US011975063B2

(12) United States Patent
Collins et al.

(10) Patent No.: US 11,975,063 B2
(45) Date of Patent: May 7, 2024

(54) RECOMBINANT CHIMERIC BOVINE/HUMAN PARAINFLUENZA VIRUS 3 EXPRESSING RSV G AND ITS USE

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Peter L. Collins, Silver Spring, MD (US); Ursula J. Buchholz, Silver Spring, MD (US); Bo Liang, Bethesda, MD (US); Shirin Munir, Bethesda, MD (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 47 days.

(21) Appl. No.: 17/590,631

(22) Filed: Feb. 1, 2022

(65) Prior Publication Data
US 2022/0226458 A1 Jul. 21, 2022

Related U.S. Application Data

(63) Continuation of application No. 16/616,873, filed as application No. PCT/US2018/034848 on May 29, 2018, now Pat. No. 11,273,214.

(60) Provisional application No. 62/512,111, filed on May 29, 2017.

(51) Int. Cl.
A61K 39/12 (2006.01)
A61K 39/00 (2006.01)
C07K 14/005 (2006.01)
C12N 15/86 (2006.01)

(52) U.S. Cl.
CPC ............ A61K 39/12 (2013.01); C07K 14/005 (2013.01); C12N 15/86 (2013.01); A61K 2039/5254 (2013.01); A61K 2039/5256 (2013.01); A61K 2039/543 (2013.01); A61K 2039/575 (2013.01); C12N 2760/18534 (2013.01); C12N 2760/18571 (2013.01); C12N 2760/18643 (2013.01)

(58) Field of Classification Search
CPC ............ A61K 39/12; A61K 2039/5254; A61K 2039/5256; A61K 2039/543; A61K 2039/575; C07K 14/005; C12N 15/86; C12N 2760/18534; C12N 2760/18571; C12N 2760/18643; C12N 2760/18641
See application file for complete search history.

(56) References Cited

U.S. PATENT DOCUMENTS

| 6,764,685 | B1 | 7/2004 | Haller et al. |
| 7,192,593 | B2 | 3/2007 | Murphy et al. |
| 7,201,907 | B1 | 4/2007 | Schmidt et al. |
| 7,208,161 | B1 | 4/2007 | Murphy et al. |
| 7,250,171 | B1 | 7/2007 | Tao et al. |
| 7,622,123 | B2 | 11/2009 | Skiadopoulos et al. |
| 7,632,508 | B2 | 12/2009 | Schmidt et al. |
| 2009/0017517 | A1 | 1/2009 | Schickli et al. |
| 2009/0263883 | A1 | 10/2009 | Haller et al. |
| 2010/0119547 | A1 | 5/2010 | Haller et al. |
| 2011/0097355 | A1 | 4/2011 | Morrison |
| 2012/0045471 | A1 | 2/2012 | Haller et al. |

FOREIGN PATENT DOCUMENTS

| JP | 2002-502241 | 1/2002 |
| JP | 2003-516148 | 5/2003 |
| JP | 2005-518209 | 6/2005 |
| WO | WO 1998/53078 A1 | 11/1998 |
| WO | WO 2001/42445 A2 | 6/2001 |
| WO | WO2001/70032 A1 | 9/2001 |
| WO | WO 2003/072725 A2 | 9/2003 |
| WO | WO 2016/118642 A1 | 7/2016 |
| WO | WO 2017/100759 A1 | 6/2017 |

OTHER PUBLICATIONS

Bernstein et al., "Phase 1 Study of the Safety and Immunogenicity of a Live, Attenuated Respiratory Syncytial Virus and Parainfluenza Virus Type 3 Vaccine in Seronegative Children," Ped Infect Dis J. 31.2: 109-114, Feb. 2012.
Boyoglu-Barnum et al., "Mutating the CX3C Motif in the G Protein Should Make a Live Respiratory Syncytial Virus Vaccine Safer and More Effective," J Virol. 91.10: e02059-16, May 2017.
Bukreyev et al., "The Secreted G Protein of Human Respiratory Syncytial Virus Antagonizes Antibody-Mediated Restriction of Replication Involving Macrophages and Complement," J Virol. 86.19: 10880-10884, Oct. 2012.
Chirkova et al., "Respiratory Syncytial Virus G Protein CX3C Motif Impairs Human Airway Epithelial and Immune Cell Responses," J Virol. 87.24: 13466-13479, Dec. 2013.
Collins et al., "Nucleotide Sequences for the Gene Junctions of Human Respiratory Syncytial Virus Reveal Distinctive Features of Intergenic Structure and Gene Order," Proc Natl Acad Sci USA 83.13: 4594-4598, Jul. 1986.

(Continued)

Primary Examiner — Rachel B Gill
(74) Attorney, Agent, or Firm — Klarquist Sparkman, LLP

(57) ABSTRACT

Recombinant chimeric bovine/human parainfluenza virus 3 (rB/HPIV3) vectors expressing Respiratory Syncytial Virus (RSV) G protein or a recombinant RSV G protein, as well as methods of their use and manufacture, are provided. The rB/HPIV3 vector comprises a genome comprising a heterologous gene encoding the RSV G protein or the recombinant RSV G protein. Nucleic acid molecules comprising the sequence of the genome or antigenome of the disclosed rB/HPIV3 vectors are also provided. The disclosed rB/HPIV3 vectors can be used, for example, to induce an immune response to RSV and HPIV3 in a subject.

20 Claims, 23 Drawing Sheets

Specification includes a Sequence Listing.

(56) References Cited

OTHER PUBLICATIONS

Collins et al., "Gene Overlap and Site-Specific Attenuation of Transcription of the Viral Polymerase L Gene of Human Respiratory Syncytial Virus," Proc Natl Acad Sci USA 84.15: 5134-5138, Aug. 1987.

Collins et al., "Production of Infectious Human Respiratory Syncytial Virus from Cloned cDNA Confirms an Essential Role for the Transcription Elongation Factor from the 5' Proximal Open Reading Frame of the M2 mRNA in Gene Expression and Provides a Capability for Vaccine Development," Proc Natl Acad Sci USA 92.25: 11563-11567, Dec. 1995.

Corry et al., "Preventing Cleavage of the Respiratory Syncytial Virus Attachment Protein in Vero Cells Rescues the Infectivity of Progeny Virus for Primary Human Airway Cultures," J Virol. 90.3: 1311-1320, Feb. 2016.

Eshagi, et al., "Genetic Variability of Human Respiratory Syncytial Virus A Strains Circulating in Ontario: A Novel Genotype with a 72 Nucleotide G Gene Duplication," PLoS One 7.3: 1-10, Mar. 2012.

Harcourt et al., "Respiratory Syncytial Virus G Protein and G Protein CX3C Motif Adversely Affect CX3CR1+ T Cell Responses," J Immunol. 176.3: 1600-1608, Feb. 2006.

Ilyushina et al., "Comparative Study of Influenza Virus Replication in MDCK Cells and in Primary Cells Derived from Adenoids and Airway Epithelium," J Virol. 86.21: 11725-11734, Nov. 2012.

International Search Report and Written Opinion, dated Sep. 4, 2018, by the European Patent Office, for PCT Application No. PCT/US2018/034848, 14 pp.

Johnson et al., "Priming with Secreted Glycoprotein G of Respiratory Syncytial Virus (RSV) Augments Interleukin-5 Production and Tissue Eosinophilia After RSV Challenge," J Virol. 72.4: 2871-2880, Apr. 1998.

Johnson et al., "Respiratory Syncytial Virus Glycoprotein G Interacts with DC-SIGN and L-SIGN to Activate ERK1 and ERK2," J Virol. 86.3: 1339-1347, Feb. 2012.

Johnson et al., "Respiratory Syncytial Virus Uses CX3CR1 as a Receptor on Primary Human Airway Epithelial Cultures," PLoS Pathogens 11.12: e1005318, Dec. 2015.

Joyce, et al., "Iterative Structure-Based Improvement of a Respiratory Syncytial Virus Fusion Glycoprotein Vaccine," Nat Struct Mol Biol. 23.9: 811-820, Sep. 2016.

Karron et al., "Respiratory Syncytial Virus (RSV) SH and G Proteins are not Essential for Viral Replication In Vitro: Clinical Evaluation and Molecular Characterization of a Cold-Passaged, Attenuated RSV Subgroup B Mutant," Proc Natl Acad Sci USA 94.25: 13961-13966, Dec. 1997.

Karron et al., "Identification of a Recombinant Live Attenuated Respiratory Syncytial Virus Vaccine Candidate that is Highly Attenuated in Infants," J Infect Diseases 191.7: 1093-1104, Apr. 2005.

Karron et al., "Evaluation of Two Chimeric Bovine-Human Parainfluenza Virus Type 3 Vaccines in Infants and Young Children," Vaccine 30.26: 3975-3981, Jun. 2012.

Kolakofsky, "Paramyxovirus RNA Synthesis, mRNA Editing, and Genome Hexamer Phase: A Review," Virology 498: 94-98, Aug. 2016.

Liang, et al., "Chimeric Bovine/Human Parainfluenza Virus Type 3 Expressing Respiratory Syncytial Virus (RSV) F Glycoprotein: Effect of Insert Position on Expression, Replication, Immunogenicity, Stability, and Protection Against RSV Infection," J Virol. 88.8: 4237-4250, Apr. 2014.

Liang, et al., "Enhanced Neutralizing Antibody Response Induced by Respiratory Syncytial Virus Prefusion F Protein Expressed by a Vaccine Candidate," J Virol. 89.18: 9549-9510, Sep. 2015.

Liang et al., "Packaging and Prefusion Stabilization Separately and Additively Increase the Quantity and Quality of Respiratory Syncytial Virus (RSV)-Neutralizing Antibodies Induced by an RSV Fusion Protein Expressed by a Parainfluenza Virus Vector," J Virol. 90.21: 10022-10038, Nov. 2016.

Liang et al., "Improved Prefusion Stability, Optimized Codon Usage, and Augmented Virion Packaging Enhance the Immunogenicity of Respiratory Syncytial Virus Fusion Protein in a Vectored-Vaccine Candidate," J Virol. 91.15: e00189-17, Aug. 2017.

Liang et al., "Effects of Alterations to the CX3C Motif and Secreted Form of Human Respiratory Syncytial Virus (RSV) G Protein on Immune Responses to a Parainfluenza Virus Vector Expressing the RSV G Protein," J Virol. 93.7: e02043-18, Apr. 2019.

Mackow et al., "Attenuated Human Parainfluenza Virus Type 1 (HPIV1) Expressing the Fusion Glycoprotein of Human Respiratory Syncytial Virus (RSV) as a Bivalent HPIV1/RSV Vaccine," J Virol. 89.20: 10319-10332, Oct. 2015.

Maher et al., "Recombinant Respiratory Syncytial Virus Lacking Secreted Glycoprotein G is Attenuated, Non-Pathogenic but Induces Protective Immunity," Microbes Infect. 6.12: 1049-1055, Oct. 2004.

Munir et al., "Nonstructural Proteins 1 and 2 of Respiratory Syncytial Virus Suppress Maturation of Human Dendritic Cells," J Virol. 82.17: 8780-8796, Sep. 2008.

Polack et al., "The Cysteine-Rich Region of Respiratory Syncytial Virus Attachment Protein Inhibits Innate Immunity Elicited by the Virus and Endotoxin," PNAS 102.25: 8996-9001, Jun. 2005.

Roberts et al., "The Membrane-Associated and Secreted Forms of the Respiratory Syncytial Virus Attachment Glycoprotein G are Synthesized from Alternative Initiation Codons," J Virol. 68.7: 4538-4546, Jul. 1994.

Schaap-Nutt et al., "Growth Restriction of an Experimental Live Attenuated Human Parainfluenza Virus Type 2 Vaccine in Human Ciliated Airway Epithelium In Vitro Parallels Attenuation in African Green Monkeys," Vaccine 28.15: 2788-2798, Mar. 2010.

Schmidt et al., "Bovine Parainfluenza Virus Type 3 (BPIV3) Fusion and Hemagglutinin-Neuraminidase Glycoproteins Make an Important Contribution to the Restricted Replication of BPIV3 in Primates," J Virol. 74.19: 8922-8929, Oct. 2000.

Schmidt et al., "Recombinant Bovine/Human Parainfluenza Virus Type 3 (B/HPIV3) Expressing the Respiratory Syncytial Virus (RSV) G and F Proteins Can be Used to Achieve Simultaneous Mucosal Immunization Against RSV and HPIV3," J Virol. 75.10: 4594-4603, May 2001.

Schneider-Ohrum et al., "Immunization with Low Doses of Recombinant Postfusion or Prefusion Respiratory Syncytial Virus F Primes for Vaccine-Enhanced Disease in the Cotton Rat Model Independently of the Presence of a Th1-Biasing (GLA-SE) or Th2-Biasing (Alum) Adjuvant," J Virol. 91.8: e02180-16, Apr. 2017.

Shingai et al., "Soluble G Protein of Respiratory Syncytial Virus Inhibits Toll-Like Receptor 3/4-Mediated IFN-beta Induction," Internat Immunol. 20.9: 1169-1180, Jul. 2008.

Tang et al., "Effects of Human Metapneumovirus and Respiratory Syncytial Virus Antigen Insertion in Two 3' Proximal Genome Positions of Bovine/Human Parainfluenza Virus Type 3 on Virus Replication and Immunogenicity," J Virol. 77.20: 10819-10828, Oct. 2003.

Tao et al., "A Live Attenuated Recombinant Chimeric Parainfluenza Virus (PIV) Candidate Vaccine Containing the Hemagglutinin-Neuraminidase and Fusion Glycoproteins of PIV1 and the Remaining Proteins from PIV3 Induces Resistance to PIV1 Even in Animals Immune to PIV3," Vaccine 18.14: 1359-1366, Jan. 2000.

Teng et al., "Contribution of the Respiratory Syncytial Virus G Glycoprotein and Its Secreted and Membrane-Bound Forms to Virus Replication In Vitro and In Vivo," Virology 289.2: 283-296, Oct. 2001.

Trento, et al., "Major Changes in the G Protein of Human Respiratory Syncytial Virus Isolates Introduced by a Duplication of 60 Nucleotides," J Gen Virol. 84.11: 3115-3120, Nov. 2003.

Tripp et al., "CX3C Chemokine Mimicry by Respiratory Syncytial Virus G Glycoprotein," Nature Immunol. 2.8: 732-738, Aug. 2001.

Yang et al., "Implication of Respiratory Syncytial Virus (RSV) F Transgene Sequence Heterogeneity Observed in Phase 1 Evaluation of MEDI-534, a Live Attenuated Parainfluenza Type 3 Vectored RSV Vaccine," Vaccine 31.26: 2822-2827, Jun. 2013.

Zhang et al., "Respiratory Syncytial Virus Infection of Human Airway Epithelial Cells is Polarized, Specific to Ciliated Cells, and Without Obvious Cytopathology," J Virol. 76.11: 5654-5666, Jun. 2002.

(56) References Cited

OTHER PUBLICATIONS

Zhang et al., "Infection of Ciliated Cells by Human Parainfluenza Virus Type 3 in an In Vitro Model of Human Airway Epithelium," *J Virol.* 79.2: 1113-1124, Jan. 2005.

Zhivaki et al., "Respiratory Syncytial Virus Infects Regulatory B Cells in Human Neonates via Chemokine Receptor CX3CR1 and Promotes Lung Disease Severity," *Immunity* 46.2: 301-314, Feb. 2017.

FIG. 1A rB/HPIV3-RSV G

*Asc* I — 3' leader — N GE `GGCGCGCCAGTAAGAAAAACTTAGGATTAATGA` — P GS — RSV G — P GS `AGTAAGAAAAACTTAGGATTAATGA`CCTGCAGGATG — M — F — HN — L — 5' trailer

I263T-T370P XX

SEQ ID NO: 32

RSV G TAGTGATAGCTTAGCGGGCGCGCCAGCAACAGTAAGAAAAACTTAGGATTAATGGA

SEQ ID NO: 33

*Asc* I — N GE — P GS (i) wtG — M48 — 298 aa (ii) mG — M48I — 298 aa (iii) sG — M48 — 251 aa ***

(iv) G_B3CT — 30 — 291 aa ***

(v) G_B3TMCT — 56 — 289 aa ***

(vi) G_dCX3C — C186R — 298 aa (vii) G_wCX4C — A186 — 299 aa ***

(viii) G_dCX3C_B3CT — C186R — 30 — 291 aa ***

(ix) G_dCX3C_B3TMCT — C186R — 56 — 289 aa ***

(x) wtG/GS-opt

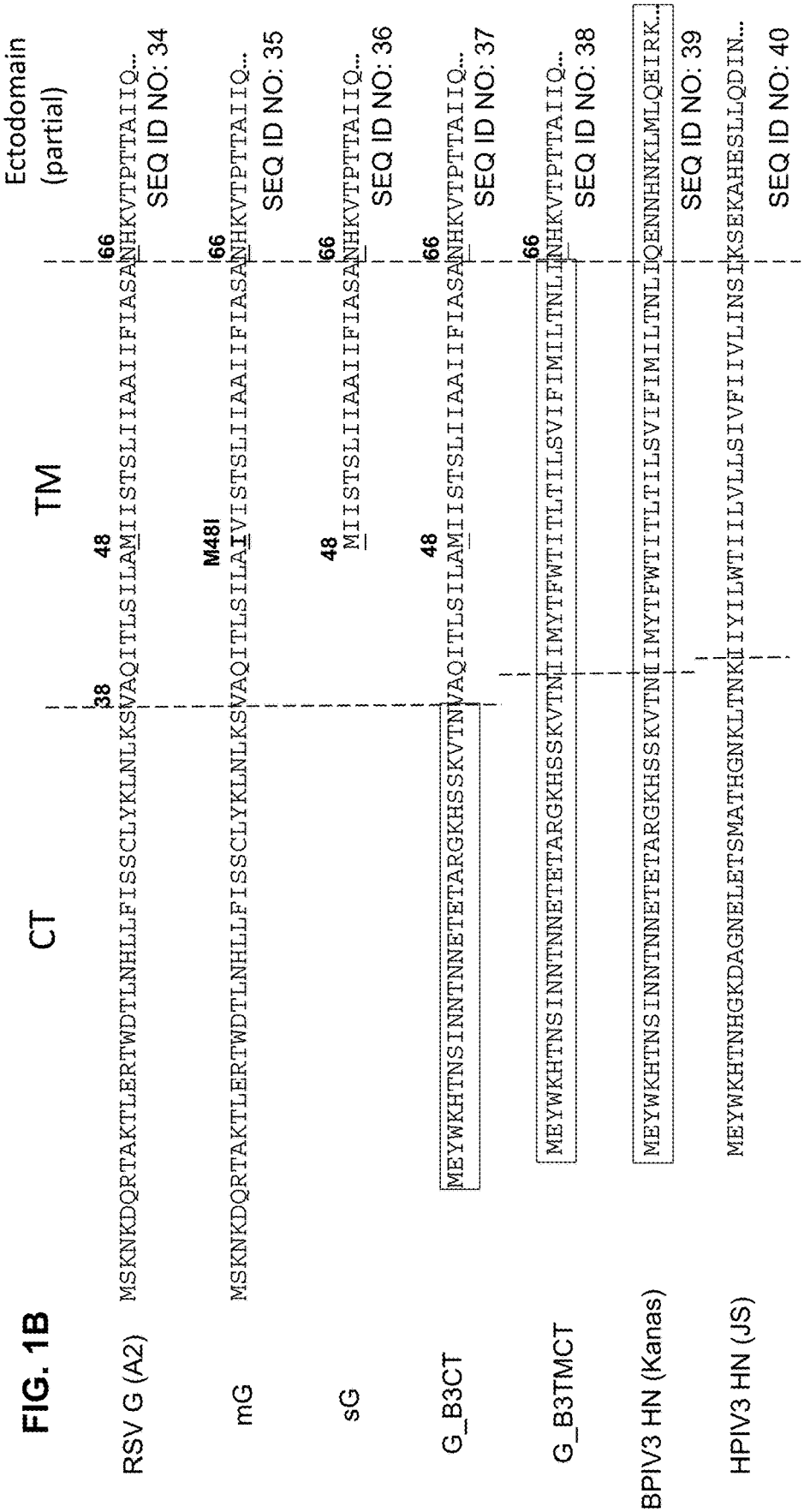

FIG. 1C

|  | 182 | 183 | 184 | 185 | 186 |  |
|---|---|---|---|---|---|---|
| Unmodified CX3C | C<br>TGC | W<br>TGG | A<br>GCT | I<br>ATC |  | C<br>TGC |
| dCX3C | C<br>TGC | W<br>TGG | A<br>GCT | I<br>ATC |  | R<br>CGC |
| wCX4C | C<br>TGC | W<br>TGG | A<br>GCT | I<br>ATC | A<br>GCA | C<br>TGC |

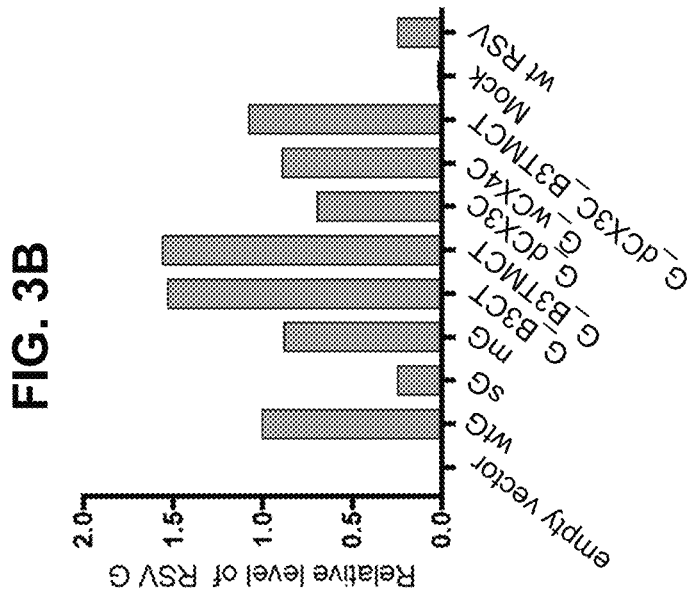
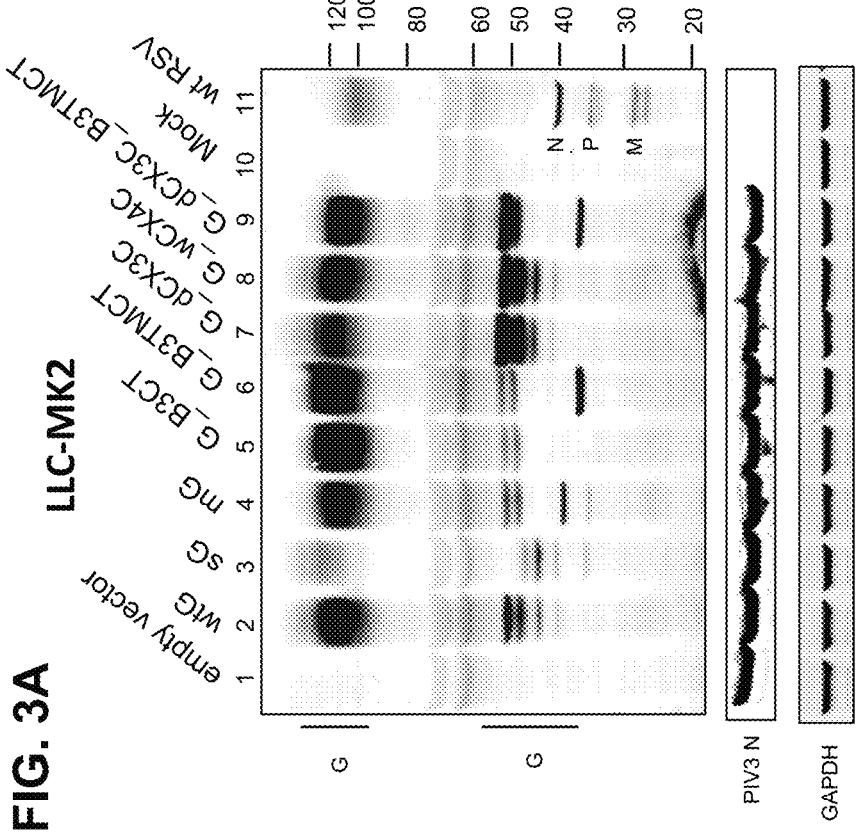
FIG. 3A
FIG. 3B

Goat anti-RSV (ab20531) + MS456

131-2G + MS456

FIG. 6B
wt RSV

FIG. 6D

FIG. 6C rB/HPIV3-wt G rB/HPIV3-sG

FIG. 6G

FIG. 6H rB/HPIV3-G_B3CT

FIG. 6J

FIG. 6I rB/HPIV3-G_B3TMCT rB/HPIV3-Empty vector

FIG. 8A
RSV A2 neutralizing, with complement

FIG. 8B
HPIV3 neutralizing, with complement

FIG. 8C

RSV B1 neutralizing, with complement

FIG. 8D

RSV A2 CWAIS neutralizing, with complement

FIG. 8E

RSV A2 neutralizing, without complement (Bar chart with y-axis: Log$_2$(PRNT$_{60}$) ranging from 1 to 14; x-axis categories:
1. rB/HPIV3
2. wtG
3. sG
4. mG
5. G_B3CT
6. G_B3TMCT
7. G_dCX3C
8. G_wCX4C
9. G_dCX3C_B3CT
10. G_dCX3C_B3TMCT
11. wt RSV
RSVF)

FIG. 9A
wt RSV replication in NT

FIG. 9B
wt RSV replication in Lungs

Protection against wt RSV A2 challenge

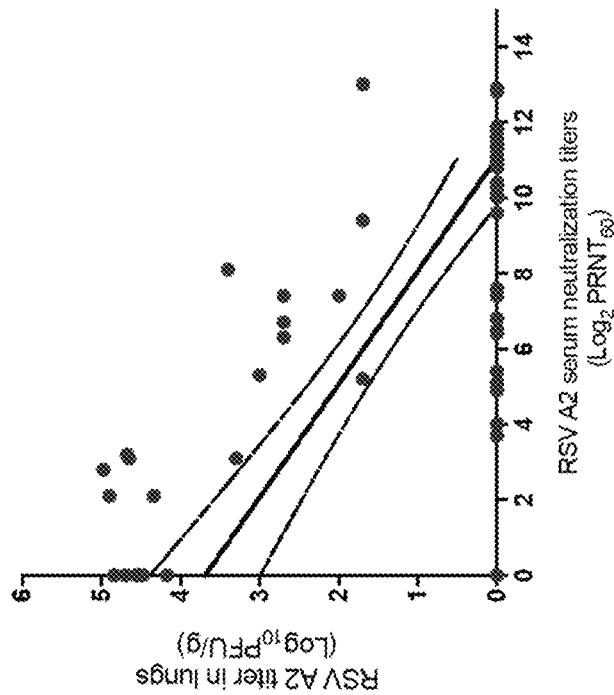
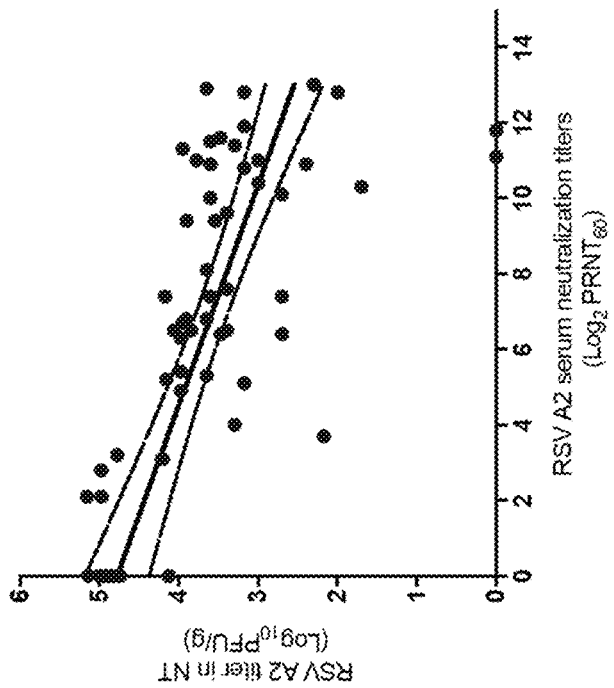

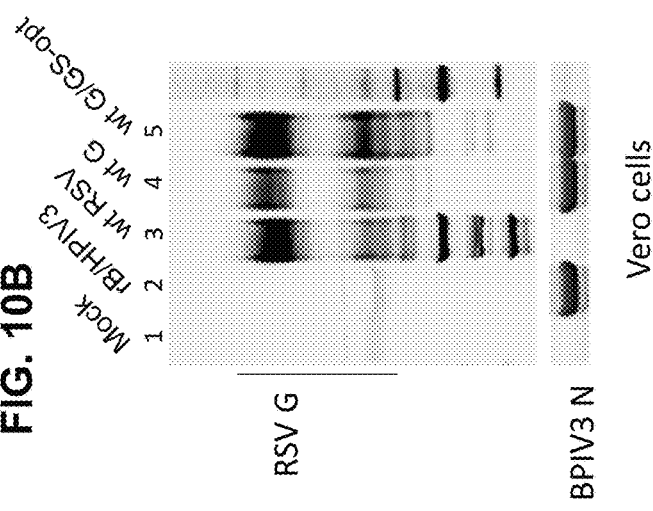
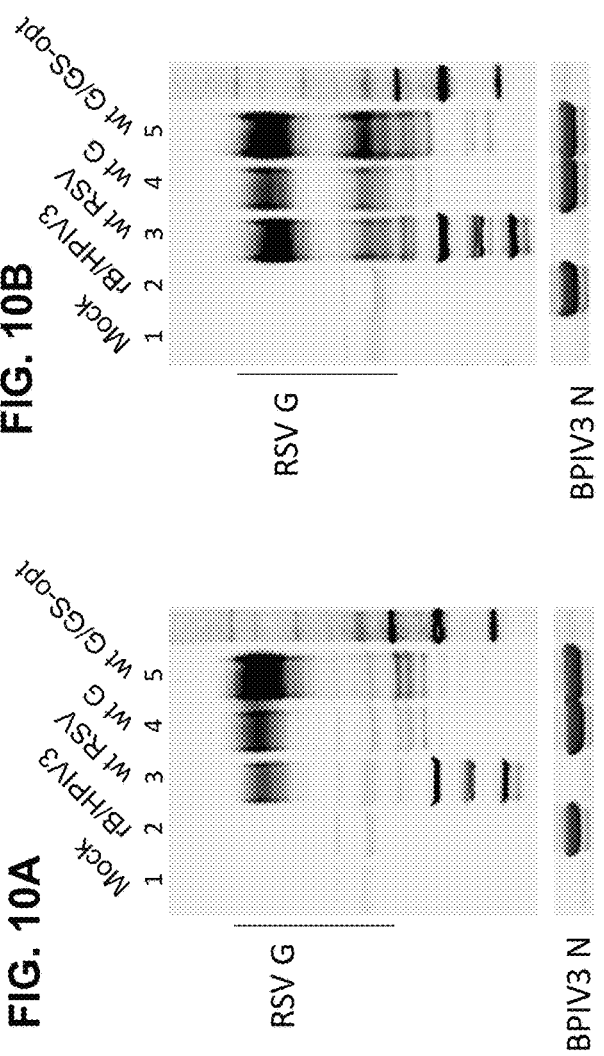
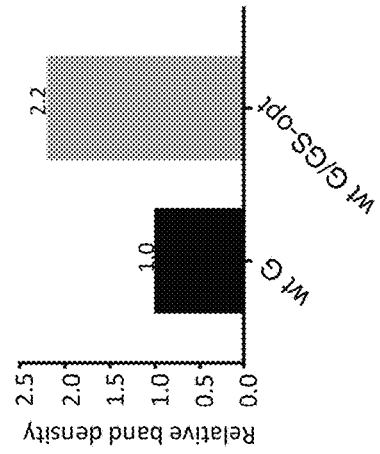
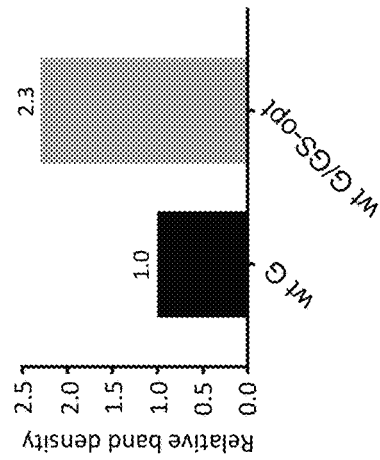

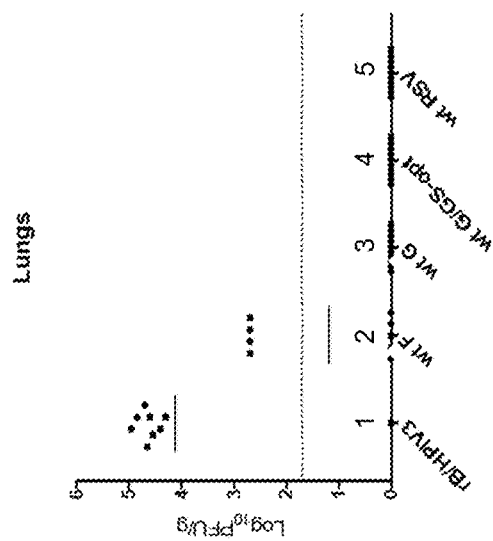
FIG. 12A
FIG. 12B
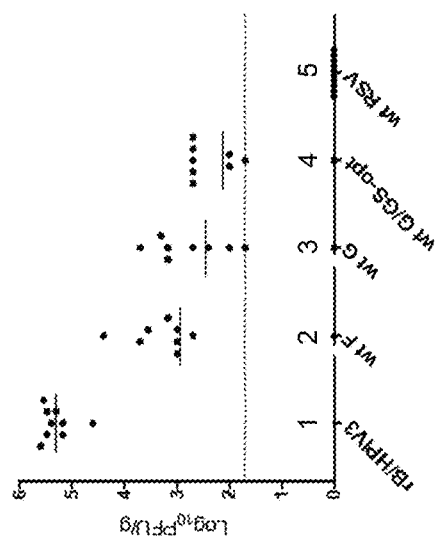
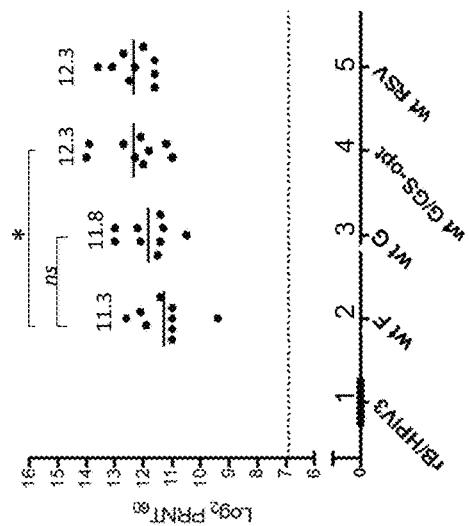
FIG. 11

RECOMBINANT CHIMERIC BOVINE/HUMAN PARAINFLUENZA VIRUS 3 EXPRESSING RSV G AND ITS USE

CROSS REFERENCE TO RELATED APPLICATION

This application is a continuation of U.S. application Ser. No. 16/616,873, filed Nov. 25, 2019, which is the U.S. National Stage of International Application No. PCT/US2018/034848, filed May 29, 2018, which was published in English under PCT Article 21(2), which in turn claims the benefit of U.S. Provisional Application No. 62/512,111, filed May 29, 2017, all of which are herein incorporated by reference in their entireties.

FIELD

This disclosure relates to recombinant chimeric bovine/human parainfluenza virus 3 (rB/HPIV3) vectors expressing Respiratory Syncytial Virus (RSV) G protein, or a recombinant RSV G protein, and use of the rB/HPIV3 vector, for example, to induce an immune response to RSV and HPIV3 in a subject.

PARTIES TO A JOINT RESEARCH AGREEMENT

This invention was made under Public Health Service Cooperative Research and Development Agreement (PHS-CRADA) No. 2013-0810 between the National Institute of Allergy and Infectious Disease at the National Institutes of Health and Sanofi Pasteur, Inc.

BACKGROUND

RSV is an enveloped non-segmented negative-strand RNA virus in the family Pneumoviridae, genus *Orthopneumovirus*. It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems. Passive immunization currently is used to prevent severe illness caused by RSV infection, especially in infants with prematurity, bronchopulmonary dysplasia, or congenital heart disease. Despite the burden of RSV infection in certain populations, development of an effective RSV vaccine remains elusive.

Parainfluenza viruses (PIV) are closely related enveloped non-segmented negative-strand RNA viruses that belong to the closely related family Paramyxoviridae. PIVs include members of the genus *Respirovirus* (including PIV1, PIV3, Sendai virus) and *Rubulavirus* (including PIV2, PIV4, PIV5). The human parainfluenza viruses (HPIVs, serotypes 1, 2, and 3) are second only to RSV in causing severe respiratory infections in infants and children worldwide, with HPIV3 being the most relevant of the HPIVs in terms of disease impact. The HPIV3 genome is approximately 15.5 kb, with a gene order of 3'-N-P-M-F-HN-L. Each gene encodes a separate mRNA that encodes a major protein: N, nucleoprotein; P, phosphoprotein; M, matrix protein; F, fusion glycoprotein; HN, hemagglutinin-neuraminidase glycoprotein; L, large polymerase protein, with the P gene containing additional open reading frames encoding the accessory C and V proteins. Similar to RSV, development of an effective HPIV vaccine remains elusive.

Major challenges to developing pediatric vaccines against RSV and HPIV3 include the immaturity of the immune system during infancy, immune-suppression by maternal antibodies, inefficient immune protection at the superficial epithelium of the respiratory tract, and vaccine-induced enhanced disease that has been observed in studies with inactivated or subunit RSV and HPIV3 vaccines in virus-naïve recipients. Further, prior studies of a live-attenuated rB/HPIV3 vector expressing an RSV antigen (RSV F protein) revealed disappointing immunogenicity to RSV that was deemed insufficient for vaccine use.

Thus, despite substantial effort, a need remains for a safe and effective immunogen that induces a protective immune response to RSV and HPIV3, particularly in pediatric subjects.

SUMMARY

Recombinant chimeric bovine/human parainfluenza virus 3 (rB/HPIV3) vectors expressing RSV G or variants thereof ("rB/HPIV3-RSV G" vectors) are provided herein. The disclosed rB/HPIV3-RSV G vectors comprise a genome comprising, in a 3'-to-5' order, a 3' leader region, a BPIV3 N gene, a heterologous gene, BPIV3 P and M genes, HPIV3 F and HN genes, a BPIV3 L gene, and a 5' trailer region. The heterologous gene encodes one of: (a) a RSV G protein comprising an RSV G ectodomain, transmembrane domain, and cytoplasmic tail; (b) a recombinant RSV G protein comprising a RSV G ectodomain, a BPIV3 HN transmembrane domain, and a BPIV3 HN cytoplasmic tail; (c) a recombinant RSV G protein comprising a RSV G ectodomain, a HPIV3 HN transmembrane domain, and a HPIV3 HN cytoplasmic tail; or (d) a recombinant RSV G protein comprising a RSV G ectodomain, a HPIV1 HN transmembrane domain, and a HPIV1 HN cytoplasmic tail. The HPIV3 HN gene encodes a HPIV3 HN protein comprising 263T and 370P amino acid assignments. The rB/HPIV3 vectors disclosed herein are infectious, attenuated, and self-replicating, and can be used to induce an immune response to RSV and HPIV3.

In some embodiments, the heterologous gene encoding the wild-type (wt) RSV G protein or recombinant RSV G protein can be codon-optimized for expression in human cells.

Also provided herein are methods and compositions related to the expression of the disclosed viruses. For example, isolated polynucleotide molecules that include a nucleic acid sequence encoding the genome or antigenome of the described viruses are disclosed.

Immunogenic compositions including the rB/HPIV3-RSV G are also provided. The compositions can further include an adjuvant. Methods of eliciting an immune response in a subject by administering an effective amount of a disclosed rB/HPIV3-RSV G to the subject are also disclosed. In some embodiments, the subject is a human subject, for example, a human subject between 1 and 6 months of age, or between 1 and 12 months of age, or between 1 and 18 months of age, or older.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1C. Map of the rB/HPIV3 genome and added RSV G gene of rB/HPIV3-RSV G vectors, and diagrams and features of modified RSV G proteins included in the vectors. (FIG. 1A) rB/HPIV3 gene map and G protein diagrams. The rB/HPIV3 gene map is shown at the top, and the second line shows the details of the sequence flanking the RSV strain A2 G gene inserted at the second gene position, between the vector N and P genes, using the indicated AscI sites (underlined). N GE: gene end signal from the BPIV3 N gene: P GS: gene start signal from the BPIV3 P gene; M48: AUG codon 48 of the RSV G open reading frame (ORF) that can serve as an alternative translational start site; CX3C (G amino acids 182-186): fractalkine motif, conserved among RSV strains; the TGA stop codon of the G ORF is emboldened and underlined. An additional TAG stop codon is underlined with * and was included in those G protein inserts indicated with *: this trinucleotide was added when needed to adjust the sequence length to conform to the "rule of six" (see Kolakofsky Virology 498:94-98, 2016). Several diagrams of RSV G protein structures are shown, including: (i) wt G, unmodified wild-type RSV G; (ii) mG, expressing only the transmembrane form of RSV G (mG) due to the M48I mutation that ablates expression of secreted G (sG); (iii) sG, expressing only sG, due to deletion of the first 47 codons, so that the ORF begins with the M48 codon; (iv) G_B3CT, with the cytoplasmic tail (CT) of RSV G replaced by the CT of BPIV3 HN; (v) G_B3TMCT, with the transmembrane domain (TM) and CT of RSV G replaced by the TM and CT of BPIV3 HN; (vi) G_dCX3C, with the C186R mutation ablating the CX3C motif (yielding CX3R); (vii) G_wCX4C, with the addition of A186 to ablate the CX3C motif (yielding CX3AC); (viii) G_dCX3C_B3CT, with the C186R mutation ablating the CX3C motif, and bearing the CT of BPIV3 HN; (ix) G_dCX3C_B3TMCT, with the C186R mutation ablating the CX3C motif, and bearing the TM and CT of BPIV3 HN; (x) wt G/GS-opt, GenScript codon-optimized wt G. (FIG. 1B) Amino acid sequences of the TM and CT domains of wt RSV G protein (top); and the following modified versions of RSV G: mG, sG, G_B3CT, and G_B3TMCT; and the wt BPIV3 HN (strain Kansas), and wt HPIV3 HN (strain JS). The sequences were aligned according to the beginning of the G ectodomain at amino acid 66. The presumed CT, TM, and ectodomains are demarcated with dashed lines, and BPIV3 HN sequences are boxed. Note that the N-terminus of sG is that of the primary translation product, which subsequently gets trimmed proteolytically to yield a predominant N-terminus at N66, or a secondary N-terminus at 175. (FIG. 1C) Sequence of the unmodified CX3C motif of wt G protein (top line, showing protein (SEQ ID NO: 41) and nucleotide (SEQ ID NO: 42) sequence), the dCX3C version in which the CX3C motif is disrupted by a C186R missense mutation (middle line, showing protein (SEQ ID NO: 43) and nucleotide (SEQ ID NO: 44) sequence), and the wCX4C version in which the CX3C motif is disrupted by the addition of an alanine codon following codon 185 (bottom line, showing protein (SEQ ID NO: 45) and nucleotide (SEQ ID NO: 46) sequence). The conserved cysteine residues are in bold; mutated nucleotides in dCX3C and wCX4C are underlined.

Figures 2A, 2B, 2C, 2D:
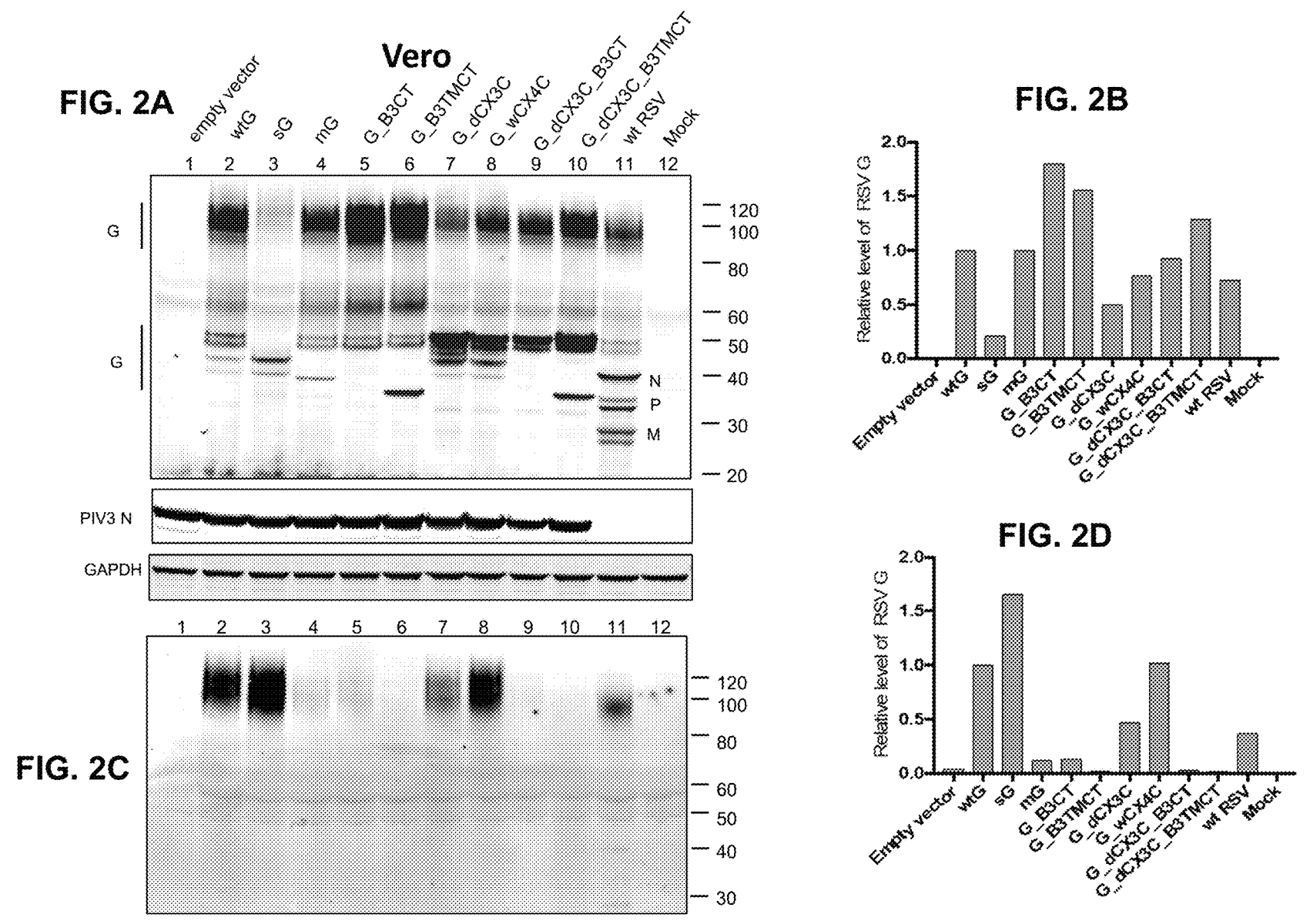

FIGS. 2A-2D. Western blot analysis of modified RSV G proteins expressed in Vero cells from the rB/HPIV3-RSV G vectors. Vero cells were infected with the indicated rB/HPIV3-RSV G vector or wt RSV at an MOI of 10 $TCID_{50}$ or 3 PFU per cell, respectively. At 24 hours post-infection (h.p.i.), the cells were harvested for analysis, and at 48 h.p.i., the overlying cell culture medium supernatants from duplicate cultures were harvested for analysis. The cells and medium supernatants were analyzed separately by gel electrophoresis under denaturing and reducing conditions followed by Western blotting with antisera raised separately against RSV and HPIV3, followed by secondary antibodies conjugated with infrared fluorescent dyes, and the relative levels of the large predominant band of fully glycosylated, 90-120 kDa RSV G protein were quantified densitometric analysis using an Odyssey imaging system (LiCor). (FIG. 2A) Western blots of proteins from infected cells. Top panel: the bars to the left indicate fully and partially glycosylated forms of RSV G (upper and lower bars, respectively), lane 11 shows in addition the RSV N, P, M proteins expressed by wt RSV. Middle panel: BPIV3 N protein. Bottom panel: GAPDH protein used as loading control. (FIG. 2B) Relative levels of fully glycosylated (90-120 kDa) RSV G quantified from the experiment in part A by densitometry using the LiCor Image Studio software calibrated using the GAPDH signal and normalized to wt G (lane 2) set as 1.0. (FIG. 2C) Western blot of G protein in cell culture medium supernatants. (FIG. 2D) Relative levels of fully glycosylated G protein from FIG. 2C, normalized to wt G.

FIGS. 3A and 3B. Western blot analysis of RSV G expression from rB/HPIV3-RSV G vectors in LLC-MK2 cells. LLC-MK2 cells were infected with the indicated rB/HPIV3-RSV G constructs or wt RSV as described in FIG. 2A. Cells were harvested at 24 h.p.i. processed, and subjected to by Western blot analysis with antisera raised separately against RSV and HPIV3 as described in FIGS. 2A and 2B. (FIG. 3A) Western blot showing expression of RSV G (top panel), BPIV3 N (middle panel), and GAPDH (bottom panel) as a loading control. (FIG. 3B) Relative levels of fully glycosylated (90-120 kDa) RSV G quantified from FIG. 3A and normalized to wt G (lane 2) as 1.0.

(FIG. 4A) Images of plaques that were probed with rabbit antisera raised separately against HPIV3 and RSV, and a goat hyperimmune serum to RSV (ab20531, Abcam): HPIV3 antigens alone were visualized as green, RSV G protein alone as red, and co-expression as yellow. (FIG. 4B) Images of plaques that were probed with the same HPIV3-specific rabbit hyperimmune serum and RSV G mAb 131-2G specific to the CX3C domain: HPIV3 antigens alone were visualized as green, RSV G containing the 131-2G epitope alone was red, and co-expression was yellow.

(FIG. 5A) Western blot of empty rB/HPIV3 vector (lane 1), vector expressing wt RSV G (lane 2), vectors expressing the indicated modified forms of RSV G (lanes 3-5), and wt RSV (lane 6). The upper panel was probed with polyclonal RSV antibodies, showing the fully-glycosylated 90-120 kDa form of G, evident in lane 5, and RSV structural proteins N, P, M, and G proteins including a smaller, broad band of G (~48-62 kDa) often observed with Vero cells (lane 6) as previously described (Corry et al. *J. Virol.* 90:1311-1320, 2015). The bottom panel shows the BPIV3 N protein. (FIG. 5B) RSV G packaging efficiency based on quantification of FIG. 5A and normalized to wt G (lane 2) as 1.0.

Figure 6B:
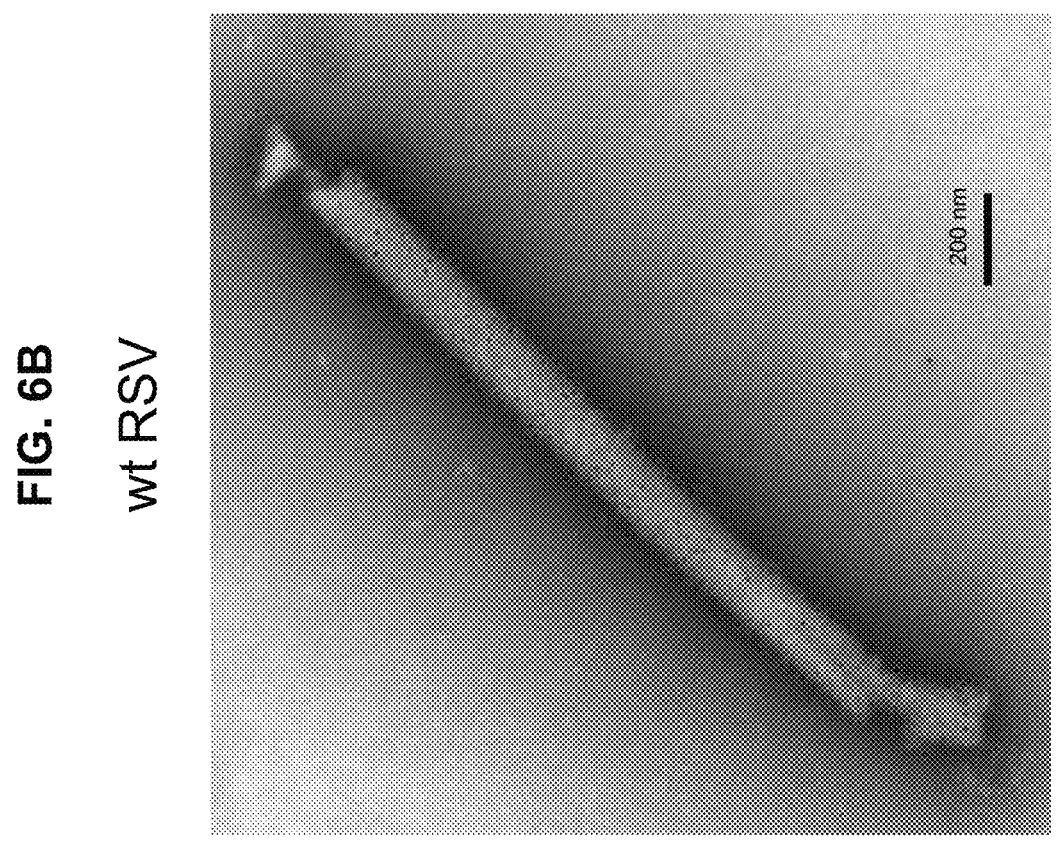
Figures 6C, 6D:
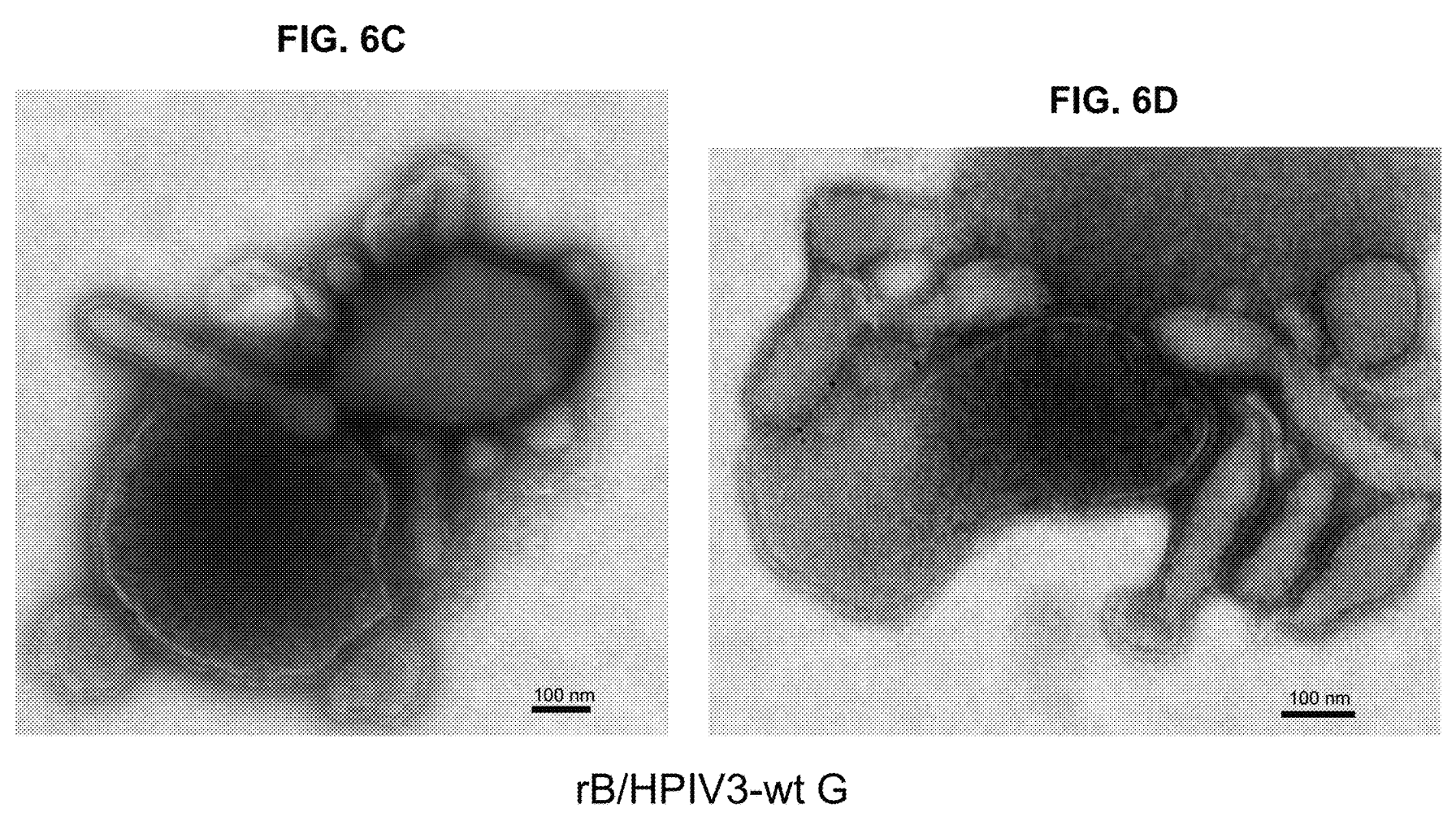
Figures 6G, 6H:
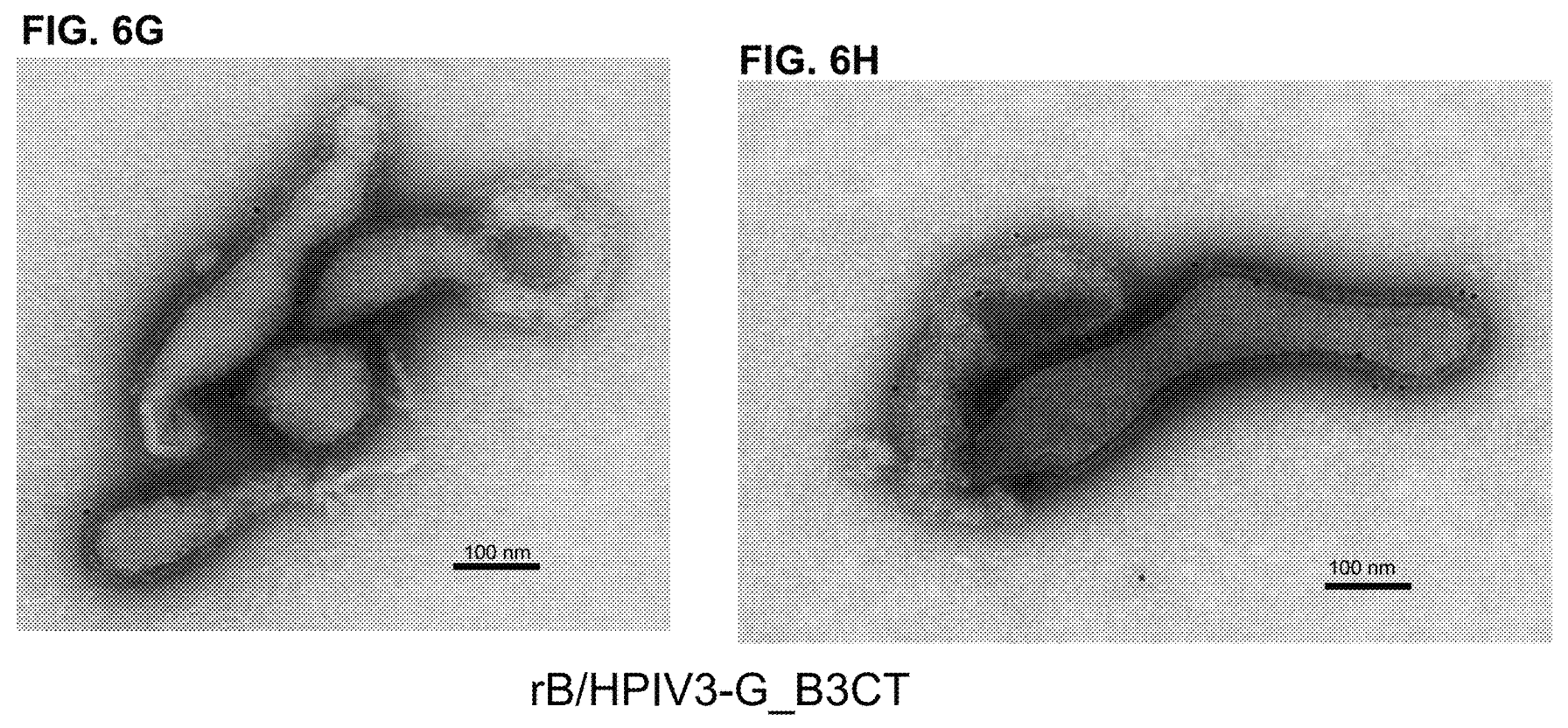
Figures 6I, 6J:
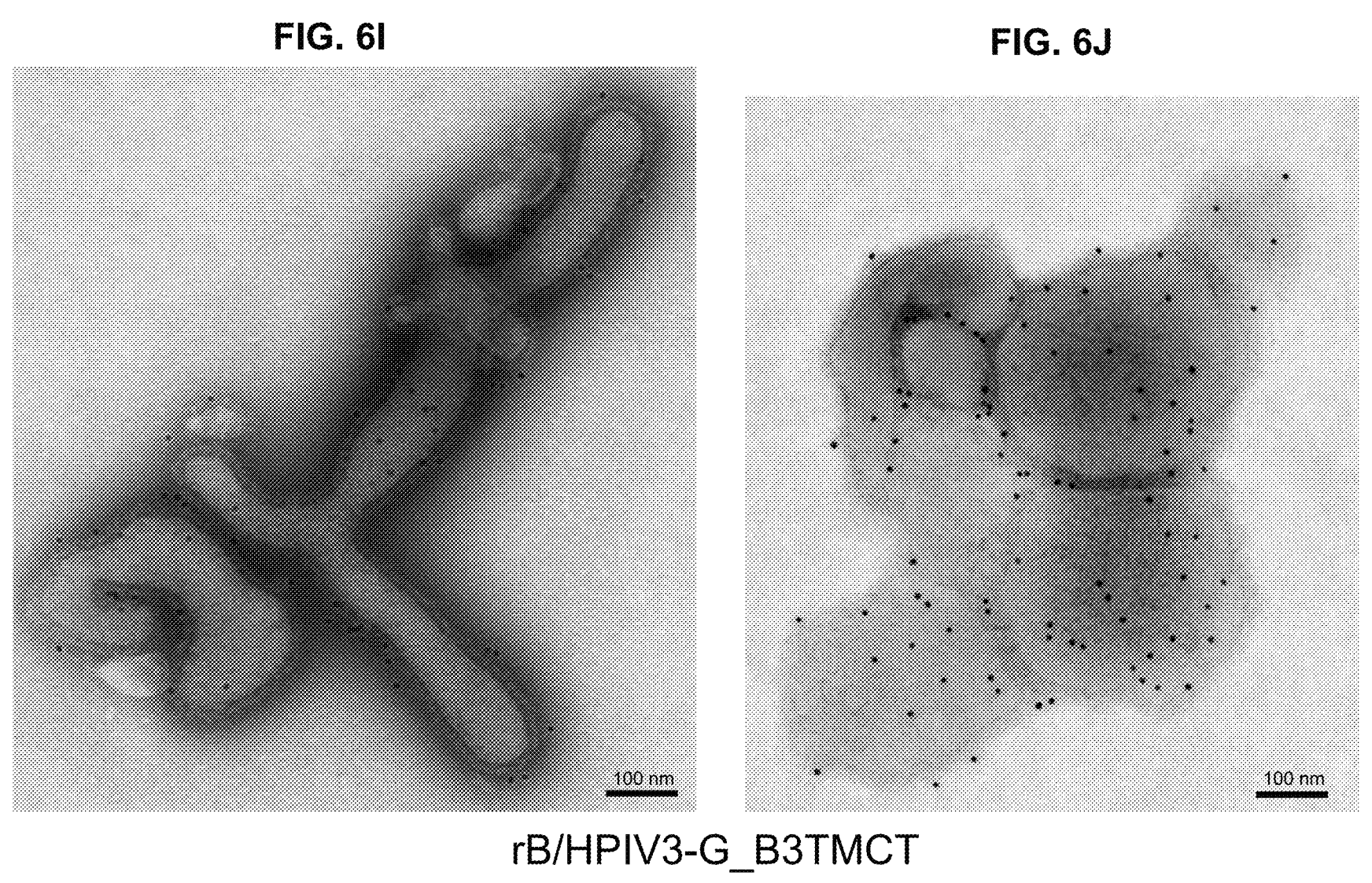

FIGS. 6A-6L. Imaging of packaged RSV G in virions by transmission electron microscopy (TEM) with immune-gold labeling. Purified virions from the preparations described in FIG. 5 were incubated with G-specific mouse MAb 131-2G (specific to the CX3C domain) and polyclonal goat anti-mouse secondary antibodies conjugated with 10 nm gold particles. Selected representative virion images are shown for: wt RSV (FIGS. 6A and 6B), rB/HPIV3 vector expressing wt RSV G (FIGS. 6C and 6D), rB/HPIV3 vector expressing only sG (FIGS. 6E and 6F), rB/HPIV3 vector expressing chimeric RSV G with CT of BPIV3 HN (FIGS. 6G and 6H), rBHPIV3 vector expressing chimeric RSV G with TM and CT of BPIV3 HN (FIGS. I and 6J), and empty rB/HPIV3 vector (FIGS. 6K and 6L).

FIGS. 8A-8E. RSV- and HPIV3-neutralizing serum antibody titers induced by rB/HPIV3-RSV G vectors and wt RSV in immunized hamsters. Hamsters in groups of six were infected IN by $10^5$ $TCID_{50}$ of the indicated rB/HPIV3-RSV G vector or $10^6$ PFU of wt RSV. Sera were collected on day 28 post-immunization. The serum neutralization titers were determined by 60% plaque reduction neutralization assay ($PRNT_{60}$) on Vero cell monolayers. For comparison, sera from a group of hamsters immunized with the same dose of vector expressing unmodified wt RSV F (from a separate experiment performed in essentially the same way) were included in RSV neutralization assays. Neutralization titers against: wt RSV, with complement (FIG. 8A), HPIV3, with complement (FIG. 8B), RSV B1, of subgroup B, with complement (FIG. 8C), RSV CX3C mutant (CWAIS), with complement (FIG. 8D), and wt RSV, without complement (FIG. 8E), are shown. The limit of detection is indicated with a dashed line. Each dot represents the titer of an individual animal. The bars indicate the mean titers of the groups; and error bars represent the SEM. The statistical significance of differences in mean titers among all groups in each assay was analyzed using one-way ANOVA followed by Tukey-Kramer test. Mean titers designated with the same letter (A, B, C or D) are not statistically different. In FIG. 8A, a Student t-test was carried out between the two indicated groups (2 and 12), with the significance of the difference shown as a P value.

FIGS. 9A-9D. Protection of immunized hamsters against wt RSV A2 challenge. Hamsters in groups of six were immunized IN with $10^5$ $TCID_{50}$ of the indicated rB/HPIV3-RSV G vector or $10^6$ PFU of wt RSV as described in FIGS. 8 and 31 days later were challenged IN by $10^6$ PFU of wt RSV. On day 3 post-challenge, animals were sacrificed and viral titers were determined in homogenates of the (FIG. 9A) nasal turbinates (NT) and (FIG. 9B) lungs by plaque assay in Vero cells. The limit of detection is indicated with a dashed line. Each dot represents the titer of an individual animal. Mean titers are indicated as short horizontal bars. The statistical significance of differences in mean titers among all groups was analyzed using one-way ANOVA followed by Tukey-Kramer test. Mean titers of groups designated with a same letter (A, B, C or D) are not statistically different. In FIGS. 9C and 9D, the RSV challenge virus titers for individual animals in the nasal turbinates (FIG. 9C) and lungs (FIG. 9D) were plotted versus the corresponding titers of complement-dependent serum RSV-neutralizing antibodies collected 28 days following vector immunization (from FIG. 8A). Pearson's linear regression model (statistical software Prism 7.0) was used to show the correlation of the neutralization titers ($Log2PRNT60$) and viral titer ($Log10PFU/g$), shown by solid lines. The R squared values were 0.45 for NT and 0.51 for lungs: the R squared value indicates how well the data fit into the model (values range from 0 to 1, with a greater value indicating increased fit). The dotted lines indicate 95% confidence intervals.

FIGS. 10A-10D. Expression of G protein from a B/HPIV3 vector bearing a G ORF that was codon-optimized for human translation (construct (x) in FIG. 1A, or wt G/GS-opt). The accumulation of G protein in LLC-MK2 and Vero cells infected with rB/HPIV3 vectors expressing wt G or wt G/GS-opt was evaluated by Western blot analysis (FIGS. 10A and 10B). The LLC-MK2 (10A) and Vero (10B) cells were infected with the indicated rB/HPIV3-RSV-G vector or wt RSV at an MOI of 10 $TCID_{50}$ or 3 PFU per cell, respectively. At 24 hours post-infection, the cells were harvested and lysates prepared and analyzed by gel electrophoresis under denaturing and reducing conditions followed by Western blotting with antisera raised against RSV, followed by secondary antibodies conjugated with infrared fluorescent dyes, and the bound antibodies were visualized using an Odyssey imaging system (LiCor). Quantification of band intensities in Western blot analysis indicated that there was 2.3-fold increase of RSV G expression by codon-optimization in LLC-MK2 cells (FIG. 10C) and 2.2-fold increase in Vero cells (FIG. 10D).

FIG. 11 RSV-neutralizing serum antibody titers induced by rB/HPIV3-RSV-G vectors expressing codon-optimized or non-optimized G ORFs in immunized hamsters. Hamsters in groups of nine were infected IN by $10^4$ $TCID_{50}$ of the indicated rB/HPIV3-RSV G vectors (lanes 1-4) or $10^6$ PFU of wt RSV (lane 5). Sera were collected on day 28 post-immunization. The serum neutralization titers were determined by 60% plaque reduction neutralization assay ($PRNT_{60}$) on Vero cell monolayers in the presence of added complement. Neutralization titers against wt RSV, with added complement are shown. Lane 1, empty rB/HPIV3 vector; lane 2, wt F, unmodified wild-type RSV F, specifically the "Non-HEK/non-opt" construct that was described in a patent application (PCT/US2016/014154) and a previous publication (Liang, et al., *J. Virol.* 89: 9499-9510, 2015); lane 3, wt G, wild-type RSV G of A2 strain; lane 4, wt G/GS-opt, a GenScript optimized wild-type G of A2 strain, having the same amino acid sequence as the wt G construct in lane 3; lane 5, wt RSV, wild-type RSV A2 as control. The limit of detection is indicated with a dashed line. Each dot represents the titer of an individual animal. The horizontal lines indicate the mean titers of the groups. The statistical significance of differences in mean titers among all groups in each assay was analyzed using unpaired two-tailed student t-test :* indicates P<0.05; ns=not significant.

FIGS. 12A-12B Replication of wt RSV challenge in hamsters previously infected with the indicated rB/HPIV3-RSV-G or RSV-F vector or wt RSV. Hamsters infected in FIG. 11 were challenged intranasally 30 days later with $10^6$ PFU of wt RSV in total volume of 100 ul in both nostrils. Nasal turbinates (NT) and lungs were collected on day 3 after challenge and homogenized. Titers of RSV in nasal turbinates (FIG. 12A) and lungs (FIG. 12B) were determined by plaque assays in Vero monolayers. The horizontal lines indicate the mean value of titers in that group. Limit of detected is shown by a dashed line.

SEQUENCE LISTING

Figure 4A:
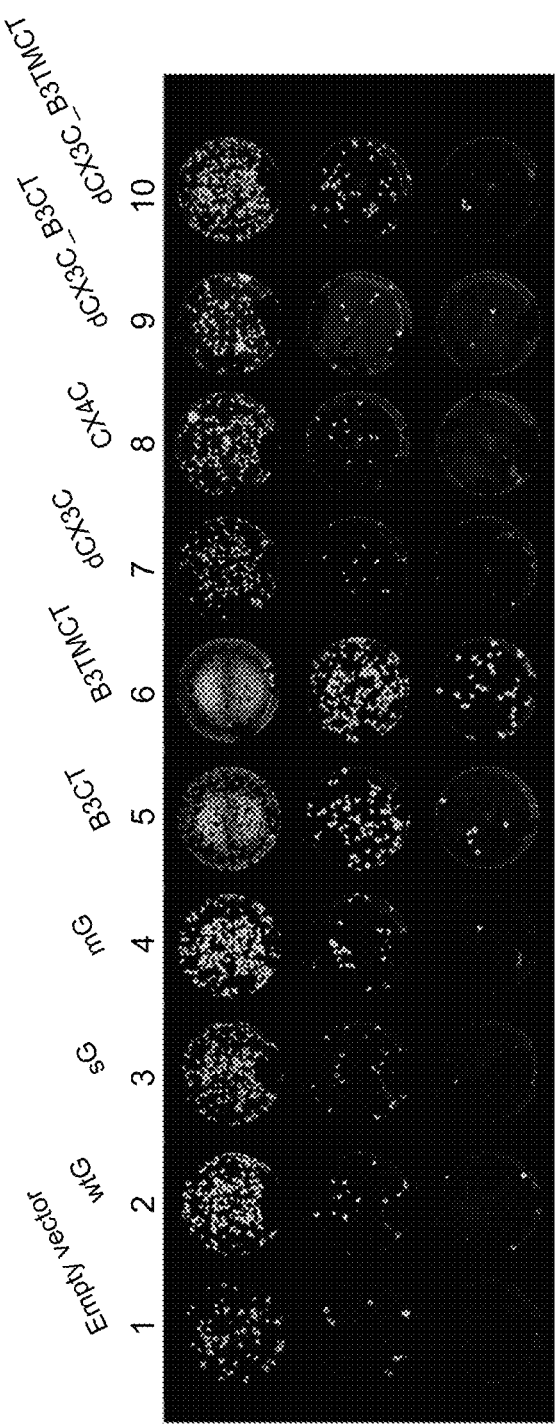
FIGS. 4A and 4B. Double-staining plaque assays characterizing expression of modified forms of RSV G protein from rB/HPIV3-RSV G. rB/HPIV3 constructs expressing the indicated modified G proteins were inoculated in 10-fold dilution series on Vero cell monolayers in 24-well plates and incubated under methyl cellulose overlay for 6 days. The monolayers were fixed with 80% methanol and analyzed with the indicated primary antibodies followed by secondary antibodies conjugated to infrared dye.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence_Listing.txt" (approximately 266,240 bytes), which was created on Jan. 28, 2022, and which is incorporated by reference herein.

DETAILED DESCRIPTION

Major challenges to developing pediatric vaccines against RSV and HPIV3 include the immaturity of the immune system during infancy, immune-suppression by maternal antibodies, inefficient immune protection at the superficial epithelium of the respiratory tract, and vaccine-induced enhanced disease that has been observed in studies with inactivated or subunit RSV and HPIV3 vaccines in virus-naïve recipients (Kim et al., *Amer. J. Epidemiol.* 89:422-434, 1969; Ottolini et al., *Viral Immunol.* 13:231-236, 2000; Schneider-Ohrum et al., *J. Virol.* 91:e02180-16, 2017). Further, although immunization with a live-attenuated rB/HPIV3 vector expressing an RSV antigen (unmodified RSV F protein) did not prime vaccine-induced enhanced disease, clinical trial assessment revealed disappointing RSV immunogenicity (Bernstein, et al. 2012. Pediatric Infectious Disease Journal 31:109-114). Thus, despite substantial effort, a need remains for an effective immunogen that induces a protective immune response to RSV and/or HPIV3.

The present disclosure provides recombinant chimeric bovine/human parainfluenza virus 3 (rB/HPIV3) vectors expressing RSV G or variants thereof ("rB/HPIV3-RSV G" vectors) that meet the above-discussed need. For example, as described in the examples, of nine different rB/HPIV3-RSV G vectors, one vector (rB/HPIV3 comprising a heterologous gene encoding wt RSV G) produced an immune response to RSV in an animal model that provided titers of serum RSV-neutralizing antibodies assayed in the presence of complement that were not significantly different than those induced by wt RSV infection, even though the RSV was administered at a 10-fold higher dose, was not attenuated, and bears both the F and G neutralization antigens.

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the term "comprises" means "includes." Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. Adjuvants are described, for example, in Singh (ed.) Vaccine Adjuvants and Delivery Systems. Wiley-Interscience, 2007.

Administration: The introduction of a composition into a subject by a chosen route. Administration can be local or systemic. For example, if the chosen route is intranasal, the composition (such as a composition including a disclosed rB/HPIV3-RSV G vector) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid.

Attenuated: A virus that is "attenuated" or has an "attenuated phenotype" refers to a virus that has decreased virulence compared to a reference virus under similar conditions of infection. Attenuation usually is associated with decreased virus replication as compared to replication of a reference wild-type virus under similar conditions of infection, and thus "attenuation" and "restricted replication" often are used synonymously. In some hosts (typically non-natural hosts, including experimental animals), disease is not evident during infection with a reference virus in question, and restriction of virus replication can be used as a surrogate marker for attenuation. In some embodiments, a disclosed rB/HPIV3-RSV G vector that is attenuated exhibits at least about 10-fold or greater decrease, such as at least about 100-fold or greater decrease in virus titer in the upper or lower respiratory tract of a mammal compared to non-attenuated, wild type virus titer in the upper or lower respiratory tract, respectively, of a mammal of the same species under the same conditions of infection. Examples of mammals include, but are not limited to, humans, mice, rabbits, rats, hamsters, such as for example *Mesocricetus auratus*, and non-human primates, such as for example *Ceropithiecus aethiops*. An attenuated rB/HPIV3-RSV G vector may display different phenotypes including without limitation altered growth, temperature sensitive growth, host range restricted growth, or plaque size alteration.

Cytoplasmic Tail (CT): A contiguous region of a transmembrane protein that includes a terminus (either N- or C-terminus) of the protein and extends into the cytoplasm of a cell or enveloped virus from the cytoplasmic surface of the cell membrane or viral envelope. In the case of a type I transmembrane protein, the CT includes the C-terminus of the protein. In the case of a type II transmembrane protein, the CT includes the N-terminus of the protein.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Gene: A nucleic acid sequence that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

A "gene" of a rB/HPIV3 vector as described herein refers to a portion of the rB/HPIV3 genome encoding an mRNA and typically begins at the upstream (3') end with a gene-start (GS) signal and ends at the downstream (5') end with the gene-end (GE) signal. In this context, the term gene also embraces what is referred to as a "translational open reading frame", or ORF, particularly in the case where a protein, such as C, is expressed from an additional ORF rather than from a unique mRNA. To construct a disclosed rB/HPIV3 vector, one or more genes or genome segments may be deleted, inserted or substituted in whole or in part.

Heterologous: Originating from a different genetic source. A heterologous gene included in a recombinant genome is a gene that does not originate from that genome. In one specific, non-limiting example, a heterologous gene encoding an ectodomain of a RSV G protein is included in the genome of a rB/HPIV3 vector as described herein.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Infectious and Self-Replicating Virus: A virus that is capable of entering and replicating in a cultured cell or cell of an animal or human host to produce progeny virus capable of the same activity.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic composition: A preparation of immunogenic material capable of stimulating an immune response, which in some examples can be administered for the prevention, amelioration, or treatment of infectious or other types of disease. The immunogenic material may include attenuated or killed microorganisms (such as bacteria or viruses), or antigenic proteins, peptides or DNA derived from them. Immunogenic compositions comprise an antigen (such as a virus) that induces a measurable T cell response against the antigen, or induces a measurable B cell response (such as production of antibodies) against the antigen. In one example, an immunogenic composition comprises a disclosed rB/HPIV3-RSV G that induces a measurable CTL response against RSV and HPIV3, or induces a measurable B cell response (such as production of antibodies) against RSV and HPIV3, when administered to a subject. For in vivo use, the immunogenic composition will typically include a recombinant virus in a pharmaceutically acceptable carrier and may also include other agents, such as an adjuvant.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% pure, such as at least 75%, 80%, 90%, 95%, 98%, 99%, or even 99.9% pure.

Linker: A bi-functional molecule that can be used to link two molecules into one contiguous molecule. Non-limiting examples of peptide linkers include glycine-serine linkers.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "polynucleotide." A nucleic acid molecule is usually at least 10 bases in length, unless otherwise specified. The term includes single- and double-stranded forms of DNA. A nucleic acid molecule may include either or both naturally occurring and modified nucleotides linked together by naturally occurring and/or non-naturally occurring nucleotide linkages.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Parainfluenza virus (PIV): A number of enveloped non-segmented negative-sense single-stranded RNA viruses from family Paramyxoviridae that are descriptively grouped together. This includes all of the members of genus *Respirovirus* (e.g., HPIV1, HPIV3) and a number of members of genus *Rubulavirus* (e.g. HPIV2, HPIV4, PIV5). PIVs are made up of two structural modules: (1) an internal ribonucleoprotein core, or nucleocapsid, containing the viral genome, and (2) an outer, roughly spherical lipoprotein envelope. The PIV genome is approximately 15,000 nucleotides in length and encodes at least eight polypeptides. These proteins include the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins. The gene order is 3'-N-P-M-F-HN-L-5', and each gene encodes a separate protein encoding mRNA, with the P gene containing one or more additional open reading frames (ORFs) encoding accessory proteins.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic.

A polypeptide has an amino terminal (N-terminal) end and a carboxy terminal (C-terminal) end. "Polypeptide" is used interchangeably with peptide or protein, and is used herein to refer to a polymer of amino acid residues.

Recombinant: A recombinant nucleic acid molecule or protein is one that has a sequence that is not naturally occurring: for example, includes one or more nucleic acid substitutions, deletions or insertions, and/or has a sequence that is made by an artificial combination of two otherwise separated segments of sequence. This artificial combination can be accomplished, for example, by chemical synthesis, targeted mutation of a naturally occurring nucleic acid molecule or protein, or, artificial manipulation of isolated segments of nucleic acids, for example, by genetic engineering techniques. A recombinant virus is one that includes a genome that includes a recombinant nucleic acid molecule.

Recombinant chimeric bovine/human parainfluenza virus 3 (rB/HPIV3): A chimeric PIV3 comprising a genome comprising a combination of BPIV3 and HPIV3 genes that together make up the full complement of PIV3 genes in the PIV3 genome (N, P, M, F, HN, and L genes). The disclosed rB/HPIV3 vectors are based on a BPIV3 genome having F and HN genes replaced with the corresponding genes from HPIV3 (one example of which is discussed in Schmidt A C et al., *J. Virol.* 74:8922-8929, 2000). The structural and functional genetic elements that control gene expression, such as gene start and gene end sequences and genome and anti-genome promoters, are BPIV3 structural and functional genetic elements. The rB/HPIV3 vectors described herein are infectious, self-replicating, and attenuated.

In some embodiments, a heterologous gene encoding RSV G protein or variant thereof is inserted between the N and P genes of the rB/HPIV3 genome to generate a "rB/HPIV3-RSV G" vector. The disclosed rB/HPIV3-RSV G vectors are infectious, self-replicating, and attenuated, and can be used to induce a bivalent immune response to RSV and HPIV3 in a subject.

Respiratory Syncytial Virus (RSV): An enveloped non-segmented negative-sense single-stranded RNA virus of the family Pneumoviridae, genus *Orthopneumovirus*. The RSV genome is ~15,000 nucleotides in length and includes 10 genes encoding 11 proteins, including the glycoproteins SH, G and F. The F protein mediates fusion, allowing entry of the virus into the cell cytoplasm and also promoting the formation of syncytia. Two antigenic subgroups of human RSV strains have been described, the A and B subgroups, based primarily on differences in the antigenicity of the G glycoprotein. RSV strains for other species are also known, including bovine RSV. Several animal models of infection by human RSV and closely-related animal counterparts are available, including model organisms infected with human RSV, as well as model organisms infected with species-specific RSV, such as use of bRSV infection in cattle (see, e.g., Bern et al., *Am J, Physiol. Lung Cell Mol. Physiol.,* 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

RSV G protein: An RSV envelope glycoprotein that is a type II membrane protein and facilitates attachment of RSV to host cell membranes.

The RSV G protein is expressed during RSV infection in two forms. One is the full-length transmembrane form (mG), which is expressed on the cell surface and is packaged into the virus particle. The other form is an N-terminally-truncated, secreted form, sG. The full-length G protein (mG) is a type II protein that has an N-terminal cytoplasmic tail (CT, predicted to comprise amino acids 1-37 in strain A2, see FIG. 1B), a hydrophobic transmembrane domain (TM, comprising approximately amino acids 38-65, see FIG. 1B), and an ectodomain (comprising approximately amino acids 66-298). The sG form is relatively abundant in RSV-infected cell cultures, and is produced by alternative translation initiation at the second AUG codon (M48) in the ORF, whose corresponding position in the protein lies within the TM domain (see FIG. 1B). The N-terminus is then subjected to intracellular proteolytic trimming that creates a new N-terminus at N66 (FIG. 1B).

The ectodomain of RSV G protein comprises two large divergent domains that flank a short central conserved region at amino acids 164-186. The divergent domains have a high content of proline, alanine, threonine, and serine amino acids, and (for strain A2) an estimated four N-linked and 24-25 O-linked carbohydrate side chains. The central conserved domain contains a cysteine noose (i.e., a tight turn stabilized by two disulfide bonds) that bears a conserved CX3C motif (CWAIC, amino acids 182-186 of the A2 strain). The mG and sG forms are believed to be essentially the same with regard to glycosylation and protein structure except that mG forms a multimer that probably is a trimer or tetramer, whereas sG remains a monomer.

An exemplary RSV G protein sequence is provided herein as SEQ ID NO: 22.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

When determining sequence identity between two sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013).

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm nih gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

In one examples, once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Homologs and variants of a polypeptide (such as a RSV G ectodomain) are typically characterized by possession of at least about 75%, for example at least about 80%, 85%, 90%, 91%, 92%, 93%, 94%, 95%, 96%, 97%, 98% or 99% sequence identity counted over the full-length alignment with the amino acid sequence of interest. As used herein, reference to "at least 90% identity" or similar language refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals. In an example, a subject is a human. In a particular example, the subject is a newborn infant. In an additional example, a subject is selected that is in need of inhibiting an RSV infection and/or a HPIV3 infection. For example, the subject is either uninfected and at risk of RSV infection and/or HPIV3 infection or is infected in need of treatment.

Transmembrane domain (TM): An amino acid sequence that spans a lipid bilayer, such as the lipid bilayer of a cell or virus or virus-like particle.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides or DNA derived from them. An attenuated vaccine is a virulent organism that has been modified to produce a less virulent form, but nevertheless retains the ability to elicit antibodies and cell-mediated immunity against the virulent form. An inactivated (killed) vaccine is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

II. rB/HPIV3-RSV G Vectors

Recombinant chimeric viral vectors comprising a BPIV3 genome with the encoding sequences of the BPIV3 HN and F genes replaced by encoding sequences of the corresponding HPIV3 HN and F gene, and further comprising a heterologous gene encoding a RSV G protein (such as a wild-type RSV G protein) or a variant thereof are provided herein. These recombinant chimeric viral vectors are referred as "rB/HPIV3-RSV G" vectors.

The rB/HPIV3-RSV G genome contains a full complement of PIV3 genes. Therefore, the rB/HPIV3-RSV G vectors are infectious and replication-competent, but are attenuated in rhesus monkeys and humans due to the BPIV3 backbone, and the presence of the heterologous gene.

The genome of the rB/HPIV3-RSV G vectors comprises the heterologous gene encoding RSV G or a variant thereof, HPIV3 F and HN genes, BPIV3 N, P, M, and L genes, and BPIV3 genomic promoter (3' leader region) and 5' trailer region, with the order of 3'-leader region—BPIV3 N, heterologous gene, BPIV3 P, BPIV3 M, HPIV3 F, HPIV3 HN, BPIV3L —5'-trailer. Exemplary nucleic acid sequences of these genes and proteins encoded thereby are provided herein, as are structural and functional genetic elements that control gene expression, such as gene start and gene end sequences and genome and anti-genome promoters.

An exemplary BPIV3 genome sequence (Kansas stain) is provided as GenBank Acc. No. AF178654.1, which is incorporated by reference herein in its entirety. An exemplary HPIV3 JS strain genome sequence is provided as GenBank Acc. No. Z11575.1, which is incorporated by reference herein in its entirety. In some embodiments, sequences from these strains can be used to construct the rB/HPIV3 aspect of the rB/HPIV3-RSV G vector, for example, as described in Schmidt et al., (*J. Virol.* 74:8922-8929, 2000). In some such embodiments, the HN protein encoded by the HPIV3 HN gene can be modified to have threonine and proline residues at positions 263 and 370, respectively.

In some embodiments, the rB/HPIV3-RSV G vector comprises a genome comprising HPIV3 F and HN genes and BPIV3 N, P, M, and L genes encoding HPIV3 F and HN proteins and BPIV3 N, P, C, V, M, and L proteins as set forth below, or encoding HPIV3 F and HN proteins and BPIV3 N, P, C, V, M, and L proteins individually having at least 90% (such as at least 95% or at least 98%) sequence identity to the corresponding HPIV3 F and HN protein or BPIV3 N, P, C, V, M, and L protein set forth below:

BPIV3 N (GenBank Acc. No.: AAF28254.1, encoded by
nucleotides 111-1658 of GenBank No. AF178654.1)
(SEQ ID NO: 1)
MLSLFDTFSARRQENITKSAGGAVIPGQKNTVSIFALGPSITDDNDKMTL

ALLFLSHSLDNEKQHAQRAGFLVSLLSMAYANPELYLTSNGSNADVKYVI

YMIEKDPGRQKYGGFVVKTREMVYEKTTDWMFGSDLEYDQDNMLQNGRST

STIEDLVHTFGYPSCLGALIIQVWIILVKAITSISGLRKGFFTRLEAFRQ

DGTVKSSLVLSGDAVEQIGSIMRSQQSLVTLMVETLITMNTGRNDLTTIE

KNIQIVGNYIRDAGLASFFNTIRYGIETRMAALTLSTLRPDINRLKALIE

LYLSKGPRAPFICILRDPVHGEFAPGNYPALWSYAMGVAVVQNKAMQQYV

TGRSYLDIEMFQLGQAVARDAESQMSSILEDELGVTQEAKQSLKKHMKNI

SSSDTTFHKPTGGSAIEMAIDEEAGQPESRGDQDQGDEPRSSIVPYAWAD

ETGNDNQTESTTEIDSIKTEQRNIRDRLNKRLNEKRKQSDPRSTDITNNT

NQTEIDDLFSAFGSN

BPIV3 P (GenBank Acc. No.: AAF28255, encoded by
nucleotides 1784-3574 of GenBank No. AF178654)
(SEQ ID NO: 2)
MEDNVQNNQIMDSWEEGSGDKSSDISSALDIIEFILSTDSQENTADSNEI

NTGTTRLSTTIYQPESKTTETSKENSGPANKNRQFGASHERATETKDRNV

NQETVQGGYRRGSSPDSRTETMVTRRISRSSPDPNNGTQIQEDIDYNEVG

EMDKDSTKREMRQFKDVPVKVSGSDAIPPTKQDGDGDDGRGLESISTFDS

GYTSIVTAATLDDEEELLMKNNRPRKYQSTPQNSDKGIKKGVGRPKDTDK

QSSILDYELNFKGSKKSQKILKASTNTGEPTRPQNGSQGKRITSWNILNS

ESGNRTESTNQTHQTSTSGQNHTMGPSRTTSEPRIKTQKTDGKEREDTEE

STRFTERAITLLQNLGVIQSAAKLDLYQDKRVVCVANVLNNADTASKIDF

LAGLMIGVSMDHDTKLNQIQNEILSLKTDLKKMDESHRRLIENQKEQLSL

ITSLISNLKIMTERGGKKDQPEPSGRTSMIKTKAKEEKIKKVRFDPLMET

QGIEKNIPDLYRSIEKTPENDTQIKSEINRLNDESNATRLVPRRISSTMR

SLIIIINNSNLSSKAKQSYINELKLCKSDEEVSELMDMFNEDVSSQ

BPIV3 C (encoded by nucleotide 1794-2399 of
GenBank No. AF178654)
(SEQ ID NO: 3)
MFKTIKSWILGKRDQEINHLTSHRPSTSLNSYSAPTPKRTRQTAMKSTQE

PQDLARQSTNLNPKQQKQARKIVDQLTKIDSLGHHTNVPQRQKIEMLIRR

LYREDIGEEAAQIVELRLWSLEESPEAAQILTMEPKSRKILITMKLERWI

RTLLRGKCDNLKMFQSRYQEVMPFLQQNKMETVMMEEAWNLSVHLIQDIP

V

BPIV3 V (encoded by nucleotide 1784-3018 of
GenBank No. AF178654 with an inserted nucleotide g
between nucleotide 2505-2506 at a gene editing
site located at nucleotide 2500-2507)
(SEQ ID NO: 4)
MEDNVQNNQIMDSWEEGSGDKSSDISSALDIIEFILSTDSQENTADSNEI

NTGTTRLSTTIYQPESKTTETSKENSGPANKNRQFGASHERATETKDRNV

NQETVQGGYRRGSSPDSRTETMVTRRISRSSPDPNNGTQIQEDIDYNEVG

EMDKDSTKREMRQFKDVPVKVSGSDAIPPTKQDGDGDDGRGLESISTFDS

GYTSIVTAATLDDEEELLMKNNRPRKYQSTPQNSDKGIKKGGWKAKRHRQ

TIINIGLRTQLQRIEEEPENPQSQHEYRRTNKTTEWIPGEENHILEHPQQ

RERQSNRINKPNPSDINLGTEPHNGTKQNNLRTKDQDTKDGWKGKRGHRR

EHSIYRKGDYIITESWCNPICSKIRPIPRQESCVCGECPKQCRYCIKDRL

PSRFDDRSVNGS

-continued

BPIV3 M (GenBank Acc. No.: AAF28256, encoded by
nucleotides 3735-4790 of GenBank No. AF178654)
(SEQ ID NO: 5)
MSITNSTIYTFPESSFSENGNIEPLPLKVNEQRKAIPHIRVVKIGDPPKH

GSRYLDVFLLGFFEMERSKDRYGSISDLDDDPSYKVCGSGSLPLGLARYT

GNDQELLQAATKLDIEVRRTVKATEMIVYTVQNIKPELYPWSSRLRKGML

FDANKVALAPQCLPLDRGIKFRVIFVNCTAIGSITLFKIPKSMALLSLPN

TISINLQVHIKTGVQTDSKGVVQILDEKGEKSLNFMVHLGLIKRKMGRMY

SVEYCKQKIEKMRLLFSLGLVGGISFHVNATGSISKTLASQLAFKREICY

PLMDLNPHLNSVIWASSVEITRVDAVLQPSLPGEFRYYPNIIAKGVGKIR

Q

HPIV3 F (encoded by nucleotides 5072-6691 of
GenBank No. Z11575)
(SEQ ID NO: 6)
MPTSILLIITTMIMASFCQIDITKLQHVGVLVNSPKGMKISQNFETRYLI

LSLIPKIEDSNSCGDQQIKQYKKLLDRLIIPLYDGLRLQKDVIVTNQESN

ENTDPRTKRFFGGVIGTIALGVATSAQITAAVALVEAKQARSDIEKLKEA

IRDTNKAVQSVQSSIGNLIVAIKSVQDYVNKEIVPSIARLGCEAAGLQLG

IALTQHYSELTNIFGDNIGSLQEKGIKLQGIASLYRTNITEIFTTSTVDK

YDIYDLLFTESIKVRVIDVDLNDYSITLQVRLPLLTRLLNTQIYKVDSIS

YNIQNREWYIPLPSHIMTKGAFLGGADVKECIEAFSSYICPSDPGFVLNH

EIESCLSGNISQCPRTTVTSDIVPRYAFVNGGVVANCITTTCTCNGIGNR

INQPPDQGVKIITHKECSTIGINGMLFNTNKEGTLAFYTPNDITLNNSVA

LDPIDISIELNKAKSDLEESKEWIRRSNQKLDSIGNWHQSSTTIIIILIM

IIILFIINITIITIAIKYYRIQKRNRVDQNDKPYVLTNK

HPIV3 wt HN (encoded by nucleotides 6806-8524 of
GenBank No. Z11575)
(SEQ ID NO: 7)
MEYWKHTNHGKDAGNELETSMATHGNKLTNKIIYILWTIILVLLSIVFII

VLINSIKSEKAHESLLQDINNEFMEITEKIQMASDNTNDLIQSGVNTRLL

TIQSHVQNYIPISLTQQMSDLRKFISEITIRNDNQEVLPQRITHDVGIKP

LNPDDFWRCTSGLPSLMKTPKIRLMPGPGLLAMPTTVDGCVRTPSLVIND

LIYAYTSNLITRGCQDIGKSYQVLQIGIITVNSDLVPDLNPRISHTFNIN

DNRKSCSLALLNTDVYQLCSTPKVDERSDYASSGIEDIVLDIVNYDGSIS

TTRFKNNNISFDQPYAALYPSVGPGIYYKGKIIFLGYGGLEHPINENVIC

NTTGCPGKTQRDCNQASHSPWFSDRRMVNSIIVVDKGLNSIPKLKVWTIS

MRQNYWGSEGRLLLLGNKIYIYTRSTSWHSKLQLGIIDITDYSDIRIKWT

WHNVLSRPGNNECPWGHSCPDGCITGVYTDAYPLNPTGSIVSSVILDSQK

SRVNPVITYSTATERVNELAILNRTLSAGYTTTSCITHYNKGYCFHIVEI

NHKSLNTFQPMLFKTEIPKSCS

In some embodiments, the HPIV3 HN gene in rB/HPIV3 vector encodes a HPIV3 HN protein comprising the amino acid sequence set forth as:

(SEQ ID NO: 8)
MEYWKHTNHGKDAGNELETSMATHGNKLTNKIIYILWTIILVLLSIVFII

VLINSIKSEKAHESLLQDINNEFMEITEKIQMASDNTNDLIQSGVNTRLL

TIQSHVQNYIPISLTQQMSDLRKFISEITIRNDNQEVLPQRITHDVGIKP

LNPDDFWRCTSGLPSLMKTPKIRLMPGPGLLAMPTTVDGCVRTPSLVIND

LIYAYTSNLITRGCQDIGKSYQVLQIGIITVNSDLVPDLNPRISHTFNIN

DNRKSCSLALLNIDVYQLCSTPKVDERSDYASSGIEDIVLDIVNYDGSIS

TTRFKNNNISFDQPYAALYPSVGPGIYYKGKIIFLGYGGLEHPINENVIC

NTTGCPGKTQRDCNQASHSTWFSDRRMVNSIIVVDKGLNSIPKLKVWTIS

MRQNYWGSEGRLLLLGNKIYIYTRSTSWHSKLQLGIIDITDYSDIRIKWT

WHNVLSRPGNNECPWGHSCPDGCITGVYTDAYPLNPTGSIVSSVILDSQK

SRVNPVITYSTATERVNELAILNRTLSAGYTTTSCITHYNKGYCFHIVEI

NHKSLNTFQPMLFKTEIPKSCS

The HN protein shown as SEQ ID NO: 7 comprises 263T and 370P amino acid assignments. As discussed in the examples, rB/HPIV3-RSV G including an HN protein with 263T and 370P amino acid assignments can be recovered and passaged with substantially reduced occurrence of adventitious mutations, which increases the efficiency of virus production, analysis, and manufacture. Any of the rB/HPIV3-RSV G vectors provided herein can comprise a HPIV3 HN gene encoding HN protein with 263T and 370P amino acid assignments (for example, introduced into the HN protein by I263T and T370P amino acid substitutions). An exemplary DNA sequence encoding SEQ ID NO: 7 is provided as follows:

(SEQ ID NO: 9)
atggaatactggaagcataccaatcacggaaaggatgctggtaatgagct ggagacgtctatggctactcatggcaacaagctcactaataagataatat acatattatggacaataatcctggtgttattatcaatagtcttcatcata gtgctaattaattccatcaaaagtgaaaaggcccacgaatcattgctgca agacataaataatgagtttatggaaattacagaaaagatccaaatggcat cggataataccaatgatctaatacagtcaggagtgaatacaaggcttctt acaattcagagtcatgtccagaattacataccaatatcattgacacaaca gatgtcagatcttaggaaattcattagtgaaattacaattagaaatgata atcaagaagtgctgccacaaagaataacacatgatgtaggtataaaacct ttaaatccagatgattttggagatgcacgtctggtcttccatctttaat gaaaactccaaaaataaggttaatgccagggccgggattattagctatgc caacgactgttgatggctgtgttagaactccgtctttagttataaatgat ctgatttatgcttatacctcaaatctaattactcgaggttgtcaggatat aggaaaatcatatcaagtcttacagatagggataataactgtaaactcag acttggtacctgacttaaatcctaggatctctcataccttttaacataaat gacaataggaagtcatgttctctagcactcctaaatatagatgtatatca -continued

```
actgtgttcaactcccaaagttgatgaaagatcagattatgcatcatcag gcatagaagatattgtacttgatattgtcaattatgatggttcaatctca acaacaagatttaagaataataacataagctttgatcaaccatatgctgc actatacccatctgttggaccagggatatactacaaaggcaaaataatat ttctcgggtatggaggtcttgaacatccaataaatgagaatgtaatctgc aacacaactgggtgcccgggaaaacacagagagactgtaatcaagcatc tcatagtacttggttttcagataggaggatggtcaactccatcattgttg ttgacaaaggcttaaactcaattccaaaattgaaagtatggacgatatct atgcgacaaaattactgggggtcagaaggaaggttacttctactaggtaa caagatctatatatacaagatctacaagttggcatagcaagttacaat taggaataattgatattactgattacagtgatataaggataaaatggaca tggcataatgtgctatcaagaccaggaaacaatgaatgtccatgggaca ttcatgtccagatggatgtataacaggagtatatactgatgcatatccac tcaatcccacagggagcattgtgtcatctgtcatattagactcacaaaaa tcgagagtgaacccagtcataacttactcaacagcaaccgaaagagtaaa cgagctggccatcctaaacagaacactctcagctggatatcaacaacaa gctgcattacacactataacaaaggatattgttttcatatagtagaaata aatcataaaagcttaaacacatttcaacccatgttgttcaaaacagagat tccaaaaagctgcagttaa
```

BPIV3 L (GenBank Acc. No.: AAF28259, encoded by nucleotides 8640-15341 of GenBank No. AF178654)
(SEQ ID NO: 10)

```
MDTESHSGTTSDILYPECHLNSPIVKGKIAQLHTIMSLPQPYDMDDDSIL

IITRQKIKLNKLDKRQRSIRKLRSVLMERVSDLGKYTFIRYPEMSSEMFQ

LCIPGINNKINELLSKASKTYNQMTDGLRDLWVTILSKLASKNDGSNYDI

NEDISNISNVHMTYQSDKWYNPFKTWFTIKYDMRRLQKAKNEITFNRHKD

YNLLEDQKNILLIHPELVLILDKQNYNGYIMTPELVLMYCDVVEGRWNIS

SCAKLDPKLQSMYYKGNNLWEIIDGLFSTLGERTFDIISLLEPLALSLIQ

TYDPVKQLRGAFLNHVLSEMELIFAAECTTEEIPNVDYIDKILDVFKEST

IDEIAEIFSFFRTFGHPPLEASIAAEKVRKYMYTEKCLKFDTINKCHAIF

CTIIINGYRERHGGQWPPVTLPVHAHEFIINAYGSNSAISYENAVDYYKS

FIGIKFDKFIEPQLDEDLTIYMKDKALSPKKSNWDTVYPASNLLYRTNVS

HDSRRLVEVFIADSKFDPHQVLDYVESGYWLDDPEFNISYSLKEKEIKQE

GRLFAKMTYKMRATQVLSETLLANNIGKFFQENGMVKGEIELLKRLTTIS

MSGVPRYNEVYNNSKSHTEELQAYNAISSSNLSSNQKSKKFEFKSTDIYN

DGYETVSCFLTTDLKKYCLNWRYESTALFGDTCNQIFGLKELFNWLHPRL

EKSTIYVGDPYCPPSDIEHLPLDDHPDSGFYVHNPKGGIEGFCQKLWTLI

SISAIHLAAVKIGVRVTAMVQGDNQAIAVTTRVPNNYDYKVKKEIVYKDV

VRFFDSLREVMDDLGHELKLNETIISSKMFIYSKRIYYDGRILPQALKAL

SRCVFWSETIIDETRSASSNLATSFAKAIENGYSPVLGYVCSIFKNIQQL

YIALGMNINPTITQNIKDQYFRNIHWMQYASLIPASVGGFNYMAMSRCFV

RNIGDPTVAALADIKRFIKANLLDRGVLYRIMNQEPGESSFLDWASDPYS

CNLPQSQNITTMIKNITARNVLQDSPNPLLSGLFTSTMIEEDEELAEFLM

DRRIILPRVAHDILDNSLTGIRNAIAGMLDTTKSLIRVGISRGGLTYNLL

RKISNYDLVQYETLSKTLRLIVSDKIKYEDMCSVDLAISLRQKMWMHLSG

GRMINGLETPDPLELLSGVIITGSEHCRICYSTEGESPYTWMYLPGNLNI

GSAETGIASLRVPYFGSVTDERSEAQLGYIKNLSKPAKAAIRIAMIYTWA

FGNDEISWMEASQIAQTRANFTLDSLKILTPVTTSTNLSHRLKDTATQMK

FSSTSLIRVSRFITISNDNMSIKEANETKDTNLIYQQVMLTGLSVFEYLF

RLEESTGHNPMVMHLHIEDGCCIKESYNDEHINPESTLELIKYPESNEFI

YDKDPLKDIDLSKLMVIRDHSYTIDMNYWDDTDIVHAISICTAVTIADTM

SQLDRDNLKELVVIANDDDINSLITEFLTLDILVFLKTFGGLLVNQFAYT

LYGLKIEGRDPIWDYIMRTLKDTSHSVLKVLSNALSHPKVFKRFWDCGVL

NPIYGPNTASQDQVKLALSICEYSLDLFMREWLNGASLEIYICDSDMEIA

NDRRQAFLSRHLAFVCCLAEIASFGPNLLNLTYLERLDELKQYLDLNIKE

DPTLKYVQVSGLLIKSFPSTVTYVRKTAIKYLRIRGINPPETIEDWDPIE

DENILDNIVKTVNDNCSDNQKRNKSSYFWGLALKNYQVVKIRSITSDSEV

NEASNVTTHGMTLPQGGSYLSHQLRLFGVNSTSCLKALELSQILMREVKK

DKDRLFLGEGAGAMLACYDATLGPAINYYNSGLNITDVIGQRELKIFPSE

VSLVGKKLGNVTQILNRVRVLFNGNPNSTWIGNMECESLIWSELNDKSIG

LVHCDMEGAIGKSEETVLHEHYSIIRITYLIGDDDVVLVSKIIPTITPNW

SKILYLYKLYWKDVSVVSLKTSNPASTELYLISKDAYCTVMEPSNLVLSK

LKRISSIEENNLLKWIILSKRKNNEWLQHEIKEGERDYGIMRPYHTALQI

FGFQINLNHLAREFLSTPDLTNINNIIQSFTRTIKDVMFEWVNITHDNKR

HKLGGRYNLFPLKNKGKLRLLSRRLVLSWISLSLSTRLLTGRFPDEKFEN

RAQTGYVSLADIDLESLKLLSRNIVKNYKEHIGLISYWFLTKEVKILMKL

IGGVKLLGIPKQYKELEDRSSQGYEYDNEFDID
```

The encoding sequences of the HPIV3 F and HN genes and the BPIV3 N, P, M, and L genes in the rB/HPIV3-RSV G vector are flanked by appropriate gene start and gene-end sequences to facilitate expression from the viral genome. For example, in some embodiments, the encoding sequences of the HPIV3 F and HN genes and the BPIV3 N, P, M, and L genes can be flanked by BPIV3 gene-start and gene end sequences as follows:

| Gene | Gene start | SEQ ID | Gene end | SEQ ID |
|------|------------|--------|----------|--------|
| N | aggattaaagac | 11 | aaataagaaaaa | 16 |
| P | aggattaaag | 12 | aaataagaaaaa | 17 |
| M | aggattaaag | 12 | aaataaaggataatcaaaaa | 18 |
| F | aggacaaaag | 13 | aattataaaaaa | 19 |
| HN | aggagtaaag | 14 | aaatataaaaaa | 20 |
| L | aggagcaaag | 15 | aaagtaagaaaaa | 21 |

Further, the rB/HPIV3-RSV G vector comprises appropriate genome and anti-genome promoters, such as those of the BPIV3 Kansas strain as set forth in GenBank Acc. No.

AF178654, which provides genomic promoter as nucleotides 1-96 and the antigenomic promoter as nucleotides 15361-15456.

The genome of the rB/HPIV3-RSV G comprises a heterologous gene encoding a native RSV G protein or a variant thereof, such as a recombinant RSV G protein comprising BPIV3 HN transmembrane and/or cytoplasmic tail sequences in place of the native RSV G transmembrane and/or cytoplasmic tail sequences. Human RSV can be classified into two groups: A and B. Groups A and B include subgroups A1, A2, B1, and B2, based mainly on sequence variability of the attachment (G) and fusion (F) proteins. The heterologous gene included in the genome of the rB/HPIV3-RSV G can encode a RSV G protein and/or an RSV G ectodomain from (or derived from) any human RSV group (such as Group A or Group B) or subgroup of human RSV (such as subgroup A1, A2, B1, or B2).

An exemplary human RSV G protein sequence from subgroup A2 is set forth below:

(SEQ ID NO: 22)
MSKNKDQRTAKTLERTWDTLNHLLFISSCLYKLNLKSVAQITLSILAMII

STSLIIAAIIFIASANHKVTPTTAIIQDATSQIKNTTPTYLTQNPQLGIS

PSNPSEITSQITTILASTTPGVKSTLQSTTVKTKNTTTTQTQPSKPTTKQ

RQNKPPSKPNNDFHFEVFNFVPCSICSNNPTCWAICKRIPNKKPGKKTTT

KPTKKPTLKTTKKDPKPQTTKSKEVPTTKPTEEPTINTTKTNIITTLLTS

NTTGNPELTSQMETFHSTSSEGNPSPSQVSTTSEYPSQPSSPPNTPRQ

In some embodiments, the heterologous gene included in the genome of the rB/HPIV3-RSV G encodes a RSV G protein comprising or consisting of the amino acid sequence set forth as SEQ ID NO: 22, or an amino acid sequence at least 90% (such as at least 95% or at least 98%) identical to SEQ ID NO: 22

An exemplary human RSV G ectodomain sequence from subgroup A2 is set forth below:

(SEQ ID NO: 23)
NHKVTPTTAIIQDATSQIKNTTPTYLTQNPQLGISPSNPSEITSQITTIL

ASTTPGVKSTLQSTTVKTKNTTTTQTQPSKPTTKQRQNKPPSKPNNDFHF

EVFNFVPCSICSNNPTCWAICKRIPNKKPGKKTTTKPTKKPTLKTTKKDP

KPQTTKSKEVPTTKPTEEPTINTTKTNIITTLLTSNTTGNPELTSQMETF

HSTSSEGNPSPSQVSTTSEYPSQPSSPPNTPRQ

In some embodiments, the heterologous gene encodes a recombinant RSV G ectodomain comprising or consisting of the amino acid sequence set forth as SEQ ID NO: 23, or an amino acid sequence at least 90% (such as at least 95% or at least 98%) identical to SEQ ID NO: 23. The ectodomain is linked to appropriate transmembrane domain and cytoplasmic tail sequences, such as those set forth herein.

An exemplary human RSV G protein sequence from RSV A/Maryland/001/11 is set forth below:

(SEQ ID NO: 47)
MSKTKDQRTAKTLERTWDTLNHLLFISSCLYKLNLKSIAQITLSILAMI

ISTSLIIAAIIFIASANHKVTLTTAIIQDATNQIKNTTPTYLTQNPQLG

ISLSNLSETTSKPTTILALTTPNAESTPQSTTVKTKNTTTTQIQPSKPT

TKQRQNKPQNKPNNDFHFEVFNFVPCSICSNNPTCWAICKRIPNKKPGR

KTTTKPTKQPAIKTTKKDPKPQTTKPKEVLTTKPTEKPTINTTKTNIRT

TLLTSNITENQEHTSQKETLHSTTSEGNPSPSQVYTTSEYLSQSLSPSN

TTRW

In some embodiments, the heterologous gene included in the genome of the rB/HPIV3-RSV G encodes a RSV G protein comprising or consisting of the amino acid sequence set forth as SEQ ID NO: 47, or an amino acid sequence at least 90% (such as at least 95% or at least 98%) identical to SEQ ID NO: 47.

An exemplary human RSV G ectodomain sequence from RSV A/Maryland/001/11 is set forth below:

(SEQ ID NO: 48)
NHKVTLTTAIIQDATNQIKNTTPTYLTQNPQLGISLSNLSETTSKPTTI

LALTTPNAESTPQSTTVKTKNTTTTQIQPSKPTTKQRQNKPQNKPNNDF

HFEVFNFVPCSICSNNPTCWAICKRIPNKKPGRKTTTKPTKQPAIKTTK

KDPKPQTTKPKEVLTTKPTEKPTINTTKTNIRTTLLTSNITENQEHTSQ

KETLHSTTSEGNPSPSQVYTTSEYLSQSLSPSNTTRW

In some embodiments, the heterologous gene encodes a recombinant RSV G ectodomain comprising or consisting of the amino acid sequence set forth as SEQ ID NO: 48, or an amino acid sequence at least 90% (such as at least 95% or at least 98%) identical to SEQ ID NO: 48. The ectodomain is linked to appropriate transmembrane domain and cytoplasmic tail sequences, such as those set forth herein.

An exemplary human RSV G protein sequence from Subgroup B (B1, AAB82435.1, see Karron et al., Proc. Natl. Acad. Sci. U.S.A. 94, 13961-6, 1997) is set forth below:

(SEQ ID NO: 49)
MSKHKNQRTARTLEKTWDTLNHLIVISSCLYRLNLKSIAQIALSVLAMI

ISTSLIIAAIIFIISANHKVTLTTVTVQTIKNHTEKNITTYLTQVPPER

VSSSKQPTTTSPIHTNSATTSPNTKSETHHTTAQTKGRTTTSTQTNKPS

TKPRLKNPPKKPKDDYHFEVFNFVPCSICGNNQLCKSICKTIPSNKPKK

KPTIKPTNKPTTKTTNKRDPKTPAKTTKKETTTNPTKKPTLTTTERDTS

TSQSTVLDTTTLEHTIQQQSLHSTTPENTPNSTQTPTASEPSTSNSTQN

TQSHA

In some embodiments, the heterologous gene included in the genome of the rB/HPIV3-RSV G encodes a RSV G protein comprising or consisting of the amino acid sequence set forth as SEQ ID NO: 49, or an amino acid sequence at least 90% (such as at least 95% or at least 98%) identical to SEQ ID NO: 49.

An exemplary human RSV G ectodomain sequence from Subgroup B (B1, AAB82435.1) is set forth below:

(SEQ ID NO: 50)
NHKVTLTTVTVQTIKNHTEKNITTYLTQVPPERVSSSKQPTTTSPIHTN

SATTSPNTKSETHHTTAQTKGRTTTSTQTNKPSTKPRLKNPPKKPKDDY

HFEVFNFVPCSICGNNQLCKSICKTIPSNKPKKKPTIKPTNKPTTKTTN

-continued

KRDPKTPAKTTKKETTTNPTKKPTLTTTERDTSTSQSTVLDTTTLEHTI

QQQSLHSTTPENTPNSTQTPTASEPSTSNSTQNTQSHA

In some embodiments, the heterologous gene encodes a recombinant RSV G ectodomain comprising or consisting of the amino acid sequence set forth as SEQ ID NO: 50, or an amino acid sequence at least 90% (such as at least 95% or at least 98%) identical to SEQ ID NO: 50. The ectodomain is linked to appropriate transmembrane domain and cytoplasmic tail sequences, such as those set forth herein.

An exemplary human RSV G protein sequence from Subgroup A (genotype ON1; ON67-1210A, AEQ98758.1, Eshagi A. et al., Plos One 7(3):e32807, 2012 is set forth below:

(SEQ ID NO: 51)
MSKTKDQRTAKTLERTWDTLNHLLFISSCLYKLNLKSIAQITLSILAMI

ISTSLIIAAIIFIASANHKVTLTTAIIQDATNQIKNTTPTYLTQNPQLG

ISFSNLSGTTSQSTTILASTTPSAESTPQSTTVKIKNTTTTQILPSKPT

TKQRQNKPQNKPNNDFHFEVFNFVPCSICSNNPTCWAICKRIPNKKPGK

KTTTKPTKKPTLKTTKKDPKPQTTKPKEVLTTKPTGKPTINTTKTNIRT

TLLTSNTKGNPEHTSQEETLHSTTSEGYLSPSQVYTTSGQEETLHSTTS

EGYLSPSQVYTTSEYLSQSLSSSNTTK

In some embodiments, the heterologous gene included in the genome of the rB/HPIV3-RSV G encodes a RSV G protein comprising or consisting of the amino acid sequence set forth as SEQ ID NO: 51, or an amino acid sequence at least 90% (such as at least 95% or at least 98%) identical to SEQ ID NO: 51.

An exemplary human RSV G ectodomain sequence from Subgroup A (genotype ON1; ON67-1210A, AEQ98758.1, Eshagi A. et al., Plos One 7(3):e32807, 2012) is set forth below:

(SEQ ID NO: 52)
NHKVTLTTAIIQDATNQIKNTTPTYLTQNPQLGISFSNLSGTTSQSTTI

LASTTPSAESTPQSTTVKIKNTTTTQILPSKPTTKQRQNKPQNKPNNDF

HFEVFNFVPCSICSNNPTCWAICKRIPNKKPGKKTTTKPTKKPTLKTTK

KDPKPQTTKPKEVLTTKPTGKPTINTTKTNIRTTLLTSNTKGNPEHTSQ

EETLHSTTSEGYLSPSQVYTTSGQEETLHSTTSEGYLSPSQVYTTSEYL

SQSLSSSNTTK

In some embodiments, the heterologous gene encodes a recombinant RSV G ectodomain comprising or consisting of the amino acid sequence set forth as SEQ ID NO: 52, or an amino acid sequence at least 90% (such as at least 95% or at least 98%) identical to SEQ ID NO: 52. The ectodomain is linked to appropriate transmembrane domain and cytoplasmic tail sequences, such as those set forth herein.

An exemplary human RSV G protein sequence from Subgroup B (genotype BA1; BA4128/99B, AAQ16179.1, Trento A. et al., J. Gen. Virol. 84, 3115-3120, 2003) is set forth below:

(SEQ ID NO: 53)
MSKNKNQRTARTLEKTWDTLNHLIVISSCLYKLNLKSIAQIALSVLAMI

ISTSLIIAAIIFIISANHKVTLTTVTVQTIKNHTEKNITTYLTQVSPER

VSPSKQLTTTPPIYTNSATISPNTKSETHHTTAQTKGRTTTPTQNNKPS

TKPRPKNPPKKPKDDYHFEVFNFVPCSICGNNQLCKSICKTIPSNKPKK

KPTIKPTNKPPTKTTNKRDPKKLAKTLKKETTINPTKKPTPKTTERDTS

TSQSTVLDTTTSKHTERDTSTSQSTVLDTTTSKHTIQQQSLHSTTPENT

PNSTQTPTASEPSTSNSTQKL

In some embodiments, the heterologous gene included in the genome of the rB/HPIV3-RSV G encodes a RSV G protein comprising or consisting of the amino acid sequence set forth as SEQ ID NO: 53, or an amino acid sequence at least 90% (such as at least 95% or at least 98%) identical to SEQ ID NO: 53.

An exemplary human RSV G ectodomain sequence from Subgroup B (genotype BA1; BA4128/99B, AAQ16179.1, Trento A. et al., J. Gen. Virol. 84, 3115-20, 2003) is set forth below:

(SEQ ID NO: 54)
NHKVTLTTVTVQTIKNHTEKNITTYLTQVSPERVSPSKQLTTTPPIYTN

SATISPNTKSETHHTTAQTKGRTTTPTQNNKPSTKPRPKNPPKKPKDDY

HFEVFNFVPCSICGNNQLCKSICKTIPSNKPKKKPTIKPTNKPPTKTTN

KRDPKKLAKTLKKETTINPTKKPTPKTTERDTSTSQSTVLDTTTSKHTE

RDTSTSQSTVLDTTTSKHTIQQQSLHSTTPENTPNSTQTPTASEPSTSN

STQKL

In some embodiments, the heterologous gene encodes a recombinant RSV G ectodomain comprising or consisting of the amino acid sequence set forth as SEQ ID NO: 54, or an amino acid sequence at least 90% (such as at least 95% or at least 98%) identical to SEQ ID NO: 54. The ectodomain is linked to appropriate transmembrane domain and cytoplasmic tail sequences, such as those set forth herein.

In some embodiments, the heterologous gene encodes a recombinant RSV G protein comprising an RSV G ectodomain and transmembrane domain linked to a cytoplasmic tail of a BPIV3 HN protein, a HPIV3 HN protein, or a HPIV1 HN protein. In some embodiments, the heterologous gene encodes a recombinant RSV G protein comprising an RSV G ectodomain linked to a transmembrane domain and cytoplasmic tail of a BPIV3 HN protein, a HPIV3 HN protein, or a HPIV1 HN protein. As discussed in the Examples, swapping the PIV HN transmembrane and cytoplasmic tail protein sequences with the RSV G transmembrane and cytoplasmic tail protein sequences promotes membrane insertion and packaging of the type-II membrane protein into the virion envelope. It is believed that an increase in the amount of RSV G ectodomain exposed on the surface of the virion envelope leads to a corresponding increase in the immune response to the RSV G ectodomain.

The transmembrane domain and cytoplasmic tail of an exemplary RSV G sequence from RSV A2 are set forth as follows:

RSV G CT:
                                          SEQ ID NO: 24
MSKNKDQRTAKTLERTWDTLNHLLFISSCLYKLNLKS,

RSV G TM:
                                          SEQ ID NO: 25
VAQITLSILAMIISTSLIIAAIIFIASA.

RSV G TM + CT:
                                          SEQ ID NO: 26
MSKNKDQRTAKTLERTWDTLNHLLFISSCLYKLNLKSVAQITLSILAMI
ISTSLIIAAIIFIASA,

Further, the cytoplasmic tail and transmembrane domain of an exemplary BPIV3 HN protein are set forth as follows:

BPIV3 HN CT:
                                          SEQ ID NO: 27
MEYWKHTNSINNTNNETETARGKHSSKVTN,

BPIV3 HN TM:
                                          SEQ ID NO: 28
IIMYTFWTITLTILSVIFIMILTNLI,

BPIV3 HN TM + CT:
                                          SEQ ID NO: 29
MEYWKHTNSINNTNNETETARGKHSSKVTNIIMYTFWTITLTILSVIFI
MILTNLI,

Further, the cytoplasmic tail and transmembrane domain of an exemplary HPIV3 HN protein are set forth as follows:

HPIV3 HN CT:
                                          SEQ ID NO: 55
MEYWKHTNHGKDAGNELETSMATHGNKLTNK,

HPIV3 HN TM:
                                          SEQ ID NO: 56
IIYILWTIILVLLSIVFIIVLINSI,

HPIV3 HN TM + CT:
                                          SEQ ID NO: 57
MEYWKHTNHGKDAGNELETSMATHGNKLTNKIIYILWTIILVLLSIVFI
IVLINSI,

Further, the cytoplasmic tail and transmembrane domain of an exemplary HPIV1 HN protein are set forth as follows:

HPIV1 HN CT:
                                          SEQ ID NO: 58
MAEKGKTNSSYWSTTRNDNSTVNTHINTPAGRTHW,

HPIV1 HN TM:
                                          SEQ ID NO: 59
ILLIATTMHTVLSFIIMILCIDLII,

HPIV1 HN TM + CT:
                                          SEQ ID NO: 60
MAEKGKTNSSYWSTTRNDNSTVNTHINTPAGRTHWILLIATTMHTVLSF
IIMILCIDLII,

The human RSV G, BPIV3 HN, HPIV3 HN, and HPIV1 HN proteins exhibit remarkable sequence conservation across corresponding viral subgroups. Accordingly, the cytoplasmic tail and transmembrane domain sequences of an RSV G protein can readily be identified and swapped for the corresponding sequences of a BPIV3, HPIV3, or HPIV1 HN protein as needed when constructing the heterologous gene included in the rB/HPIV3-RSV G vector.

An exemplary amino acid sequence of a recombinant RSV G comprising a RSV G ectodomain and transmembrane domain from RSV A2, and a BPIV3 HN cytoplasmic tail is provided below:

(SEQ ID NO: 30)
MEYWKHTNSINNTNNETETARGKHSSKVTNVAQITLSILAMIISTSLII

AAIIFIASANHKVTPTTAIIQDATSQIKNTTPTYLTQNPQLGISPSNPS

EITSQITTILASTTPGVKSTLQSTTVKTKNTTTTQTQPSKPTTKQRQNK

PPSKPNNDFHFEVFNFVPCSICSNNPTCWAICKRIPNKKPGKKTTTKPT

KKPTLKTTKKDPKPQTTKSKEVPTTKPTEEPTINTTKTNIITTLLTSNT

TGNPELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 30, or an amino acid sequence at least 90% (such as at least 95% or at least 98%) identical to SEQ ID NO: 30.

An exemplary amino acid sequence of a recombinant RSV G comprising the RSV G ectodomain from RSV A2 and BPIV3 HN transmembrane domain and cytoplasmic tail is provided below:

(SEQ ID NO: 31)
MEYWKHTNSINNTNNETETARGKHSSKVTNIIMYTFWTITLTILSVIFI

MILTNLINHKVTPTTAIIQDATSQIKNTTPTYLTQNPQLGISPSNPSEI

TSQITTILASTTPGVKSTLQSTTVKTKNTTTTQTQPSKPTTKQRQNKPP

SKPNNDFHFEVFNFVPCSICSNNPTCWAICKRIPNKKPGKKTTTKPTKK

PTLKTTKKDPKPQTTKSKEVPTTKPTEEPTINTTKTNIITTLLTSNTTG

NPELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 31, or an amino acid sequence at least 90% (such as at least 95% or at least 98%) identical to SEQ ID NO: 31.

An exemplary amino acid sequence of a recombinant RSV G comprising a RSV G ectodomain and transmembrane domain from RSV B (B1, GenBank AAB82435.1), and a BPIV3 HN cytoplasmic tail is provided below:

(SEQ ID NO: 61)
MEYWKHTNSINNTNNETETARGKHSSKVTNIAQIALSVLAMIISTSLII

AAIIFIISANHKVTLTTVTVQTIKNHTEKNITTYLTQVPPERVSSSKQP

TTTSPIHTNSATTSPNTKSETHHTTAQTKGRTTTSTQTNKPSTKPRLKN

PPKKPKDDYHFEVFNFVPCSICGNNQLCKSICKTIPSNKPKKKPTIKPT

NKPTTKTTNKRDPKTPAKTTKKETTTNPTKKPTLTTTERDTSTSQSTVL

DTTTLEHTIQQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 61, or an amino acid sequence at least 90% (such as at least 95% or at least 98%) identical to SEQ ID NO: 61.

An exemplary amino acid sequence of a recombinant RSV G comprising the RSV G ectodomain from RSV B (B1, GenBank AAB82435.1) and BPIV3 HN transmembrane domain and cytoplasmic tail is provided below:

(SEQ ID NO: 62)
MEYWKHTNSINNTNNETETARGKHSSKVTNIIMYTFWTITLTILSVIFIMI

LTNLINHKVTLTTVTVQTIKNHTEKNITTYLTQVPPERVSSSKQPTTTSPI

HTNSATTSPNTKSETHHTTAQTKGRTTTSTQTNKPSTKPRLKNPPKKPKDD

YHFEVFNFVPCSICGNNQLCKSICKTIPSNKPKKKPTIKPTNKPTTKTTNK

RDPKTPAKTTKKETTTNPTKKPTLTTTERDTSTSQSTVLDTTTLEHTIQQQ

SLHSTTPENTPNSTQTPTASEPSTSNSTQNTQSHA

In some embodiments, the heterologous gene encodes a recombinant RSV G comprising or consisting of the amino acid sequence set forth as SEQ ID NO: 62, or an amino acid sequence at least 90% (such as at least 95% or at least 98%) identical to SEQ ID NO: 62.

An exemplary amino acid sequence of a recombinant RSV G comprising a RSV G ectodomain and transmembrane domain from RSV A/Maryland/001/11, and a BPIV3 HN cytoplasmic tail is provided below:

(SEQ ID NO: 63)
MEYWKHTNSINNTNNETETARGKHSSKVTNIAQITLSILAMIISTSLIIAA

IIFIASANHKVTLTTAIIQDATNQIKNTTPTYLTQNPQLGISLSNLSETTS

KPTTILALTTPNAESTPQSTTVKTKNTTTTQIQPSKPTTKQRQNKPQNKPN

NDFHFEVFNFVPCSICSNNPTCWAICKRIPNKKPGRKTTTKPTKQPAIKTT

KKDPKPQTTKPKEVLTTKPTEKPTINTTKTNIRTTLLTSNITENQEHTSQK

ETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 63, or an amino acid sequence at least 90% (such as at least 95% or at least 98%) identical to SEQ ID NO: 63.

An exemplary amino acid sequence of a recombinant RSV G comprising the RSV G ectodomain from RSV A/Maryland/001/11 and BPIV3 HN transmembrane domain and cytoplasmic tail is provided below:

(SEQ ID NO: 64)
MEYWKHTNSINNTNNETETARGKHSSKVTNIIMYTFWTITLTILSVIFIMI

LTNLINHKVTLTTAIIQDATNQIKNTTPTYLTQNPQLGISLSNLSETTSKP

TTILALTTPNAESTPQSTTVKTKNTTTTQIQPSKPTTKQRQNKPQNKPNND

FHFEVFNFVPCSICSNNPTCWAICKRIPNKKPGRKTTTKPTKQPAIKTTKK

DPKPQTTKPKEVLTTKPTEKPTINTTKTNIRTTLLTSNITENQEHTSQKET

LHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 64, or an amino acid sequence at least 90% (such as at least 95% or at least 98%) identical to SEQ ID NO: 64.

An exemplary amino acid sequence of a recombinant RSV G comprising a RSV G ectodomain and transmembrane domain from RSV ON1, and a BPIV3 HN cytoplasmic tail is provided below:

(SEQ ID NO: 65)
MEYWKHTNSINNTNNETETARGKHSSKVTNIAQITLSILAMIISTSLIIAA

IIFIASANHKVTLTTAIIQDATNQIKNTTPTYLTQNPQLGISFSNLSGTTS

QSTTILASTTPSAESTPQSTTVKIKNTTTTQILPSKPTTKQRQNKPQNKPN

NDFHFEVFNFVPCSICSNNPTCWAICKRIPNKKPGKKTTTKPTKKPTLKTT

KKDPKPQTTKPKEVLTTKPTGKPTINTTKTNIRTTLLTSNTKGNPEHTSQE

ETLHSTTSEGYLSPSQVYTTSGQEETLHSTTSEGYLSPSQVYTTSEYLSQS

LSSSNTTK

In some embodiments, the heterologous gene encodes a recombinant RSV G comprising or consisting of the amino acid sequence set forth as SEQ ID NO: 65, or an amino acid sequence at least 90% (such as at least 95% or at least 98%) identical to SEQ ID NO: 65.

An exemplary amino acid sequence of a recombinant RSV G comprising the RSV G ectodomain from RSV ON1, and BPIV3 HN transmembrane domain and cytoplasmic tail is provided below:

(SEQ ID NO: 66)
MEYWKHTNSINNTNNETETARGKHSSKVTNIIMYTFWTITLTILSVIFIMI

LTNLINHKVTLTTAIIQDATNQIKNTTPTYLTQNPQLGISFSNLSGTTSQS

TTILASTTPSAESTPQSTTVKIKNTTTTQILPSKPTTKQRQNKPQNKPNND

FHFEVFNFVPCSICSNNPTCWAICKRIPNKKPGKKTTTKPTKKPTLKTTKK

DPKPQTTKPKEVLTTKPTGKPTINTTKTNIRTTLLTSNTKGNPEHTSQEET

LHSTTSEGYLSPSQVYTTSGQEETLHSTTSEGYLSPSQVYTTSEYLSQSLS

SSNTTK

In some embodiments, the heterologous gene encodes a recombinant RSV G comprising or consisting of the amino acid sequence set forth as SEQ ID NO: 66, or an amino acid sequence at least 90% (such as at least 95% or at least 98%) identical to SEQ ID NO: 66.

An exemplary amino acid sequence of a recombinant RSV G comprising a RSV G ectodomain and transmembrane domain from RSV BA1, and a BPIV3 HN cytoplasmic tail is provided below:

(SEQ ID NO: 67)
MEYWKHTNSINNTNNETETARGKHSSKVTNIAQIALSVLAMIISTSLIIAA

IIFIISANHKVTLTTVTVQTIKNHTEKNITTYLTQVSPERVSPSKQLTTTP

PIYTNSATISPNTKSETHHTTAQTKGRTTTPTQNNKPSTKPRPKNPPKKPK

DDYHFEVFNFVPCSICGNNQLCKSICKTIPSNKPKKKPTIKPTNKPPTKTT

NKRDPKKLAKTLKKETTINPTKKPTPKTTERDTSTSQSTVLDTTTSKHTER

DTSTSQSTVLDTTTSKHTIQQQSLHSTTPENTPNSTQTPTASEPSTSNSTQ

KL

In some embodiments, the heterologous gene encodes a recombinant RSV G comprising or consisting of the amino acid sequence set forth as SEQ ID NO: 67, or an amino acid sequence at least 90% (such as at least 95% or at least 98%) identical to SEQ ID NO: 67.

An exemplary amino acid sequence of a recombinant RSV G comprising the RSV G ectodomain from RSV BA1, and BPIV3 HN transmembrane domain and cytoplasmic tail is provided below:

(SEQ ID NO: 68)
MEYWKHTNSINNTNNETETARGKHSSKVTNIIMYTFWTITLTILSVIFIMI

LTNLINHKVTLTTVTVQTIKNHTEKNITTYLTQVSPERVSPSKQLTTTPPI

YTNSATISPNTKSETHHTTAQTKGRTTTPTQNNKPSTKPRPKNPPKKPKDD

YHFEVFNFVPCSICGNNQLCKSICKTIPSNKPKKKPTIKPTNKPPTKTTNK

RDPKKLAKTLKKETTINPTKKPTPKTTERDTSTSQSTVLDTTTSKHTERDT

STSQSTVLDTTTSKHTIQQQSLHSTTPENTPNSTQTPTASEPSTSNSTQKL

In some embodiments, the heterologous gene encodes a recombinant RSV G comprising or consisting of the amino acid sequence set forth as SEQ ID NO: 68, or an amino acid sequence at least 90% (such as at least 95% or at least 98%) identical to SEQ ID NO: 68.

An exemplary amino acid sequence of a recombinant RSV G comprising a RSV G ectodomain and transmembrane domain from RSV A2, and a HPIV3 HN cytoplasmic tail is provided below:

(SEQ ID NO: 69)
MEYWKHTNHGKDAGNELETSMATHGNKLTNKVAQITLSILAMIISTSLIIA

AIIFIASANHKVTPTTAIIQDATSQIKNTTPTYLTQNPQLGISPSNPSEIT

SQITTILASTTPGVKSTLQSTTVKTKNTTTTQTQPSKPTTKQRQNKPPSKP

NNDFHFEVFNFVPCSICSNNPTCWAICKRIPNKKPGKKTTTKPTKKPTLKT

TKKDPKPQTTKSKEVPTTKPTEEPTINTTKTNIITTLLTSNTTGNPELTSQ

METFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 69, or an amino acid sequence at least 90% (such as at least 95% or at least 98%) identical to SEQ ID NO: 69.

An exemplary amino acid sequence of a recombinant RSV G comprising the RSV G ectodomain from RSV A2 and HPIV3 HN transmembrane domain and cytoplasmic tail is provided below:

(SEQ ID NO: 70)
MEYWKHTNHGKDAGNELETSMATHGNKLTNKIIYILWTIILVLLSIVFIIV

LINSINHKVTPTTAIIQDATSQIKNTTPTYLTQNPQLGISPSNPSEITSQI

TTILASTTPGVKSTLQSTTVKTKNTTTTQTQPSKPTTKQRQNKPPSKPNND

FHFEVFNFVPCSICSNNPTCWAICKRIPNKKPGKKTTTKPTKKPTLKTTKK

DPKPQTTKSKEVPTTKPTEEPTINTTKTNIITTLLTSNTTGNPELTSQMET

FHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 70, or an amino acid sequence at least 90% (such as at least 95% or at least 98%) identical to SEQ ID NO: 70.

An exemplary amino acid sequence of a recombinant RSV G comprising a RSV G ectodomain and transmembrane domain from RSV B (B1, GenBank AAB82435.1), and a HPIV3 HN cytoplasmic tail is provided below:

(SEQ ID NO: 71)
MEYWKHTNHGKDAGNELETSMATHGNKLTNKIAQIALSVLAMIISTSLIIA

AIIFIISANHKVTLTTVTVQTIKNHTEKNITTYLTQVPPERVSSSKQPTTT

SPIHTNSATTSPNTKSETHHTTAQTKGRTTTSTQTNKPSTKPRLKNPPKKP

KDDYHFEVFNFVPCSICGNNQLCKSICKTIPSNKPKKKPTIKPTNKPTTKT

TNKRDPKTPAKTTKKETTTNPTKKPTLTTTERDTSTSQSTVLDTTTLEHTI

QQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 71, or an amino acid sequence at least 90% (such as at least 95% or at least 98%) identical to SEQ ID NO: 71.

An exemplary amino acid sequence of a recombinant RSV G comprising the RSV G ectodomain from RSV B (B1, GenBank AAB82435.1) and HPIV3 HN transmembrane domain and cytoplasmic tail is provided below:

(SEQ ID NO: 72)
MEYWKHTNHGKDAGNELETSMATHGNKLTNKIIYILWTIILVLLSIVFIIV

LINSINHKVTLTTVTVQTIKNHTEKNITTYLTQVPPERVSSSKQPTTTSPI

HTNSATTSPNTKSETHHTTAQTKGRTTTSTQTNKPSTKPRLKNPPKKPKDD

YHFEVFNFVPCSICGNNQLCKSICKTIPSNKPKKKPTIKPTNKPTTKTTNK

RDPKTPAKTTKKETTTNPTKKPTLTTTERDTSTSQSTVLDTTTLEHTIQQQ

SLHSTTPENTPNSTQTPTASEPSTSNSTQNTQSHA

In some embodiments, the heterologous gene encodes a recombinant RSV G comprising or consisting of the amino acid sequence set forth as SEQ ID NO: 72, or an amino acid sequence at least 90% (such as at least 95% or at least 98%) identical to SEQ ID NO: 72.

An exemplary amino acid sequence of a recombinant RSV G comprising a RSV G ectodomain and transmembrane domain from RSV A/Maryland/001/11, and a HPIV3 HN cytoplasmic tail is provided below:

(SEQ ID NO: 73)
MEYWKHTNHGKDAGNELETSMATHGNKLTNKIAQITLSILAMIISTSLIIA

AIIFIASANHKVTLTTAIIQDATNQIKNTTPTYLTQNPQLGISLSNLSETT

SKPTTILALTTPNAESTPQSTTVKTKNTTTTQIQPSKPTTKQRQNKPQNKP

NNDFHFEVFNFVPCSICSNNPTCWAICKRIPNKKPGRKTTTKPTKQPAIKT

TKKDPKPQTTKPKEVLTTKPTEKPTINTTKTNIRTTLLTSNITENQEHTSQ

KETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 73, or an amino acid sequence at least 90% (such as at least 95% or at least 98%) identical to SEQ ID NO: 73.

An exemplary amino acid sequence of a recombinant RSV G comprising the RSV G ectodomain from RSV A/Maryland/001/11 and HPIV3 HN transmembrane domain and cytoplasmic tail is provided below:

(SEQ ID NO: 74)
MEYWKHTNHGKDAGNELETSMATHGNKLTNKIIYILWTIILVLLSIVFIIV
LINSINHKVTLTTAIIQDATNQIKNTTPTYLTQNPQLGISLSNLSETTSKP
TTILALTTPNAESTPQSTTVKTKNTTTTQIQPSKPTTKQRQNKPQNKPNND
FHFEVFNFVPCSICSNNPTCWAICKRIPNKKPGRKTTTKPTKQPAIKTTKK
DPKPQTTKPKEVLTTKPTEKPTINTTKTNIRTTLLTSNITENQEHTSQKET
LHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 74, or an amino acid sequence at least 90% (such as at least 95% or at least 98%) identical to SEQ ID NO: 74.

An exemplary amino acid sequence of a recombinant RSV G comprising a RSV G ectodomain and transmembrane domain from RSV ON1, and a HPIV3 HN cytoplasmic tail is provided below:

(SEQ ID NO: 75)
MEYWKHTNHGKDAGNELETSMATHGNKLTNKIAQITLSILAMIISTSLIIA
AIIFIASANHKVTLTTAIIQDATNQIKNTTPTYLTQNPQLGISFSNLSGTT
SQSTTILASTTPSAESTPQSTTVKIKNTTTTQILPSKPTTKQRQNKPQNKP
NNDFHFEVFNFVPCSICSNNPTCWAICKRIPNKKPGKKTTTKPTKKPTLKT
TKKDPKPQTTKPKEVLTTKPTGKPTINTTKTNIRTTLLTSNTKGNPEHTSQ
EETLHSTTSEGYLSPSQVYTTSGQEETLHSTTSEGYLSPSQVYTTSEYLSQ
SLSSSNTTK

In some embodiments, the heterologous gene encodes a recombinant RSV G comprising or consisting of the amino acid sequence set forth as SEQ ID NO: 75, or an amino acid sequence at least 90% (such as at least 95% or at least 98%) identical to SEQ ID NO: 75.

An exemplary amino acid sequence of a recombinant RSV G comprising the RSV G ectodomain from RSV ON1, and HPIV3 HN transmembrane domain and cytoplasmic tail is provided below:

(SEQ ID NO: 76)
MEYWKHTNHGKDAGNELETSMATHGNKLTNKIIYILWTIILVLLSIVFIIV
LINSINHKVTLTTAIIQDATNQIKNTTPTYLTQNPQLGISFSNLSGTTSQS
TTILASTTPSAESTPQSTTVKIKNTTTTQILPSKPTTKQRQNKPQNKPNND
FHFEVFNFVPCSICSNNPTCWAICKRIPNKKPGKKTTTKPTKKPTLKTTKK
DPKPQTTKPKEVLTTKPTGKPTINTTKTNIRTTLLTSNTKGNPEHTSQEET
LHSTTSEGYLSPSQVYTTSGQEETLHSTTSEGYLSPSQVYTTSEYLSQSLS
SSNTTK

In some embodiments, the heterologous gene encodes a recombinant RSV G comprising or consisting of the amino acid sequence set forth as SEQ ID NO: 76, or an amino acid sequence at least 90% (such as at least 95% or at least 98%) identical to SEQ ID NO: 76.

An exemplary amino acid sequence of a recombinant RSV G comprising a RSV G ectodomain and transmembrane domain from RSV BA1, and a HPIV3 HN cytoplasmic tail is provided below:

(SEQ ID NO: 77)
MEYWKHTNHGKDAGNELETSMATHGNKLTNKIAQIALSVLAMIISTSLII
AAIIFIISANHKVTLTTVTVQTIKNHTEKNITTYLTQVSPERVSPSKQLT
TTPPIYTNSATISPNTKSETHHTTAQTKGRTTTPTQNNKPSTKPRPKNPP
KKPKDDYHFEVFNFVPCSICGNNQLCKSICKTIPSNKPKKKPTIKPTNKP
PTKTTNKRDPKKLAKTLKKETTINPTKKPTPKTTERDTSTSQSTVLDTTT
SKHTERDTSTSQSTVLDTTTSKHTIQQQSLHSTTPENTPNSTQTPTASEP
STSNSTQKL

In some embodiments, the heterologous gene encodes a recombinant RSV G comprising or consisting of the amino acid sequence set forth as SEQ ID NO: 77, or an amino acid sequence at least 90% (such as at least 95% or at least 98%) identical to SEQ ID NO: 77.

An exemplary amino acid sequence of a recombinant RSV G comprising the RSV G ectodomain from RSV BA1, and HPIV3 HN transmembrane domain and cytoplasmic tail is provided below:

(SEQ ID NO: 78)
MEYWKHTNHGKDAGNELETSMATHGNKLTNKIIYILWTIILVLLSIVFII
VLINSINHKVTLTTVTVQTIKNHTEKNITTYLTQVSPERVSPSKQLTTTP
PIYTNSATISPNTKSETHHTTAQTKGRTTTPTQNNKPSTKPRPKNPPKKP
KDDYHFEVFNFVPCSICGNNQLCKSICKTIPSNKPKKKPTIKPTNKPPTK
TTNKRDPKKLAKTLKKETTINPTKKPTPKTTERDTSTSQSTVLDTTTSKH
TERDTSTSQSTVLDTTTSKHTIQQQSLHSTTPENTPNSTQTPTASEPSTS
NSTQKL

In some embodiments, the heterologous gene encodes a recombinant RSV G comprising or consisting of the amino acid sequence set forth as SEQ ID NO: 78, or an amino acid sequence at least 90% (such as at least 95% or at least 98%) identical to SEQ ID NO: 78.

An exemplary amino acid sequence of a recombinant RSV G comprising a RSV G ectodomain and transmembrane domain from RSV A2, and a HPIV1 HN cytoplasmic tail is provided below:

(SEQ ID NO: 79)
MAEKGKTNSSYWSTTRNDNSTVNTHINTPAGRTHWVAQITLSILAMIIST
SLIIAAIIFIASANHKVTPTTAIIQDATSQIKNTTPTYLTQNPQLGISPS
NPSEITSQITTILASTTPGVKSTLQSTTVKTKNTTTTQTQPSKPTTKQRQ
NKPPSKPNNDFHFEVFNFVPCSICSNNPTCWAICKRIPNKKPGKKTTTKP
TKKPTLKTTKKDPKPQTTKSKEVPTTKPTEEPTINTTKTNIITTLLTSNT
TGNPELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 79, or an amino acid sequence at least 90% (such as at least 95% or at least 98%) identical to SEQ ID NO: 79.

An exemplary amino acid sequence of a recombinant RSV G comprising the RSV G ectodomain from RSV A2 and HPIV1 HN transmembrane domain and cytoplasmic tail is provided below:

(SEQ ID NO: 80)
MAEKGKTNSSYWSTTRNDNSTVNTHINTPAGRTHWILLIATTMHTVLSFI

IMILCIDLIINHKVTPTTAIIQDATSQIKNTTPTYLTQNPQLGISPSNPS

EITSQITTILASTTPGVKSTLQSTTVKTKNTTTTQTQPSKPTTKQRQNKP

PSKPNNDFHFEVFNFVPCSICSNNPTCWAICKRIPNKKPGKKTTTKPTKK

PTLKTTKKDPKPQTTKSKEVPTTKPTEEPTINTTKTNIITTLLTSNTTGN

PELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 80, or an amino acid sequence at least 90% (such as at least 95% or at least 98%) identical to SEQ ID NO: 80.

An exemplary amino acid sequence of a recombinant RSV G comprising a RSV G ectodomain and transmembrane domain from RSV B (B1, GenBank AAB82435.1), and a HPIV1 HN cytoplasmic tail is provided below:

(SEQ ID NO: 81)
MAEKGKTNSSYWSTTRNDNSTVNTHINTPAGRTHWIAQIALSVLAMIIST

SLIIAAIIFIISANHKVTLTTVTVQTIKNHTEKNITTYLTQVPPERVSSS

KQPTTTSPIHTNSATTSPNTKSETHHTTAQTKGRTTTSTQTNKPSTKPRL

KNPPKKPKDDYHFEVFNFVPCSICGNNQLCKSICKTIPSNKPKKKPTIKP

TNKPTTKTTNKRDPKTPAKTTKKETTTNPTKKPTLTTTERDTSTSQSTVL

DTTTLEHTIQQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 81, or an amino acid sequence at least 90% (such as at least 95% or at least 98%) identical to SEQ ID NO: 81.

An exemplary amino acid sequence of a recombinant RSV G comprising the RSV G ectodomain from RSV B (B1, GenBank AAB82435.1) and HPIV1 HN transmembrane domain and cytoplasmic tail is provided below:

(SEQ ID NO: 82)
MAEKGKTNSSYWSTTRNDNSTVNTHINTPAGRTHWILLIATTMHTVLSFI

IMILCIDLIINHKVTLTTVTVQTIKNHTEKNITTYLTQVPPERVSSSKQP

TTTSPIHTNSATTSPNTKSETHHTTAQTKGRTTTSTQTNKPSTKPRLKNP

PKKPKDDYHFEVFNFVPCSICGNNQLCKSICKTIPSNKPKKKPTIKPTNK

PTTKTTNKRDPKTPAKTTKKETTTNPTKKPTLTTTERDTSTSQSTVLDTT

TLEHTIQQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 82, or an amino acid sequence at least 90% (such as at least 95% or at least 98%) identical to SEQ ID NO: 82.

An exemplary amino acid sequence of a recombinant RSV G comprising a RSV G ectodomain and transmembrane domain from RSV A/Maryland/001/11, and a HPIV1 HN cytoplasmic tail is provided below:

(SEQ ID NO: 83)
MAEKGKTNSSYWSTTRNDNSTVNTHINTPAGRTHWIAQITLSILAMIIST

SLIIAAIIFIASANHKVTLTTAIIQDATNQIKNTTPTYLTQNPQLGISLS

NLSETTSKPTTILALTTPNAESTPQSTTVKTKNTTTTQIQPSKPTTKQRQ

NKPQNKPNNDFHFEVFNFVPCSICSNNPTCWAICKRIPNKKPGRKTITKP

TKQPAIKTTKKDPKPQTTKPKEVLITKPTEKPTINTTKINIRTILLTSNI

TENQEHTSQKETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 83, or an amino acid sequence at least 90% (such as at least 95% or at least 98%) identical to SEQ ID NO: 83.

An exemplary amino acid sequence of a recombinant RSV G comprising the RSV G ectodomain from RSV A/Maryland/001/11 and HPIV1 HN transmembrane domain and cytoplasmic tail is provided below:

(SEQ ID NO: 84)
MAEKGKTNSSYWSTTRNDNSTVNTHINTPAGRTHWILLIATTMHTVLSFI

IMILCIDLIINHKVTLTTAIIQDATNQIKNTTPTYLTQNPQLGISLSNLS

ETTSKPTTILALTTPNAESTPQSTTVKTKNTTTTQIQPSKPTTKQRQNKP

QNKPNNDFHFEVFNFVPCSICSNNPTCWAICKRIPNKKPGRKTTTKPTKQ

PAIKTTKKDPKPQTTKPKEVLTTKPTEKPTINTTKTNIRTTLLTSNITEN

QEHTSQKETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 84, or an amino acid sequence at least 90% (such as at least 95% or at least 98%) identical to SEQ ID NO: 84.

An exemplary amino acid sequence of a recombinant RSV G comprising a RSV G ectodomain and transmembrane domain from RSV ON1, and a HPIV1 HN cytoplasmic tail is provided below:

(SEQ ID NO: 85)
MAEKGKTNSSYWSTTRNDNSTVNTHINTPAGRTHWIAQITLSILAMIIST

SLIIAAIIFIASANHKVTLTTAIIQDATNQIKNTTPTYLTQNPQLGISFS

NLSGTTSQSTTILASTTPSAESTPQSTTVKIKNTTTTQILPSKPTTKQRQ

NKPQNKPNNDFHFEVFNFVPCSICSNNPTCWAICKRIPNKKPGKKTTTKP

TKKPTLKTTKKDPKPQTTKPKEVLTTKPTGKPTINTTKTNIRTTLLTSNT

KGNPEHTSQEETLHSTTSEGYLSPSQVYTTSGQEETLHSTTSEGYLSPSQ

VYTTSEYLSQSLSSSNTTK

In some embodiments, the heterologous gene encodes a recombinant RSV G comprising or consisting of the amino acid sequence set forth as SEQ ID NO: 85, or an amino acid sequence at least 90% (such as at least 95% or at least 98%) identical to SEQ ID NO: 85.

An exemplary amino acid sequence of a recombinant RSV G comprising the RSV G ectodomain from RSV ON1, and HPIV1 HN transmembrane domain and cytoplasmic tail is provided below:

(SEQ ID NO: 86)
MAEKGKTNSSYWSTTRNDNSTVNTHINTPAGRTHWILLIATTMHTVLSFI

IMILCIDLIINHKVTLTTAIIQDATNQIKNTTPTYLTQNPQLGISFSNLS

GTTSQSTTILASTTPSAESTPQSTTVKIKNTTTTQILPSKPTTKQRQNKP

QNKPNNDFHFEVFNFVPCSICSNNPTCWAICKRIPNKKPGKKTTTKPTKK

PTLKTTKKDPKPQTTKPKEVLTTKPTGKPTINTTKTNIRTTLLTSNTKGN

PEHTSQEETLHSTTSEGYLSPSQVYTTSGQEETLHSTTSEGYLSPSQVYT

TSEYLSQSLSSSNTTK

In some embodiments, the heterologous gene encodes a recombinant RSV G comprising or consisting of the amino acid sequence set forth as SEQ ID NO: 86, or an amino acid sequence at least 90% (such as at least 95% or at least 98%) identical to SEQ ID NO: 86.

An exemplary amino acid sequence of a recombinant RSV G comprising a RSV G ectodomain and transmembrane domain from RSV BA1, and a HPIV1 HN cytoplasmic tail is provided below:

(SEQ ID NO: 87)
MAEKGKTNSSYWSTTRNDNSTVNTHINTPAGRTHWIAQIALSVLAMIIST

SLIIAAIIFIISANHKVTLTTVTVQTIKNHTEKNITTYLTQVSPERVSPS

KQLTTTPPIYTNSATISPNTKSETHHTTAQTKGRTTTPTQNNKPSTKPRP

KNPPKKPKDDYHFEVFNFVPCSICGNNQLCKSICKTIPSNKPKKKPTIKP

TNKPPTKTTNKRDPKKLAKTLKKETTINPTKKPTPKTTERDTSTSQSTVL

DTTTSKHTERDTSTSQSTVLDTTTSKHTIQQQSLHSTTPENTPNSTQTPT

ASEPSTSNSTQKL

In some embodiments, the heterologous gene encodes a recombinant RSV G comprising or consisting of the amino acid sequence set forth as SEQ ID NO: 87, or an amino acid sequence at least 90% (such as at least 95% or at least 98%) identical to SEQ ID NO: 87.

An exemplary amino acid sequence of a recombinant RSV G comprising the RSV G ectodomain from RSV BA1, and HPIV1 HN transmembrane domain and cytoplasmic tail is provided below:

(SEQ ID NO: 88)
MAEKGKENSSYWSTERNDNSTVNTHINTPAGRTHWILLIATTMHTVLSFI

IMILCIDLIINHKVTLETVEVQTIKNHTEKNITTYLTQVSPERVSPSKQL

ETTPPITINSATISPNEKSETHHTTAQTKGRETTPTQNNKPSTKPRPKNP

PKKPKDDYHFEVFNFVPCSICGNNQLCKSICKTIPSNKPKKKPTIKPENK

PPEKTENKRDPKKLAKTLKKETTINPTKKPTPKTTERDTSTSQSTVLDTT

ESKHTERDTSTSQSTVLDTTTESKHTIQQQSLHSTTPENTPNSTQTPTAS

EPSTSNSTQKL

In some embodiments, the heterologous gene encodes a recombinant RSV G comprising or consisting of the amino acid sequence set forth as SEQ ID NO: 88, or an amino acid sequence at least 90% (such as at least 95% or at least 98%) identical to SEQ ID NO: 88.

In additional embodiments, the heterologous gene of the rB/HPIV3-RSV G comprises a sequence encoding a wild-type RSV G or variant thereof that has been codon-optimized for expression in a human cell. For example, the encoding sequence of the heterologous gene can be codon-optimized for human expression using a GeneArt (GA), DNA2.0 (D2), or GenScript (GS) optimization algorithm. Non-limiting examples of nucleic acid sequences encoding the RSV G protein that have been codon-optimized for expression in a human cell are provided as follows:

"GS" codon optimized DNA coding sequence
for wt G from RSV A2:
(SEQ ID NO: 89)
atgtcaaagaacaaggatcagagaactgccaagaccctggaaagaacctg ggacacctgaaccacctgctgtttatctcaagctgcctgtacaagctga atctgaaaagtgtggcccagatcaccctgtcaattctggctatgatcatt tcaacaagcctgatcattgccgctatcattttcatcgcaagcgccaacca caaggtcaccccaccacagctatcattcaggacgcaacatcccagatta agaacactaccccacctatctgacacagaatcctcagctgggaatctcc ccatctaacccctcagagattaccagccagatcacaactattctggcctc caccacacctggcgtgaagtccactctgcagtctactaccgtcaagacca aaaatacaactaccacacagacacagccttctaagccaactaccaaacag cggcagaataagcccctagtaaaccaaacaatgacttccattttgaggt gttcaactttgtcccatgcagcatctgttccaacaatcccacctgctggg ccatctgtaagagaattccaaacaagaaacccggcaagaagaccactacc aaacctactaagaaaccaaccctgaagacaactaagaaagatcctaaacc acagaccacaaagtctaaagaagtgcccactaccaagcctacagaggaac caactatcaacacaactaagactaacatcatcaccacactgctgacaagc aacactaccggcaatcccgagctgaccagccagatggaaacctttcactc cacaagctccgaggggaatcccagtccttcacaggtgtctacaactagtg aataccccagccagccttctagtccacccaacaccctaggcagtga Codon optimized (Biobasic) DNA coding sequence for wt G from RSV A/Maryland/001/11:
(SEQ ID NO: 95)
atgtctaagacaaaggatcagcggacagccaaaacactggaacggacatg ggataccctgaatcacctcctcttcatcagcagttgcctgtacaagctca atctgaagtccatcgcccagatcactctctccatccttgccatgatcatc tctacaagcctcatcattgccgcaattatcttcatcgccagcgctaacca caaggtcacccttaccacagccattattcaggatgccaccaaccagatca agaacacaaccccctacctacctgacacagaaccctcagcttggaatttca ctgagcaacctgtccgaaaccacatctaaacctacaaccatcttggctct gaccacaccaaacgccgagtccacccccacaaagtaccacagtgaagacca aaaacaccacaaccacacagattcagccaagcaagcctacaactaagcaa aggcagaacaagccacagaacaaacccaacaacgactttcactttgaggt gttcaactttgtgcctgctccatttgctccaacaaccctacctgttggg ctatctgcaagaggatccccaacaagaagcccggcaggaagactactact aagcctactaaacagccagccattaagaccactaagaaggacccaaagcc acagacaaccaagccaaggaggtgctcactaccaagcccactgagaagc ccaccattaacaccactaaaaccaacatccgcacaacattgctgacatca -continued aacattacagagaaccaggagcacacaagccagaaggagacactgcatag cactacatccgaaggcaatcccagcccaagccaggtctatactacctcag agtacctgtcccagagcctgagccctagcaacactactagatggtag Codon optimized (Biobasic) DNA coding sequence for
wt G from RSV B1:
(SEQ ID NO: 90)
agtctaaacacaagaatcagcggaccgcccggaccttggaaaagacttgg gatacccttaaccaccttatcgtgatttcctcctgcctgtaccgcctcaa cctcaagagcattgctcagatcgcgctctcagtgctggccatgataatct ccacttccttgataattgccgccattatcttcattatttctgcaaaccac aaagtcaccctgaccaccgttaccgtgcaaaccattaaaaaccacacgga gaagaacatcactacatacctgactcaggttcccccggagcgagtgagca gctccaagcagcccacaacaacaagccctatccatacaaattcagcaaca acaagtccaaacacaaagtctgaaacgcatcacacaaccgctcagacgaa aggcaggaccacaacatccacccagactaataaacccagtactaagccta gactgaagaaccctcccaagaaacctaaggacgactatcatttcgaggtg tttaattttgtaccttgcagcatctgtggcaacaatcagctctgcaaaag catctgtaagaccatcccgtctaataagccaaagaagaagcccacgataa aaccaacaaataaaccaactaccaagacaacaaataagagggacccaaag accccgctaaaactaccaagaaggagactaccaccaacccgacaaagaa acccaccctgacgactactgagagagatacttcaacttcacaaagcaccg tcctggatacaactaccctggagcacacaatccagcaacagagcctgcat agtactacgcctgaaaacactccaaactctacccagacgcccacagcctc agaaccttctacctccaatagtacccaaaatacccagagtcatgcatag In some embodiments, the genome of the rB/HPIV3-RSV G vector comprises an antigenomic cDNA sequence set forth as any one of SEQ ID NOs: 85-88.

Non-limiting examples of methods of generating a recombinant parainfluenza virus (such as a rB/HPIV3) including a heterologous gene, methods of attenuating the viruses (e.g., by recombinant or chemical means), as well as viral sequences and reagents for use in such methods are provided in U.S. Patent Publications 2012/0045471, 2010/0119547, 2009/0263883, 2009/0017517, U.S. Pat. Nos. 7,632,508, 7,622,123, 7,250,171, 7,208,161, 7,201,907, 7,192,593, PCT Pub. No. WO 2016/118642, Liang et al. (J. Virol, 88(8): 4237-4250, 2014), and Tang et al. (J Virol, 77(20):10819-10828, 2003), each of which is incorporated by reference herein. In some embodiments, these methods can be modified as needed using the description provided herein to construct a disclosed rB/HPIV3-RSV G vector.

The genome of the rB/HPIV3-RSV G vector can include one or more variations (for example, mutations that cause an amino acid deletion, substitution, or insertion) as long as the resulting the rB/HPIV3-RSV G retains the desired biological function, such as a level of attenuation or immunogenicity. These variations in sequence can be naturally occurring variations or they can be engineered through the use of genetic engineering technique.

Other mutations involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986)) can be shortened or lengthened or changed in sequence content, and the naturally-occurring gene overlap (Collins et al., Proc. Natl. Acad. Sci. USA 84:5134-5138 (1987)) can be removed or changed to a different intergenic region by the methods described herein.

In another embodiment, a sequence surrounding a translational start site (preferably including a nucleotide in the −3 position) of a selected viral gene is modified, alone or in combination with introduction of an upstream start codon, to modulate gene expression by specifying up- or down-regulation of translation.

Alternatively, or in combination with other modifications disclosed herein, gene expression can be modulated by altering a transcriptional GS signal of a selected gene(s) of the virus. In additional embodiments, modifications to a transcriptional GE signal can be incorporated into the viral genome.

In addition to the above described modifications to rB/HPIV3-RSV G, different or additional modifications to the genome can be made to facilitate manipulations, such as the insertion of unique restriction sites in various intergenic regions (e.g., a unique Asc I site between the N and P genes) or elsewhere. Nontranslated gene sequences can be removed to increase capacity for inserting foreign sequences.

Introduction of the foregoing modifications into rB/HPIV3-RSV G can be achieved by a variety of well-known methods. Examples of such techniques are found in see, e.g., Sambrook et al. (Molecular Cloning: A Laboratory Manual, 4$^{th}$ ed., Cold Spring Harbor, New York, 2012) and Ausubel et al. (In Current Protocols in Molecular Biology, John Wiley & Sons, New York, through supplement 104, 2013). Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. A mutated subfragment can then be assembled into the complete antigenome or genome cDNA. Mutations can vary from single nucleotide changes to replacement of large cDNA pieces containing one or more genes or genome regions.

The disclosed embodiments of rB/HPIV3-RSV G are self-replicating, that is they are capable of replicating following infection of an appropriate host cell, and have an attenuated phenotype, for example when administered to a human subject. Preferably, the rB/HPIV3-RSV G is attenuated about 3- to 500-fold or more in the upper respiratory tract and about 100 to 5000 fold or more in the lower respiratory tract in a mammal compared to control HPIV3. In some embodiments, it is preferred that the level of viral replication in vitro is sufficient to provide for production of virus for use on a wide spread scale. In some embodiments, it is preferred that the level of viral replication of attenuated paramyxovirus in vitro is at least $10^6$, more preferably at least $10^7$, and most preferably at least $10^8$ per ml.

In some embodiments, the rB/HPIV3-RSV G vectors can be produced using the reverse genetics recombinant DNA-based technique (Collins, et al. 1995. Proc Natl Acad Sci USA 92:11563-11567). This system allows de novo recovery of infectious virus entirely from cDNA in a qualified cell substrate under defined conditions. Reverse genetics provides a means to introduce predetermined mutations into the rB/HPIV3-RSV G genome via the cDNA intermediate. Specific attenuating mutations were characterized in preclinical studies and combined to achieve the desired level of attenuation. Derivation of vaccine viruses from cDNA minimizes the risk of contamination with adventitious agents and helps to keep the passage history brief and well documented. Once recovered, the engineered virus strains propagate in the same manner as a biologically derived virus. As a result of passage and amplification, the virus does not contain recombinant DNA from the original recovery.

To propagate rB/HPIV3-RSV G vectors for immunization and other purposes, a number of cell lines which allow for viral growth may be used. Parainfluenza virus grows in a variety of human and animal cells. Preferred cell lines for propagating attenuated rB/HPIV3-RSV G virus for immunization include HEp-2 cells, FRhL-DBS2 cells, LLC-MK2 cells, MRC-5 cells, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by standard clarification procedures, e.g., centrifugation, and may be further purified as desired using known procedures.

The rB/HPIV3-RSV G vectors can be tested in various well known and generally accepted in vitro and in vivo models to confirm adequate attenuation, resistance to phenotypic reversion, and immunogenicity. In in vitro assays, the modified virus is tested for temperature sensitivity of virus replication or "ts phenotype," and for the small plaque phenotype. Modified virus also may be evaluated in an in vitro human airway epithelium (HAE) model, which appears to provide a means of ranking viruses in the order of their relative attenuation in non-human primates and humans (Zhang et al., 2002 J Virol 76:5654-5666; Schaap-Nutt et al., 2010 Vaccine 28:2788-2798; Ilyushina et al., 2012 J Virol 86:11725-11734). Modified viruses are further tested in animal models of HPIV3 or RSV infection. A variety of animal models (e.g., murine, cotton rat, and primate) are available.

Immunogenicity of a rB/HPIV3-RSV G vector can be assessed in an animal model (such as a non-human primate, for example an African green monkey), for example, by determining the number of animals that form antibodies to RSV and HPIV3 after one immunization and after a second immunization, and by measuring the magnitude of that response. In some embodiments, a rB/HPIV3-RSV G has sufficient immunogenicity if about 60 to 80% of the animals develop antibodies after the first immunization and about 80 to 100% of the animals develop antibodies after the second immunization. Preferably, the immune response protects against infection by both RSV and HPIV3.

Also provided are isolated polynucleotides comprising or consisting of the genome or antigenome of a disclosed rB/HPIV3-RSV G vector, vectors comprising the polynucleotides, and host cells comprising the polynucleotides or vectors.

IV. Immunogenic Compositions

Immunogenic compositions comprising a disclosed rB/HPIV3-RSV G vector and a pharmaceutically acceptable carrier are also provided. Such compositions can be administered to a subject by a variety of modes, for example, by an intranasal route. Standard methods for preparing administrable immunogenic compositions are described, for example, in such publications as *Remingtons Pharmaceutical Sciences*, 19$^{th}$ Ed., Mack Publishing Company, Easton, Pennsylvania, 1995.

Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized Lyophilized preparations are combined with a sterile solution prior to administration for either single or multiple dosing.

The immunogenic composition can contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic composition can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance the immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the recombinant virus, and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the immunogenic composition can include a rB/HPIV3-RSV G encoding an RSV G ectodomain from one particular RSV subgroup or strain and also a recombinant rB/HPIV3-RSV G encoding an RSV G ectodomain from a different RSV subgroup or strain. For example, the composition can include rB/HPIV3-RSV G including recombinant RSV G proteins from subtype A and subtype B RSV. The different viruses can be in an admixture and administered simultaneously, or administered separately. Due to the phenomenon of cross-protection among certain strains of RSV, immunization with one rB/HPIV3-RSV G encoding a RSV G ectodomain from a first strain may protect against several different strains of the same or different subgroup.

In some instances it may be desirable to combine the immunogenic composition including the rB/HPIV3-RSV G, with other pharmaceutical products (e.g., vaccines) which induce protective responses to other viral agents, particularly those causing other childhood illnesses. For example, a composition including a rB/HPIV3-RSV G as described herein can also include other vaccines recommended by the Advisory Committee on Immunization Practices (ACIP; cdc.gov/vaccines/acip/index.html) for the targeted age group (e.g., infants from approximately one to six months of age). These additional vaccines include, but are not limited to, IN-administered vaccines. As such, a rB/HPIV3-RSV G as described herein may be administered simultaneously with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the immunogenic composition can be provided in unit dosage form for use to induce an immune response in a subject, for example, to prevent HPIV3 and/or RSV infection in the subject. A unit dosage form contains a suitable single preselected dosage for administration to a subject, or suitable marked or measured multiples of two or more preselected unit dosages, and/or a metering mechanism for administering the unit dose or multiples thereof.

V. Methods of Eliciting an Immune Response

Provided herein are methods of eliciting an immune response in a subject by administering an immunogenic composition containing a disclosed rB/HPIV3-RSV G to the subject. Upon immunization, the subject responds by producing antibodies specific for one or more of RSV G protein and HPIV3 HN and F proteins. In addition, innate and cell-mediated immune responses are induced, which can provide antiviral effectors as well as regulating the immune response. As a result of the immunization the host becomes at least partially or completely immune to HPIV3 and/or RSV infection, or resistant to developing moderate or severe HPIV3 and/or RSV disease, particularly of the lower respiratory tract.

Because nearly all humans are infected with RSV and HPIV3 by the age of 5, the entire birth cohort is included as a relevant population for immunization. This could be done, for example, by beginning an immunization regimen anytime from birth to 6 months of age, from 6 months of age to 5 years of age, in pregnant women (or women of childbearing age) to protect their infants by passive transfer of antibody, family members of newborn infants or those still in utero, and subjects greater than 50 years of age. The scope of this disclosure is meant to include maternal immunization. In several embodiments, the subject is a human subject that is seronegative for RSV, HPIV3, and/or HPIV1 specific antibodies. In additional embodiments, the subject is no more than one year old, such as no more than 6 months old, no more than 3 months, or no more than 1 month old.

Subjects at greatest risk of RSV and/or HPIV infection with severe symptoms (e.g. requiring hospitalization) include children with prematurity, bronchopulmonary dysplasia, and congenital heart disease are most susceptible to severe disease. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. In some embodiments, these subjects can be selected for administration of a disclosed rB/HPIV3-RSV G.

The immunogenic compositions containing the rB/HPIV3-RSV G are administered to a subject susceptible to or otherwise at risk of RSV and/or HPIV3 infection in an "effective amount" which is sufficient to induce or enhance the individual's immune response capabilities against RSV and/or HPIV3. The immunogenic composition may be administered by any suitable method, including but not limited to, via injection, aerosol delivery, nasal spray, nasal droplets, oral inoculation, or topical application. In a preferred embodiment, the attenuated virus is administered according to established human intranasal administration protocols (e.g., as discussed in Karron et al. JID 191:1093-104, 2005). Briefly, adults or children are inoculated intranasally via droplet with an effective amount of the rB/HPIV3-RSV G, typically in a volume of 0.5 ml of a physiologically acceptable diluent or carrier. This has the advantage of simplicity and safety compared to parenteral immunization with a non-replicating virus. It also provides direct stimulation of local respiratory tract immunity, which plays a major role in resistance to RSV and HPIV3. Further, this mode of vaccination effectively bypasses the immunosuppressive effects of HPIV3- and RSV-specific maternally-derived serum antibodies, which typically are found in the very young. Also, while the parenteral administration of RSV antigens can sometimes be associated with immunopathologic complications, this has not been observed with a live virus.

In all subjects, the precise amount of immunogen administered and the timing and repetition of administration will be determined by various factors, including the patient's state of health and weight, the mode of administration, the nature of the formulation, etc. Dosages will generally range from about 3.0 $\log_{10}$ to about 6.0 $\log_{10}$ plaque forming units ("PFU") or more of virus per patient, more commonly from about 4.0 $\log_{10}$ to 5.0 $\log_{10}$ PFU virus per patient. In one embodiment, about 5.0 $\log_{10}$ to 6.0 $\log_{10}$ PFU per patient may be administered during infancy, such as between 1 and 6 months of age, and one or more additional booster doses could be given 2-6 months or more later. In another embodiment, young infants could be given a dose of about 5.0 $\log_{10}$ to 6.0 $\log_{10}$ PFU per patient at approximately 2, 4, and 6 months of age, which is the recommended time of administration of a number of other childhood vaccines. In yet another embodiment, an additional booster dose could be administered at approximately 10-15 months of age. The embodiments of rB/HPIV3-RSV G described herein, and immunogenic compositions thereof, are administered to a subject in an amount effective to induce or enhance an immune response against the HPIV3 and RSV antigens included in the rB/HPIV3-RSV G in the subject. An effective amount will allow some growth and proliferation of the virus, in order to produce the desired immune response, but will not produce viral-associated symptoms or illnesses. Based on the guidance provided herein and knowledge in the art, the proper amount of rB/HPIV3-RSV G to use for immunization cane determined.

A desired immune response is to inhibit subsequent infection with RSV and/or HPIV3. The RSV and/or HPIV3infection does not need to be completely inhibited for the method to be effective. For example, administration of an effective amount of a disclosed rB/HPIV3-RSV G can decrease subsequent RSV and/or HPIV3infection (for example, as measured by infection of cells, or by number or percentage of subjects infected by RSV and/or HPIV3) by a desired amount, for example by at least 10%, at least 20%, at least 50%, at least 60%, at least 70%, at least 80%, at least 90%, at least 95%, at least 98%, or even at least 100%

(prevention of detectable RSV and/or HPIV3 infection), as compared to a suitable control.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, hamster, cotton rat, bovine, ovine, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease).

Administration of the rB/HPIV3-RSV G to a subject can elicit the production of an immune response that is protective against serious lower respiratory tract disease, such as pneumonia and bronchiolitis, or croup, when the subject is subsequently infected or re-infected with a wild-type RSV or HPIV3. While the naturally circulating virus is still capable of causing infection, particularly in the upper respiratory tract, there is a reduced possibility of rhinitis as a result of the immunization and a possible boosting of resistance by subsequent infection by wild-type virus. Following immunization, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup. To achieve higher levels of cross-protection, for example, against heterologous strains of another subgroup, subjects can be immunized with multiple immunogenic compositions that together comprise rB/HPIV3-RSV G with genomes encoding a RSV G proteins from at least one predominant strain of both RSV subgroups A and B.

An immunogenic composition including one or more of the disclosed rB/HPIV3-RSV G viruses can be used in coordinate (or prime-boost) immunization protocols or combinatorial formulations. It is contemplated that there can be several boosts, and that each boost can be a different disclosed immunogen. It is also contemplated in some examples that the boost may be the same immunogen as another boost, or the prime. In certain embodiments, novel combinatorial immunogenic compositions and coordinate immunization protocols employ separate immunogens or formulations, each directed toward eliciting an anti-viral immune response, such as an immune response to RSV and HPIV3 proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measures by flow cytometry or for cytotoxic activity against indicator target cells displaying RSV antigens. In this regard, individuals are also monitored for signs and symptoms of upper respiratory illness.

EXAMPLES

The following examples are provided to illustrate particular features of certain embodiments, but the scope of the claims should not be limited to those features exemplified.

Example 1

Identification of rB/HPIV3 Vectors Expressing RSV G or Variants Thereof for Induction of a Protective Immune Response to RSV and HPIV3

This example describes development, production, and evaluation of a rB/HPIV3 vector to express wt G protein of RSV A2 strain, and variants thereof, from the second gene position, between the vector N and P genes.

The vector backbone used in this example is a chimera of bovine PIV3 (Kansas strain) and human PIV3 (JS strain), called rB/HPIV3 (Schmidt et al., 2000, *J. Virol.* 74:8922-8929). This vector consists of BPIV3 in which the genes encoding the F and HN glycoproteins (the two PIV3 neutralization antigens and major protective antigens) have been replaced by their counterparts from HPIV3. HPIV3 and BPIV3 are very closely-related viruses, and the rB/HPIV3 chimera contains all of the PIV3 genes and is fully replication-competent, but is attenuated in rhesus monkeys and humans due to the BPIV3 backbone (Karron et al., 2012, Vaccine 30:3975-3981).

A version of the rB/HPIV3 with the wild type (wt) RSV F gene inserted in the second gene position (N-P), called MEDI-534, previously was evaluated in HPIV3- and RSV-seronegative infants and children (Bernstein et al., *Ped. Infect. Dis., J.* 31:109-114, 2012). MEDI-534 was attenuated and well-tolerated (as was the empty rB/HPIV3 vector in a different study in seronegative children, Karron et al., 2012, Vaccine 30:3975-3981). However, while all vaccine recipients seroconverted against HPIV3, only half developed detectable serum RSV-neutralizing antibodies analyzed by a micro-neutralization assay in the absence of added complement. There also was loss of RSV F protein expression by substantial proportions of vector that had been recovered in nasal washes from vaccinees (Yang et al., Vaccine 31:2822-2827, 2013). An advantage of the rB/HPIV3 vector system is that, because rB/HPIV3 expressing RSV wt F protein was shown to be safe and well-tolerated in seronegative children, as noted above (Bernstein et al., 2012, Pediatr. Infect. Dis. J. 31:109-114), versions with improved RSV inserts can be anticipated to be similarly well-tolerated, putting them on a fast track for clinical development.

The rB/HPIV3-RSV G vectors were designed so that the RSV G gene was flanked by BPIV3 transcription regulatory elements including a gene end (GE) signal copied from the N gene, a gene start (GS) signal copied from the P gene, and CTT trinucleotide intergenic regions (FIG. 1A). Additionally, the HN gene of the rB/HPIV3 includes 263T and 370P amino acid assignments, which results in virus that could be recovered and passaged with substantially reduced appearance of adventitious mutations to increase the efficiency of virus production, analysis, and manufacture.

RSV G and RSV G Variants

The RSV G protein is expressed during RSV infection in two forms. One is the full-length transmembrane form (mG), which is expressed on the cell surface and is packaged into the virus particle.

The other form is an N-terminally-truncated, secreted form, sG. The full-length G protein (mG) is a type II protein that has an N-terminal cytoplasmic tail (CT, predicted to comprise amino acids 1-37 in strain A2, see FIG. 1B), a hydrophobic transmembrane domain (TM, comprising approximately amino acids 38-65, see FIG. 1B), and an ectodomain (comprising approximately amino acids 66-298). The sG form is produced by alternative translation initiation at the second AUG codon (M48) in the ORF, whose corresponding position in the protein lies within the TM domain (see FIG. 1B). The N-terminus is then subjected to intracellular proteolytic trimming that creates a new N-terminus at N66 (FIG. 1B).

The ectodomain of G consists of two large divergent domains that flank a short central conserved region at amino acids 164-186. The divergent domains have a high content of proline, alanine, threonine, and serine amino acids, and (for strain A2) an estimated four N-linked and 24-25 O-linked carbohydrate side chains. The central conserved domain contains a cysteine noose (i.e., a tight turn stabilized by two disulfide bonds) that bears a conserved CX3C motif (CWAIC, 182-186 aa of the A2 strain). The mG and sG forms are believed to be essentially the same with regard to glycosylation and protein structure except that mG forms a multimer that probably is a trimer or tetramer, whereas sG remains a monomer.

A CX3C domain also occurs in the chemokine called fractalkine (FIG. 1C), and the sequences flanking the CX3C domains in RSV G and fractalkine also share sequence relatedness (Tripp et al., *Nature Immunol.* 2:732-738, 2001). The G protein has been shown to mimic fractalkine in the ability to induce leukocyte chemotaxis in vitro (Tripp et al., 2001, *Nature Immunol* 2:732-738), and also binds to the fractalkine receptor CX3CR1, which can initiate RSV infection (Tripp et al., 2001, *Nature Immunol* 2:732-738; Johnson et al., 2015, *PLoS Pathog.* 11:e1005318). Like the G protein, fractalkine is expressed as a full-length transmembrane form and a truncated secreted form. For fractalkine, the full-length transmembrane form acts as an adhesion molecule that interacts with the fractalkine receptor CX3CR1 expressed on T cells, NK cells, and monocytes; and the secreted form acts as a chemoattractant for the same cell types. The role of the CX3C domain in RSV attachment seems straight-forward (i.e., allowing the virus to bind to cells expressing CX3CR1), but the effects of the CX3C domain and sG on host immunity remain unclear. In principle, ablation of the CX3C domain and/or the expression of sG would be expected to reduce the chemotactic influx of immune cells and might reduce disease, and this is supported by several studies with mutant RSVs (e.g., Maher et al., 2004, *Microbes Infect.* 6:1049-1055; Boyoglu-Barnum et al., 2017, *J. Virol.*, 91(10): e02059-16), although there also are contradictory data (e.g. Harcourt et al., 2006, *J. Immunol.* 176:1600-1608). Other effects of G also have been described: e.g., sG was shown to act as an antigen decoy to reduce neutralization by antibodies, and also appeared to interfere with clearance of RSV by macrophages and complement (Bukreyev et al., *J. Virol.*, 86(19): 10880-4, 2012). As another example, in vitro, the G protein interfered with human dendritic cell activation (Johnson et al., 2012, *J. Virol.* 86:1339-1347). In addition, the binding of RSV to CX3CR1 expressed on human neonatal regulatory B cells lead to a Th2-polarized response (Zhivaki et al., 2017, *Immunity* 46:301-314). Thus, the effects of the G protein, including its sG form and CX3C motif, on host immunity are incompletely understood and likely are complex.

RSV G and nine derivatives thereof are shown in FIG. 1A (constructs (i)-(x)), which are described below:

Constructs (i) is wt RSV G. The wt RSV G used in this example is from subgroup A2 and has the amino acid sequence set forth as:

(SEQ ID NO: 22)
MSKNKDQRTAKTLERTWDTLNHLLFISSCLYKLNLKSVAQITLSILAMII

STSLIIAAIIFIASANHKVTPTTAIIQDATSQIKNTTPTYLTQNPQLGIS

PSNPSEITSQITTILASTTPGVKSTLQSTTVKTKNTTTTQTQPSKPTTKQ

RQNKPPSKPNNDFHFEVFNFVPCSICSNNPTCWAICKRIPNKKPGKKTTT

KPTKKPTLKTTKKDPKPQTTKSKEVPTTKPTEEPTINTTKTNIITTLLTS

NTTGNPELTSQMETFHSTSSEGNPSPSQVSTTSEYPSQPSSPPNTPRQ

Constructs (ii) and (iii) in FIG. 1A encode the mG and sG forms of G protein. The mG construct was made by ablating expression of sG by a M48I mutation (FIG. 1B), and the sG construct was made by deletion of the first 47 codons of the G ORF so that codon M48 initiates the ORF (FIG. 1B); as described previously, the protein subsequently gets trimmed intracellularly to a major product with an N-terminus of N66 (Roberts et al., *J. Virol.*, 68(7): 4538-4546, 1994, Teng et al., *J. Virol.* 289:283-296, 2001).

Constructs (iv) and (v) in FIG. 1A (G_B3CT and G_B3TMCT) are chimeric proteins that have the CT and TMCT of wt G replaced by those of the vector BPIV3 HN protein (see FIG. 1B) to promote efficient packaging of RSV G into the vector particles. It is believed that the presence in RSV G of CT or TMCT domains from the vector HN protein would promote homologous interactions with internal vector proteins such as M and N to facilitate the incorporation of RSV G into the viral particle. Identification of the sequence boundaries of the TM and CT of BPIV3 HN was determined by inspection and alignment with HPIV3 HN (FIG. 1B).

Constructs (vi) and (vii) in FIG. 1A (G_dCX3C and G_wCX4C) have mutations that ablate the CX3C motif in the G protein: specifically, G_dCX3C has a C186R mutation that changes the assignment of the second cysteine residue in the CX3C motif (FIG. 1C), and G_wCX4C has the insertion of an alanine residue between positions 185 and 186 that disrupts the spacing of the motif (FIG. 1C).

In constructs (viii) and (ix) in FIG. 1A, the C186R mutation also was made in combination with the B3CT and B3TMCT substitutions (G_dCX3C_B3CT and G_dCX3C_B3TMCT).

In addition, a construct encoding wt G was codon-optimized for human expression by GenScript (wt G/GS-opt, FIG. 1A, form x).

The range of RSV G variants allowed assessment of the effects of sG, the CX3C motif, the CT and TMCT mutations, and codon optimization on the immunogenicity of the RSV G protein. In addition, possible effects on the immune response to the rB/HPIV3 vector could also be assessed. In this context, PIV3 is a suitable surrogate for RSV because it is a related respiratory virus that has general similarities in epidemiology, tissue tropism, and disease. In addition, the RSV G insert is not needed for replication of the PIV vector, removing this confounding factor. Thus, effects on vector immunogenicity, as well as possible changes in immunologic restriction of vector replication, were assessed.

Full antigenomic cDNA sequences for rB/HPIV3-RSV wtG (construct (i)), rB/HPIV3-RSV wt G/GS-opt (construct (x)), rB/HPIV3-RSV G_B3TMCT (construct (v)), rB/HPIV3-RSV G_B3CT (construct (iv)) are provided in the exemplary sequences section below.

Virus Replication and RSV G Expression

The rB/HPIV3 vectors expressing various forms of RSV G replicated efficiently in LLC-MK2 cells (7.6-8.6 $\log_{10}TCID_{50}$/ml). No growth defect was observed with any construct.

The intracellular expression of RSV G by the various constructs was evaluated in Vero (FIGS. 2A and 2B) and LLC-MK2 (FIG. 3) cells by Western blot analysis. Cells were infected with each vector at a multiplicity of infection (MOI) of 10 $TCID_{50}$ (50% tissue culture infection doses) per cell, or by wt RSV at MOI of 3 plaque formation units (PFU) per cell. Cells were harvested at 24 h post-infection (p.i.) and cell lysates were prepared, subjected to gel electrophoresis under denaturing and reducing conditions, and analyzed by Western blotting using polyclonal antibodies against RSV and HPIV3.

Intracellular RSV G expressed by the rB/HPIV3 vector expressing wt RSV G (FIG. 2A, lane 2) and by wt RSV (lane 11) was detected as a predominant diffuse band of 90-120 kD (FIG. 2A), which corresponds to the fully glycosylated form, and as less abundant bands of 35-50 kD that represent processing intermediates of the G protein with incomplete O-glycosylation. Expression of the various G protein species described above by the mG construct was essentially the same as for wt G (FIGS. 2A and 2B, lane 4 versus 2). In contrast, the sG construct had only a trace amount of the large diffuse band, consistent with efficient secretion. The sG construct also had versions of the incompletely-glycosylated bands of the G protein that were reduced in size due to the N-terminal truncation. The CT and TMCT substitutions increased expression of the large G band by 50-80%, an effect that is unexplained (FIGS. 2A and 2B, lanes 5 and 6 versus 2). In contrast, CX3C ablation reduced the accumulation of the large G band by 20-50% percent, which appeared to be due at least in part to an increase in the accumulation of the 35-50 kD incompletely-glycosylated forms (FIGS. 2A and 2B, lanes 7 and 8 versus 2). The reduction in accumulation of the large G band associated with the CX3C mutations was compensated for when combined with the B3CT and B3TMCT substitutions (FIGS. 2A and 2B, lanes 9 and 10). There were no significant differences in the expression of the BPIV3 N protein between the constructs, including the empty vector (FIG. 2A), suggesting that none of the forms of the RSV G had much effect on vector gene expression in vitro. Intracellular expression of the RSV G and BPIV3 N protein in LLC-MK2 cells (FIGS. 3A and 3B) followed similar patterns as their expression in Vero cells.

Secretion of RSV G was evaluated from Vero cell cultures that were infected in parallel as described above and incubated for 48 h (FIG. 2C, 2D). The overlying medium was collected and clarified by centrifugation at 10,000×g for 60 min in order to remove debris as well as rB/HPIV3 virions. The clarified supernatants were then subjected to Western blot analysis with polyclonal antibodies against RSV and HPIV3. In the case of cells infected with rB/HPIV3 expressing wt G (FIG. 2C, lane 2) or infected with RSV (lane 11), the only form of G protein that was detected in the clarified, virus-depleted medium was the large, diffuse 90-120 kD species, indicating only the completely glycosylated form of G was secreted into medium (FIG. 2C, lanes 2 and 11). As expected, very little G protein was detected in the medium from cells infected with the mG construct (FIGS. 2C and 2D, lane 4), while sG protein produced by the sG construct was 70% more abundant than with the wt G construct (FIGS. 2C and 2D, lane 3 versus 2). Ablation of the CX3C by either mutation appeared to slightly decrease the expression of sG protein (FIGS. 2C and 2D, lanes 7 and 8), which likely was due to the overall reduced expression (FIGS. 2A and 2B, lanes 7 and 8). The B3CT and B3TMCT substitution completely abrogated the expression of sG protein (FIGS. 2C and 2D, lanes 5-6 and 9-10). This perhaps was not surprising in the case of B3TMCT, since the native M48 codon that normally is used to initiate synthesis of sG protein is located in the TM domain of G that was replaced with the TM domain from HPIV3 HN protein (although two other AUG codons are present in the HPIV3 HN TM domain that apparently were not utilized, FIG. 1B). In the case of the B3CT substitution, the native TM with its M48 codon is present, and it is not known why it was not utilized. One possibility is that the nucleotide sequence upstream of this region influences initiation at the M48 codon.

The stability of RSV G expression by the rB/HPIV3 constructs following passage in vitro was determined by a double-staining plaque assay (FIG. 4A), similar to assays described previously for rB/HPIV3 constructs expressing the RSV F protein (Liang et al., *J. Virol.*, 89(18): 9499-9510, 2015). Briefly, Vero cells were infected with 10-fold serially diluted viral stocks and incubated under methyl cellulose overlay until plaques formed. Plaques were fixed and stained with primary rabbit anti-HPIV3 or goat anti-RSV antibodies followed by species-specific secondary antibodies conjugated to infrared dye (PIV3, green; RSV, red) (FIG. 4A). Co-expression of HPIV3 antigens and RSV G by a single PFU was visualized as yellow. All of the vector stocks expressing RSV G were found to have almost 100% of PFU expressing RSV G, with the exception that this could not be determined in the case of the sG construct because the rapid secretion of G into the medium precluded staining of the plaques for this protein (FIG. 4A, column 3).

Figure 4B:
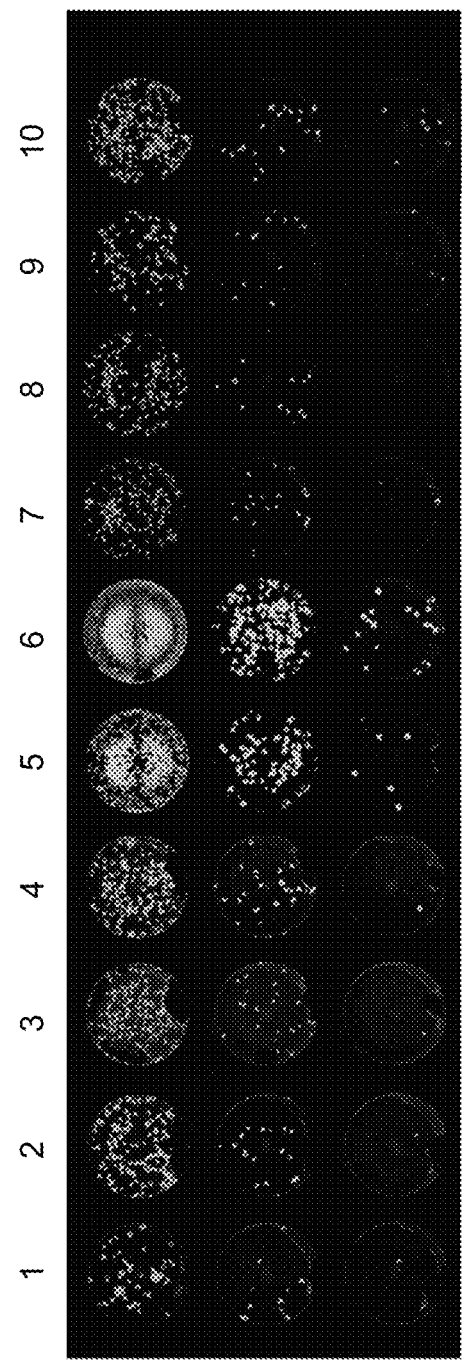

Additionally, a double-plaque assay was performed using an RSV G MAb (131-2G) that is specific to the CX3C domain (FIG. 4B). This antibody bound to plaques for all of the versions of G in which the CX3C motif was intact (FIG. 4B lanes 2, 4, 5, 6) except for sG (lane 3), but did not bind to the versions with mutations in the CX3C motif (FIG. 4B, lanes 7-10). This indicated that ablation of CX3C motif disrupted the 131-2G binding epitope on RSV G, and was confirmation of the absence of an intact CX3C motif in these mutants.

RSV G Packaging

Figure 5B:
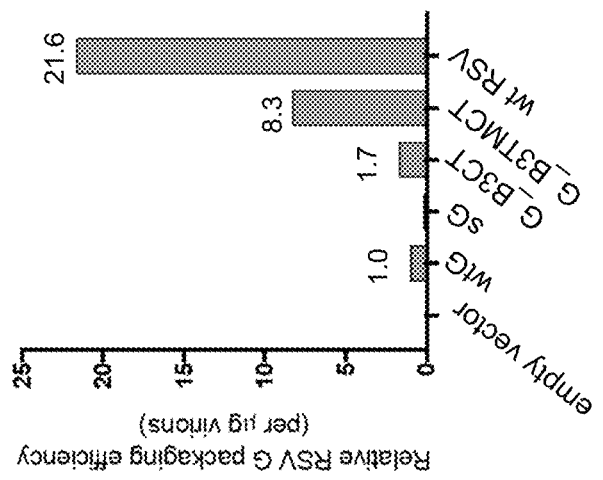
FIGS. 5A and 5B. Quantification of RSV G packaging efficiency by Western blot analysis of purified rB/HPIV3-RSV G particles. LLC-MK2 and Vero cells were infected with, respectively, 0.01 $TCID_{50}$ of the indicated rB/HPIV3-RSV G construct or 0.1 PFU of wt RSV. The cultures were harvested on day 4 and clarified cell culture medium supernatants were subjected to centrifugation on discontinuous 30%/60% w/v sucrose gradients. Purified virions were harvested from the sucrose interface and pelleted by centrifugation. Approximately 4 µg of each virus were subjected to gel electrophoresis under denaturing and reducing conditions. Western blots were prepared and analyzed with antisera raised separately against RSV and HPIV3.
Figure 5A:
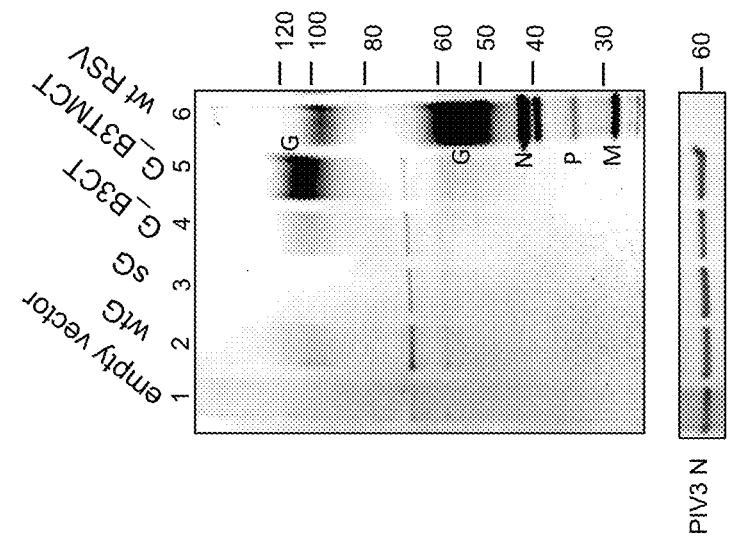
Figure 6A:
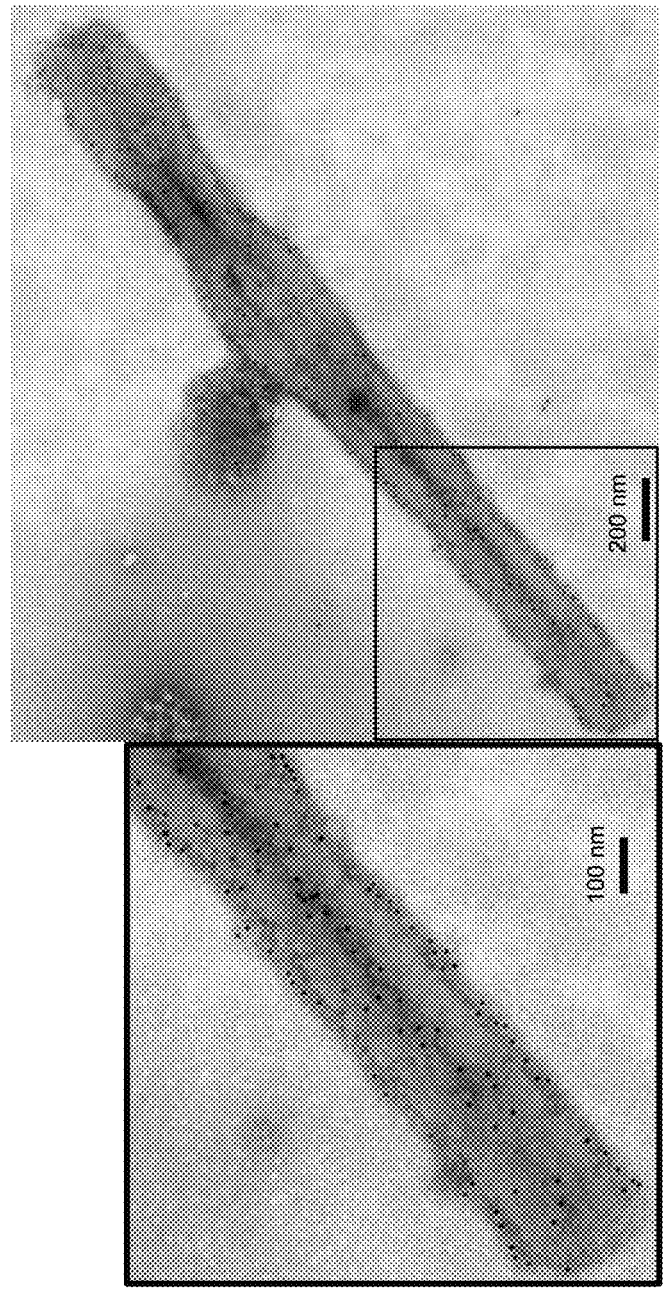
Figures 6E, 6F:
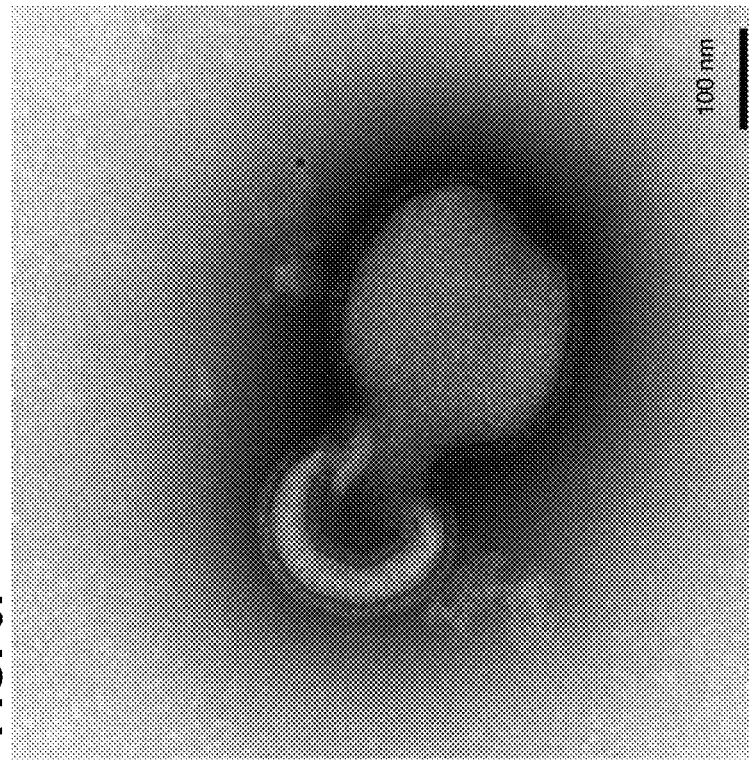
Figure 6L:
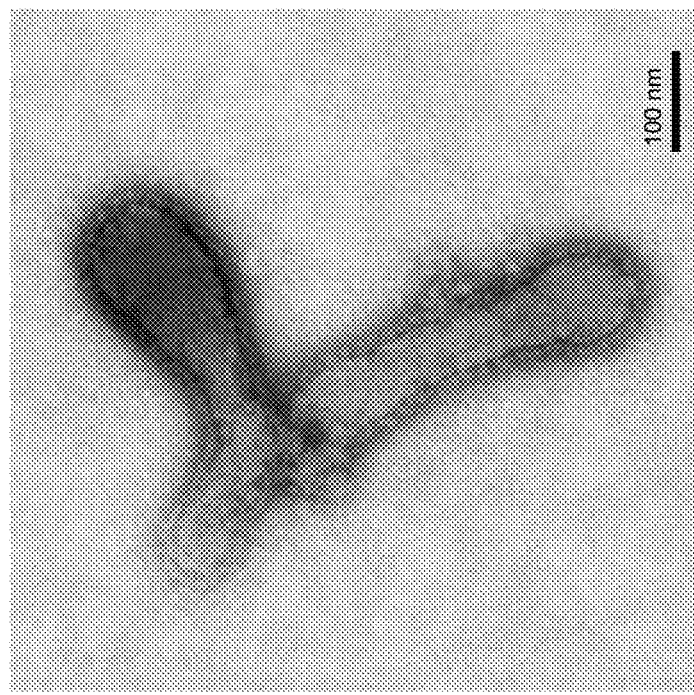
Figure 6K:

To evaluate the packaging efficiency of RSV G into rB/HPIV3 virions, empty vector and various vectors expressing versions of RSV G were propagated in LLC-MK2, and wt RSV was propagated in Vero cells. The medium overlying the cells was harvested, clarified by low speed centrifugation, and subjected to centrifugation on 30%-60% discontinuous sucrose gradients. For each construct, four micrograms of purified virus were analyzed by Western blot (FIG. 5A) and were quantified and normalized relative to wt G as 1.0. This showed that the unmodified wt G was detectable in vector virions as a very faint band (FIG. 5A, lane 2), and its packaging efficiency was less than 5% per μg of virion protein that of wt RSV (FIGS. 5A and 5B, lanes 2 and 6). Note that most of the G protein that was packaged in RSV virions grown in Vero cells had a lower molecular weight (50-60 kD) than the normally predominant 90-120 kD form. This was previously shown to arise due to cleavage by the cellular protease cathepsin L during long incubations in that particular cell line (Corry et al., 2015, *J. Virol.* 90:1311-1320). In the quantitation shown in FIG. 5B, both forms were quantified for wt RSV. The TMCT substitution from the BPIV3 HN protein enhanced the packaging efficiency of RSV G by 8.3-fold (FIGS. 5A and B, lanes 2 and 5), and the same magnitude of effect also was observed for the G_dCX3C_B3TMCT construct. The BPIV3 HN CT substitution alone only marginally increased the packaging of RSV G into vector virions (FIGS. 5A and 5B, lanes 2 and 4). As expected, sG protein was not packaged in the vector (FIG. 5A, lane 3).

The packaging of RSV G was also visualized by immunegold labeling and transmission electron microscopy (TEM, FIG. 6). Purified virions prepared as described above (FIG. 5) were labeled by incubation with MAb 131-2G followed by anti-mouse IgG conjugated with gold particles. The specimens were imaged by TEM as previously described (Liang et al., *J. Virol.,* 90(21): 10022-10038, 2016). The results showed that wt RSV virions had extensive antibody staining, indicative of a high density of packaging of the RSV G protein (FIGS. 6A and 6B). In contrast, virions of rB/HPIV3-wt G had only sporadic labeling (FIGS. 6C and 6D), and many virions had no detectable G. There was essentially no antibody binding to virions of vector expressing the sG protein (FIGS. 6E and 6F). The B3CT substitution appeared to slightly increase antibody binding (FIGS. 6G and 6H), while the B3TMCT substitution greatly improved the efficiency of antibody binding (FIGS. 6I and 6J). Empty vector virions were not labeled with the immunegold particles (FIGS. 6K and 6L). Thus, the densities of RSV G displayed in TEM analysis were in agreement with the efficiency of G packaging quantified by Western blot.

In Vivo Replication, Immunogenicity and Protection

The replication, immunogenicity, and protective efficacy of the vectors were evaluated in a hamster model (FIGS. 7-9, respectively). To evaluate replication, hamsters in groups of six were immunized IN with $10^5$TCID$_{50}$ of the indicated vector or $10^6$ PFU of wt RSV. Lungs and nasal turbinates were collected on day 5 after immunization, and the titers of the rB/HPIV3 vectors were determined by TCID$_{50}$ hemadsorption assays on LLC-MK2 cell monolayers, whereas RSV titers were determined by plaque assay on Vero monolayers. In the nasal turbinates, all of the vectors bearing an RSV G insert replicated to similar titers as the empty rB/HPIV3 vector (FIG. 7A), whereas in the lungs the vectors bearing an RSV G insert all were slightly more attenuated than the empty vector, although the differences were not significant (FIG. 7B). There were no significant differences between the replication of the various vectors expressing various forms of RSV G. Thus, for example, the expression of sG, or lack of expression of sG, or presence of the CX3C motif, or the absence of this motif, did not have an impact on the immunobiological milieu of the hamster lung sufficient to affect the replication of the rB/HPIV3 vector, which has the same tissue tropism as RSV (Zhang et al., *J. Virol.* 76:5654-5666, 2002; Zhang et al., *J. Virol.* 79:1113-1124, 2005) and shares many similarities in biology.

To evaluate immunogenicity, hamsters were immunized with vectors and wt RSV as described above, and sera were collected on days 0 and 28 post-immunization, In vitro 60% plaque reduction neutralization assays were carried out to quantify the serum RSV- and HPIV3-neutralizing antibody titers (FIG. 8).

Serum RSV-neutralizing antibody titers were determined in vitro on Vero cells by a 60%-plaque reduction neutralization titer (PRNT$_{60}$) assay using recombinant RSV that expresses the green fluorescent protein (RSV-GFP, Munir et al., *J. Virol.* 82:8780-8796, 2008). Assays were done in the presence or absence of added complement. The presence of complement can confer virus-lysis and steric-hindrance capabilities that give neutralization activity to otherwise non-neutralizing antibodies, and that can enhance the neutralization activity of poorly-neutralizing antibodies, whereas neutralization in the absence of complement depends on the direct capability of the antibodies (Yoder et al. 2004, J. Med. Virol. 72:688-694). Thus, assays done without complement provide a more stringent evaluation, and detect only those antibodies that can directly neutralize RSV (Liang et al., *J. Virol.,* 89(18): 9499-9510, 2015).

When serum RSV-neutralizing antibody titers were evaluated by a neutralization assay performed with added complement, vectors expressing wt G, mG, G_B3CT and G_B3TMCT were shown to induce similarly high titers (>1:1024) that are not statistically different from that induced by a 10-fold higher ($10^6$ PFU) of wt (i.e., not attenuated) RSV (FIG. 8A, lanes 2, 4-6 versus 11). In contrast, the sG construct did not induce detectable serum RSV neutralization antibodies (FIG. 8A, lane 3), despite its robust secretory expression (FIG. 2C, lane 3). Interestingly, CX3C ablation drastically reduced the RSV serum neutralization titers (FIG. 8A, lanes 7-10), indicating the role of the CX3C motif for the induction of RSV-neutralizing antibodies. Thus, ablating the expression of sG, or ablating the CX3C motif, did not increase the immunogenicity of the G protein, as would have been expected if these features interfered significantly with host immunity On the contrary, the CX3C motif contributed substantially to inducing a strong RSV-neutralizing antibody response. To compare G- versus F-induced neutralization activity, sera of hamsters immunized with the same dose of rB/HPIV3 expressing unmodified wild-type (wt) RSV F from a previous study (Liang et al., *J. Virol.,* 89(18): 9499-9510, 2015) were assayed in parallel (FIG. 8A, lane 12). The wt G induced slightly lower titers of RSV serum neutralization antibodies than wt F, but the difference was not statistically significant (FIG. 8A, lanes 2 and 12).

When serum HPIV3-neutralizing antibody titers (i.e., against the vector) were evaluated by an assay with added complement, all of the vectors expressing various forms of RSV G were similarly immunogenic (FIG. 8B, lanes 2-10), with the exception of the G_B3TMCT construct which induced a slightly but significantly lower level of serum HPIV3-neutralizing antibodies than the empty vector (FIG. 8B, lanes 1 and 6). The lower titer induced by the G_B3TMCT construct suggested that the enhanced packaging of RSV G by its TMCT substitution interfered with vector replication efficiency in vivo, perhaps by reducing the packaging of vector HN protein. Thus, the presence or absence of the sG protein or the CX3C motif in the expressed G protein did not have a significant effect on the antibody response against the vector.

Hamster sera were also assayed for neutralizing serum antibodies against a subgroup B strain of RSV (B1). While the neutralization activity against the B1 strain remained similarly high for wt RSV and wt F sera (FIG. 8C, lanes 11-12), the B1 cross-neutralization activities induced by RSV G constructs were substantially reduced (FIG. 8C, lanes 2 and 4-6), and disruption of the CX3C motif almost completely abolished the neutralization activity (FIG. 8C, lanes 7-10). This indicates that the G protein of RSV G A2 induced moderate titers of cross-subgroup neutralizing antibodies; furthermore, this was highly dependent upon the presence of CX3C motif.

To further characterize the role of the CX3C motif in the induction of RSV-neutralizing antibodies, an A2 RSV strain bearing a mutated CX3C (CWAIS) of G was used to analyze the serum RSV-neutralizing titers in the presence of added complement (FIG. 8D). While the serum neutralizing activity against the CX3C-mutated RSV induced by the four CX3C-ablation mutants (FIG. 8D, lanes 7-10) remained relatively low compared to wt RSV and vector expressing wt F (FIG. 8D, lanes 11 and 12), the neutralization activity in sera of wt G, mG, G_B3CT and G_B3TMCT against this CWAIS mutant were equally low (FIG. 8D, lanes 2 and 4-6). This was further confirmation that the CX3C domain is a major neutralization epitope of the G protein.

The titers of serum neutralizing antibodies, measured in the presence of complement, against wt RSV A2 (from FIG. 8A), wt RSV B1 (from FIG. 8C), and RSV A2 CWAIS (from FIG. 8D) are shown in Table 1. This further illustrates that ablation of sG (resulting in mG) did not result in increased immunogenicity; that packaging of G into the vector particle did not increase immunogenicity; and that ablation of the CX3C motif strongly reduced immunogenicity.

TABLE 1

The relative mean RSV serum neutralization titers induced by $10^5$ TCID$_{50}$ vectors compared to that induced by $10^6$ PFU wt RSV A2 in hamsters. All titers were determined in the presence of complement.

| Viruses for immunization | Strains of RSV used in neutralization assays | | |
|---|---|---|---|
| | RSV A2 | RSV B1 | RSV A2 CWAIS |
| Empty vector | <4 | <4 | <4 |
| sG | <4 | <4 | <4 |
| wtG | 3040 | 226 | 52 |
| mG | 2077 | 152 | 16 |
| G_B3CT | 1746 | 125 | 25 |
| G_B3TMCT | 1911 | 70 | 25 |
| G_dCX3C | 40 | <4 | 21 |
| G_wCX4C | 58 | 4 | 35 |
| G_dCX3C_B3CT | 83 | 6 | 42 |
| G_dCX3C_B3TMCT | 54 | <4 | 36 |
| wt RSV A2 | 6339 | 2521 | 4640 |
| RSV F | 6889 | 3040 | 6654 |

Serum RSV-neutralizing antibody titers were also evaluated by a neutralization assay performed in the absence of added complement (FIG. 8E) which provides a more stringent assessment of neutralization activity. The complement-independent assay showed that, while both wt RSV and vector-expressed wt F induced moderate titers of complement-independent serum RSV-neutralizing antibodies (FIG. 8E, lanes 11 and 12), the G constructs induced relatively low titers of serum antibodies capable of neutralizing RSV in the absence of complement in vitro (FIG. 8E, lanes 2-10). This result is offered with the caveat that Vero cells are deficient in the CX3CR1 receptor that may play a significant role in attachment in vivo (Johnson SM et al., 2015, PLoS Pathog., 11:e1005318), and therefore this Vero-based assay may fail to detect G-specific neutralizing antibodies. This may be resolved by a neutralization assay using an in vitro model of mucociliary human airway epithelium (HAE), which does express the CX3CR1 receptor (Johnson SM et al., 2015, PLoS Pathog., 11:e1005318), although HAE cultures are not very amenable to in vitro neutralization assays.

To measure protective efficacy, the hamsters that were immunized in the experiment in FIG. 8 were challenged IN with $10^6$ PFU of wt RSV on day 31 post-immunization. Hamsters were sacrificed 3 days later. Nasal turbinates and lungs were collected and homogenized for RSV plaque assay titration (FIG. 9). In the nasal turbinates, vector expressing wt G (FIG. 9A, lane 2) was significantly more protective than any of the other G constructs (lanes 3-10). In contrast, the sG construct was not protective (FIG. 9A, lane 3), correlating with its inability to induce RSV-neutralizing antibody (FIG. 9A, lane 3). Constructs mG, G_B3CT and G_B3TMCT induced substantial protection (FIG. 9A, lanes 4-6); while CX3C ablation (lanes 7 and 8) drastically reduced the protection compared to the unmodified wt G (lane 2), to a level that was not statistically different from sG and the empty vector (lanes 1 and 3). Enhanced packaging of the dCX3C mutant by B3CT and B3TMCT (FIG. 9A, lanes 9 and 10) appeared to slightly improve the protective efficacy to the level that was significantly better than sG and the empty vector (lanes 1 and 3). Only the wt RSV inoculation achieved complete protection in the nasal turbinates (FIG. 9A, lane 11). Superior protection with wt RSV was not unexpected, since it was administered at a 10-fold higher dose, it is not attenuated, it bears both the F and G neutralization antigens, and it expresses all of the viral antigens and thus would induce a broader cellular immune response. In studies with PIVs in hamsters, internal proteins in chimeric viruses have been shown to induce protection in a short term (1-2 month) challenge, but this wanes by four months (Tao T et al., 2000, Vaccine 18:1359-1366).

Vector-induced protection against RSV was much better in the lungs than in the nasal turbinates. The vectors expressing wt G, mG, G_B3CT, and B_B3TMCT conferred almost complete protection (FIG. 9B, lanes 2 and 4-6). But the vectors expressing any of the four CXC3 ablation mutants were less protective, with 1-3 hamsters per group not completely protected (FIG. 9B, lanes 7-10). As was observed in the nasal turbinates, the TMCT substitution exhibited some improvement of protection with the dCX3C construct (FIG. 9B, lane 10).

The titers of serum RSV-neutralizing antibodies on day 28 following the initial immunization (measured for individual animals in the presence of added complement, from FIG. 8A), were plotted versus the titers of challenge RSV in the nasal turbinates (from FIG. 9A) and lungs (from FIG. 9B) of the same individuals, resulting in the plots shown in FIGS. 9C and 9D, respectively. This showed that protection against challenge RSV replication in either the nasal turbinates or lungs, indicated by a reduction in challenge virus titer, was strongly correlated with the titer of serum complement-dependent RSV neutralizing antibodies (FIGS. 9C and D, respectively).

Codon-Optimized G ORF (wtG/GS-opt)

A rB/HPIV3 construct expressing a RSV G ORF that was codon-optimized for human expression (GenScript), with no changes to amino acid coding (wtG/GS-opt, construct (x) in FIG. 1A), replicated in Vero and LLCMK-2 cells with a high level of efficiency similar to that of the other vectors. The intracellular expression of G protein by construct wtG/GS-opt in LLC-MK2 cells and Vero cells was evaluated by Western blot analysis. The LLC-MK2 and Vero cells were infected with rB/HPIV3 expressing wtG/GS-opt or wtG at a MOI of 10 TCID$_{50}$ per cell, or with wt RSV at an MOI of 3 PFU per cell. Cells were harvested at 24 hours post infection and cell lysates were prepared, subjected to gel electrophoresis under denaturing and reducing conditions, and analyzed by Western blotting using polyclonal antibodies against RSV (FIGS. 10A and B). This showed that the codon-optimized version was expressed approximately 2.2- to 2.3-fold more efficiently than the non-optimized wt ORF (FIGS. 10C and D.

Figure 7A:
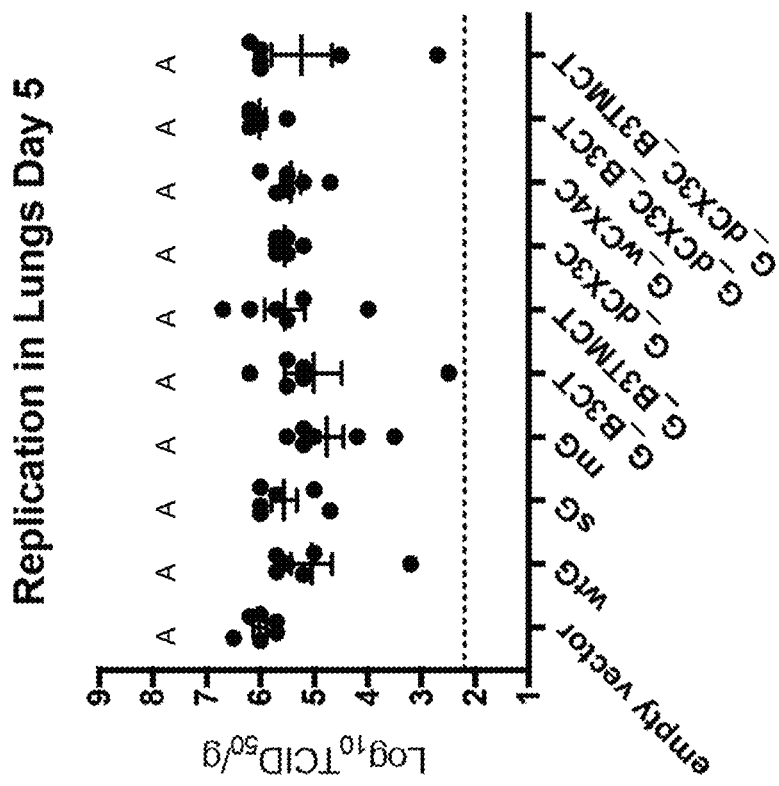
FIGS. 7A and 7B. Replication of rB/HPIV3-RSV G vectors in the upper and lower respiratory tracts of hamsters. Hamsters in groups of six were infected intranasally (IN) with $10^5 TCID_{50}$ of vector or $10^6$ PFU of wt RSV. Nasal turbinates and lungs were collected on day 5 post-immunization and homogenized. Titers of vectors in nasal turbinates (FIG. 7A) and lungs (FIG. 7B) were determined by $TCID_{50}$ hemadsorption assays on LLC-MK2 cells. The limit of detection of $TCID_{50}$ is indicated as dashed line. Mean titer and standard error of the mean (SEM) are shown as horizontal line with error bars. The statistical significance of differences in mean titers among all groups in the present study was analyzed using one-way ANOVA followed by Tukey-Kramer test. The mean titers of any two groups designated with a same letter (A, or B) are not statistically different.
Figure 7B:
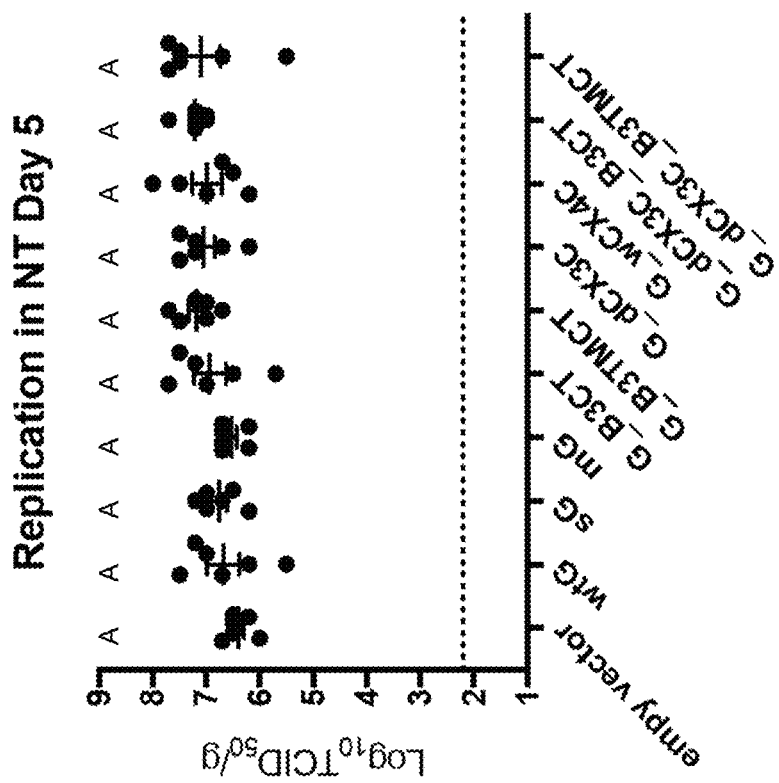

The in vivo replication and immunogenicity of rB/HPIV3 expressing the codon-optimized G ORF was evaluated in parallel with rB/HPIV3 expressing the unmodified wt G ORF. Following the methods described in FIG. 7, hamsters in groups of nine were immunized IN with $10^4$ TCID$_{50}$ of the indicated vector or $10^6$ PFU of wt RSV. Sera were collected on day 28 after immunization. Hamsters were challenged intranasally on day 30 with $10^6$ PFU of wt RSV. Lungs and nasal turbinates were collected on day 3 after challenge. The titers of challenge RSV replication were determined by plaque assay on Vero monolayers. Serum RSV-neutralizing antibody titers were evaluated by plaque reduction neutralization in the presence of complement (FIG. 11). The serum RSV-neutralizing antibody titer induced by wild-type G (wt G) was slightly higher than that induced by wild-type F (wt F), although the difference was not significant (FIG. 11, lanes 2 and 3). But the codon-optimized wild-type G (wtG/GS-opt) induced a 2-fold higher titer of serum RSV-neutralizing antibodies than the wt F, which was statistically significant (FIG. 11, lanes 2 and 4). This indicated that GS codon-optimization of RSV G enhanced the immunogenicity of the rB/HPIV3-RSV G vector. Similar to their trend in the induction of serum RSV-neutralizing antibodies, the wt G and wt G/GS-opt conferred increased protection against RSV challenge in the nasal turbinates compared to wt F (FIG. 12A). In the lungs, wt G and wtG/GS-opt conferred complete protection, as with the wt RSV (FIG. 12B, lanes 3-5), while wt F was only partially protective (FIG. 12B, lane 2). These results indicated that rB/HPIV3 expressing wt G was more immunogenic and protective than rB/HPIV3 expressing wt F in hamsters; and the GenScript codon-optimization of RSV G enhanced its immunogenicity and protective efficacy.

Blocking RSV Infection of Ciliated Airway Epithelial Cells by RSV G-Induced Serum Antibodies Vero cells are known to be deficient in the CX3CR1 surface protein that has been identified as a major receptor for G-mediated attachment in vivo (Johnson S M et al., 2015, PLoS Pathog., 11:e1005318). Thus, an important component of virus neutralization by G-induced antibodies might be missed by neutralization assays in Vero cells. To better evaluate the neutralization activity of G-induced serum antibodies, we performed a serum neutralization assay using an in vitro model of differentiated mucociliary human airway epithelium (HAE) that has been shown to be a close facsimile of in vivo HAE, and which does express CX3CR1 (Johnson S M et al., 2015, PLoS Pathog., 11:e1005318).

Figure 13:
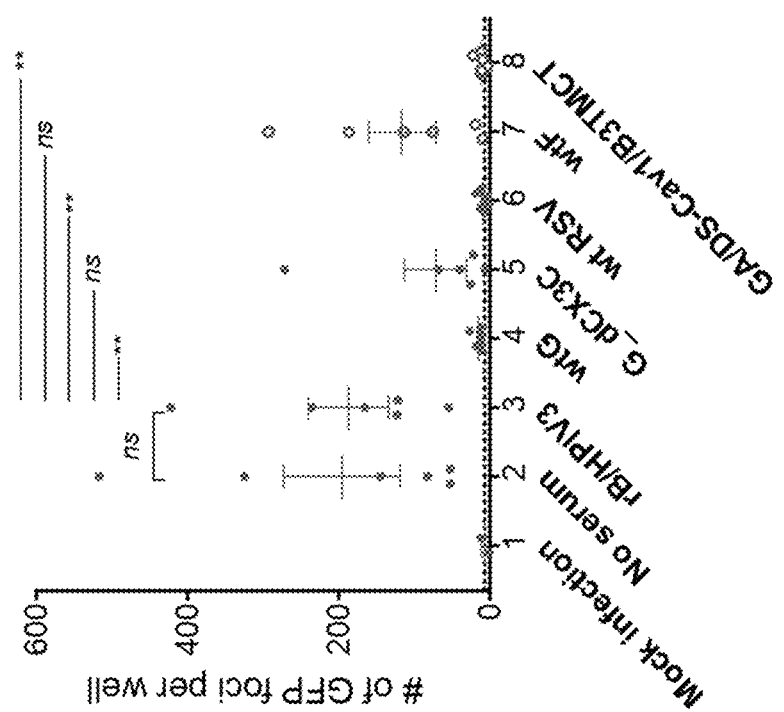
FIG. 13. Evaluation of the ability of serum RSV-neutralizing antibodies to block RSV-GFP infection in an in vitro model of primary differentiated mucociliary human airway epithelial (HAE) tissue. Aliquots of RSV-GFP were incubated for 30 min at 37° C. with the indicated hamster serum in the absence of added complement, from the experiment shown in FIGS. 7 and 8, and were then inoculated onto HAE cultures (one well per sample). After 60 min at 37° C., the inoculum was removed and the cultures were incubated for 48 hours. The GFP foci of infected cells were imaged and quantified, and the mean of each set of duplicates was calculated. Significant differences were identified by an unpaired t test:** indicates P<0.01; ns=not significant.

HAE cells were differentiated in culture at an air-liquid interface. Full differentiation was verified by the formation of ciliated cells and tight junctions imaged by confocal microscopy. Sera of immunized hamsters from the experiment shown in FIG. 8 were tested for the ability to block RSV infection in the HAE model. Equal aliquots of RSV-GFP (A2 strain) were pre-incubated with hamster serum in the absence of added complement, and then used to infect HAE cultures. The inocula was removed after infection and cells were cultured at the air-liquid interface. At 48 hours post infection, the GFP foci of infected cells were visualized and quantified (FIG. 13). In the uninfected culture, there was a background of approximately 6 foci per culture insert (FIG. 13, lane 1), likely due to autofluorescent cells. In the RSV-GFP infected culture, an average of approximately 200 (ranging from 53 to 518) GFP fluorescent foci were detected (FIG. 13, lane 2). Pre-incubation of RSV-GFP with sera from hamsters infected with the empty vector had no effect in RSV infection in HAE cells (FIG. 13, lane 3). Remarkably, the sera from hamsters immunized with wt G or wt RSV almost completely prevented the infection (FIG. 13, lanes 4 and 6). Surprisingly, the sera from hamsters immunized by the vector expressing wt RSV F displayed little inhibitory activity in this model; but the sera from hamsters immunized by the vector expressing a stabilized prefusion F (from a previous study and used here as a positive control for high-quality neutralizing antibody response) completed blocked the RSV infection (FIG. 13, lane 8). Interestingly, the sera of hamsters infected with the G_dCX3C construct were only partially protective compared with sera with wt G (FIG. 13, lanes 4 and 5). These results indicated that the wt RSV G induced high-quality neutralizing antibodies that can effectively prevent RSV infection in HAE in the absence of added complement. In addition, the integrity of the CX3C motif was important for the induction of serum neutralization antibodies by RSV G. Unexpectedly, in this assay, the neutralizing activity of sera raised against wt G was greater than for wt F, likely reflecting an effect on attachment. These results indicate antibodies to RSV G are particularly effective in neutralization of RSV in an in vitro model of HAE that closely resembles authentic HAE, and therefore the G protein may be an effective antigen to include in an RSV vaccine.

Conclusion

A number of studies have provided data indicating that the CX3C motif in the RSV G protein and expression of the soluble form of RSV G (sG) has various deleterious effects on host immune responses to RSV infection. This has been reported to include reduced dendritic cell activation (Johnson et al., 2012, J. Virol. 86:1339-1347), augmented inflammatory responses (Johnson et al., 1998, J. Virol. 72:2871-2880), inhibition of innate immunity (Shingai et al., 2008, Int. Immunol. 20:1169-1180; Polack et al 2005, Proc. Natl. Acad. Sci. USA 102:8996-9001), and inhibition of immune cell responses (Chirkova et al., 2013, J. Virol. 87:13466-13479), among other activities. Based on these studies, it was expected that ablation of the CX3C motif and/or sG should make a safer, more immunogenic vaccine (e.g., Boyoglu-Barnum et al., "Mutating the CX3C Motif in the G Protein Should Make a Live Respiratory Syncytial Virus Vaccine Safer and More Effective," J. Virol., 91(10): e02059-16, 2017; Chirkova et al., 2013, J. Virol. 87:13466-13479).

Surprisingly, data provided in the present example indicate that the mG construct (construct (ii), FIG. 1A), from which expression of sG was ablated, was modestly less immunogenic and protective than wt G protein, when expressed from the rB/HPIV3 vector. The finding that ablation of expression of the sG protein did not increase immunogenicity and protection was contrary to the postulated role of sG in impairing immune responses. Furthermore, the enhanced expression of sG on its own did not affect vector replication or vector immunogenicity. This was evident in comparing wtG (that expresses sG) with mG (that does not), and evaluating the effects of expression of sG protein alone (construct (iii), FIG. 1A), none of which affected vector replication or immunogenicity. Thus, there was no evidence that sG affected the host immune response in a manner that significantly affected RSV G immunogenicity and protective efficacy, or vector replication and immunogenicity.

Additionally, ablation of the CX3C motif greatly reduced the immunogenicity of RSV G (whether assayed with or without complement) and protective efficacy against RSV. Thus, contrary to the studies discussed above, this region of RSV G provides a positive effect on RSV immunogenicity and protective efficacy. Ablating the CX3C domain also did not significantly affect vector replication or immunogenicity. Thus, this motif did not alter the pulmonary immune milieu sufficient to affect vector replication or immunogenicity.

This example shows that features of the RSV G protein such as sG protein and the CX3C motif do not impair the immunogenicity and protective efficacy of the G protein expressed from a rB/HPIV3 vector. rB/HPIV3-based immunogens expressing wt G ectodomain were identified as preferred for inducing an immune response to RSV G. Surprisingly, the wt G construct induced titers of serum RSV-neutralizing antibodies assayed in the presence of complement that were not significantly different than those induced by wt RSV, even though RSV was administered at a 10-fold higher dose, is not attenuated, and bears both the F and G neutralization antigens. Additionally, the HAE assay (FIG. 13) showed that antibodies induced by wt G completely blocked infection in a model that closely mimics in vivo HAE, the predominant site of RSV replication in vivo, whereas antibodies induced by wt F did not. The RSV G protein is often considered to be a secondary neutralization and protective antigen compared to F. The present data revise this view and indicate that the G protein can improve neutralization (and likely protection). This suggests that the inclusion of vector expressing RSV G to an RSV immunization protocol improved neutralization and protection, a contribution that is not appreciated by conventional neutralization assays that do not involve the CX3CR receptor for RSV.

Exemplary Antigenomic cDNA Sequences:

```
rB/HPIV3-RSV wt G (SEQ ID NO: 91):
accaaacaagagaagagactggtttgggaatattaattcaaataaaaattaacttaggattaaagaactttaccgaaagg taaggggaaagaaatcctaagagcttagccatgttgagtctattcgacacattcagtgcgcgtaggcaggagaacataac gaaatcagctggtggggctgttattcccgggcaaaaaaacactgtgtctatatttgctcttggaccatcaataacagatg acaatgataaaatgacattggctcttctcttttttgtctcattctttagacaatgaaaagcagcatgcgcaaagagctgga tttttagtttctctgttatcaatggcttatgccaacccagaattatatttaacatcaaatggtagtaatgcagatgttaa atatgttatctacatgatagagaaagacccaggaagacagaaatatggtgggtttgtcgtcaagactagagagatggttt atgaaaagacaactgattggatgttcgggagtgatcttgagtatgatcaagacaatatgttgcaaaatggtagaagcact tctacaatcgaggatcttgttcatacttttggatatccatcgtgtcttggagcccttataatccaagtttggataatact tgttaaggctataaccagtatatcaggattgaggaaaggattctttactcggttagaagcatttcgacaagatggaacag ttaaatccagtctagtgttgagcggtgatgcagtagaacaaattggatcaattatgaggtcccaacagagcttggtaaca ctcatggttgaaacactgataacaatgaacacaggcaggaatgatctgacaacaatagaaaagaatatacagattgtagg aaactacatcagagatgcaggtcttgcttcattttttcaacacaatcagatatggcattgagactagaatggcagctctaa ctctgtctacccttagaccggatatcaacagactcaaggcactgatcgagttatatctatcaaaggggccacgtgctcct tttatatgcatttttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactgggggtcacacaagaagccaag caaagcttgaagaaacacatgaagaacatcagcagttcagatacaacctttcataagcctacaggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaaggaaacagagtgacccgagatcaactgacatcac aaacaacacaaatcaaactgaaatagatgatttgttcagtgcattcggaagcaactagtcacaaagagatgaccaggcgc gccaagtaagaaaaacttaggattaatggacctgcaggatgtccaaaaacaaggaccaacgcaccgctaagacattagaa aggacctgggacactctcaatcatttattattcatatcatcgtgcttatataagttaaatcttaaatctgtagcacaaat cacattatccattctggcaatgataatctcaacttcacttataattgcagccatcatattcatagcctcggcaaaccaca aagtcacaccaacaactgcaatcatacaagatgcaacaagccagatcaagaacacaaccccaacatacctcacccagaat cctcagcttggaatcagtccctctaatccgtctgaaattacatcacaaatcaccaccatactagcttcaacaacaccagg agtcaagtcaaccctgcaatccacaacagtcaagaccaaaaacacaacaacaactcaaacacaacccagcaagcccacca caaaacaacgccaaaacaaaccaccaagcaaacccaataatgattttcactttgaagtgttcaactttgtaccctgcagc atatgcagcaacaatccaacctgctgggctatctgcaaaagaataccaaacaaaaaaaccaggaaagaaaaccactaccaa
```

-continued

```
gcccacaaaaaaaccaaccctcaagacaaccaaaaaagatcccaaacctcaaaccactaaatcaaaggaagtacccacca ccaagcccacagaagagccaaccatcaacaccaccaaaacaaacatcataactacactactcacctccaacaccacagga aatccagaactcacaagtcaaatggaaaccttccactcaacttcctccgaaggcaatccaagcccttctcaagtctctac aacatccgagtacccatcacaaccttcatctccacccaacacaccacgccagtgatagctagcggcgcgccagcaacaag taagaaaaacttaggattaatggaaattatccaatccagagacggaaggacaaatccagaatccaaccacaactcaatca accaaagattcatggaagacaatgttcaaaacaatcaaatcatggattcttgggaagagggatcaggagataaatcatct gacatctcatcggccctcgacatcattgaattcatactcagcaccgactcccaagagaacacggcagacagcaatgaaat caacacaggaaccacaagacttagcacgacaatctaccaacctgaatccaaaacaacagaaacaagcaaggaaaatagtg gaccagctaacaaaaatcgacagtttggggcatcacacgaacgtgccacagagacaaaagatagaaatgttaatcaggag actgtacagggaggatataggagaggaagcagcccagatagtagaactgagactatggtcactcgaagaatctccagaag cagcccagatcctaacaatggaacccaaatccaggaagatattgattacaatgaagttggagagatggataaggactcta ctaagagggaaatgcgacaattttaaagatgttccagtcaaggtatcaggaagtgatgccattcctccaacaaaacaagat ggagacggtgatgatggaagaggcctggaatctatcagtacatttgattcaggatataccagtatagtgactgccgcaac actagatgacgaagaagaactccttatgaagaacaacaggccaagaaagtatcaatcaacaccccagaacagtgacaagg gaattaaaaaaggggttggaaggccaaaagacacagacaaacaatcatcaatattggactacgaactcaacttcaaagga tcgaagaagagccagaaaatcctcaaagccagcacgaatacaggagaaccaacaagaccacagaatggatcccaggggaa gagaatcacatcctggaacatcctcaacagcgagagcggcaatcgaacagaatcaacaaaccaaacccatcagacatcaa cctcgggacagaaccacacaatgggaccaagcagaacaacctccgaaccaaggatcaagacacaaaagacggatggaaag gaaagagaggacacagaagagagcactcgatttacagaaagggcgattacattattacagaatcttggtgtaatccaatc tgcagcaaaattagacctataccaagacaagagagttgtgtgtgtggcgaatgtcctaaacaatgcagatactgcatcaa agatagacttcctagcaggtttgatgataggagtgtcaatggatcatgataccaaattaaatcagattcagaacgagata ttaagtttgaaaactgatcttaaaaagatggatgaatcacatagaagactaattgagaatcaaaaagaacaattatcact gatcacatcattaatctcaaatcttaaaattatgacagagagaggagggaagaaggaccaaccagaacctagcgggagga catccatgatcaagacaaaagcaaaagaagagaaaataaagaaagtcaggtttgaccctcttatggaaacacagggcatc gagaaaaacatccctgacctctatagatcaatagagaaaacaccagaaaacgacacacagatcaaatcagaaataaacag attgaatgatgaatccaatgccactagattagtacctagaagaataagcagtacaatgagatcattaataataatcatta acaacagcaatttatcatcaaaagcaaagcaatcatacatcaacgaactcaagctctgcaagagtgacgaggaagtgtct gagttgatggacatgttcaatgaggatgtcagctcccagtaaaccgccaaccaagggtcaacaccaagaaaaccaatagc acaaaacagccaatcagagaccaccccaatacaccaaaccaatcaacacataacaaagatcgcggccgcatagatgatta agaaaaacttaggatgaaaggactaatcaatcctccgaaacaatgagcatcaccaactccacaatctacacattcccaga atcctctttctccgagaatggcaacatagagccgttaccactcaaggtcaatgaacagagaaaggccatacctcatatta gggttgtcaagataggagatccgcccaaacatggatccagatatctggatgtcttttactgggcttctttgagatggaa aggtcaaaagacaggtatgggagcataagtgatctagatgatgatccaagttacaaggtttgtggctctggatcattgcc acttgggttggctagatacaccggaaatgatcaggaactcctacaggctgcaaccaagctcgatatagaagtaagaagaa ctgtaaaggctacggagatgatagtttacactgtacaaaacatcaaacctgaactatatccatggtccagtagattaaga aaagggatgttatttgacgctaataaggttgcacttgctcctcaatgtcttccactagatagagggataaaattcagggt gatatttgtgaactgcacagcaattggatcaataactctattcaaaatccctaagtccatggcattgttatcattgccta atacaatatcaataaatctacaagtacatatcaaaacaggagttcagacagattccaaaggagtagttcagattctagat gaaaaggtgaaaaatcactaaatttcatggttcatctcgggttgatcaaaaggaagatgggcagaatgtactcagttga atattgtaagcagaagatcgagaagatgagattattattctcattgggattagttggagggatcagcttccacgtcaacg
```

-continued

```
caactggctctatatcaaagacattagcaagtcaattagcattcaaaagagaaatctgctatcccctaatggatctgaat
ccacacttaaattcagttatatgggcatcatcagttgaaattacaagggtagatgcagttctccagccttcattacctgg
cgaattcagatactacccaaacatcatagcaaaaggggtcgggaaaatcagacagtaaaatcaacaaccctgatatccac
cggtgtattaagccgaagcaaataaaggataatcaaaaacttaggacaaaagaggtcaataccaacaactattagcagtc
acactcgcaagaataagagagaagggaccaaaaaagtcaaataggagaaatcaaaacaaaaggtacagaacaccagaaca
acaaaatcaaaacatccaactcactcaaaacaaaaattccaaaagagaccggcaacacaacaagcactgaacacaatgcc
aacttcaatactgctaattattacaaccatgatcatggcatctttctgccaaatagatatcacaaaactacagcacgtag
gtgtattggtcaacagtcccaaagggatgaagatatcacaaaactttgaaacaagatatctaattttgagcctcatacca
aaatagaagactctaactcttgtggtgaccaacagatcaagcaatacaagaagttattggatagactgatcatccctttt
atatgatggattaagattacagaaagatgtgatagtaaccaatcaagaatccaatgaaaacactgatcccagaacaaaac
gattctttggaggggtaattggaaccattgctctgggagtagcaacctcagcacaaattacagcggcagttgctctggtt
gaagccaagcaggcaagatcagacatcgaaaaactcaaagaagcaattagggacacaaacaaagcagtgcagtcagttca
gagctccataggaaatttaatagtagcaattaaatcagtccaggattatgttaacaaagaaatcgtgccatcgattgcga
ggctaggttgtgaagcagcaggacttcaattaggaattgcattaacacagcattactcagaattaacaaacatatttggt
gataacataggatcgttacaagaaaaggaataaaattacaaggtatagcatcattataccgcacaaatatcacagaaat
attcacaacatcaacagttgataaatatgatatctatgatctgttatttacagaatcaataaaggtgagagttatagatg
ttgacttgaatgattactcaatcaccctccaagtcagactccctttattaactaggctgctgaacactcagatctacaaa
gtagattccatatcatataacatccaaaacagagaatggtatatccctcttcccagccatatcatgacgaaaggggcatt
tctaggtggagcagacgtcaaagaatgtatagaagcattcagcagctatatatgcccttctgatccaggatttgtattaa
accatgaaatagagagctgcttatcaggaaacatatcccaatgtccaagaacaacggtcacatcagacattgttccaaga
tatgcatttgtcaatggaggagtggttgcaaactgtataacaaccacctgtacatgcaacgaattggtaatagaatcaa
tcaaccacctgatcaaggagtaaaaattataacacataaagaatgtagtacaataggtatcaacggaatgctgttcaata
caaataaagaaggaactcttgcattctatacaccaaatgatataacactaaacaattctgttgcacttgatccaattgac
atatcaatcgagctcaacaaggccaaatcagatctagaagaatcaaaagaatggataagaaggtcaaatcaaaaactaga
ttctattggaaattggcatcaatctagcactacaatcataattttttgataatgatcattatattgtttataattaata
taacgataattacaattgcaattaagtattacagaattcaaaagagaaatcgagtggatcaaaatgacaagccatatgta
ctaacaaacaaataacatatctacagatcattagatattaaaattataaaaaacttaggagtaaagttacgcaatccaac
tctactcatataattgaggaaggacccaatagacaaatccaaattcgagatggaatactggaagcataccaatcacggaa
aggatgctggtaatgagctggagacgtctatggctactcatggcaacaagctcactaataagataatatacatattatgg
acaataatcctggtgttattatcaatagtcttcatcatagtgctaattaattccatcaaaagtgaaaaggcccacgaatc
attgctgcaagacataaataatgagtttatgaaattacagaaaagatccaaatggcatcggataataccaatgatctaa
tacagtcaggagtgaatacaaggcttcttacaattcagagtcatgtccagaattacataccaatatcattgacacaacag
atgtcagatcttaggaaattcattagtgaaattacaattagaaatgataatcaagaagtgctgccacaaagaataacaca
tgatgtaggtataaaacctttaaatccagatgatttttggagatgcacgtctggtcttccatctttaatgaaaactccaa
aaataaggttaatgccagggccgggattattagctatgccaacgactgttgatggctgtgttagaactccgtctttagtt
ataaatgatctgatttatgcttatacctcaaatctaattactcgaggttgtcaggatataggaaaatcatatcaagtctt
acagatagggataataactgtaaactcagacttggtacctgacttaaatcctaggatctctcatacctttaacataaatg
acaataggaagtcatgttctctagcactcctaaatacagatgtatatcaactgtgttcaactcccaaagttgatgaaaga
tcagattatgcatcatcaggcatagaagatattgtacttgatattgtcaattatgatggttcaatctcaacaacaagatt
taagaataataacataagctttgatcaaccatatgctgcactatacccatctgttggaccagggatatactacaaaggca
aaataatatttctcgggtatggaggtcttgaacatccaataaatgagaatgtaatctgcaacacaactgggtgccccggg
```

-continued aaaacacagagagactgtaatcaagcatctcatagtccatggttttcagataggaggatggtcaactccatcattgttgt tgacaaaggcttaaactcaattccaaaattgaaagtatggacgatatctatgcgacaaaattactggggtcagaaggaa ggttacttctactaggtaacaagatctatatatatacaagatctacaagttggcatagcaagttacaattaggaataatt gatattactgattacagtgatataaggataaaatggacatggcataatgtgctatcaagaccaggaaacaatgaatgtcc atggggacattcatgtccagatggatgtataacaggagtatatactgatgcatatccactcaatcccacagggagcattg tgtcatctgtcatattagactcacaaaaatcgagagtgaacccagtcataacttactcaacagcaaccgaaagagtaaac gagctggccatcctaaacagaacactctcagctggatatacaacaacaagctgcattacacactataacaaggatattg ttttcatatagtagaaataaatcataaaagcttaaacacatttcaacccatgttgttcaaaacagagattccaaaaagct gcagttaatcataattaaccataatatgcatcaatctatctataatacaagtatatgataagtaatcagcaatcagacaa tagacgtacggaaataataaaaaacttaggagaaaagtgtgcaagaaaaatggacaccgagtcccacagcggcacaacat ctgacattctgtaccctgaatgtcacctcaattctcctatagttaaaggaaagatagcacaactgcatacaataatgagt ttgcctcagccctacgatatggatgatgattcaatactgattattactagacaaaaaattaaactcaataaattagataa aagacaacggtcaattaggaaattaagatcagtcttaatggaaagagtaagtgatctaggtaaatataccttatcagat atccagagatgtctagtgaaatgttccaattatgtatacccggaattaataataaaataaatgaattgctaagtaaagca agtaaaacatataatcaaatgactgatggattaagagatctatgggttactatactatcgaagttagcatcgaaaaatga tggaagtaattatgatatcaatgaagatattagcaatatatcaaatgttcacatgacttatcaatcagacaaatggtata atccattcaagacatggtttactattaagtatgacatgagaagattacaaaaagccaaaatgagattacattcaatagg cataaagattataatctattagaagaccaaaagaatatattgctgatacatccagaactcgtcttaatattagataaaca aaattacaatgggtatataatgactcctgaattggtactaatgtattgtgatgtagttgaagggaggtggaatataagtt catgtgcaaaattggatcctaagttacaatcaatgtattataagggtaacaatttatgggaaataatagatggactattc tcgaccttaggagaaagaacatttgacataatatcactattagaaccacttgcattatcgctcattcaaacttatgaccc ggttaaacagctcaggggggcttttttaaatcacgtgttatcagaaatggaattaatatttgcagctgagtgtacaacag aggaaatacctaatgtggattatatagataaaattttagatgtgttcaaagaatcaacaatagatgaaatagcagaaatt ttctcttttcttccgaacttttggacaccctccattagaggcgagtatagcagcagagaaagttagaaagtatatgtatac tgagaaatgcttgaaatttgatactatcaataaatgtcatgctatttttttgtacaataattataaatggatatagagaaa gacatggtggtcaatggcctccagttacattacctgtccatgcacatgaatttatcataaatgcatacggatcaaattct gccatatcatatgagaatgctgtagattattataagagcttcataggaataaaatttgacaagtttatagagcctcaatt ggatgaagacttaactatttatatgaaagataaagcattatccccaaagaaatcaaactgggacacagtctatccagctt caaacctgttataccgcactaatgtgtctcatgattcacgaagattggttgaagtatttatagcagatagtaaatttgat ccccaccaagtattagattacgtagaatcaggatattggctggatgatcctgaatttaatatctcatatagtttaaagaa gaaagaaataaaacaagaaggtagacttttttgcaaaaatgacatacaagatgagggctcacacaagtattatcagaaacat tattggcgaataatatagggaaattcttccaagagaatgggatggttaaaggagaaattgaattactcaagagactaaca acaatatctatgtctggagttccgcggtataatgaggtatacaataattcaaaaagtcacacagaagaacttcaagctta taatgcaattagcagttccaatttatcttctaatcagaagtcaaagaagtttgaatttaaatctacagatatatacaatg atggatacgaaaccgtaagctgcttcttaacgacagatcttaaaaaatattgtttaaattggaggtatgaatcaacagct ttattcggtgatacttgtaatcagatatttgggttaaaggaattatttaattggctgcaccctcgccttgaaaagagtac aatatatgttggagatccttattgcccgccatcagatattgaacatttaccacttgatgaccatcctgattcaggattt atgttcataatcctaaaggaggaatagaagggttttgccaaaagttatggacactcatatctatcagtgcaatacattta gcagctgtcaaaatcggtgtaagagttactgcaatggttcaaggggataatcaagccatagctgttaccacaagagtacc taataattatgattataaagttaagaaagagattgtttataaagatgtggtaagattttttgattccttgagagaggtga -continued

```
tggatgatctgggtcatgagctcaaactaaatgaaactataataagtagtaaaatgtttatatatagcaaaaggatatac tatgacggaagaatccttcctcaggcattaaaagcattgtctagatgtgttttttggtctgaaacaatcatagatgagac aagatcagcatcctcaaatctggctacatcgtttgcaaaggccattgagaatggctactcacctgtattgggatatgtat gctcaatcttcaaaaatatccaacagttgtatatagcgcttggaatgaatataaacccaactataacccaaaatattaaa gatcaatatttcaggaatattcattggatgcaatatgcctccttaatccctgctagtgtcggaggatttaattatatggc catgtcaaggtgttttgtcagaaacattggagatcctacagtcgctgcgttagccgatattaaaagatttataaaagcaa atttgttagatcgaggtgtcctttacagaattatgaatcaagaaccaggcgagtcttcttttttagactgggcctcagat ccctattcatgtaacttaccacaatctcaaaatataaccaccatgataaagaatataactgcaagaaatgtactacagga ctcaccaaacccattactatctggattatttacaagtacaatgatagaagaggatgaggaattagctgagttcctaatgg acaggagaataatcctcccaagagttgcacatgacattttagataattctcttactggaattaggaatgctatagctggt atgttggatacaacaaaatcactaattcgagtagggataagcagaggaggattaacctataacttattaagaaagataag caactatgatcttgtacaatatgagacacttagtaaaactttaagactaatagtcagtgacaagattaagtatgaagata tgtgctcagtagacctagccatatcattaagacaaaaaatgtggatgcatttatcaggaggaagaatgataaatggactt gaaactccagatcctttagagttactgtctggagtaataatacaggatctgaacattgtaggatatgttattcaactga aggtgaaagcccatatacatggatgtatttaccaggcaatcttaatataggatcagctgagacaggaatagcatcattaa gggtcccttactttggatcagttacagatgagagatctgaagcacaattagggtatatcaaaaatctaagcaaaccagct aaggctgctataagaatagcaatgatatatacttgggcatttgggaatgacgaaatatcttggatggaagcatcacagat tgcacaaacacgtgcaaactttacattggatagcttaaagattttgacaccagtgacaacatcaacaaatctatcacaca ggttaaaagatactgctactcagatgaaattttctagtacatcacttattagagtaagcaggttcatcacaatatctaat gataatatgtctattaaagaagcaaatgaaactaaagatacaaatcttatttatcaacaggtaatgttaacaggattaag tgtatttgaatatctatttaggttagaggagagtacaggacataaccctatggtcatgcatctacatatagaggatggat gttgtataaaagagagttacaatgatgagcatatcaatccggagtctacattagagttaatcaaatacctgagagtaat gaatttatatatgataaggaccctttaaaggatatagatctatcaaaattaatggttataagagatcattcttatacaat tgacatgaattactgggatgacacagatattgtacatgcaatatcaatatgtactgcagttacaatagcagatacaatgt cgcagctagatcgggataatcttaaggagctggttgtgattgcaaatgatgatgatattaacagtctgataactgaattt ctgaccctagatatactagtgtttctcaaaacatttggagggttactcgtgaatcaatttgcatatacccttatggatt gaaaatagaaggaagggatcccatttgggattatataatgagaacattaaaagacacctcacattcagtacttaaagtat tatctaatgcactatctcatccaaaagtgtttaagagattttgggattgtggagttttgaatcctatttatggtcctaat actgctagtcaagatcaagttaagcttgctctctcgatttgcgagtactccttggatctatttatgagagaatggttgaa tggagcatcacttgagatctatatctgtgatagtgacatggaaatagcaaatgacagaagacaagcatttctctcaagac atcttgcctttgtgtgttgtttagcagagatagcatcttttggaccaaatttattaaatctaacatatctagagagactt gatgaattaaaacaatacttagatctgaacatcaaagaagatcctactcttaaatatgtgcaagtatcaggactgttaat taaatcattcccctcaactgttacgtatgtaaggaaaactgcgattaagtatctgaggattcgtggtattaatccgcctg aaacgattgaagattgggatcccatagaagatgagaatatcttagacaatattgttaaaactgtaaatgacaattgcagt gataatcaaagagaaataaaagtagttatttctggggattagctctaaagaattatcaagtcgtgaaaataagatccat aacgagtgattctgaagttaatgaagcttcgaatgttactacacatggaatgacacttcctcagggaggaagttatctat cacatcagctgaggttatttggagtaaacagtacaagttgtcttaaagctcttgaattatcacaaatcttaatgagggaa gttaaaaagataaagatagactcttttaggagaaggagcaggagctatgttagcatgttatgatgctacactcggtcc tgcaataaattattataattctggtttaaatattacagatgtaattggtcaacgggaattaaaaatcttcccatcagaag tatcattagtaggtaaaaaactaggaaatgtaacacagattcttaatcgggtgagggtgttatttaatgggaatcccaat tcaacatggataggaaatatggaatgtgagagtttaatatggagtgaattaaatgataagtcaattggtttagtacattg
```

-continued tgacatggagggagcgataggcaaatcagaagaaactgttctacatgaacattatagtattattaggattacatatttaa tcggggatgatgatgttgtcctagtatcaaaaattataccaactattactccgaattggtctaaaatactctatctatac aagttgtattggaaggatgtaagtgtagtgtcccttaaaacatccaatcctgcctcaacagagctttatttaatttcaaa agatgcttactgtactgtaatggaacccagtaatcttgttttatcaaaacttaaaaggatatcatcaatagaagaaaata atctattaaagtggataatcttatcaaaaaggaagaataacgagtggttacagcatgaaatcaaagaaggagaaagggat tatgggataatgaggccatatcatacagcactgcaaattttggattccaaattaacttaaatcacttagctagagaatt tttatcaactcctgatttaaccaacattaataatataattcaagttttacaagaacaattaaagatgttatgttcgaat gggtcaatatcactcatgacaataaaagacataaattaggaggaagatataatctattcccgcttaaaaataaggggaaa ttaagattattatcacgaagattagtactaagctggatatcattatccttatcaaccagattactgacgggccgttttcc agatgaaaaatttgaaaatagggcacagaccggatatgtatcattggctgatattgatttagaatccttaaagttattat caagaaatattgtcaaaaattacaaagaacacataggattaatatcatactggttttgaccaaagaggtcaaaatacta atgaagcttataggaggagtcaaactactaggaattcctaaacagtacaaagagttagaggatcgatcatctcagggtta tgaatatgataatgaatttgatattgattaatacataaaaacataaaataaaacacctattcctcacccattcacttcca acaaaatgaaaagtaagaaaaacatgtaatatatatataccaaacagagttttttctcttgtttggt rB/HPIV3- RSV wt G/GS-opt (SEQ ID NO: 92):
accaaacaagagaagagactggtttgggaatattaattcaaataaaaattaacttaggattaaagaactttaccgaaagg taaggggaaagaaatcctaagagcttagccatgttgagtctattcgacacattcagtgcgcgtaggcaggagaacataac gaaatcagctggtggggctgttattcccgggcaaaaaaacactgtgtctatatttgctcttggaccatcaataacagatg acaatgataaaatgacattggctcttctcttttttgtctcattctttagacaatgaaaagcagcatgcgcaaagagctgga tttttagtttctctgttatcaatggcttatgccaacccagaattatatttaacatcaaatggtagtaatgcagatgttaa atatgttatctacatgatagagaaagacccaggaagacagaaatatggtgggtttgtcgtcaagactagagagatggttt atgaaaagacaactgattggatgttcgggagtgatcttgagtatgatcaagacaatatgttgcaaaatggtagaagcact tctacaatcgaggatcttgttcatacttttggatatccatcgtgtcttggagcccttataatccaagtttggataatact tgttaaggctataaccagtatatcaggattgaggaaaggattctttactcggttagaagcatttcgacaagatggaacag ttaaatccagtctagtgttgagcggtgatgcagtagaacaaattggatcaattatgaggtcccaacagagcttggtaaca ctcatggttgaaacactgataacaatgaacacaggcaggaatgatctgacaacaatagaaaagaatatacagattgtagg aaactacatcagagatgcaggtcttgcttcattttttcaacacaatcagatatggcattgagactagaatggcagctctaa ctctgtctacccttagaccggatatcaacagactcaaggcactgatcgagttatatctatcaaaggggccacgtgctcct tttatatgcattttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactgggggtcacacaagaagccaag caaagcttgaagaaacacatgaagaacatcagcagttcagatacaacctttcataagcctacaggggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaaggaaacagagtgacccgagatcaactgacatcac aaacaacacaaatcaaactgaaatagatgatttgttcagtgcattcggaagcaactagtcacaaagagatgaccaggcgc gccaagtaagaaaaacttaggattaatggacctgcaggatgtcaaagaacaaggatcagagaactgccaagaccctggaa agaacctgggacacccctgaaccacctgctgtttatctcaagctgcctgtacaagctgaatctgaaagtgtggcccagat caccctgtcaattctggctatgatcatttcaacaagcctgatcattgccgctatcattttcatcgcaagcgccaaccaca aggtcacccccaccacagctatcattcaggacgcaacatcccagattaagaacactaccccccacctatctgacacagaat cctcagctgggaatctccccatctaacccctcagagattaccagccagatcacaactattctggcctccaccacacctgg -continued

```
cgtgaagtccactctgcagtctactaccgtcaagaccaaaaatacaactaccacacagacacagccttctaagccaacta ccaaacagcggcagaataagcccctagtaaaccaaacaatgacttccattttgaggtgttcaactttgtcccatgcagc atctgttccaacaatcccacctgctgggccatctgtaagagaattccaaacaagaaacccggcaagaagaccactaccaa acctactaagaaaccaaccctgaagacaactaagaaagatcctaaaccacagaccacaaagtctaaagaagtgcccacta ccaagcctacagaggaaccaactatcaacacaactaagactaacatcatcaccacactgctgacaagcaacactaccggc aatcccgagctgaccagccagatggaaaccttcactccacaagctccgaggggaatcccagtccttcacaggtgtctac aactagtgaataccccagccagccttctagtccacccaacacccctaggcagtgatagctagcggcgcgccagcaacaag taagaaaaacttaggattaatggaaattatccaatccagagacggaaggacaaatccagaatccaaccacaactcaatca accaaagattcatggaagacaatgttcaaaacaatcaaatcatggattcttgggaagagggatcaggagataaatcatct gacatctcatcggccctcgacatcattgaattcatactcagcaccgactcccaagagaacacggcagacagcaatgaaat caacacaggaaccacaagacttagcacgacaatctaccaacctgaatccaaaacaacagaaacaagcaaggaaaatagtg gaccagctaacaaaaatcgacagtttggggcatcacacgaacgtgccacagagacaaaagatagaaatgttaatcaggag actgtacagggaggatataggagaggaagcagcccagatagtagaactgagactatggtcactcgaagaatctccagaag cagcccagatcctaacaatggaacccaaatccaggaagatattgattacaatgaagttggagagatggataaggactcta ctaagagggaaatgcgacaatttaaagatgttccagtcaaggtatcaggaagtgatgccattcctccaacaaaacaagat ggagacggtgatgatggaagaggcctggaatctatcagtacatttgattcaggatataccagtatagtgactgccgcaac actagatgacgaagaagaactccttatgaagaacaacaggccaagaaagtatcaatcaacacccccagaacagtgacaagg gaattaaaaaagggggttggaaggccaaaagacacagacaaacaatcatcaatattggactacgaactcaacttcaaagga tcgaagaagagccagaaaatcctcaaagccagcacgaatacaggagaaccaacaagaccacagaatggatcccagggaa gagaatcacatcctggaacatcctcaacagcgagagcggcaatcgaacagaatcaacaaaccaaacccatcagacatcaa cctcgggacagaaccacacaatgggaccaagcagaacaacctccgaaccaaggatcaagacacaaaagacggatggaaag gaaagagaggacacagaagagagcactcgatttacagaaagggcgattacattattacagaatcttggtgtaatccaatc tgcagcaaaattagacctataccaagacaagagagttgtgtgtgtggcgaatgtcctaaacaatgcagatactgcatcaa agatagacttcctagcaggtttgatgataggagtgtcaatggatcatgataccaaattaaatcagattcagaacgagata ttaagtttgaaaactgatcttaaaaagatggatgaatcacatagaagactaattgagaatcaaaaagaacaattatcact gatcacatcattaatctcaaatcttaaaattatgacagagagaggagggaagaaggaccaaccagaacctagcgggagga catccatgatcaagacaaaagcaaaagaagagaaaataaagaaagtcaggtttgaccctcttatggaaacacagggcatc gagaaaacatccctgacctctatagatcaatagagaaaacaccagaaaacgacacacagatcaaatcagaaataaacag attgaatgatgaatccaatgccactagattagtacctagaagaataagcagtacaatgagatcattaataataatcatta acaacagcaatttatcatcaaaagcaaagcaatcatacatcaacgaactcaagctctgcaagagtgacgaggaagtgtct gagttgatggacatgttcaatgaggatgtcagctcccagtaaaccgccaaccaagggtcaacaccaagaaaaccaatagc acaaaacagccaatcagagaccaccccaatacaccaaaccaatcaacacataacaaagatcgcggccgcatagatgatta agaaaaacttaggatgaaaggactaatcaatcctccgaaacaatgagcatcaccaactccacaatctacacattcccaga atcctctttctccgagaatggcaacatagagccgttaccactcaaggtcaatgaacagagaaaggccatacctcatatta gggttgtcaagataggagatccgcccaaacatggatccagatatctggatgtcttttactgggcttctttgagatggaa aggtcaaaagacaggtatgggagcataagtgatctagatgatgatccaagttacaaggtttgtggctctggatcattgcc acttgggttggctagatacaccggaaatgatcaggaactcctacaggctgcaaccaagctcgatatagaagtaagaagaa ctgtaaaggctacggagatgatagtttacactgtacaaaacatcaaacctgaactatatccatggtccagtagattaaga aaagggatgttatttgacgctaataaggttgcacttgctcctcaatgtcttccactagatagagggataaaattcagggt gatatttgtgaactgcacagcaattggatcaataactctattcaaaatccctaagtccatggcattgttatcattgccta
```

-continued

```
atacaatatcaataaatctacaagtacatatcaaaacaggagttcagacagattccaaaggagtagttcagattctagat gaaaaaggtgaaaaatcactaaatttcatggttcatctcgggttgatcaaaaggaagatgggcagaatgtactcagttga atattgtaagcagaagatcgagaagatgagattattattctcattgggattagttggagggatcagcttccacgtcaacg caactggctctatatcaaagacattagcaagtcaattagcattcaaaagagaaatctgctatcccctaatggatctgaat ccacacttaaattcagttatatgggcatcatcagttgaaattacaagggtagatgcagttctccagccttcattacctgg cgaattcagatactacccaaacatcatagcaaaaggggtcgggaaaatcagacagtaaaatcaacaaccctgatatccac cggtgtattaagccgaagcaaataaaggataatcaaaaacttaggacaaaagaggtcaataccaacaactattagcagtc acactcgcaagaataagagagaagggaccaaaaaagtcaaataggagaaatcaaacaaaaggtacagaacaccagaaca acaaaatcaaaacatccaactcactcaaaacaaaaattccaaaagagaccggcaacacaacaagcactgaacacaatgcc aacttcaatactgctaattattacaaccatgatcatggcatctttctgccaaatagatatcacaaaactacagcacgtag gtgtattggtcaacagtcccaaagggatgaagatatcacaaaactttgaaacaagatatctaattttgagcctcatacca aaaatagaagactctaactcttgtggtgaccaacagatcaagcaatacaagaagttattggatagactgatcatccctttt atatgatggattaagattacagaaagatgtgatagtaaccaatcaagaatccaatgaaaacactgatcccagaacaaaac gattctttggaggggtaattggaaccattgctctgggagtagcaacctcagcacaaattacagcggcagttgctctggtt gaagccaagcaggcaagatcagacatcgaaaaactcaaagaagcaattagggacacaaacaaagcagtgcagtcagttca gagctccataggaaatttaatagtagcaattaaatcagtccaggattatgttaacaaagaaatcgtgccatcgattgcga ggctaggttgtgaagcagcaggacttcaattaggaattgcattaacacagcattactcagaattaacaaacatatttggt gataacataggatcgttacaagaaaaaggaataaaattacaaggtatagcatcattataccgcacaaatatcacagaaat attcacaacatcaacgttgataaatatgatatctatgatctgttatttacagaatcaataaaggtgagagttatagatg ttgacttgaatgattactcaatcaccctccaagtcagactccctttattaactaggctgctgaacactcagatctacaaa gtagattccatatcatataacatccaaaacagagaatggtatatccctcttcccagccatatcatgacgaaagggggcatt tctaggtggagcagacgtcaaagaatgtatagaagcattcagcagctatatatgcccttctgatccaggatttgtattaa accatgaaatagagagctgcttatcaggaaacatatcccaatgtccaagaacaacggtcacatcagacattgttccaaga tatgcatttgtcaatggaggagtggttgcaaactgtataacaaccacctgtacatgcaacggaattggtaatagaatcaa tcaaccacctgatcaaggagtaaaaattataacacataaagaatgtagtacaataggtatcaacggaatgctgttcaata caaataaagaaggaactcttgcattctatacaccaaatgatataacactaaacaattctgttgcacttgatccaattgac atatcaatcgagctcaacaaggccaaatcagatctagaagaatcaaaagaatggataagaaggtcaaatcaaaaactaga ttctattggaaattggcatcaatctagcactacaatcataattatttgataatgatcattatattgtttataattaata taacgataattacaattgcaattaagtattacagaattcaaaagagaaatcgagtggatcaaaatgacaagccatatgta ctaacaaacaaataacatatctacagatcattagatattaaaattataaaaaacttaggagtaaagttacgcaatccaac tctactcatataattgaggaaggacccaatagacaaatccaaattcgagatggaatactggaagcataccaatcacggaa aggatgctggtaatgagctggagacgtctatggctactcatggcaacaagctcactaataagataatatacatattatgg acaataatcctggtgttattatcaatagtcttcatcatagtgctaattaattccatcaaaagtgaaaaggcccacgaatc attgctgcaagacataaataatgagtttatggaaattacagaaaagatccaaatggcatcggataataccaatgatctaa tacagtcaggagtgaatacaaggcttcttacaattcagagtcatgtccagaattacataccaatatcattgacacaacag atgtcagatcttaggaaattcattagtgaaattacaattagaaatgataatcaagaagtgctgccacaaagaataacaca tgatgtaggtataaaaccttaaatccagatgattttttggagatgcacgtctggtcttccatctttaatgaaaactccaa aaaataaggttaatgccagggccgggattattagctatgccaacgactgttgatggctgtgttagaactccgtctttagtt ataaatgatctgatttatgcttataccctcaaatctaattactcgaggttgtcaggatataggaaaatcatatcaagtctt acagatagggataataactgtaaactcagacttggtacctgacttaaatcctaggatctctcatacctttaacataaatg acaataggaagtcatgttctctagcactcctaaatacagatgtatatcaactgtgttcaactcccaaagttgatgaaaga
```

-continued

```
tcagattatgcatcatcaggcatagaagatattgtacttgatattgtcaattatgatggttcaatctcaacaacaagatt
taagaataataacataagctttgatcaaccatatgctgcactatacccatctgttggaccagggatatactacaaaggca
aaataatatttctcgggtatggaggtcttgaacatccaataaatgagaatgtaatctgcaacacaactgggtgccccggg
aaaacacagagagactgtaatcaagcatctcatagtccatggttttcagataggaggatggtcaactccatcattgttgt
tgacaaaggcttaaactcaattccaaaattgaaagtatggacgatatctatgcgacaaaattactggggtcagaaggaa
ggttacttctactaggtaacaagatctatatatatacaagatctacaagttggcatagcaagttacaattaggaataatt
gatattactgattacagtgatataaggataaaatggacatggcataatgtgctatcaagaccaggaaacaatgaatgtcc
atggggacattcatgtccagatggatgtataacaggagtatatactgatgcatatccactcaatcccacagggagcattg
tgtcatctgtcatattagactcacaaaaaatcgagagtgaacccagtcataacttactcaacagcaaccgaaagagtaaac
gagctggccatcctaaacagaacactctcagctggatatacaacaacaagctgcattacacactataacaaaggatattg
ttttcatatagtagaaataaatcataaaagcttaaacacatttcaacccatgttgttcaaaacagagattccaaaaagct
gcagttaatcataattaaccataatatgcatcaatctatctataatacaagtatatgataagtaatcagcaatcagacaa
tagacgtacggaaataataaaaaacttaggagaaaagtgtgcaagaaaaatggacaccgagtcccacagcggcacaacat
ctgacattctgtaccctgaatgtcacctcaattctcctatagttaaaggaaagatagcacaactgcatacaataatgagt
ttgcctcagccctacgatatggatgatgattcaatactgattattactagacaaaaaattaaactcaataaattagataa
aagacaacggtcaattaggaaattaagatcagtcttaatggaaagagtaagtgatctaggtaaatataccttttatcagat
atccagagatgtctagtgaaatgttccaattatgtatacccggaattaataataaaataaatgaattgctaagtaaagca
agtaaaacatataatcaaatgactgatggattaagagatctatgggttactatactatcgaagttagcatcgaaaaatga
tggaagtaattatgatatcaatgaagatattagcaatatatcaaatgttcacatgacttatcaatcagacaaatggtata
atccattcaagacatggtttactattaagtatgacatgagaagattacaaaaagccaaaaatgagattacattcaatagg
cataaagattataatctattagaagaccaaaagaatatattgctgatacatccagaactcgtcttaatattagataaaca
aaattacaatgggtatataatgactcctgaattggtactaatgtattgtgatgtagttgaagggaggtggaatataagtt
catgtgcaaaattggatcctaagttacaatcaatgtattataagggtaacaatttatgggaaataatagatggactattc
tcgaccttaggagaaagaacatttgacataatatcactattagaaccacttgcattatcgctcattcaaacttatgaccc
ggttaaacagctcaggggggctttttaaatcacgtgttatcagaaatgaattaatatttgcagctgagtgtacaacag
aggaaatacctaatgtggattatatagataaaattttagatgtgttcaaagaatcaacaatagatgaaatagcagaaatt
ttctcttttcttccgaacttttggacaccctccattagaggcgagtatagcagcagagaaagttagaaagtatatgtatac
tgagaaatgcttgaaatttgatactatcaataaatgtcatgctattttttgtacaataattataaatggatatagagaaa
gacatggtggtcaatggcctccagttacattacctgtccatgcacatgaatttatcataaatgcatacggatcaaattct
gccatatcatatgagaatgctgtagattattataagagcttcataggaataaaatttgacaagtttatagagcctcaatt
ggatgaagacttaactatttatatgaaagataaagcattatccccaaagaaatcaaactgggacacagtctatccagctt
caaacctgttataccgcactaatgtgtctcatgattcacgaagattggttgaagtatttatagcagatagtaaatttgat
ccccaccaagtattagattacgtagaatcaggatattggctggatgatcctgaatttaatatctcatatagtttaaaaga
gaaagaaataaaacaagaaggtagacttttgcaaaaatgacatacaagatgagggctacacaagtattatcagaaacat
tattggcgaataatatagggaaattcttccaagagaatgggatggttaaaggagaaattgaattactcaagagactaaca
acaatatctatgtctggagttccgcggtataatgaggtatacaataattcaaaaagtcacacagaagaacttcaagctta
taatgcaattagcagttccaatttatcttctaatcagaagtcaaagaagtttgaatttaaatctacagatatatacaatg
atggatacgaaaccgtaagctgcttcttaacgacagatcttaaaaaatattgtttaaattggaggtatgaatcaacagct
ttattcggtgatacttgtaatcagatatttgggttaaaggaattatttaattggctgcaccctcgccttgaaaagagtac
aatatatgttggagatccttattgcccgccatcagatattgaacatttaccacttgatgaccatcctgattcaggatttt
```

-continued

```
atgttcataatcctaaaggaggaatagaagggttttgccaaaagttatggacactcatatctatcagtgcaatacattta
gcagctgtcaaaatcggtgtaagagttactgcaatggttcaaggggataatcaagccatagctgttaccacaagagtacc
taataattatgattataaagttaagaaagagattgtttataaagatgtggtaagatttttttgattccttgagagaggtga
tggatgatctgggtcatgagctcaaactaaatgaaactataataagtagtaaaatgtttatatatagcaaaaggatatac
tatgacggaagaatccttcctcaggcattaaaagcattgtctagatgtgttttttggtctgaaacaatcatagatgagac
aagatcagcatcctcaaatctggctacatcgtttgcaaaggccattgagaatggctactcacctgtattgggatatgtat
gctcaatcttcaaaaatatccaacagttgtatatagcgcttggaatgaatataaacccaactataacccaaaatattaaa
gatcaatatttcaggaatattcattggatgcaatatgcctccttaatccctgctagtgtcggaggatttaattatatggc
catgtcaaggtgttttgtcagaaacattggagatcctacagtcgctgcgttagccgatattaaaagatttataaaagcaa
atttgttagatcgaggtgtcctttacagaattatgaatcaagaaccaggcgagtcttctttttttagactgggcctcagat
ccctattcatgtaacttaccacaatctcaaaatataaccaccatgataaagaatataactgcaagaaatgtactacagga
ctcaccaaacccattactatctggattatttacaagtacaatgatagaagaggatgaggaattagctgagttcctaatgg
acaggagaataatcctcccaagagttgcacatgacatttagataattctcttactggaattaggaatgctatagctggt
atgttggatacaacaaaatcactaattcgagtagggataagcagaggaggattaacctataacttattaagaaagataag
caactatgatcttgtacaatatgagacacttagtaaaactttaagactaatagtcagtgacaagattaagtatgaagata
tgtgctcagtagacctagccatatcattaagacaaaaaatgtggatgcatttatcaggaggaagaatgataaatggactt
gaaactccagatcctttagagttactgtctggagtaataataacaggatctgaacattgtaggatatgttattcaactga
aggtgaaagcccatatacatggatgtatttaccaggcaatcttaatataggatcagctgagacaggaatagcatcattaa
gggtccttactttggatcagttacagatgagagatctgaagcacaattagggtatatcaaaaatctaagcaaaccagct
aaggctgctataagaatagcaatgatatatacttgggcatttggaatgacgaaatatcttggatggaagcatcacagat
tgcacaaacacgtgcaaactttacattggatagcttaaagattttgacaccagtgacaacatcaacaaatctatcacaca
ggttaaaagatactgctactcagatgaaattttctagtacatcacttattagagtaagcaggttcatcacaatatctaat
gataatatgtctattaaagaagcaaatgaaactaaagatacaaatcttatttatcaacaggtaatgttaacaggattaag
tgtatttgaatatctatttaggttagaggagagtacaggacataaccctatggtcatgcatctacatatagaggatggat
gttgtataaaagagagttacaatgatgagcatatcaatccggagtctacattagagttaatcaaatacctgagagtaat
gaatttatatatgataaggacccctttaaaggatatagatctatcaaaattaatggttataagagatcattcttatacaat
tgacatgaattactgggatgacacagatattgtacatgcaatatcaatatgtactgcagttacaatagcagatacaatgt
cgcagctagatcgggataatcttaaggagctggttgtgattgcaaatgatgatgatattaacagtctgataactgaattt
ctgaccctagatatactagtgtttctcaaaacatttggagggttactcgtgaatcaatttgcatatacccctttatggatt
gaaaatagaaggaagggatcccatttgggattatataatgagaacattaaaagacacctcacattcagtacttaaagtat
tatctaatgcactatctcatccaaaagtgtttaagagattttgggattgtggagttttgaatcctatttatggtcctaat
actgctagtcaagatcaagttaagcttgctctctcgatttgcgagtactccttggatctatttatgagagaatggttgaa
tggagcatcacttgagatctatatctgtgatagtgacatggaaatagcaaatgacagaagacaagcatttctctcaagac
atcttgcctttgtgtgttgtttagcagagatagcatcttttggaccaaatttattaaatctaacatatctagagagactt
gatgaattaaaacaatacttagatctgaacatcaaagaagatcctactcttaaatatgtgcaagtatcaggactgttaat
taaatcattcccctcaactgttacgtatgtaaggaaaactgcgattaagtatctgaggattcgtggtattaatccgcctg
aaacgattgaagattgggatcccatagaagatgagaatatcttagacaatattgttaaaactgtaaatgacaattgcagt
gataatcaaaagagaaataaaagtagttatttctggggattagctctaaagaattatcaagtcgtgaaaataagatccat
aacgagtgattctgaagttaatgaagcttcgaatgttactacacatggaatgacacttcctcagggaggaagttatctat
cacatcagctgaggttatttggagtaaacagtacaagttgtcttaaagctcttgaattatcacaaatcttaatgagggaa
gttaaaaaagataaagatagactcttttttaggagaaggagcaggagctatgttagcatgttatgatgctacactcggtcc
``` tgcaataaattattataattctggtttaaatattacagatgtaattggtcaacgggaattaaaaatcttcccatcagaag tatcattagtaggtaaaaaactaggaaatgtaacacagattcttaatcgggtgagggtgttatttaatgggaatcccaat tcaacatggataggaaatatggaatgtgagagtttaatatggagtgaattaaatgataagtcaattggtttagtacattg tgacatggagggagcgataggcaaatcagaagaaactgttctacatgaacattatagtattattaggattacatatttaa tcggggatgatgatgttgtcctagtatcaaaaattataccaactattactccgaattggtctaaaatactctatctatac aagttgtattggaaggatgtaagtgtagtgtcccttaaaacatccaatcctgcctcaacagagctttatttaatttcaaa agatgcttactgtactgtaatggaacccagtaatcttgttttatcaaaacttaaaaggatatcatcaatagaagaaaata atctattaaagtggataatcttatcaaaaaggaagaataacgagtggttacagcatgaaatcaaagaaggagaaagggat tatgggataatgaggccatatcatacagcactgcaaattttttggattccaaattaacttaaatcacttagctagagaatt tttatcaactcctgatttaaccaacattaataatataattcaaagttttacaagaacaattaaagatgttatgttcgaat gggtcaatatcactcatgacaataaaagacataaattaggaggaagatataatctattcccgcttaaaaataaggggaaa ttaagattattcacgaagattagtactaagctggatatcattatccttatcaaccagattactgacgggccgttttcc agatgaaaaatttgaaaatagggcacagaccggatatgtatcattggctgatattgatttagaatccttaaagttattat caagaaatattgtcaaaaattacaaagaacacataggattaatatcatactggttttttgaccaaagaggtcaaaatacta atgaagcttataggaggagtcaaactactaggaattcctaaacagtacaaagagttagaggatcgatcatctcagggtta tgaatatgataatgaatttgatattgattaatacataaaaacataaaatagaaacacctattcctcacccattcacttcca acaaaatgaaaagtaagaaaaacatgtaatatatatataccaaacagagttttctcttgtttggt rB/HPIV3- RSV G_B3TMCT (SEQ ID NO: 93):
accaaacaagagaagagactggtttgggaatatattaattcaaataaaaattaacttaggattaaagaactttaccgaaagg taaggggaaagaaatcctaagagcttagccatgttgagtctattcgacacattcagtgcgcgtaggcaggagaacataac gaaatcagctggtggggctgttattcccgggcaaaaaaaacactgtgtctatatttgctcttggaccatcaataacagatg acaatgataaaatgacattggctcttctcttttgtctcattcttagacaatgaaaagcagcatgcgcaaagagctgga ttttagtttctctgttatcaatggcttatgccaacccagaattatatttaacatcaaatggtagtaatgcagatgttaa atatgttatctacatgatagagaaagacccaggaagacagaaatatggtgggtttgtcgtcaagactagagagatggttt atgaaaagacaactgattggatgttcgggagtgatcttgagtatgatcaagacaatatgttgcaaaatggtagaagcact tctacaatcgaggatcttgttcatacttttggatatccatcgtgtcttggagcccttataatccaagtttggataatact tgttaaggctataaccagtatatcaggattgaggaaaggattctttactcggttagaagcatttcgacaagatggaacag ttaaatccagtctagtgttgagcggtgatgcagtagaacaaattggatcaattatgaggtcccaacagagcttggtaaca ctcatggttgaaacactgataacaatgaacacaggcaggaatgatctgacaacaatagaaaagaatatacagattgtagg aaactacatcagagatgcaggtcttgcttcattttttcaacacaatcagatatggcattgagactagaatggcagctctaa ctctgtctaccccttagaccggatatcaacagactcaaggcactgatcgagttatatctatcaaaggggccacgtgctcct tttatatgcatttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactggggggtcacacaagaagccaag caaagcttgaagaaacacatgaagaacatcagcagttcgatacaacctttcataagcctacagggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaaggaaacagagtgacccgagatcaactgacatcac aaacaacacaaatcaaactgaaatagatgattgttcagtgcattcggaagcaactagtcacaaagagatgaccaggcgc gccaagtaagaaaaacttaggattaatggacctgcaggatgaatattggaaacacacaaacagcataaataacaccaac aatgaaaccgaaacagccagaggcaaacatagtagcaaggttacaaatatcataatgtacaccttctggacaataacatt -continued

```
aacaatattatcagtcatttttataatgatattgacaaacttaattaaccacaaagtcacaccaacaactgcaatcatac aagatgcaacaagccagatcaagaacacaaccccaacatacctcacccagaatcctcagcttggaatcagtccctctaat ccgtctgaaattacatcacaaatcaccaccatactagcttcaacaacaccaggagtcaagtcaaccctgcaatccacaac agtcaagaccaaaaacacaacaacaactcaaacacaacccagcaagccaccacaaaacaacgccaaaacaaaccaccaa gcaaacccaataatgattttcactttgaagtgttcaactttgtaccctgcagcatatgcagcaacaatccaacctgctgg gctatctgcaaaagaataccaaacaaaaaccaggaaagaaaaccactaccaagcccacaaaaaaaccaaccctcaagac aaccaaaaagatcccaaacctcaaaccactaaatcaaggaagtacccaccaccaagcccacagaagagccaaccatca acaccaccaaaacaaacatcataactacactactcacctccaacaccacaggaaatccagaactcacaagtcaaatggaa accttccactcaacttcctccgaaggcaatccaagcccttctcaagtctctacaacatccgagtacccatcacaaccttc atctccacccaacacaccacgccagtagtgatagctagcggcgcgccagcaacaagtaagaaaaacttaggattaatgga aattatccaatccagagacggaaggacaaatccagaatccaaccacaactcaatcaaccaaagattcatggaagacaatg ttcaaaacaatcaaatcatggattcttgggaagagggatcaggagataaatcatctgacatctcatcggccctcgacatc attgaattcatactcagcaccgactcccaagagaacacggcagacagcaatgaaatcaacacaggaaccacaagacttag cacgacaatctaccaacctgaatccaaaacaacagaaacaagcaaggaaaatagtggaccagctaacaaaaatcgacagt ttggggcatcacacgaacgtgccacagagacaaaagatagaaatgttaatcaggagactgtacagggaggatataggaga ggaagcagcccagatagtagaactgagactatggtcactcgaagaatctccagaagcagcccagatcctaacaatggaac ccaaatccaggaagatattgattacaatgaagttggagagatggataaggactctactaagagggaaatgcgacaattta aagatgttccagtcaaggtatcaggaagtgatgccattcctccaacaaaacaagatggagacggtgatgatggaagaggc ctggaatctatcagtacatttgattcaggatataccagtatagtgactgccgcaacactagatgacgaagaagaactcct tatgaagaacaacaggccaagaaagtatcaatcaacaccccagaacagtgacaagggaattaaaaaaggggttggaaggc caaaagacacagacaaacaatcatcaatattggactacgaactcaacttcaaaggatcgaagaagagccagaaaatcctc aaagccagcacgaatacaggagaaccaacaagaccacagaatggatcccaggggaagagaatcacatcctggaacatcct caacagcgagagcggcaatcgaacagaatcaacaaaccaaacccatcagacatcaacctcgggacagaaccacacaatgg gaccaagcagaacaacctccgaaccaaggatcaagacacaaaagacggatggaaaggaaagagaggacacagaagagagc actcgatttacagaaagggcgattacattattacagaatcttggtgtaatccaatctgcagcaaaattagacctataccaa agacaagagagttgtgtgtgtggcgaatgtcctaaacaatgcagatactgcatcaaagatagacttcctagcaggtttga tgataggagtgtcaatggatcatgataccaaattaaatcagattcagaacgagatatttaagtttgaaaactgatcttaaa aagatggatgaatcacatagaagactaattgagaatcaaaaagaacaattatcactgatcacatcattaatctcaaatct taaaattatgacagagagagggagggaagaaggaccaaccagaacctagcgggaggacatccatgatcaagacaaaagcaa aagaagagaaaataaagaaagtcaggtttgaccctcttatggaaacacagggcatcgagaaaaacatccctgacctctat agatcaatagagaaaacaccagaaaacgacacacagatcaaatcagaaataaacagattgaatgatgaatccaatgccac tagattagtacctagaagaataagcagtacaatgagatcattaataataatcattaacaacagcaatttatcatcaaaag caaagcaatcatacatcaacgaactcaagctctgcaagagtgacgaggaagtgtctgagttgatggacatgttcaatgag gatgtcagctcccagtaaaccgccaaccaagggtcaacaccaagaaaaccaatagcacaaaacagccaatcagagaccac cccaatacaccaaaccaatcaacacataacaaagatcgcggccgcatagatgattaagaaaaacttaggatgaaaggact aatcaatcctccgaaacaatgagcatcaccaactccacaatctacacattcccagaatcctctttctccgagaatggcaa catagagccgttaccactcaaggtcaatgaacagagaaaggccatacctcatattgggttgtcaagataggagatccgc ccaaacatggatccagatatctggatgtcttttttactgggcttctttgagatggaaaggtcaaaagacaggtatgggagc ataagtgatctagatgatgatccaagttacaaggtttgtggctctggatcattgccacttgggttggctagatacaccgg aaatgatcaggaactcctacaggctgcaaccaagctcgatatagaagtaagaagaactgtaaaggctacggagatgatag
```

-continued

```
tttacactgtacaaaacatcaaacctgaactatatccatggtccagtagattaagaaaagggatgttatttgacgctaat aaggttgcacttgctcctcaatgtcttccactagatagagggataaaattcagggtgatatttgtgaactgcacagcaat tggatcaataactctattcaaaatccctaagtccatggcattgttatcattgcctaatacaatatcaataaatctacaag tacatatcaaaacaggagttcagacagattccaaaggagtagttcagattctagatgaaaaaggtgaaaaatcactaaat ttcatggttcatctcgggttgatcaaaaggaagatgggcagaatgtactcagttgaatattgtaagcagaagatcgagaa gatgagattattattctcattgggattagttggagggatcagcttccacgtcaacgcaactggctctatatcaaagacat tagcaagtcaattagcattcaaaagagaaatctgctatcccctaatggatctgaatccacacttaaattcagttatatgg gcatcatcagttgaaattacaaggdagtagatgcagttctccagccttcattacctggcgaattcagatactacccaaacat catagcaaaagdgggtcgggaaaatcagacagtaaaatcaacaaccctgatatccaccggtgtattaagccgaagcaaata aaggataatcaaaaacttaggacaaaagaggtcaataccaacaactattagcagtcacactcgcaagaataagagagaag ggaccaaaaagtcaaataggagaaatcaaaacaaaaggtacagaacaccagaacaacaaaatcaaaacatccaactcac tcaaaacaaaaattccaaaagagaccggcaacacaacaagcactgaacacaatgccaacttcaatactgctaattattac aaccatgatcatggcatctttctgccaaatagatatcacaaaactacagcacgtaggtgtattggtcaacagtcccaaag ggatgaagatatcacaaaactttgaaacaagatatctaattttgagcctcataccaaaaatagaagactctaactcttgt ggtgaccaacagatcaagcaatacaagaagttattggatagactgatcatccctttatatgatggattaagattacagaa agatgtgatagtaaccaatcaagaatccaatgaaaacactgatcccagaacaaaacgattctttggagdgggtaattggaa ccattgctctgggagtagcaacctcagcacaaattacagcggcagttgctctggttgaagccaagcaggcaagatcagac atcgaaaaactcaaagaagcaattagggacacaaacaaagcagtgcagtcagttcagagctccataggaaatttaatagt agcaattaaatcagtccaggattatgttaacaaagaaatcgtgccatcgattgcgaggctaggttgtgaagcagcaggac ttcaattaggaattgcattaacacagcattactcagaattaacaaacatatttggtgataacataggatcgttacaagaa aaaggaataaaattacaaggtatagcatcattataccgcacaaatatcacagaaatattcacaacatcaacagttgataa atatgatatctatgatctgttatttacagaatcaataaaggtgagagttatagatgttgacttgaatgattactcaatca ccctccaagtcagactccctttattaactaggctgctgaacactcagatctacaaagtagattccatatcatataacatc caaaacagagaatggtatatccctcttcccagccatatcatgacgaaaggggcatttctaggtggagcagacgtcaaaga atgtatagaagcattcagcagctatatatgcccttctgatccaggatttgtattaaaccatgaaatagagagctgcttat caggaaacatatcccaatgtccaagaacaacggtcacatcagacattgttccaagatatgcatttgtcaatggaggagtg gttgcaaactgtataacaaccacctgtacatgcaacggaattggtaatagaatcaatcaaccacctgatcaaggagtaaa aattataacacataaagaatgtagtacaataggtatcaacggaatgctgttcaatacaaataaagaaggaactcttgcat tctatacaccaaatgatataacactaaacaattctgttgcacttgatccaattgacatatcaatcgagctcaacaaggcc aaatcagatctagaagaatcaaaagaatggataagaaggtcaaatcaaaaactagattctattggaaattggcatcaatc tagcactacaatcataattattttgataatgatcattatattgtttataattaatataacgataattacaattgcaatta agtattacagaattcaaaagagaaatcgagtggatcaaaatgacaagccatatgtactaacaaacaaataacatatctac agatcattagatattaaaattataaaaaacttaggagtaaagttacgcaatccaactctactcatataattgaggaagga cccaatagacaaatccaaattcgagatggaatactggaagcataccaatcacggaaaggatgctggtaatgagctggaga cgtctatggctactcatggcaacaagctcactaataagtaatatacatattatggacaataatcctggtgttattatca atagtcttcatcatagtgctaattaattccatcaaaagtgaaaaggcccacgaatcattgctgcaagacataaataatga gtttatggaaattacagaaaagatccaaatggcatcggataataccaatgatctaatacagtcaggagtgaatacaaggc ttcttacaattcagagtcatgtccagaattacataccaatatcattgacacaacagatgtcagatcttaggaaattcatt agtgaaattacaattagaaatgataatcaagaagtgctgccacaaagaataacacatgatgtaggtataaaaccttaaa tccagatgattttggagatgcacgtctggtcttccatctttaatgaaaactccaaaaataaggttaatgccagggccgg gattattagctatgccaacgactgttgatggctgtgttagaactccgtctttagttataaatgatctgatttatgcttat
```

-continued

```
acctcaaatctaattactcgaggttgtcaggatataggaaaatcatatcaagtcttacagatagggataataactgtaaa
ctcagacttggtacctgacttaaatcctaggatctctcatacctttaacataaatgacaataggaagtcatgttctctag
cactcctaaatacagatgtatatcaactgtgttcaactcccaaagttgatgaaagatcagattatgcatcatcaggcata
gaagatattgtacttgatattgtcaattatgatggttcaatctcaacaacaagatttaagaataataacataagctttga
tcaaccatatgctgcactatacccatctgttggaccagggatatactacaaaggcaaaataatatttctcgggtatggag
gtcttgaacatccaataaatgagaatgtaatctgcaacacaactgggtgccccgggaaaacacagagagactgtaatcaa
gcatctcatagtccatggttttcagataggaggatggtcaactccatcattgttgttgacaaaggcttaaactcaattcc
aaaattgaaagtatggacgatatctatgcgacaaaattactgggggtcagaaggaaggttacttctactaggtaacaaga
tctatatatatacaagatctacaagttggcatagcaagttacaattaggaataattgatattactgattacagtgatata
aggataaaatggacatggcataatgtgctatcaagaccaggaaacaatgaatgtccatggggacattcatgtccagatgg
atgtataacaggagtatatactgatgcatatccactcaatcccacagggagcattgtgtcatctgtcatattagactcac
aaaaatcgagagtgaacccagtcataacttactcaacagcaaccgaaagagtaaacgagctggccatcctaaacagaaca
ctctcagctggatatacaacaacaagctgcattacacactataacaaaggatattgttttcatatagtagaaataaatca
taaaagcttaaacacatttcaacccatgttgttcaaaacagagattccaaaaagctgcagttaatcataattaaccataa
tatgcatcaatctatctataatacaagtatatgataagtaatcagcaatcagacaatagacgtacggaaataataaaaaa
cttaggagaaaagtgtgcaagaaaaatggacaccgagtcccacagcggcacaacatctgacattctgtaccctgaatgtc
acctcaattctcctatagttaaaggaaagatagcacaactgcatacaataatgagtttgcctcagccctacgatatggat
gatgattcaatactgattattactagacaaaaaattaaactcaataaattagataaaagacaacggtcaattaggaaatt
aagatcagtcttaatggaaagagtaagtgatctaggtaaatatacctttatcagatatccagagatgtctagtgaaatgt
tccaattatgtatacccggaattaataataaaataaatgaattgctaagtaaagcaagtaaaacatataatcaaatgact
gatggattaagagatctatgggttactatactatcgaagttagcatcgaaaaatgatggaagtaattatgatatcaatga
agatattagcaatatatcaaatgttcacatgacttatcaatcagacaaatggtataatccattcaagacatggtttacta
ttaagtatgacatgagaagattacaaaaagccaaaaatgagattacattcaataggcataaagattataatctattagaa
gaccaaaagaatatattgctgatacatccagaactcgtcttaatattagataaacaaaattacaatgggtatataatgac
tcctgaattggtactaatgtattgtgatgtagttgaagggaggtggaatataagttcatgtgcaaaattggatcctaagt
tacaatcaatgtattataagggtaacaatttatgggaaataatagatggactattctcgaccttaggagaaagaacattt
gacataatatcactattagaaccacttgcattatcgctcattcaaacttatgacccggttaaacagctcaggggggcttt
ttttaaatcacgtgttatcagaaatggaattaatatttgcagctgagtgtacaacagaggaaatacctaatgtggattata
tagataaaattttagatgtgttcaaagaatcaacaatagatgaaatagcagaaattttctctttcttccgaacttttgga
caccctccattagaggcgagtatagcagcagagaaagttagaaagtatatgtatactgagaaatgcttgaaatttgatac
tatcaataaatgtcatgctatttttttgtacaataattataaatggatatagagaaagacatggtggtcaatggcctccag
ttacattacctgtccatgcacatgaatttatcataaatgcatacggatcaaattctgccatatcatatgagaatgctgta
gattattataagagcttcataggaataaaatttgacaagtttatagagcctcaattggatgaagacttaactatttatat
gaaagataaagcattatccccaaagaaatcaaactgggacacagtctatccagcttcaaacctgttataccgcactaatg
tgtctcatgattcacgaagattggttgaagtatttatagcagatagtaaatttgatccccaccaagtattagattacgta
gaatcaggatattggctggatgatcctgaatttaatatctcatatagtttaaaagagaaagaaataaaacaagaaggtag
acttttttgcaaaaatgacatacaagatgagggctacacaagtattatcagaaacattattggcgaataatatagggaaat
tcttccaagagaatgggatggttaaaggagaaattgaattactcaagagactaacaacaatatctatgtctggagttccg
cggtataatgaggtatacaataattcaaaaagtcacacagaagaacttcaagcttataatgcaattagcagttccaattt
atcttctaatcagaagtcaaagaagtttgaatttaaatctacagatatatacaatgatggatacgaaaccgtaagctgct
```

-continued

```
tcttaacgacagatcttaaaaaatattgtttaaattggaggtatgaatcaacagctttattcggtgatacttgtaatcag atatttgggttaaaggaattatttaattggctgcaccctcgcctttgaaaagagtacaatatatgttggagatccttattg cccgccatcagatattgaacatttaccacttgatgaccatcctgattcaggattttatgttcataatcctaaaggaggaa tagaagggttttgccaaaagttatggacactcatatctatcagtgcaatacatttagcagctgtcaaaatcggtgtaaga gttactgcaatggttcaaggggataatcaagccatagctgttaccacaagagtacctaataattatgattataaagttaa gaaagagattgtttataaagatgtggtaagatttttttgattccttgagagaggtgatggatgatctgggtcatgagctca aactaaatgaaactataataagtagtaaaatgtttatatatagcaaaaggatatactatgacggaagaatccttcctcag gcattaaaagcattgtctagatgtgttttttggtctgaaacaatcatagatgagacaagatcagcatcctcaaatctggc tacatcgtttgcaaaggccattgagaatggctactcacctgtattgggatatgtatgctcaatcttcaaaaatatccaac agttgtatatagcgcttggaatgaatataaacccaactataaccaaaatattaaagatcaatatttcaggaatattcat tggatgcaatatgcctccttaatccctgctagtgtcggaggatttaattatatggccatgtcaaggtgttttgtcagaaa cattggagatcctacagtcgctgcgttagccgatattaaaagatttataaaagcaaatttgttagatcgaggtgtccttt acagaattatgaatcaagaaccaggcgagtcttcttttttagactgggcctcagatccctattcatgtaacttaccacaa tctcaaaatataaccaccatgataaagaatataactgcaagaaatgtactacaggactcaccaaacccattactatctgg attatttacaagtacaatgatagaagaggatgaggaattagctgagttcctaatggacaggagaataatcctcccaagag ttgcacatgacattttagataattctcttactggaattaggaatgctatagctggtatgttggatacaacaaaatcacta attcgagtagggataagcagaggaggattaacctataacttattaagaaagataagcaactatgatcttgtacaatatga gacacttagtaaaactttaagactaatagtcagtgacaagattaagtatgaagatatgtgctcagtagacctagccatat cattaagacaaaaatgtggatgcatttatcaggaggaagaatgataaatggacttgaaactccagatcctttagagtta ctgtctggagtaataataacaggatctgaacattgtaggatatgttattcaactgaaggtgaaagcccatatacatggat gtatttaccaggcaatcttaatataggatcagctgagacaggaatagcatcattaagggtcccttactttggatcagtta cagatgagagatctgaagcacaattagggtatatcaaaaatctaagcaaaccagctaaggctgctataagaatagcaatg atatatacttgggcatttgggaatgacgaaatatcttggatggaagcatcacagattgcacaaacacgtgcaaactttac attggatagcttaaagattttgacaccagtgacaacatcaacaaatctatcacacaggttaaaagatactgctactcaga tgaaattttctagtacatcacttattagagtaagcaggttcatcacaatatctaatgataatatgtctattaaagaagca aatgaaactaaagatacaaatcttatttatcaacaggtaatgttaacaggattaagtgtatttgaatatctatttaggtt agaggagagtacaggacataacccctatggtcatgcatctacatatagaggatggatgttgtataaaagagagttacaatg atgagcatatcaatccggagtctacattagagttaatcaaatacccctgagagtaatgaatttatatatgataaggaccct ttaaaggatatagatctatcaaaattaatggttataagagatcattcttatacaattgacatgaattactgggatgacac agatattgtacatgcaatatcaatatgtactgcagttacaatagcagatacaatgtcgcagctagatcgggataatctta aggagctggttgtgattgcaaatgatgatgatattaacagtctgataactgaatttctgaccctagatatactagtgttt ctcaaaacatttggagggttactcgtgaatcaatttgcatatacccctttatggattgaaaatagaaggaagggatcccat ttgggattatataatgagaacattaaaagacacctcacattcagtacttaaagtattatctaatgcactatctcatccaa aagtgtttaagagattttgggattgtggagttttgaatcctatttatggtcctaatactgctagtcaagatcaagttaag cttgctctctcgatttgcgagtactccttggatctatttatgagagaatggttgaatggagcatcacttgagatctatat ctgtgatagtgacatggaaatagcaaatgacagaagacaagcattttctctcaagacatcttgcctttgtgtgttgtttag cagagatagcatcttttggaccaaatttattaaatctaacatatctagagagacttgatgaattaaaacaatacttagat ctgaacatcaaagaagatcctactcttaaatatgtgcaagtatcaggactgttaattaaatcattcccctcaactgttac gtatgtaaggaaaactgcgattaagtatctgaggattcgtggtattaatccgcctgaaacgattgaagattgggatccca tagaagatgagaatatcttagacaatattgttaaaactgtaaatgacaattgcagtgataatcaaaagagaaatcaaagt agttatttctggggattagctctaaagaattatcaagtcgtgaaaataagatccataacgagtgattctgaagttaatga
``` agcttcgaatgttactacacatggaatgacacttcctcagggaggaagttatctatcacatcagctgaggttatttggag taaacagtacaagttgtcttaaagctcttgaattatcacaaatcttaatgagggaagttaaaaaagataaagatagactc tttttaggagaaggagcaggagctatgttagcatgttatgatgctacactcggtcctgcaataaattattataattctgg tttaaatattacagatgtaattggtcaacgggaattaaaaatcttcccatcagaagtatcattagtaggtaaaaaactag gaaatgtaacacagattcttaatcgggtgagggtgttatttaatgggaatcccaattcaacatggataggaaatatggaa tgtgagagtttaatatggagtgaattaaatgataagtcaattggtttagtacattgtgacatggagggagcgataggcaa atcagaagaaactgttctacatgaacattatagtattattaggattacatatttaatcggggatgatgatgttgtcctag tatcaaaaattataccaactattactccgaattggtctaaaatactctatctatacaagttgtattggaaggatgtaagt gtagtgtcccttaaaacatccaatcctgcctcaacagagctttatttaatttcaaaagatgcttactgtactgtaatgga acccagtaatcttgttttatcaaaacttaaaaggatatcatcaatagaagaaaataatctattaaagtggataatcttat caaaaaggaagaataacgagtggttacagcatgaaatcaaagaaggagaaagggattatgggataatgaggccatatcat acagcactgcaaattttggattccaaattaacttaaatcacttagctagagaatttttatcaactcctgatttaaccaa cattaataatataattcaaagttttacaagaacaattaaagatgttatgttcgaatgggtcaatatcactcatgacaata aaagacataaattaggaggaagatataatctattcccgcttaaaaataaggggaaattaagattattatcacgaagatta gtactaagctggatatcattatccttatcaaccagattactgacgggccgttttccagatgaaaaatttgaaaatagggc acagaccggatatgtatcattggctgatattgatttagaatccttaaagttattatcaagaaatattgtcaaaaattaca aagaacacataggattaatatcatactggttttgaccaaagaggtcaaaatactaatgaagcttataggaggagtcaaa ctactaggaattcctaaacagtacaaagagttagaggatcgatcatctcagggttatgaatatgataatgaatttgatat tgattaatacataaaaacataaaataaaacacctattcctcacccattcacttccaacaaaatgaaaagtaagaaaaaca tgtaatatatatataccaaacagagttttctcttgtttggt rB/HPIV3-RSV G_B3CT (SEQ ID NO: 94):
accaaacaagagaagagactggtttgggaatatattaattcaaataaaaattaacttaggattaaagaactttaccgaaagg taaggggaaagaaatcctaagagcttagccatgttgagtctattcgacacattcagtgcgcgtaggcaggagaacataac gaaatcagctggtggggctgttattcccgggcaaaaaaacactgtgtctatatttgctcttggaccatcaataacagatg acaatgataaaatgacattggctcttctctttttgtctcattctttagacaatgaaaagcagcatgcgcaaagagctgga ttttagtttctctgttatcaatggcttatgccaacccagaattatatttaacatcaaatggtagtaatgcagatgttaa atatgttatctacatgatagagaaagacccaggaagacagaaatatggtgggtttgtcgtcaagactagagagatggttt atgaaaagacaactgattggatgttcgggagtgatcttgagtatgatcaagacaatatgttgcaaaatggtagaagcact tctacaatcgaggatcttgttcatacttttggatatccatcgtgtcttggagcccttataatccaagtttggataatact tgttaaggctataaccagtatatcaggattgaggaaaggattcttactcggttagaagcatttcgacaagatggaacag ttaaatccagtctagtgttgagcggtgatgcagtagaacaaattggatcaattatgaggtcccaacagagcttggtaaca ctcatggttgaaacactgataacaatgaacacaggcaggaatgatctgacaacaatagaaaagaatatacagattgtagg aaactacatcagagatgcaggtctgcttcattttttcaacacaatcagatatggcattgagactagaatggcagctctaa ctctgtctacccttagaccggatatcaacagactcaaggcactgatcgagttatctatcaaaggggccacgtgctcct tttatatgcattttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactgggggtcacacaagaagccaag caaagcttgaagaaacacatgaagaacatcagcagttcagatacaacctttcataagcctacaggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaaggaaacagagtgacccgagatcaactgacatcac -continued aaacaacacaaatcaaactgaaatagatgatttgttcagtgcattcggaagcaactagtcacaaagagatgaccaggcgc gccaagtaagaaaaacttaggattaatggacctgcaggatggaatattggaaacacacaaacagcataaataacaccaac aatgaaaccgaaacagccagaggcaaacatagtagcaaggttacaaatgtagcacaaatcacattatccattctggcaat gataatctcaacttcacttataattgcagccatcatattcatagcctcggcaaaccacaaagtcacaccaacaactgcaa tcatacaagatgcaacaagccagatcaagaacacaaccccaacatacctcacccagaatcctcagcttggaatcagtccc tctaatccgtctgaaattacatcacaaatcaccaccatactagcttcaacaacaccaggagtcaagtcaaccctgcaatc cacaacagtcaagaccaaaaacacaacaacaactcaaacacaacccagcaagcccaccacaaaacaacgccaaaacaaac caccaagcaaacccaataatgattttcactttgaagtgttcaactttgtaccctgcagcatatgcagcaacaatccaacc tgctgggctatctgcaaaagaataccaaacaaaaaaccaggaaagaaaaccactaccaagcccacaaaaaaaccaaccct caagacaaccaaaaaagatcccaaacctcaaaccactaaatcaaaggaagtacccaccaccaagcccacagaagagccaa ccatcaacaccaccaaaacaaacatcataactacactactcacctccaacaccacaggaaatccagaactcacaagtcaa atggaaaccttccactcaacttcctccgaaggcaatccaagcccttctcaagtctctacaacatccgagtacccatcaca accttcatctccacccaacacaccacgccagtagtgatagctagcggcgcgccagcaacaagtaagaaaaacttaggatt aatggaaattatccaatccagagacggaaggacaaatccagaatccaaccacaactcaatcaaccaaagattcatggaag acaatgttcaaaacaatcaaatcatggattcttgggaagagggatcaggagataaatcatctgacatctcatcggccctc gacatcattgaattcatactcagcaccgactcccaagagaacacggcagacagcaatgaaatcaacacaggaaccacaag acttagcacgacaatctaccaacctgaatccaaaacaacagaaacaagcaaggaaaatagtggaccagctaacaaaaatc gacagtttgggcatcacacgaacgtgccacagagacaaaagatagaaatgttaatcaggagactgtacagggaggatat aggagaggaagcagcccagatagtagaactgagactatggtcactcgaagaatctccagaagcagcccagatcctaacaa tggaacccaaatccaggaagatattgattacaatgaagttggagagatggataaggactctactaagagggaaatgcgac aatttaaagatgttccagtcaaggtatcaggaagtgatgccattcctccaacaaaacaagatggagacggtgatgatgga agaggcctggaatctatcagtacatttgattcaggatataccagtatagtgactgccgcaacactagatgacgaagaaga actccttatgaagaacaacaggccaagaaagtatcaatcaacaccccagaacagtgacaagggaattaaaaaagggggttg gaaggccaaaagacacagacaaacaatcatcaatattggactacgaactcaacttcaaaggatcgaagaagagccagaaa atcctcaaagccagcacgaatacaggagaaccaacaagaccacagaatggatcccaggggaagagaatcacatcctggaa catcctcaacagcgagagcggcaatcgaacagaatcaacaaaccaaacccatcagacatcaacctcgggacagaaccaca caatgggaccaagcagaacaacctccgaaccaaggatcaagacacaaaagacggatggaaaggaaagagaggacacagaa gagagcactcgatttacagaaagggcgattacattattacagaatcttggtgtaatccaatctgcagcaaaattagacct ataccaagcaagagagttgtgtgtgtggcgaatgtcctaaacaatgcagatactgcatcaaagatagacttcctagcag gtttgatgataggagtgtcaatggatcatgataccaaattaaatcagattcagaacgagatattaagtttgaaaactgat cttaaaaagatggatgaatcacatagaagactaattgagaatcaaaaagaacaattatcactgatcacatcattaatctc aaatcttaaaattatgacagagagaggagggaagaaggaccaaccagaacctagcgggaggacatccatgatcaagacaa aagcaaaagaagagaaaataaagaaagtcaggtttgaccctcttatggaaacacagggcatcgagaaaaacatccctgac ctctatagatcaatagagaaaacaccagaaaacgacacacagatcaaatcagaaataaacagattgaatgatgaatccaa tgccactagattagtacctagaagaataagcagtacaatgagatcattaataataatcattaacaacagcaatttatcat caaaagcaaagcaatcatacatcaacgaactcaagctctgcaagagtgacgaggaagtgtctgagttgatggacatgttc aatgaggatgtcagctcccagtaaaccgccaaccaagggtcaacaccaagaaaaccaatagcacaaaacagccaatcaga gaccacccaatacaccaaaccaatcaacacataacaaagatcgcggccgcatagatgattaagaaaaacttaggatgaa aggactaatcaatcctccgaaacaatgagcatcaccaactccacaatctacacattcccagaatcctctttctccgagaa tggcaacatagagccgttaccactcaaggtcaatgaacagagaaaggccatacctcatattagggttgtcaagataggag -continued

```
atccgcccaaacatggatccagatatctggatgtcttttactgggcttctttgagatggaaaggtcaaaagacaggtat
gggagcataagtgatctagatgatgatccaagttacaaggtttgtggctctggatcattgccacttgggttggctagata
caccggaaatgatcaggaactcctacaggctgcaaccaagctcgatatagaagtaagaagaactgtaaaggctacggaga
tgatagtttacactgtacaaaacatcaaacctgaactatatccatggtccagtagattaagaaaagggatgttatttgac
gctaataaggttgcacttgctcctcaatgtcttccactagatagagggataaaattcagggtgatatttgtgaactgcac
agcaattggatcaataactctattcaaaatccctaagtccatggcattgttatcattgcctaatacaatatcaataaatc
tacaagtacatatcaaaacaggagttcagacagattccaaggagtagttcagattctagatgaaaaaggtgaaaaatca
ctaaatttcatggttcatctcgggttgatcaaaaggaagatgggcagaatgtactcagttgaatattgtaagcagaagat
cgagaagatgagattattattctcatgggattagttggagggatcagcttccacgtcaacgcaactggctctatatcaa
agacattagcaagtcaattagcattcaaaagagaaatctgctatcccctaatggatctgaatccacacttaaattcagtt
atatgggcatcatcagttgaaattacaagggtagatgcagttctccagccttcattacctggcgaattcagatactaccc
aaacatcatagcaaaaggggtcgggaaaatcagacagtaaaatcaacaaccctgatatccaccggtgtattaagccgaag
caaataaaggataatcaaaaacttaggacaaaagaggtcaataccaacaactattagcagtcacactcgcaagaataaga
gagaagggaccaaaaaagtcaaataggagaaatcaaaacaaaaggtacagaacaccagaacaacaaaatcaaaacatcca
actcactcaaaacaaaattccaaaagagaccggcaacacaacaagcactgaacacaatgccaacttcaatactgctaat
tattacaaccatgatcatggcatctttctgccaaatagatatcacaaaactacagcacgtaggtgtattggtcaacagtc
ccaaagggatgaagatatcacaaaactttgaaacaagatatctaattttgagcctcataccaaaaatagaagactctaac
tcttgtggtgaccaacagatcaagcaatacaagaagttattggatagactgatcatccctttatatgatggattaagatt
acagaaagatgtgatagtaaccaatcaagaatccaatgaaaacactgatcccagaacaaaacgattctttggagggtaa
ttggaaccattgctctgggagtagcaacctcagcacaaattacagcggcagttgctctggttgaagccaagcaggcaaga
tcagacatcgaaaaactcaaagaagcaattagggacacaaacaaagcagtgcagtcagttcagagctccataggaaattt
aatagtagcaattaaatcagtccaggattatgttaacaaagaaatcgtgccatcgattgcgaggctaggttgtgaagcag
caggacttcaattaggaattgcattaacacagcattactcagaattaacaaacatatttggtgataacataggatcgtta
caagaaaaggaataaaattacaaggtatagcatcattataccgcacaaatatcacagaaatattcacaacatcaacagt
tgataaatatgatatctatgatctgttatttacagaatcaataaaggtgagagttatagatgttgacttgaatgattact
caatcaccctccaagtcagactccctttattaactaggctgctgaacactcagatctacaaagtagattccatatcatat
aacatccaaaacagagaatggtatatccctcttcccagccatatcatgacgaaaggggcatttctaggtggagcagacgt
caaagaatgtatagaagcattcagcagctatatatgcccttctgatccaggatttgtattaaaccatgaaatagagagct
gcttatcaggaaacatatcccaatgtccaagaacaacggtcacatcagacattgttccaagatatgcatttgtcaatgga
ggagtggttgcaaactgtataacaaccacctgtacatgcaacggaattggtaatagaatcaatcaaccacctgatcaagg
agtaaaaattataacacataaagaatgtagtacaataggtatcaacggaatgctgttcaatacaaataaagaaggaactc
ttgcattctatacaccaaatgatataacactaaacaattctgttgcacttgatccaattgacatatcaatcgagctcaac
aaggccaaatcagatctagaagaatcaaaagaatggataagaaggtcaaatcaaaaactagattctattggaaattggca
tcaatctagcactacaatcataattattttgataatgatcattatattgtttataattaatataacgataattacaattg
caattaagtattacagaattcaaaagagaaatcgagtggatcaaaatgacaagccatatgtactaacaaacaataacat
atctacagatcattagatattaaaattataaaaaacttaggagtaaagttacgcaatccaactctactcatataattgag
gaaggacccaatagacaaatccaaattcgagatggaatactggaagcataccaatcacggaaaggatgctggtaatgagc
tggagacgtctatggctactcatggcaacaagctcactaataagataatatacatatattggacaataatcctggtgtta
ttatcaatagtcttcatcatagtgctaattaattccatcaaaagtgaaaaggcccacgaatcattgctgcaagacataaa
taatgagtttatggaaattacagaaaagatccaaatggcatcggataataccaatgatctaatacagtcaggagtgaata
caaggcttcttacaattcagagtcatgtccagaattacataccaatatcattgacacaacagatgtcagatcttaggaaa
```

-continued

```
ttcattagtgaaattacaattagaaatgataatcaagaagtgctgccacaaagaataacacatgatgtaggtataaaacc tttaaatccagatgattttggagatgcacgtctggtcttccatctttaatgaaaactccaaaaataaggttaatgccag ggccgggattattagctatgccaacgactgttgatggctgtgttagaactccgtctttagttataaatgatctgatttat gcttatacctcaaatctaattactcgaggttgtcaggatataggaaaatcatatcaagtcttacagatagggataataac tgtaaactcagacttggtacctgacttaaatcctaggatctctcatacctttaacataaatgacaataggaagtcatgtt ctctagcactcctaaatacagatgtatatcaactgtgttcaactcccaaagttgatgaaagatcagattatgcatcatca ggcatagaagatattgtacttgatattgtcaattatgatggttcaatctcaacaacaagatttaagaataataacataag ctttgatcaaccatatgctgcactatacccatctgttggaccagggatatactacaaaggcaaaataatatttctcgggt atggaggtcttgaacatccaataaatgagaatgtaatctgcaacacaactgggtgcccgggaaaacacagagagactgt aatcaagcatctcatagtccatggttttcagataggaggatggtcaactccatcattgttgttgacaaaggcttaaactc aattccaaaattgaaagtatggacgatatctatgcgacaaaattactgggggtcagaaggaaggttacttctactaggta acaagatctatatatatacaagatctacaagttggcatagcaagttacaattaggaataattgatattactgattacagt gatataaggataaaatggacatggcataatgtgctatcaagaccaggaaacaatgaatgtccatggggacattcatgtcc agatggatgtataacaggagtatatactgatgcatatccactcaatcccacagggagcattgtgtcatctgtcatattag actcacaaaaatcgagagtgaacccagtcataacttactcaacagcaaccgaaagagtaaacgagctggccatcctaaac agaacactctcagctggatatacaacaacaagctgcattacacactataacaaaggatattgttttcatatagtagaaat aaatcataaaagcttaaacacatttcaacccatgttgttcaaaacagagattccaaaaagctgcagttaatcataattaa ccataatatgcatcaatctatctataatacaagtatatgataagtaatcagcaatcagacaatagacgtacggaaataat aaaaaacttaggagaaaagtgtgcaagaaaaatggacaccgagtcccacagcggcacaacatctgacattctgtaccctg aatgtcacctcaattctcctatagttaaaggaaagatagcacaactgcatacaataatgagtttgcctcagccctacgat atggatgatgattcaatactgattattactagacaaaaaattaaactcaataaattagataaaagacaacggtcaattag gaaattaagatcagtcttaatggaaagagtaagtgatctaggtaaatataccttatcagatatccagagatgtctagtg aaatgttccaattatgtatacccggaattaataataaaataaatgaattgctaagtaaagcaagtaaaacatataatcaa atgactgatggattaagagatctatggggttactatactatcgaagttagcatcgaaaaatgatggaagtaattatgatat caatgaagatattagcaatatatcaaatgttcacatgacttatcaatcagacaaatggtataatccattcaagacatggt ttactattaagtatgacatgagaagattacaaaaagccaaaaatgagattacattcaataggcataaagattataatcta ttagaagaccaaaagaatatattgctgatacatccagaactcgtcttaatattagataaacaaaattacaatgggtatat aatgactcctgaattggtactaatgtattgtgatgtagttgaagggaggtggaatataagttcatgtgcaaaattggatc ctaagttacaatcaatgtattataagggtaacaatttatgggaaataatagatggactattctcgaccttaggagaaaga acatttgacataatatcactattagaaccacttgcattatcgctcattcaaacttatgacccggttaaacagctcagggg ggcttttttaaatcacgtgttatcagaaatggaattaatatttgcagctgagtgtacaacagaggaaatacctaatgtgg attatatagataaaattttagatgtgttcaaagaatcaacaatagatgaaatagcagaaattttctctttcttccgaact tttggacaccctccattagaggcgagtatagcagcagagaaagttagaaagtatatgtatactgagaaatgcttgaaatt tgatactatcaataaatgtcatgctattttttgtacaataattataaatggatatagagaaagacatggtggtcaatggc ctccagttacattacctgtccatgcacatgaatttatcataaatgcatacggatcaaattctgccatatcatatgagaat gctgtagattattataagagcttcataggaataaaatttgacaagtttatagagcctcaattggatgaagacttaactat ttatatgaaagataaagcattatccccaaagaaatcaaactgggacacagtctatccagcttcaaacctgttataccgca ctaatgtgtctcatgattcacgaagattggttgaagtatttatagcagatagtaaatttgatccccaccaagtattagat tacgtagaatcaggatattggctggatgatcctgaatttaatatctcatatagtttaaaagagaaagaaatttaaaacaaga aggtagacttttgcaaaaatgacatacaagatgagggctacacaagtattatcagaaacattattggcgaataatatag
```

-continued ggaaattcttccaagagaatgggatggttaaaggagaaattgaattactcaagagactaacaacaatatctatgtctgga gttccgcggtataatgaggtatacaataattcaaaaagtcacacagaagaacttcaagcttataatgcaattagcagttc caatttatcttctaatcagaagtcaaagaagtttgaatttaaatctacagatatatacaatgatggatacgaaaccgtaa gctgcttcttaacgacagatcttaaaaaatattgtttaaattggaggtatgaatcaacagctttattcggtgatacttgt aatcagatatttgggttaaaggaattatttaattggctgcaccctcgccttgaaaagagtacaatatatgttggagatcc ttattgcccgccatcagatattgaacatttaccacttgatgaccatcctgattcaggattttatgttcataatcctaaag gaggaatagaagggttttgccaaaagttatggacactcatatctatcagtgcaatacatttagcagctgtcaaaatcggt gtaagagttactgcaatggttcaaggggataatcaagccatagctgttaccacaagagtacctaataattatgattataa agttaagaaagagattgtttataaagatgtggtaagatttttgattccttgagagaggtgatggatgatctgggtcatg agctcaaactaaatgaaactataataagtagtaaaatgtttatatatagcaaaaggatatactatgacggaagaatcctt cctcaggcattaaaagcattgtctagatgtgttttttggtctgaaacaatcatagatgagacaagatcagcatcctcaaa tctggctacatcgtttgcaaaggccattgagaatggctactcacctgtattgggatatgtatgctcaatcttcaaaaata tccaacagttgtatatagcgcttggaatgaatataaacccaactataacccaaaatattaaagatcaatatttcaggaat attcattggatgcaatatgcctccttaatccctgctagtgtcggaggatttaattatatggccatgtcaaggtgttttgt cagaaacattggagatcctacagtcgctgcgttagccgatattaaaagatttataaaagcaaatttgttagatcgaggtg tcctttacagaattatgaatcaagaaccaggcgagtcttcttttttagactgggcctcagatccctattcatgtaactta ccacaatctcaaaatataaccaccatgataaagaatataactgcaagaaatgtactacaggactcaccaaacccattact atctggattatttacaagtacaatgatagaagaggatgaggaattagctgagttcctaatggacaggagaataatcctcc caagagttgcacatgacattttagataattctcttactggaattaggaatgctatagctggtatgttggatacaacaaaa tcactaattcgagtagggataagcagaggaggattaacctataacttattaagaaagataagcaactatgatcttgtaca atatgagacacttagtaaaactttaagactaatagtcagtgacaagattaagtatgaagatatgtgctcagtagacctag ccatatcattaagacaaaaaatgtggatgcatttatcaggaggaagaatgataaatggacttgaaactccagatccttta gagttactgtctggagtaataataacaggatctgaacattgtaggatatgttattcaactgaaggtgaaagcccatatac atggatgtatttaccaggcaatcttaatataggatcagctgagacaggaatagcatcattaagggtcccttactttggat cagttacagatgagagatctgaagcacaattagggtatatcaaaaatctaagcaaaccagctaaggctgctataagaata gcaatgatatatacttgggcatttgggaatgacgaaatatcttggatggaagcatcacagattgcacaaacacgtgcaaa ctttacattggatagcttaaagattttgacaccagtgacaacatcaacaaatctatcacacaggttaaaagatactgcta ctcagatgaaattttctagtacatcacttattagagtaagcaggttcatcacaatatctaatgataatatgtctattaaa gaagcaaatgaaactaaagatacaaatcttatttatcaacaggtaatgttaacaggattaagtgtatttgaatatctatt taggttagaggagagtacaggacataaccctatggtcatgcatctacatatagaggatggatgttgtataaaagagagtt acaatgatgagcatatcaatccggagtctacattagagttaatcaaatacccctgagagtaatgaatttatatatgataag gaccctttaaaggatatagatctatcaaaattaatggttataagagatcattcttatacaattgacatgaattactggga tgacacagatattgtacatgcaatatcaatatgtactgcagttacaatagcagatacaatgtcgcagctagatcgggata atcttaaggagctggttgtgattgcaaatgatgatgatattaacagtctgataactgaatttctgaccctagatatacta gtgtttctcaaaacatttggagggttactcgtgaatcaatttgcatatacccctttatggattgaaaatagaaggaaggga tcccatttgggattatataatgagaacattaaaagacacctcacattcagtacttaaagtattatctaatgcactatctc atccaaaagtgtttaagagattttgggattgtggagttttgaatcctatttatggtcctaatactgctagtcaagatcaa gttaagcttgctctctcgatttgcgagtactccttggatctatttatgagagaatggttgaatggagcatcacttgagat ctatatctgtgatagtgacatggaaatagcaaatgacagaagacaagcatttctctcaagacatcttgcctttgtgtgtt gtttagcagagatagcatcttttggaccaaatttattaaatctaacatatctagagagacttgatgaattaaaacaatac ttagatctgaacatcaaagaagatcctactcttaaatatgtgcaagtatcaggactgttaattaaatcattcccctcaac -continued tgttacgtatgtaaggaaaactgcgattaagtatctgaggattcgtggtattaatccgcctgaaacgattgaagattggg atcccatagaagatgagaatatcttagacaatattgttaaaactgtaaatgacaattgcagtgataatcaaaagagaaat aaaagtagttatttctggggattagctctaaagaattatcaagtcgtgaaaataagatccataacgagtgattctgaagt taatgaagcttcgaatgttactacacatggaatgacacttcctcagggaggaagttatctatcacatcagctgaggttat ttggagtaaacagtacaagttgtcttaaagctcttgaattatcacaaatcttaatgagggaagttaaaaaagataaagat agactctttttaggagaaggagcaggagctatgttagcatgttatgatgctacactcggtcctgcaataaattattataa ttctggtttaaatattacagatgtaattggtcaacgggaattaaaaatcttcccatcagaagtatcattagtaggtaaaa aactaggaaatgtaacacagattcttaatcgggtgagggtgttatttaatgggaatcccaattcaacatggataggaaat atggaatgtgagagtttaatatggagtgaattaaatgataagtcaattggtttagtacattgtgacatggagggagcgat aggcaaatcagaagaaactgttctacatgaacattatagtattattaggattacatatttaatcggggatgatgatgttg tcctagtatcaaaaattataccaactattactccgaattggtctaaaatactctatctatacaagttgtattggaaggat gtaagtgtagtgtcccttaaaacatccaatcctgcctcaacagagctttatttaatttcaaaagatgcttactgtactgt aatggaacccagtaatcttgttttatcaaaacttaaaggatatcatcaatagaagaaaataatctattaaagtggataa tcttatcaaaaaggaagaataacgagtggttacagcatgaaatcaaagaaggagaaagggattatgggataatgaggcca tatcatacagcactgcaaatttttggattccaaattaacttaaatcacttagctagagaatttttatcaactcctgattt aaccaacattaataatataattcaaagttttacaagaacaattaaagatgttatgttcgaatgggtcaatatcactcatg acaataaaagacataaattaggaggaagatataatctattcccgcttaaaaataaggggaaattaagattattatcacga agattagtactaagctggatatcattatccttatcaaccagattactgacgggccgttttccagatgaaaaatttgaaaa tagggcacagaccggatatgtatcattggctgatattgatttagaatccttaaagttattatcaagaaatattgtcaaaa attacaaagaacacataggattaatatcatactggtttttgaccaaagaggtcaaaatactaatgaagcttataggagga gtcaaactactaggaattcctaaacagtacaaagagttagaggatcgatcatctcagggttatgaatatgataatgaatt tgatattgattaatacataaaaacataaaataaaacacctattcctcacccattcacttccaacaaaatgaaaagtaaga aaaacatgtaatatatatataccaaacagagtttttctcttgtttggt It will be apparent that the precise details of the methods or compositions described may be varied or modified without departing from the spirit of the described embodiments. We claim all such modifications and variations that fall within the scope and spirit of the claims below.

The invention claimed is:

1. A recombinant chimeric bovine/human parainfluenza virus 3 (rB/HPIV3), comprising:
a genome comprising, in a 3' to 5' order, a 3' leader region, a BPIV3 N gene, a heterologous gene, BPIV3 P and M genes, HPIV3 F and HN genes, a BPIV3 L gene, and a 5' trailer region;
wherein the heterologous gene encodes one of:
(a) a RSV G protein comprising an RSV G ectodomain, transmembrane domain, and cytoplasmic tail, wherein the heterologous gene is codon optimized for human expression and comprises an antigenomic cDNA sequence set forth as SEQ ID NO: 89 or 90;
(b) a recombinant RSV G protein comprising a RSV G ectodomain, a BPIV3 HN transmembrane domain, and a BPIV3 HN cytoplasmic tail;
(c) a recombinant RSV G protein comprising a RSV G ectodomain, a HPIV3 HN transmembrane domain, and a HPIV3 HN cytoplasmic tail; or
(d) a recombinant RSV G protein comprising a RSV G ectodomain, a HPIV1 HN transmembrane domain, and a HPIV1 HN cytoplasmic tail;
wherein the HPIV3 HN gene encodes a HPIV3 HN protein comprising threonine and proline residues at positions 263 and 370, wherein the residue numbering is according to the HPIV3 HN protein sequence set forth as SEQ ID NO: 7; and
wherein the recombinant B/HPIV3 is infectious, attenuated, and self-replicating.

2. The rB/HPIV3 of claim 1, wherein the RSV G ectodomain comprises or consists of the amino acid sequence set forth as any one of SEQ ID NOs: 23, 48, 50, 52, or 54 or an amino acid sequence at least 90% identical thereto.

3. The rB/HPIV3 of claim 1, wherein:
the BPIV3 HN transmembrane domain and cytoplasmic tail comprises or consists of the amino acid sequence set forth as SEQ ID NO: 29, or an amino acid sequence at least 90% identical thereto;
the HPIV3 HN transmembrane domain and cytoplasmic tail comprises or consists of the amino acid sequence set forth as SEQ ID NO: 57, or an amino acid sequence at least 90% identical thereto; or
the HPIV1 HN transmembrane domain and cytoplasmic tail comprises or consists of the amino acid sequence set forth as SEQ ID NO: 60, or an amino acid sequence at least 90% identical thereto.

4. The rB/HPIV3 of claim 1, wherein the RSV G protein comprises or consists of the amino acid sequence set forth as any one of SEQ ID NOs: 22, 47, 49, 51, 53 or an amino acid sequence at least 90% identical thereto.

5. The rB/HPIV3 of claim 1, wherein the RSV G ectodomain is from a human subtype A RSV or human subtype B RSV.

6. The rB/HPIV3 of claim 1, wherein the RSV G protein is a wild-type RSV G protein from a human subtype A RSV or human subtype B RSV.

7. The rB/HPIV3 of claim 1, wherein:
the BPIV3 N gene encodes an N protein comprising or consisting of the amino acid sequence set forth as SEQ ID NO: 1, or an amino acid sequence at least 90% identical thereto;
the BPIV3 P gene encodes P, C, and V proteins comprising or consisting of the amino acid sequences set forth as SEQ ID NOs: 2, 3, and 4, respectively, or amino acid sequences at least 90% identical thereto;
the BPIV3 M gene encodes an M protein comprising or consisting of the amino acid sequence set forth as SEQ ID NO: 5, or an amino acid sequence at least 90% identical thereto;
the HPIV3 F gene encodes an F protein comprising or consisting of the amino acid sequence set forth as SEQ ID NO: 6, or an amino acid sequence at least 90% identical thereto;
the HPIV3 HN gene encodes an HN protein comprising or consisting of the amino acid sequence set forth as SEQ ID NO: 7, or an amino acid sequence at least 90% identical to SEQ ID NO: 7; and/or
the BPIV3 L gene encodes an L protein comprising or consisting of the amino acid sequence set forth as SEQ ID NO: 10, or an amino acid sequence at least 90% identical thereto.

8. The rB/HPIV3 of claim 1, wherein the heterologous gene is codon-optimized for expression in human cells.

9. The rB/HPIV3 of claim 1, wherein the genome comprises an antigenomic cDNA sequence set forth as SEQ ID NO: 91 or 92.

10. The rB/HPIV3 of claim 1, wherein:
the rB/HPIV3 induces an immune response to RSV G protein, HPIV3 F protein, and HPIV3 HN protein; and/or
the rB/HPIV3 induces an immune response that neutralizes RSV and HPIV3.

11. A nucleic acid molecule comprising the nucleotide sequence of the genome of the rB/HPIV3 of claim 1, or an antigenomic cDNA or RNA sequence of the genome.

12. A vector comprising the isolated nucleic acid molecule of claim 11.

13. An isolated host cell comprising the nucleic acid molecule or vector of claim 11.

14. A method of producing a rB/HPIV3, comprising:
transfecting a permissive cell culture with the vector of claim 13;
incubating the cell culture for a sufficient period of time to allow for viral replication; and
purifying the replicated virus to produce the rB/HPIV3.

15. A rB/HPIV3 produced by the method of claim 14.

16. An immunogenic composition comprising the rB/HPIV3 of claim 1 and a pharmaceutically acceptable carrier.

17. A method of eliciting an immune response to respiratory syncytial virus and human parainfluenza virus 3 in a subject comprising administering the immunogenic composition of claim 16 to the subject to generate the immune response.

18. The method of claim 17, comprising intranasal administration of the immunogenic composition.

19. The method of claim 17, wherein the subject is a human;

the subject is less than one year old; and/or the immune response is a protective immune response.

20. The rB/HPIV3 of claim 1, wherein the heterologous gene encodes the RSV G protein comprising the RSV G ectodomain, transmembrane domain, and cytoplasmic tail, and wherein the heterologous gene comprises the antigenomic cDNA sequence set forth as SEQ ID NO: 89.

* * * * *

SEQUENCE LISTING

<160> NUMBER OF SEQ ID NOS: 95

<210> SEQ ID NO 1
<211> LENGTH: 515
<212> TYPE: PRT
<213> ORGANISM: bovine parainfluenza virus 3

<400> SEQUENCE: 1

Met Leu Ser Leu Phe Asp Thr Phe Ser Ala Arg Arg Gln Glu Asn Ile
1               5                   10                  15

Thr Lys Ser Ala Gly Gly Ala Val Ile Pro Gly Gln Lys Asn Thr Val
            20                  25                  30

Ser Ile Phe Ala Leu Gly Pro Ser Ile Thr Asp Asp Asn Asp Lys Met
        35                  40                  45

Thr Leu Ala Leu Leu Phe Leu Ser His Ser Leu Asp Asn Glu Lys Gln
    50                  55                  60

His Ala Gln Arg Ala Gly Phe Leu Val Ser Leu Leu Ser Met Ala Tyr

```
                65                  70                  75                  80
Ala Asn Pro Glu Leu Tyr Leu Thr Ser Asn Gly Ser Asn Ala Asp Val
                    85                  90                  95

Lys Tyr Val Ile Tyr Met Ile Glu Lys Asp Pro Gly Arg Gln Lys Tyr
                    100                 105                 110

Gly Gly Phe Val Val Lys Thr Arg Glu Met Val Tyr Glu Lys Thr Thr
                    115                 120                 125

Asp Trp Met Phe Gly Ser Asp Leu Glu Tyr Asp Gln Asp Asn Met Leu
                    130                 135                 140

Gln Asn Gly Arg Ser Thr Ser Thr Ile Glu Asp Leu Val His Thr Phe
145                 150                 155                 160

Gly Tyr Pro Ser Cys Leu Gly Ala Leu Ile Ile Gln Val Trp Ile Ile
                    165                 170                 175

Leu Val Lys Ala Ile Thr Ser Ile Ser Gly Leu Arg Lys Gly Phe Phe
                    180                 185                 190

Thr Arg Leu Glu Ala Phe Arg Gln Asp Gly Thr Val Lys Ser Ser Leu
                    195                 200                 205

Val Leu Ser Gly Asp Ala Val Glu Gln Ile Gly Ser Ile Met Arg Ser
                    210                 215                 220

Gln Gln Ser Leu Val Thr Leu Met Val Glu Thr Leu Ile Thr Met Asn
225                 230                 235                 240

Thr Gly Arg Asn Asp Leu Thr Thr Ile Glu Lys Asn Ile Gln Ile Val
                    245                 250                 255

Gly Asn Tyr Ile Arg Asp Ala Gly Leu Ala Ser Phe Phe Asn Thr Ile
                    260                 265                 270

Arg Tyr Gly Ile Glu Thr Arg Met Ala Ala Leu Thr Leu Ser Thr Leu
                    275                 280                 285

Arg Pro Asp Ile Asn Arg Leu Lys Ala Leu Ile Glu Leu Tyr Leu Ser
                    290                 295                 300

Lys Gly Pro Arg Ala Pro Phe Ile Cys Ile Leu Arg Asp Pro Val His
305                 310                 315                 320

Gly Glu Phe Ala Pro Gly Asn Tyr Pro Ala Leu Trp Ser Tyr Ala Met
                    325                 330                 335

Gly Val Ala Val Val Gln Asn Lys Ala Met Gln Gln Tyr Val Thr Gly
                    340                 345                 350

Arg Ser Tyr Leu Asp Ile Glu Met Phe Gln Leu Gly Gln Ala Val Ala
                    355                 360                 365

Arg Asp Ala Glu Ser Gln Met Ser Ser Ile Leu Glu Asp Glu Leu Gly
                    370                 375                 380

Val Thr Gln Glu Ala Lys Gln Ser Leu Lys Lys His Met Lys Asn Ile
385                 390                 395                 400

Ser Ser Ser Asp Thr Thr Phe His Lys Pro Thr Gly Gly Ser Ala Ile
                    405                 410                 415

Glu Met Ala Ile Asp Glu Glu Ala Gly Gln Pro Glu Ser Arg Gly Asp
                    420                 425                 430

Gln Asp Gln Gly Asp Glu Pro Arg Ser Ser Ile Val Pro Tyr Ala Trp
                    435                 440                 445

Ala Asp Glu Thr Gly Asn Asp Asn Gln Thr Glu Ser Thr Thr Glu Ile
                    450                 455                 460

Asp Ser Ile Lys Thr Glu Gln Arg Asn Ile Arg Asp Arg Leu Asn Lys
465                 470                 475                 480

Arg Leu Asn Glu Lys Arg Lys Gln Ser Asp Pro Arg Ser Thr Asp Ile
                    485                 490                 495
```

```
Thr Asn Asn Thr Asn Gln Thr Glu Ile Asp Asp Leu Phe Ser Ala Phe
                500                 505                 510

Gly Ser Asn
        515

<210> SEQ ID NO 2
<211> LENGTH: 596
<212> TYPE: PRT
<213> ORGANISM: bovine parainfluenza virus 3

<400> SEQUENCE: 2

Met Glu Asp Asn Val Gln Asn Asn Gln Ile Met Asp Ser Trp Glu Glu
1               5                   10                  15

Gly Ser Gly Asp Lys Ser Ser Asp Ile Ser Ser Ala Leu Asp Ile Ile
            20                  25                  30

Glu Phe Ile Leu Ser Thr Asp Ser Gln Glu Asn Thr Ala Asp Ser Asn
        35                  40                  45

Glu Ile Asn Thr Gly Thr Thr Arg Leu Ser Thr Thr Ile Tyr Gln Pro
    50                  55                  60

Glu Ser Lys Thr Thr Glu Thr Ser Lys Glu Asn Ser Gly Pro Ala Asn
65                  70                  75                  80

Lys Asn Arg Gln Phe Gly Ala Ser His Glu Arg Ala Thr Glu Thr Lys
                85                  90                  95

Asp Arg Asn Val Asn Gln Glu Thr Val Gln Gly Gly Tyr Arg Arg Gly
                100                 105                 110

Ser Ser Pro Asp Ser Arg Thr Glu Thr Met Val Thr Arg Arg Ile Ser
            115                 120                 125

Arg Ser Ser Pro Asp Pro Asn Asn Gly Thr Gln Ile Gln Glu Asp Ile
130                 135                 140

Asp Tyr Asn Glu Val Gly Glu Met Asp Lys Asp Ser Thr Lys Arg Glu
145                 150                 155                 160

Met Arg Gln Phe Lys Asp Val Pro Val Lys Val Ser Gly Ser Asp Ala
                165                 170                 175

Ile Pro Pro Thr Lys Gln Asp Gly Asp Gly Asp Asp Gly Arg Gly Leu
            180                 185                 190

Glu Ser Ile Ser Thr Phe Asp Ser Gly Tyr Thr Ser Ile Val Thr Ala
        195                 200                 205

Ala Thr Leu Asp Asp Glu Glu Glu Leu Leu Met Lys Asn Asn Arg Pro
    210                 215                 220

Arg Lys Tyr Gln Ser Thr Pro Gln Asn Ser Asp Lys Gly Ile Lys Lys
225                 230                 235                 240

Gly Val Gly Arg Pro Lys Asp Thr Asp Lys Gln Ser Ser Ile Leu Asp
                245                 250                 255

Tyr Glu Leu Asn Phe Lys Gly Ser Lys Lys Ser Gln Lys Ile Leu Lys
            260                 265                 270

Ala Ser Thr Asn Thr Gly Glu Pro Thr Arg Pro Gln Asn Gly Ser Gln
        275                 280                 285

Gly Lys Arg Ile Thr Ser Trp Asn Ile Leu Asn Ser Glu Ser Gly Asn
    290                 295                 300

Arg Thr Glu Ser Thr Asn Gln Thr His Gln Thr Ser Thr Ser Gly Gln
305                 310                 315                 320

Asn His Thr Met Gly Pro Ser Arg Thr Thr Ser Glu Pro Arg Ile Lys
                325                 330                 335

Thr Gln Lys Thr Asp Gly Lys Glu Arg Glu Asp Thr Glu Glu Ser Thr
```

```
            340                 345                 350

Arg Phe Thr Glu Arg Ala Ile Thr Leu Leu Gln Asn Leu Gly Val Ile
        355                 360                 365

Gln Ser Ala Ala Lys Leu Asp Leu Tyr Gln Asp Lys Arg Val Val Cys
    370                 375                 380

Val Ala Asn Val Leu Asn Asn Ala Asp Thr Ala Ser Lys Ile Asp Phe
385                 390                 395                 400
Leu Ala Gly Leu Met Ile Gly Val Ser Met Asp His Asp Thr Lys Leu
                405                 410                 415
Asn Gln Ile Gln Asn Glu Ile Leu Ser Leu Lys Thr Asp Leu Lys Lys
            420                 425                 430
Met Asp Glu Ser His Arg Arg Leu Ile Glu Asn Gln Lys Glu Gln Leu
        435                 440                 445
Ser Leu Ile Thr Ser Leu Ile Ser Asn Leu Lys Ile Met Thr Glu Arg
    450                 455                 460
Gly Gly Lys Lys Asp Gln Pro Glu Pro Ser Gly Arg Thr Ser Met Ile
465                 470                 475                 480
Lys Thr Lys Ala Lys Glu Glu Lys Ile Lys Lys Val Arg Phe Asp Pro
                485                 490                 495
Leu Met Glu Thr Gln Gly Ile Glu Lys Asn Ile Pro Asp Leu Tyr Arg
            500                 505                 510
Ser Ile Glu Lys Thr Pro Glu Asn Asp Thr Gln Ile Lys Ser Glu Ile
        515                 520                 525
Asn Arg Leu Asn Asp Glu Ser Asn Ala Thr Arg Leu Val Pro Arg Arg
    530                 535                 540

Ile Ser Ser Thr Met Arg Ser Leu Ile Ile Ile Ile Asn Asn Ser Asn
545                 550                 555                 560
Leu Ser Ser Lys Ala Lys Gln Ser Tyr Ile Asn Glu Leu Lys Leu Cys
                565                 570                 575
Lys Ser Asp Glu Glu Val Ser Glu Leu Met Asp Met Phe Asn Glu Asp
            580                 585                 590
Val Ser Ser Gln
        595

<210> SEQ ID NO 3
<211> LENGTH: 201
<212> TYPE: PRT
<213> ORGANISM: bovine parainfluenza virus 3

<400> SEQUENCE: 3

Met Phe Lys Thr Ile Lys Ser Trp Ile Leu Gly Lys Arg Asp Gln Glu
1               5                   10                  15

Ile Asn His Leu Thr Ser His Arg Pro Ser Thr Ser Leu Asn Ser Tyr
            20                  25                  30

Ser Ala Pro Thr Pro Lys Arg Thr Arg Gln Thr Ala Met Lys Ser Thr
        35                  40                  45

Gln Glu Pro Gln Asp Leu Ala Arg Gln Ser Thr Asn Leu Asn Pro Lys
    50                  55                  60

Gln Gln Lys Gln Ala Arg Lys Ile Val Asp Gln Leu Thr Lys Ile Asp
65                  70                  75                  80

Ser Leu Gly His His Thr Asn Val Pro Gln Arg Gln Lys Ile Glu Met
                85                  90                  95

Leu Ile Arg Arg Leu Tyr Arg Glu Asp Ile Gly Glu Glu Ala Ala Gln
            100                 105                 110
```

```
Ile Val Glu Leu Arg Leu Trp Ser Leu Glu Ser Pro Glu Ala Ala
            115                 120                 125

Gln Ile Leu Thr Met Glu Pro Lys Ser Arg Lys Ile Leu Ile Thr Met
130                 135                 140

Lys Leu Glu Arg Trp Ile Arg Thr Leu Leu Arg Gly Lys Cys Asp Asn
145                 150                 155                 160

Leu Lys Met Phe Gln Ser Arg Tyr Gln Glu Val Met Pro Phe Leu Gln
                165                 170                 175

Gln Asn Lys Met Glu Thr Val Met Met Glu Gly Ala Trp Asn Leu Ser
            180                 185                 190

Val His Leu Ile Gln Asp Ile Pro Val
            195                 200

<210> SEQ ID NO 4
<211> LENGTH: 412
<212> TYPE: PRT
<213> ORGANISM: bovine parainfluenza virus 3

<400> SEQUENCE: 4

Met Glu Asp Asn Val Gln Asn G

```
Gly Glu Glu Asn His Ile Leu Glu His Pro Gln Gln Arg Glu Arg Gln
        290                 295                 300

Ser Asn Arg Ile Asn Lys Pro Asn Pro Ser Asp Ile Asn Leu Gly Thr
305                 310                 315                 320

Glu Pro His Asn Gly Thr Lys Gln Asn Asn Leu Arg Thr Lys Asp Gln
                325                 330                 335

Asp Thr Lys Asp Gly Trp Lys Gly Lys Arg Gly His Arg Arg Glu His
                340                 345                 350

Ser Ile Tyr Arg Lys Gly Asp Tyr Ile Ile Thr Glu Ser Trp Cys Asn
            355                 360                 365

Pro Ile Cys Ser Lys Ile Arg Pro Ile Pro Arg Gln Glu Ser Cys Val
        370                 375                 380

Cys Gly Glu Cys Pro Lys Gln Cys Arg Tyr Cys Ile Lys Asp Arg Leu
385                 390                 395                 400

Pro Ser Arg Phe Asp Asp Arg Ser Val Asn Gly Ser
                405                 410

<210> SEQ ID NO 5
<211> LENGTH: 351
<212> TYPE: PRT
<213> ORGANISM: bovine parainfluenza virus 3

<400> SEQUENCE: 5

Met Ser Ile Thr Asn Ser Thr Ile Tyr Thr Phe Pro Glu Ser Ser Phe
1               5                   10                  15

Ser Glu Asn Gly Asn Ile Glu Pro Leu Pro Leu Lys Val Asn Glu Gln
            20                  25                  30

Arg Lys Ala Ile Pro His Ile Arg Val Val Lys Ile Gly Asp Pro Pro
        35                  40                  45

Lys His Gly Ser Arg Tyr Leu Asp Val Phe Leu Leu Gly Phe Phe Glu
    50                  55                  60

Met Glu Arg Ser Lys Asp Arg Tyr Gly Ser Ile Ser Asp Leu Asp Asp
65                  70                  75                  80

Asp Pro Ser Tyr Lys Val Cys Gly Ser Gly Ser Leu Pro Leu Gly Leu
                85                  90                  95

Ala Arg Tyr Thr Gly Asn Asp Gln Glu Leu Leu Gln Ala Ala Thr Lys
            100                 105                 110

Leu Asp Ile Glu Val Arg Arg Thr Val Lys Ala Thr Glu Met Ile Val
        115                 120                 125

Tyr Thr Val Gln Asn Ile Lys Pro Glu Leu Tyr Pro Trp Ser Ser Arg
    130                 135                 140

Leu Arg Lys Gly Met Leu Phe Asp Ala Asn Lys Val Ala Leu Ala Pro
145                 150                 155                 160

Gln Cys Leu Pro Leu Asp Arg Gly Ile Lys Phe Arg Val Ile Phe Val
                165                 170                 175

Asn Cys Thr Ala Ile Gly Ser Ile Thr Leu Phe Lys Ile Pro Lys Ser
            180                 185                 190

Met Ala Leu Leu Ser Leu Pro Asn Thr Ile Ser Ile Asn Leu Gln Val
        195                 200                 205

His Ile Lys Thr Gly Val Gln Thr Asp Ser Lys Gly Val Val Gln Ile
    210                 215                 220

Leu Asp Glu Lys Gly Glu Lys Ser Leu Asn Phe Met Val His Leu Gly
225                 230                 235                 240

Leu Ile Lys Arg Lys Met Gly Arg Met Tyr Ser Val Glu Tyr Cys Lys
```

```
                    245                 250                 255
Gln Lys Ile Glu Lys Met Arg Leu Leu Phe Ser Leu Gly Leu Val Gly
            260                 265                 270

Gly Ile Ser Phe His Val Asn Ala Thr Gly Ser Ile Ser Lys Thr Leu
            275                 280                 285

Ala Ser Gln Leu Ala Phe Lys Arg Glu Ile Cys Tyr Pro Leu Met Asp
        290                 295                 300

Leu Asn Pro His Leu Asn Ser Val Ile Trp Ala Ser Ser Val Glu Ile
305                 310                 315                 320

Thr Arg Val Asp Ala Val Leu Gln Pro Ser Leu Pro Gly Glu Phe Arg
                325                 330                 335

Tyr Tyr Pro Asn Ile Ile Ala Lys Gly Val Gly Lys Ile Arg Gln
                340                 345                 350

<210> SEQ ID NO 6
<211> LENGTH: 539
<212> TYPE: PRT
<213> ORGANISM: human parainfluenza virus 3

<400> SEQUENCE: 6

Met Pro Thr Ser Ile Leu Leu Ile Ile Thr Thr Met Ile Met Ala Ser
1               5                   10                  15

Phe Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr
        35                  40                  45

Leu Ile Leu Ser Leu Ile Pro Lys Ile Glu Asp Ser Asn Ser Cys Gly
    50                  55                  60

Asp Gln Gln Ile Lys Gln Tyr Lys Lys Leu Leu Asp Arg Leu Ile Ile
65                  70                  75                  80

Pro Leu Tyr Asp Gly Leu Arg Leu Gln Lys Asp Val Ile Val Thr Asn
                85                  90                  95

Gln Glu Ser Asn Glu Asn Thr Asp Pro Arg Thr Lys Arg Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270
```

```
Asp Tyr Ser Ile Thr Leu Gln Val Arg Leu Pro Leu Leu Thr Arg Leu
            275                 280                 285

Leu Asn Thr Gln Ile Tyr Lys Val Asp Ser Ile Ser Tyr Asn Ile Gln
        290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Ile
                340                 345                 350

Glu Ser Cys Leu Ser Gly Asn Ile Ser Gln Cys Pro Arg Thr Thr Val
            355                 360                 365

Thr Ser Asp Ile Val Pro Arg Tyr Ala Phe Val Asn Gly Gly Val Val
        370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Ser Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Ile Leu Ile Met Ile Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
    530                 535

<210> SEQ ID NO 7
<211> LENGTH: 572
<212> TYPE: PRT
<213> ORGANISM: human parainfluenza virus 3

<400> SEQUENCE: 7

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110
```

```
Ser Leu Thr Gln Gln Met Ser Asp Leu Arg Lys Phe Ile Ser Glu Ile
        115                 120                 125

Thr Ile Arg Asn Asp Asn Gln Glu Val Leu Pro Gln Arg Ile Thr His
130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
                180                 185                 190

Thr Pro Ser Leu Val Ile Asn Asp Leu Ile Tyr Ala Tyr Thr Ser Asn
                195                 200                 205

Leu Ile Thr Arg Gly Cys Gln Asp Ile Gly Lys Ser Tyr Gln Val Leu
        210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Gly Ser Ile Ser Thr Thr Arg Phe
        290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Val Ile Cys Asn Thr
                340                 345                 350

Thr Gly Cys Pro Gly Lys Thr Gln Arg Asp Cys Asn Gln Ala Ser His
            355                 360                 365

Ser Pro Trp Phe Ser Asp Arg Arg Met Val Asn Ser Ile Ile Val Val
        370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
                420                 425                 430

Gln Leu Gly Ile Ile Asp Ile Thr Asp Tyr Ser Asp Ile Arg Ile Lys
            435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
                500                 505                 510

Thr Glu Arg Val Asn Glu Leu Ala Ile Leu Asn Arg Thr Leu Ser Ala
            515                 520                 525
```

-continued

```
Gly Tyr Thr Thr Thr Ser Cys Ile Thr His Tyr Asn Lys Gly Tyr Cys
            530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
                565                 570

<210> SEQ ID NO 8
<211> LENGTH: 572
<212> TYPE: PRT
<213> ORGANISM: human parainfluenza virus 3

<400> SEQUENCE: 8

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
            85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
            115                 120                 125

Thr Ile Arg Asn Asp Asn Gln Glu Val Leu Pro Gln Arg Ile Thr His
        130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Ile Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Gly Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335
```

Tyr Gly Gly Leu Glu His Pro Ile Asn Glu Asn Val Ile Cys Asn Thr
              340                 345                 350

Thr Gly Cys Pro Gly Lys Thr Gln Arg Asp Cys Asn Gln Ala Ser His
              355                 360                 365

Ser Thr Trp Phe Ser Asp Arg Arg Met Val Asn Ser Ile Ile Val Val
    370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                  405                 410                 415

Asn Lys Ile Tyr Ile Tyr Thr Arg Ser Thr Ser Trp His Ser Lys Leu
              420                 425                 430

Gln Leu Gly Ile Ile Asp Ile Thr Asp Tyr Ser Asp Ile Arg Ile Lys
              435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                  485                 490                 495

Asp Ser Gln Lys Ser Arg Val Asn Pro Val Ile Thr Tyr Ser Thr Ala
              500                 505                 510

Thr Glu Arg Val Asn Glu Leu Ala Ile Leu Asn Arg Thr Leu Ser Ala
              515                 520                 525

Gly Tyr Thr Thr Thr Ser Cys Ile Thr His Tyr Asn Lys Gly Tyr Cys
    530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
                  565                 570

<210> SEQ ID NO 9
<211> LENGTH: 1719
<212> TYPE: DNA
<213> ORGANISM: human parainfluenza virus 3

<400> SEQUENCE: 9
atggaatact ggaagcatac caatcacgga aaggatgctg gtaatgagct ggagacgtct      60
atggctactc atggcaacaa gctcactaat aagataatat acatattatg gacaataatc     120
ctggtgttat tatcaatagt cttcatcata gtgctaatta attccatcaa aagtgaaaag     180
gcccacgaat cattgctgca agacataaat aatgagttta tggaaattac agaaaagatc     240
caaatggcat cggataatac caatgatcta atacagtcag gagtgaatac aaggcttctt     300
acaattcaga gtcatgtcca gaattacata ccaatatcat gacacaaca gatgtcagat     360 cttaggaaat tcattagtga aattacaatt agaaatgata tcaagaagt gctgccacaa     420 agaataacac atgatgtagg tataaaacct ttaaatccag atgatttttg gagatgcacg     480
tctggtcttc catctttaat gaaaactcca aaaataaggt taatgccagg ccgggatta     540 ttagctatgc aacgactgt tgatggctgt gttagaactc cgtctttagt tataaatgat     600
ctgatttatg cttataccct aaatctaatt actcgaggtt gtcaggatat aggaaaatca     660
tatcaagtct tacagatagg gataataact gtaaactcag acttggtacc tgacttaaat     720
cctaggatct ctcataccct taacataaat gacaatagga agtcatgttc tctagcactc     780

-continued

```
ctaaatatag atgtatatca actgtgttca actcccaaag ttgatgaaag atcagattat    840
gcatcatcag gcatagaaga tattgtactt gatattgtca attatgatgg ttcaatctca    900
acaacaagat ttaagaataa taacataagc tttgatcaac catatgctgc actataccca    960
tctgttggac cagggatata ctacaaaggc aaaataatat ttctcgggta tggaggtctt   1020
gaacatccaa taaatgagaa tgtaatctgc aacacaactg ggtgccccgg gaaaacacag   1080
agagactgta atcaagcatc tcatagtact tggttttcag ataggaggat ggtcaactcc   1140
atcattgttg ttgacaaagg cttaaactca attccaaaat tgaaagtatg gacgatatct   1200
atgcgacaaa attactgggg gtcagaagga aggttacttc tactaggtaa caagatctat   1260
atatatacaa gatctacaag ttggcatagc aagttacaat taggaataat tgatattact   1320
gattacagtg atataaggat aaaatggaca tggcataatg tgctatcaag accaggaaac   1380
aatgaatgtc catggggaca ttcatgtcca gatggatgta taacaggagt atatactgat   1440
gcatatccac tcaatcccac agggagcatt gtgtcatctg tcatattaga ctcacaaaaa   1500
tcgagagtga acccagtcat aacttactca acagcaaccg aaagagtaaa cgagctggcc   1560
atcctaaaca gaacactctc agctggatat acaacaacaa gctgcattac acactataac   1620
aaaggatatt gttttcatat agtagaaata aatcataaaa gcttaaacac atttcaaccc   1680
atgttgttca aaacagagat tccaaaaagc tgcagttaa                          1719
```

```
<210> SEQ ID NO 10
<211> LENGTH: 2233
<212> TYPE: PRT
<213> ORGANISM: bovine parainfluenza virus 3

<400> SEQUENCE: 10
```

```
Met Asp Thr Glu Ser His Ser Gly Thr Thr Ser Asp Ile Leu Tyr Pro
1               5                   10                  15

Glu Cys His Leu Asn Ser Pro Ile Val Lys Gly Lys Ile Ala Gln Leu
            20                  25                  30

His Thr Ile Met Ser Leu Pro Gln Pro Tyr Asp Met Asp Asp Asp Ser
        35                  40                  45

Ile Leu Ile Ile Thr Arg Gln Lys Ile Lys Leu Asn Lys Leu Asp Lys
    50                  55                  60

Arg Gln Arg Ser Ile Arg Lys Leu Arg Ser Val Leu Met Glu Arg Val
65                  70                  75                  80

Ser Asp Leu Gly Lys Tyr Thr Phe Ile Arg Tyr Pro Glu Met Ser Ser
                85                  90                  95

Glu Met Phe Gln Leu Cys Ile Pro Gly Ile Asn Asn Lys Ile Asn Glu
            100                 105                 110

Leu Leu Ser Lys Ala Ser Lys Thr Tyr Asn Gln Met Thr Asp Gly Leu
        115                 120                 125

Arg Asp Leu Trp Val Thr Ile Leu Ser Lys Leu Ala Ser Lys Asn Asp
    130                 135                 140

Gly Ser Asn Tyr Asp Ile Asn Glu Asp Ile Ser Asn Ile Ser Asn Val
145                 150                 155                 160

His Met Thr Tyr Gln Ser Asp Lys Trp Tyr Asn Pro Phe Lys Thr Trp
                165                 170                 175

Phe Thr Ile Lys Tyr Asp Met Arg Arg Leu Gln Lys Ala Lys Asn Glu
            180                 185                 190

Ile Thr Phe Asn Arg His Lys Asp Tyr Asn Leu Leu Glu Asp Gln Lys
        195                 200                 205
```

```
Asn Ile Leu Leu Ile His Pro Glu Leu Val Leu Ile Leu Asp Lys Gln
        210                 215                 220
Asn Tyr Asn Gly Tyr Ile Met Thr Pro Glu Leu Val Leu Met Tyr Cys
225                 230                 235                 240
Asp Val Val Glu Gly Arg Trp Asn Ile Ser Ser Cys Ala Lys Leu Asp
                245                 250                 255
Pro Lys Leu Gln Ser Met Tyr Tyr Lys Gly Asn Asn Leu Trp Glu Ile
            260                 265                 270
Ile Asp Gly Leu Phe Ser Thr Leu Gly Glu Arg Thr Phe Asp Ile Ile
        275                 280                 285
Ser Leu Leu Glu Pro Leu Ala Leu Ser Leu Ile Gln Thr Tyr Asp Pro
290                 295                 300
Val Lys Gln Leu Arg Gly Ala Phe Leu Asn His Val Leu Ser Glu Met
305                 310                 315                 320
Glu Leu Ile Phe Ala Ala Glu Cys Thr Thr Glu Glu Ile Pro Asn Val
                325                 330                 335
Asp Tyr Ile Asp Lys Ile Leu Asp Val Phe Lys Glu Ser Thr Ile Asp
            340                 345                 350
Glu Ile Ala Glu Ile Phe Ser Phe Phe Arg Thr Phe Gly His Pro Pro
        355                 360                 365
Leu Glu Ala Ser Ile Ala Ala Glu Lys Val Arg Lys Tyr Met Tyr Thr
370                 375                 380
Glu Lys Cys Leu Lys Phe Asp Thr Ile Asn Lys Cys His Ala Ile Phe
385                 390                 395                 400
Cys Thr Ile Ile Ile Asn Gly Tyr Arg Glu Arg His Gly Gly Gln Trp
                405                 410                 415
Pro Pro Val Thr Leu Pro Val His Ala His Glu Phe Ile Ile Asn Ala
            420                 425                 430
Tyr Gly Ser Asn Ser Ala Ile Ser Tyr Glu Asn Ala Val Asp Tyr Tyr
        435                 440                 445
Lys Ser Phe Ile Gly Ile Lys Phe Asp Lys Phe Ile Glu Pro Gln Leu
450                 455                 460
Asp Glu Asp Leu Thr Ile Tyr Met Lys Asp Lys Ala Leu Ser Pro Lys
465                 470                 475                 480
Lys Ser Asn Trp Asp Thr Val Tyr Pro Ala Ser Asn Leu Leu Tyr Arg
                485                 490                 495
Thr Asn Val Ser His Asp Ser Arg Arg Leu Val Glu Val Phe Ile Ala
            500                 505                 510
Asp Ser Lys Phe Asp Pro His Gln Val Leu Asp Tyr Val Glu Ser Gly
        515                 520                 525
Tyr Trp Leu Asp Asp Pro Glu Phe Asn Ile Ser Tyr Ser Leu Lys Glu
530                 535                 540
Lys Glu Ile Lys Gln Glu Gly Arg Leu Phe Ala Lys Met Thr Tyr Lys
545                 550                 555                 560
Met Arg Ala Thr Gln Val Leu Ser Glu Thr Leu Leu Ala Asn Asn Ile
                565                 570                 575
Gly Lys Phe Phe Gln Glu Asn Gly Met Val Lys Gly Glu Ile Glu Leu
            580                 585                 590
Leu Lys Arg Leu Thr Thr Ile Ser Met Ser Gly Val Pro Arg Tyr Asn
        595                 600                 605
Glu Val Tyr Asn Asn Ser Lys Ser His Thr Glu Glu Leu Gln Ala Tyr
610                 615                 620
```

```
Asn Ala Ile Ser Ser Ser Asn Leu Ser Ser Asn Gln Lys Ser Lys Lys
625                 630                 635                 640

Phe Glu Phe Lys Ser Thr Asp Ile Tyr Asn Asp Gly Tyr Glu Thr Val
                645                 650                 655

Ser Cys Phe Leu Thr Thr Asp Leu Lys Lys Tyr Cys Leu Asn Trp Arg
                660                 665                 670

Tyr Glu Ser Thr Ala Leu Phe Gly Asp Thr Cys Asn Gln Ile Phe Gly
                675                 680                 685

Leu Lys Glu Leu Phe Asn Trp Leu His Pro Arg Leu Glu Lys Ser Thr
690                 695                 700

Ile Tyr Val Gly Asp Pro Tyr Cys Pro Pro Ser Asp Ile Glu His Leu
705                 710                 715                 720

Pro Leu Asp Asp His Pro Asp Ser Gly Phe Tyr Val His Asn Pro Lys
                725                 730                 735

Gly Gly Ile Glu Gly Phe Cys Gln Lys Leu Trp Thr Leu Ile Ser Ile
                740                 745                 750

Ser Ala Ile His Leu Ala Ala Val Lys Ile Gly Val Arg Val Thr Ala
                755                 760                 765

Met Val Gln Gly Asp Asn Gln Ala Ile Ala Val Thr Thr Arg Val Pro
770                 775                 780

Asn Asn Tyr Asp Tyr Lys Val Lys Lys Glu Ile Val Tyr Lys Asp Val
785                 790                 795                 800

Val Arg Phe Phe Asp Ser Leu Arg Glu Val Met Asp Asp Leu Gly His
                805                 810                 815

Glu Leu Lys Leu Asn Glu Thr Ile Ile Ser Ser Lys Met Phe Ile Tyr
                820                 825                 830

Ser Lys Arg Ile Tyr Tyr Asp Gly Arg Ile Leu Pro Gln Ala Leu Lys
                835                 840                 845

Ala Leu Ser Arg Cys Val Phe Trp Ser Glu Thr Ile Ile Asp Glu Thr
850                 855                 860

Arg Ser Ala Ser Ser Asn Leu Ala Thr Ser Phe Ala Lys Ala Ile Glu
865                 870                 875                 880

Asn Gly Tyr Ser Pro Val Leu Gly Tyr Val Cys Ser Ile Phe Lys Asn
                885                 890                 895

Ile Gln Gln Leu Tyr Ile Ala Leu Gly Met Asn Ile Asn Pro Thr Ile
                900                 905                 910

Thr Gln Asn Ile Lys Asp Gln Tyr Phe Arg Asn Ile His Trp Met Gln
                915                 920                 925

Tyr Ala Ser Leu Ile Pro Ala Ser Val Gly Gly Phe Asn Tyr Met Ala
930                 935                 940

Met Ser Arg Cys Phe Val Arg Asn Ile Gly Asp Pro Thr Val Ala Ala
945                 950                 955                 960

Leu Ala Asp Ile Lys Arg Phe Ile Lys Ala Asn Leu Leu Asp Arg Gly
                965                 970                 975

Val Leu Tyr Arg Ile Met Asn Gln Glu Pro Gly Glu Ser Ser Phe Leu
                980                 985                 990

Asp Trp Ala Ser Asp Pro Tyr Ser Cys Asn Leu Pro Gln Ser Gln Asn
                995                 1000                1005

Ile Thr Thr Met Ile Lys Asn Ile Thr Ala Arg Asn Val Leu Gln
        1010                1015                1020

Asp Ser Pro Asn Pro Leu Leu Ser Gly Leu Phe Thr Ser Thr Met
        1025                1030                1035

Ile Glu Glu Asp Glu Glu Leu Ala Glu Phe Leu Met Asp Arg Arg
```

```
                    1040                1045                1050

Ile  Ile  Leu  Pro  Arg  Val  Ala  His  Asp  Ile  Leu  Asp  Asn  Ser  Leu
               1055                1060                1065

Thr  Gly  Ile  Arg  Asn  Ala  Ile  Ala  Gly  Met  Leu  Asp  Thr  Thr  Lys
     1070                1075                1080

Ser  Leu  Ile  Arg  Val  Gly  Ile  Ser  Arg  Gly  Gly  Leu  Thr  Tyr  Asn
     1085                1090                1095

Leu  Leu  Arg  Lys  Ile  Ser  Asn  Tyr  Asp  Leu  Val  Gln  Tyr  Glu  Thr
     1100                1105                1110

Leu  Ser  Lys  Thr  Leu  Arg  Leu  Ile  Val  Ser  Asp  Lys  Ile  Lys  Tyr
     1115                1120                1125

Glu  Asp  Met  Cys  Ser  Val  Asp  Leu  Ala  Ile  Ser  Leu  Arg  Gln  Lys
     1130                1135                1140

Met  Trp  Met  His  Leu  Ser  Gly  Gly  Arg  Met  Ile  Asn  Gly  Leu  Glu
     1145                1150                1155

Thr  Pro  Asp  Pro  Leu  Glu  Leu  Leu  Ser  Gly  Val  Ile  Ile  Thr  Gly
     1160                1165                1170

Ser  Glu  His  Cys  Arg  Ile  Cys  Tyr  Ser  Thr  Glu  Gly  Glu  Ser  Pro
     1175                1180                1185

Tyr  Thr  Trp  Met  Tyr  Leu  Pro  Gly  Asn  Leu  Asn  Ile  Gly  Ser  Ala
     1190                1195                1200

Glu  Thr  Gly  Ile  Ala  Ser  Leu  Arg  Val  Pro  Tyr  Phe  Gly  Ser  Val
     1205                1210                1215

Thr  Asp  Glu  Arg  Ser  Glu  Ala  Gln  Leu  Gly  Tyr  Ile  Lys  Asn  Leu
     1220                1225                1230

Ser  Lys  Pro  Ala  Lys  Ala  Ala  Ile  Arg  Ile  Ala  Met  Ile  Tyr  Thr
     1235                1240                1245

Trp  Ala  Phe  Gly  Asn  Asp  Glu  Ile  Ser  Trp  Met  Glu  Ala  Ser  Gln
     1250                1255                1260

Ile  Ala  Gln  Thr  Arg  Ala  Asn  Phe  Thr  Leu  Asp  Ser  Leu  Lys  Ile
     1265                1270                1275

Leu  Thr  Pro  Val  Thr  Thr  Ser  Thr  Asn  Leu  Ser  His  Arg  Leu  Lys
     1280                1285                1290

Asp  Thr  Ala  Thr  Gln  Met  Lys  Phe  Ser  Ser  Thr  Ser  Leu  Ile  Arg
     1295                1300                1305

Val  Ser  Arg  Phe  Ile  Thr  Ile  Ser  Asn  Asp  Asn  Met  Ser  Ile  Lys
     1310                1315                1320

Glu  Ala  Asn  Glu  Thr  Lys  Asp  Thr  Asn  Leu  Ile  Tyr  Gln  Gln  Val
     1325                1330                1335

Met  Leu  Thr  Gly  Leu  Ser  Val  Phe  Glu  Tyr  Leu  Phe  Arg  Leu  Glu
     1340                1345                1350

Glu  Ser  Thr  Gly  His  Asn  Pro  Met  Val  Met  His  Leu  His  Ile  Glu
     1355                1360                1365

Asp  Gly  Cys  Cys  Ile  Lys  Glu  Ser  Tyr  Asn  Asp  Glu  His  Ile  Asn
     1370                1375                1380

Pro  Glu  Ser  Thr  Leu  Glu  Leu  Ile  Lys  Tyr  Pro  Glu  Ser  Asn  Glu
     1385                1390                1395

Phe  Ile  Tyr  Asp  Lys  Asp  Pro  Leu  Lys  Asp  Ile  Asp  Leu  Ser  Lys
     1400                1405                1410

Leu  Met  Val  Ile  Arg  Asp  His  Ser  Tyr  Thr  Ile  Asp  Met  Asn  Tyr
     1415                1420                1425

Trp  Asp  Asp  Thr  Asp  Ile  Val  His  Ala  Ile  Ser  Ile  Cys  Thr  Ala
     1430                1435                1440
```

```
Val Thr Ile Ala Asp Thr Met Ser Gln Leu Asp Arg Asp Asn Leu
    1445            1450                1455

Lys Glu Leu Val Val Ile Ala Asn Asp Asp Ile Asn Ser Leu
    1460            1465                1470

Ile Thr Glu Phe Leu Thr Leu Asp Ile Leu Val Phe Leu Lys Thr
    1475            1480                1485

Phe Gly Gly Leu Leu Val Asn Gln Phe Ala Tyr Thr Leu Tyr Gly
    1490            1495                1500

Leu Lys Ile Glu Gly Arg Asp Pro Ile Trp Asp Tyr Ile Met Arg
    1505            1510                1515

Thr Leu Lys Asp Thr Ser His Ser Val Leu Lys Val Leu Ser Asn
    1520            1525                1530

Ala Leu Ser His Pro Lys Val Phe Lys Arg Phe Trp Asp Cys Gly
    1535            1540                1545

Val Leu Asn Pro Ile Tyr Gly Pro Asn Thr Ala Ser Gln Asp Gln
    1550            1555                1560

Val Lys Leu Ala Leu Ser Ile Cys Glu Tyr Ser Leu Asp Leu Phe
    1565            1570                1575

Met Arg Glu Trp Leu Asn Gly Ala Ser Leu Glu Ile Tyr Ile Cys
    1580            1585                1590

Asp Ser Asp Met Glu Ile Ala Asn Asp Arg Arg Gln Ala Phe Leu
    1595            1600                1605

Ser Arg His Leu Ala Phe Val Cys Cys Leu Ala Glu Ile Ala Ser
    1610            1615                1620

Phe Gly Pro Asn Leu Leu Asn Leu Thr Tyr Leu Glu Arg Leu Asp
    1625            1630                1635

Glu Leu Lys Gln Tyr Leu Asp Leu Asn Ile Lys Glu Asp Pro Thr
    1640            1645                1650

Leu Lys Tyr Val Gln Val Ser Gly Leu Leu Ile Lys Ser Phe Pro
    1655            1660                1665

Ser Thr Val Thr Tyr Val Arg Lys Thr Ala Ile Lys Tyr Leu Arg
    1670            1675                1680

Ile Arg Gly Ile Asn Pro Pro Glu Thr Ile Glu Asp Trp Asp Pro
    1685            1690                1695

Ile Glu Asp Glu Asn Ile Leu Asp Asn Ile Val Lys Thr Val Asn
    1700            1705                1710

Asp Asn Cys Ser Asp Asn Gln Lys Arg Asn Lys Ser Ser Tyr Phe
    1715            1720                1725

Trp Gly Leu Ala Leu Lys Asn Tyr Gln Val Val Lys Ile Arg Ser
    1730            1735                1740

Ile Thr Ser Asp Ser Glu Val Asn Glu Ala Ser Asn Val Thr Thr
    1745            1750                1755

His Gly Met Thr Leu Pro Gln Gly Gly Ser Tyr Leu Ser His Gln
    1760            1765                1770

Leu Arg Leu Phe Gly Val Asn Ser Thr Ser Cys Leu Lys Ala Leu
    1775            1780                1785

Glu Leu Ser Gln Ile Leu Met Arg Glu Val Lys Lys Asp Lys Asp
    1790            1795                1800

Arg Leu Phe Leu Gly Glu Gly Ala Gly Ala Met Leu Ala Cys Tyr
    1805            1810                1815

Asp Ala Thr Leu Gly Pro Ala Ile Asn Tyr Tyr Asn Ser Gly Leu
    1820            1825                1830
```

```
Asn Ile Thr Asp Val Ile Gly Gln Arg Glu Leu Lys Ile Phe Pro
1835                1840                1845

Ser Glu Val Ser Leu Val Gly Lys Lys Leu Gly Asn Val Thr Gln
1850                1855                1860

Ile Leu Asn Arg Val Arg Val Leu Phe Asn Gly Asn Pro Asn Ser
1865                1870                1875

Thr Trp Ile Gly Asn Met Glu Cys Glu Ser Leu Ile Trp Ser Glu
1880                1885                1890

Leu Asn Asp Lys Ser Ile Gly Leu Val His Cys Asp Met Glu Gly
1895                1900                1905

Ala Ile Gly Lys Ser Glu Glu Thr Val Leu His Glu His Tyr Ser
1910                1915                1920

Ile Ile Arg Ile Thr Tyr Leu Ile Gly Asp Asp Val Val Leu
1925                1930                1935

Val Ser Lys Ile Ile Pro Thr Ile Thr Pro Asn Trp Ser Lys Ile
1940                1945                1950

Leu Tyr Leu Tyr Lys Leu Tyr Trp Lys Asp Val Ser Val Val Ser
1955                1960                1965

Leu Lys Thr Ser Asn Pro Ala Ser Thr Glu Leu Tyr Leu Ile Ser
1970                1975                1980

Lys Asp Ala Tyr Cys Thr Val Met Glu Pro Ser Asn Leu Val Leu
1985                1990                1995

Ser Lys Leu Lys Arg Ile Ser Ser Ile Glu Glu Asn Asn Leu Leu
2000                2005                2010

Lys Trp Ile Ile Leu Ser Lys Arg Lys Asn Asn Glu Trp Leu Gln
2015                2020                2025

His Glu Ile Lys Glu Gly Glu Arg Asp Tyr Gly Ile Met Arg Pro
2030                2035                2040

Tyr His Thr Ala Leu Gln Ile Phe Gly Phe Gln Ile Asn Leu Asn
2045                2050                2055

His Leu Ala Arg Glu Phe Leu Ser Thr Pro Asp Leu Thr Asn Ile
2060                2065                2070

Asn Asn Ile Ile Gln Ser Phe Thr Arg Thr Ile Lys Asp Val Met
2075                2080                2085

Phe Glu Trp Val Asn Ile Thr His Asp Asn Lys Arg His Lys Leu
2090                2095                2100

Gly Gly Arg Tyr Asn Leu Phe Pro Leu Lys Asn Lys Gly Lys Leu
2105                2110                2115

Arg Leu Leu Ser Arg Arg Leu Val Leu Ser Trp Ile Ser Leu Ser
2120                2125                2130

Leu Ser Thr Arg Leu Leu Thr Gly Arg Phe Pro Asp Glu Lys Phe
2135                2140                2145

Glu Asn Arg Ala Gln Thr Gly Tyr Val Ser Leu Ala Asp Ile Asp
2150                2155                2160

Leu Glu Ser Leu Lys Leu Leu Ser Arg Asn Ile Val Lys Asn Tyr
2165                2170                2175

Lys Glu His Ile Gly Leu Ile Ser Tyr Trp Phe Leu Thr Lys Glu
2180                2185                2190

Val Lys Ile Leu Met Lys Leu Ile Gly Gly Val Lys Leu Leu Gly
2195                2200                2205

Ile Pro Lys Gln Tyr Lys Glu Leu Glu Asp Arg Ser Ser Gln Gly
2210                2215                2220

Tyr Glu Tyr Asp Asn Glu Phe Asp Ile Asp
```

```
              2225            2230

<210> SEQ ID NO 11
<211> LENGTH: 12
<212> TYPE: DNA
<213> ORGANISM: bovine parainfluenza virus 3

<400> SEQUENCE: 11
aggattaaag ac                                                          12

<210> SEQ ID NO 12
<211> LENGTH: 10
<212> TYPE: DNA
<213> ORGANISM: bovine parainfluenza virus 3

<400> SEQUENCE: 12
aggattaaag                                                             10

<210> SEQ ID NO 13
<211> LENGTH: 10
<212> TYPE: DNA
<213> ORGANISM: bovine parainfluenza virus 3

<400> SEQUENCE: 13
aggacaaaag                                                             10

<210> SEQ ID NO 14
<211> LENGTH: 10
<212> TYPE: DNA
<213> ORGANISM: bovine parainfluenza virus 3

<400> SEQUENCE: 14
aggagtaaag                                                             10

<210> SEQ ID NO 15
<211> LENGTH: 10
<212> TYPE: DNA
<213> ORGANISM: bovine parainfluenza virus 3

<400> SEQUENCE: 15
aggagcaaag                                                             10

<210> SEQ ID NO 16
<211> LENGTH: 12
<212> TYPE: DNA
<213> ORGANISM: bovine parainfluenza virus 3

<400> SEQUENCE: 16
aaataagaaa aa                                                          12

<210> SEQ ID NO 17
<211> LENGTH: 12
<212> TYPE: DNA
<213> ORGANISM: bovine parainfluenza virus 3

<400> SEQUENCE: 17
aaataagaaa aa                                                          12

<210> SEQ ID NO 18
<211> LENGTH: 20
<212> TYPE: DNA
<213> ORGANISM: bovine parainfluenza virus 3

<400> SEQUENCE: 18
```
aaataaagga taatcaaaaa                                                   20

<210> SEQ ID NO 19
<211> LENGTH: 12
<212> TYPE: DNA
<213> ORGANISM: bovine parainfluenza virus 3

<400> SEQUENCE: 19
aattataaaa aa                                                           12

<210> SEQ ID NO 20
<211> LENGTH: 12
<212> TYPE: DNA
<213> ORGANISM: bovine parainfluenza virus 3

<400> SEQUENCE: 20
aaatataaaa aa                                                           12

<210> SEQ ID NO 21
<211> LENGTH: 13
<212> TYPE: DNA
<213> ORGANISM: bovine parainfluenza virus 3

<400> SEQUENCE: 21
aaagtaagaa aaa                                                          13

<210> SEQ ID NO 22
<211> LENGTH: 298
<212> TYPE: PRT
<213> ORGANISM: respiratory syncytial virus

<400> SEQUENCE: 22

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

```
Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295
```

<210> SEQ ID NO 23
<211> LENGTH: 233
<212> TYPE: PRT
<213> ORGANISM: respiratory syncytial virus

<400> SEQUENCE: 23

```
Asn His Lys Val Thr Pro Thr Thr Ala Ile Ile Gln Asp Ala Thr Ser
1               5                   10                  15

Gln Ile Lys Asn Thr Thr Pro Thr Tyr Leu Thr Gln Asn Pro Gln Leu
            20                  25                  30

Gly Ile Ser Pro Ser Asn Pro Ser Glu Ile Thr Ser Gln Ile Thr Thr
        35                  40                  45

Ile Leu Ala Ser Thr Thr Pro Gly Val Lys Ser Thr Leu Gln Ser Thr
50                  55                  60

Thr Val Lys Thr Lys Asn Thr Thr Thr Thr Gln Thr Gln Pro Ser Lys
65                  70                  75                  80

Pro Thr Thr Lys Gln Arg Gln Asn Lys Pro Pro Ser Lys Pro Asn Asn
                85                  90                  95

Asp Phe His Phe Glu Val Phe Asn Phe Val Pro Cys Ser Ile Cys Ser
            100                 105                 110

Asn Asn Pro Thr Cys Trp Ala Ile Cys Lys Arg Ile Pro Asn Lys Lys
        115                 120                 125

Pro Gly Lys Lys Thr Thr Thr Lys Pro Thr Lys Lys Pro Thr Leu Lys
    130                 135                 140

Thr Thr Lys Lys Asp Pro Lys Pro Gln Thr Thr Lys Ser Lys Glu Val
145                 150                 155                 160

Pro Thr Thr Lys Pro Thr Glu Glu Pro Thr Ile Asn Thr Thr Lys Thr
                165                 170                 175

Asn Ile Ile Thr Thr Leu Leu Thr Ser Asn Thr Thr Gly Asn Pro Glu
            180                 185                 190

Leu Thr Ser Gln Met Glu Thr Phe His Ser Thr Ser Ser Glu Gly Asn
        195                 200                 205

Pro Ser Pro Ser Gln Val Ser Thr Thr Ser Glu Tyr Pro Ser Gln Pro
    210                 215                 220

Ser Ser Pro Pro Asn Thr Pro Arg Gln
225                 230
```

<210> SEQ ID NO 24
<211> LENGTH: 37
<212> TYPE: PRT
<213> ORGANISM: respiratory syncytial virus

<400> SEQUENCE: 24

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser
            35

<210> SEQ ID NO 25
<211> LENGTH: 28
<212> TYPE: PRT
<213> ORGANISM: respiratory syncytial virus

<400> SEQUENCE: 25

Val Ala Gln Ile Thr Leu Ser Ile Leu Ala Met Ile Ile Ser Thr Ser
1               5                   10                  15

Leu Ile Ile Ala Ala Ile Ile Phe Ile Ala Ser Ala
            20                  25

<210> SEQ ID NO 26
<211> LENGTH: 65
<212> TYPE: PRT
<213> ORGANISM: respiratory syncytial virus

<400> SEQUENCE: 26

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala
65

<210> SEQ ID NO 27
<211> LENGTH: 30
<212> TYPE: PRT
<213> ORGANISM: bovine parainfluenza virus 3

<400> SEQUENCE: 27

Met Glu Tyr Trp Lys His Thr Asn Ser Ile Asn Asn Thr Asn Glu
1               5                   10                  15

Thr Glu Thr Ala Arg Gly Lys His Ser Ser Lys Val Thr Asn
            20                  25                  30

<210> SEQ ID NO 28
<211> LENGTH: 26
<212> TYPE: PRT
<213> ORGANISM: bovine parainfluenza virus 3

<400> SEQUENCE: 28

Ile Ile Met Tyr Thr Phe Trp Thr Ile Thr Leu Thr Ile Leu Ser Val
1               5                   10                  15

Ile Phe Ile Met Ile Leu Thr Asn Leu Ile
            20                  25

<210> SEQ ID NO 29
<211> LENGTH: 56
<212> TYPE: PRT
```

<213> ORGANISM: bovine parainfluenza virus 3

<400> SEQUENCE: 29

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
                20                  25                  30

Met Tyr Thr Phe Trp Thr Ile Thr Leu Thr Ile Leu Ser Val Ile Phe
            35                  40                  45

Ile Met Ile Leu Thr Asn Leu Ile
    50                  55

<210> SEQ ID NO 30
<211> LENGTH: 291
<212> TYPE: PRT
<213> ORGANISM: Artificial Sequence
<220> FEATURE:
<223> OTHER INFORMATION: Recombinant RSV G protein

<400> SEQUENCE: 30

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Val Ala
                20                  25                  30

Gln Ile Thr Leu Ser Ile Leu Ala Met Ile Ile Ser Thr Ser Leu Ile
            35                  40                  45

Ile Ala Ala Ile Ile Phe Ile Ala Ser Ala Asn His Lys Val Thr Pro
    50                  55                  60

Thr Thr Ala Ile Ile Gln Asp Ala Thr Ser Gln Ile Lys Asn Thr Thr
65                  70                  75                  80

Pro Thr Tyr Leu Thr Gln Asn Pro Gln Leu Gly Ile Ser Pro Ser Asn
                85                  90                  95

Pro Ser Glu Ile Thr Ser Gln Ile Thr Thr Ile Leu Ala Ser Thr Thr
            100                 105                 110

Pro Gly Val Lys Ser Thr Leu Gln Ser Thr Thr Val Lys Thr Lys Asn
        115                 120                 125

Thr Thr Thr Thr Gln Thr Gln Pro Ser Lys Pro Thr Thr Lys Gln Arg
    130                 135                 140

Gln Asn Lys Pro Pro Ser Lys Pro Asn Asn Asp Phe His Phe Glu Val
145                 150                 155                 160

Phe Asn Phe Val Pro Cys Ser Ile Cys Ser Asn Asn Pro Thr Cys Trp
                165                 170                 175

Ala Ile Cys Lys Arg Ile Pro Asn Lys Lys Pro Gly Lys Lys Thr Thr
            180                 185                 190

Thr Lys Pro Thr Lys Lys Pro Thr Leu Lys Thr Thr Lys Lys Asp Pro
        195                 200                 205

Lys Pro Gln Thr Thr Lys Ser Lys Glu Val Pro Thr Thr Lys Pro Thr
    210                 215                 220

Glu Glu Pro Thr Ile Asn Thr Thr Lys Thr Asn Ile Ile Thr Thr Leu
225                 230                 235                 240

Leu Thr Ser Asn Thr Thr Gly Asn Pro Glu Leu Thr Ser Gln Met Glu
                245                 250                 255

Thr Phe His Ser Thr Ser Ser Glu Gly Asn Pro Ser Pro Ser Gln Val
            260                 265                 270

Ser Thr Thr Ser Glu Tyr Pro Ser Gln Pro Ser Ser Pro Pro Asn Thr
        275                 280                 285

Pro Arg Gln
    290

<210> SEQ ID NO 31
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 31

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Pro Thr Thr
50                  55                  60

Ala Ile Ile Gln Asp Ala Thr Ser Gln Ile Lys Asn Thr Thr Pro Thr
65                  70                  75                  80

Tyr Leu Thr Gln Asn Pro Gln Leu Gly Ile Ser Pro Ser Asn Pro Ser
                85                  90                  95

Glu Ile Thr Ser Gln Ile Thr Thr Ile Leu Ala Ser Thr Thr Pro Gly
            100                 105                 110

Val Lys Ser Thr Leu Gln Ser Thr Thr Val Lys Thr Lys Asn Thr Thr
        115                 120                 125

Thr Thr Gln Thr Gln Pro Ser Lys Pro Thr Thr Lys Gln Arg Gln Asn
130                 135                 140

Lys Pro Pro Ser Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Lys Lys Thr Thr Thr Lys
            180                 185                 190

Pro Thr Lys Lys Pro Thr Leu Lys Thr Thr Lys Lys Asp Pro Lys Pro
        195                 200                 205

Gln Thr Thr Lys Ser Lys Glu Val Pro Thr Thr Lys Pro Thr Glu Glu
    210                 215                 220

Pro Thr Ile Asn Thr Thr Lys Thr Asn Ile Ile Thr Thr Leu Leu Thr
225                 230                 235                 240

Ser Asn Thr Thr Gly Asn Pro Glu Leu Thr Ser Gln Met Glu Thr Phe
                245                 250                 255

His Ser Thr Ser Ser Glu Gly Asn Pro Ser Pro Ser Gln Val Ser Thr
            260                 265                 270

Thr Ser Glu Tyr Pro Ser Gln Pro Ser Ser Pro Pro Asn Thr Pro Arg
        275                 280                 285

Gln

<210> SEQ ID NO 32
<211> LENGTH: 46
<212> TYPE: DNA
<213> ORGANISM: Artificial Sequence
<220> FEATURE:
<223> OTHER INFORMATION: Recombinant vector sequence

<400> SEQUENCE: 32

```
ggcgcgccaa gtaagaaaaa cttaggatta atggacctgc aggatg        46
```

<210> SEQ ID NO 33
<211> LENGTH: 55
<212> TYPE: DNA
<213> ORGANISM: Artificial Sequence
<220> FEATURE:
<223> OTHER INFORMATION: Recombinant vector sequence
<400> SEQUENCE: 33

```
tagtgatagc tagcggcgcg ccagcaacaa gtaagaaaaa cttaggatta atgga        55
```

<210> SEQ ID NO 34
<211> LENGTH: 77
<212> TYPE: PRT
<213> ORGANISM: respiratory syncytial virus
<400> SEQUENCE: 34

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
                20                  25                  30

Leu Asn Leu Lys Ser Val Ala Gln Ile Thr Leu Ser Ile Leu Ala Met
            35                  40                  45

Ile Ile Ser Thr Ser Leu Ile Ile Ala Ala Ile Ile Phe Ile Ala Ser
        50                  55                  60

Ala Asn His Lys Val Thr Pro Thr Thr Ala Ile Ile Gln
65                  70                  75
```

<210> SEQ ID NO 35
<211> LENGTH: 77
<212> TYPE: PRT
<213> ORGANISM: respiratory syncytial virus
<400> SEQUENCE: 35

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
                20                  25                  30

Leu Asn Leu Lys Ser Val Ala Gln Ile Thr Leu Ser Ile Leu Ala Ile
            35                  40                  45

Val Ile Ser Thr Ser Leu Ile Ile Ala Ala Ile Ile Phe Ile Ala Ser
        50                  55                  60

Ala Asn His Lys Val Thr Pro Thr Thr Ala Ile Ile Gln
65                  70                  75
```

<210> SEQ ID NO 36
<211> LENGTH: 30
<212> TYPE: PRT
<213> ORGANISM: respiratory syncytial virus
<400> SEQUENCE: 36

```
Met Ile Ile Ser Thr Ser Leu Ile Ile Ala Ala Ile Ile Phe Ile Ala
1               5                   10                  15

Ser Ala Asn His Lys Val Thr Pro Thr Thr Ala Ile Ile Gln
                20                  25                  30
```

<210> SEQ ID NO 37
<211> LENGTH: 70
<212> TYPE: PRT

<213> ORGANISM: Artificial sequence
<220> FEATURE:
<223> OTHER INFORMATION: Recombinant RSV G protein

<400> SEQUENCE: 37

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Val Ala
            20                  25                  30

Gln Ile Thr Leu Ser Ile Leu Ala Met Ile Ile Ser Thr Ser Leu Ile
        35                  40                  45

Ile Ala Ala Ile Ile Phe Ile Ala Ser Ala Asn His Lys Val Thr Pro
    50                  55                  60

Thr Thr Ala Ile Ile Gln
65                  70
```

<210> SEQ ID NO 38
<211> LENGTH: 68
<212> TYPE: PRT
<213> ORGANISM: Artificial sequence
<220> FEATURE:
<223> OTHER INFORMATION: Recombinant RSV G protein

<400> SEQUENCE: 38

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Pro Thr Thr
    50                  55                  60

Ala Ile Ile Gln
65
```

<210> SEQ ID NO 39
<211> LENGTH: 71
<212> TYPE: PRT
<213> ORGANISM: bovine parainfluenza virus 3

<400> SEQUENCE: 39

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Gln Glu Asn Asn His Asn Lys Leu
    50                  55                  60

Met Leu Gln Glu Ile Arg Lys
65                  70
```

<210> SEQ ID NO 40
<211> LENGTH: 70
<212> TYPE: PRT
<213> ORGANISM: human parainfluenza virus 3

<400> SEQUENCE: 40

```
Met Glu Tyr Trp Lys His Thr Asn His Gly Lys Asp Ala Gly Asn Glu
1               5                   10                  15
```

```
Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn
65                  70

<210> SEQ ID NO 41
<211> LENGTH: 5
<212> TYPE: PRT
<213> ORGANISM: respiratory syncytial virus

<400> SEQUENCE: 41

Cys Trp Ala Ile Cys
1               5

<210> SEQ ID NO 42
<211> LENGTH: 15
<212> TYPE: DNA
<213> ORGANISM: respiratory syncytial virus

<400> SEQUENCE: 42
tgctgggcta tctgc                                                15

<210> SEQ ID NO 43
<211> LENGTH: 5
<212> TYPE: PRT
<213> ORGANISM: Artificial sequence
<220> FEATURE:
<223> OTHER INFORMATION: Recombinant RSV G protein

<400> SEQUENCE: 43

Cys Trp Ala Ile Arg
1               5

<210> SEQ ID NO 44
<211> LENGTH: 15
<212> TYPE: DNA
<213> ORGANISM: Artificial sequence
<220> FEATURE:
<223> OTHER INFORMATION: Recombinant RSV G protein

<400> SEQUENCE: 44
tgctgggcta tccgc                                                15

<210> SEQ ID NO 45
<211> LENGTH: 6
<212> TYPE: PRT
<213> ORGANISM: Artificial sequence
<220> FEATURE:
<223> OTHER INFORMATION: Recombinant RSV G protein

<400> SEQUENCE: 45

Cys Trp Ala Ile Ala Cys
1               5

<210> SEQ ID NO 46
<211> LENGTH: 18
<212> TYPE: DNA
<213> ORGANISM: Artificial sequence
<220> FEATURE:
<223> OTHER INFORMATION: Recombinant RSV G protein
```

```
<400> SEQUENCE: 46
tgctgggcta tcgcatgc                                                    18

<210> SEQ ID NO 47
<211> LENGTH: 298
<212> TYPE: PRT
<213> ORGANISM: respiratory syncytial virus

<400> SEQUENCE: 47
```

Met Ser Lys Thr Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Leu Thr Thr Ala Ile Ile Gln Asp Ala Thr
65                  70                  75                  80

Asn Gln Ile Lys Asn Thr Thr Pro Thr Tyr Leu Thr Gln Asn Pro Gln
                85                  90                  95

Leu Gly Ile Ser Leu Ser Asn Leu Ser Glu Thr Thr Ser Lys Pro Thr
            100                 105                 110

Thr Ile Leu Ala Leu Thr Thr Pro Asn Ala Glu Ser Thr Pro Gln Ser
        115                 120                 125

Thr Thr Val Lys Thr Lys Asn Thr Thr Thr Thr Gln Ile Gln Pro Ser
    130                 135                 140

Lys Pro Thr Thr Lys Gln Arg Gln Asn Lys Pro Gln Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Arg Lys Thr Thr Thr Lys Pro Thr Lys Gln Pro Ala Ile
        195                 200                 205

Lys Thr Thr Lys Lys Asp Pro Lys Pro Gln Thr Thr Lys Pro Lys Glu
    210                 215                 220

Val Leu Thr Thr Lys Pro Thr Glu Lys Pro Thr Ile Asn Thr Thr Lys
225                 230                 235                 240

Thr Asn Ile Arg Thr Thr Leu Leu Thr Ser Asn Ile Thr Glu Asn Gln
                245                 250                 255

Glu His Thr Ser Gln Lys Glu Thr Leu His Ser Thr Thr Ser Glu Gly
            260                 265                 270

Asn Pro Ser Pro Ser Gln Val Tyr Thr Thr Ser Glu Tyr Leu Ser Gln
        275                 280                 285

Ser Leu Ser Pro Ser Asn Thr Thr Arg Trp
    290                 295

```
<210> SEQ ID NO 48
<211> LENGTH: 233
<212> TYPE: PRT
<213> ORGANISM: respiratory syncytial virus

<400> SEQUENCE: 48
```

Asn His Lys Val Thr Leu Thr Thr Ala Ile Ile Gln Asp Ala Thr Asn

-continued

```
1               5                   10                  15

Gln Ile Lys Asn Thr Thr Pro Thr Tyr Leu Thr Gln Asn Pro Gln Leu
            20                  25                  30

Gly Ile Ser Leu Ser Asn Leu Ser Glu Thr Thr Ser Lys Pro Thr Thr
        35                  40                  45

Ile Leu Ala Leu Thr Thr Pro Asn Ala Glu Ser Thr Pro Gln Ser Thr
    50                  55                  60

Thr Val Lys Thr Lys Asn Thr Thr Thr Thr Gln Ile Gln Pro Ser Lys
65                  70                  75                  80

Pro Thr Thr Lys Gln Arg Gln Asn Lys Pro Gln Asn Lys Pro Asn Asn
                85                  90                  95

Asp Phe His Phe Glu Val Phe Asn Phe Val Pro Cys Ser Ile Cys Ser
            100                 105                 110

Asn Asn Pro Thr Cys Trp Ala Ile Cys Lys Arg Ile Pro Asn Lys Lys
        115                 120                 125

Pro Gly Arg Lys Thr Thr Thr Lys Pro Thr Lys Gln Pro Ala Ile Lys
    130                 135                 140

Thr Thr Lys Lys Asp Pro Lys Pro Gln Thr Thr Lys Pro Lys Glu Val
145                 150                 155                 160

Leu Thr Thr Lys Pro Thr Glu Lys Pro Thr Ile Asn Thr Thr Lys Thr
                165                 170                 175

Asn Ile Arg Thr Thr Leu Leu Thr Ser Asn Ile Thr Glu Asn Gln Glu
            180                 185                 190

His Thr Ser Gln Lys Glu Thr Leu His Ser Thr Thr Ser Glu Gly Asn
        195                 200                 205

Pro Ser Pro Ser Gln Val Tyr Thr Thr Ser Glu Tyr Leu Ser Gln Ser
    210                 215                 220

Leu Ser Pro Ser Asn Thr Thr Arg Trp
225                 230

<210> SEQ ID NO 49
<211> LENGTH: 299
<212> TYPE: PRT
<213> ORGANISM: respiratory syncytial virus

<400> SEQUENCE: 49

Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Thr Ser Pro Ile His
            100                 105                 110

Thr Asn Ser Ala Thr Thr Ser Pro Asn Thr Lys Ser Glu Thr His His
        115                 120                 125

Thr Thr Ala Gln Thr Lys Gly Arg Thr Thr Thr Ser Thr Gln Thr Asn
    130                 135                 140
```

```
Lys Pro Ser Thr Lys Pro Arg Leu Lys Asn Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Pro Thr Ile Lys Pro Thr Asn Lys Pro Thr Thr
        195                 200                 205

Lys Thr Thr Asn Lys Arg Asp Pro Lys Thr Pro Ala Lys Thr Thr Lys
    210                 215                 220

Lys Glu Thr Thr Thr Asn Pro Thr Lys Lys Pro Thr Leu Thr Thr Thr
225                 230                 235                 240

Glu Arg Asp Thr Ser Thr Ser Gln Ser Thr Val Leu Asp Thr Thr Thr
                245                 250                 255

Leu Glu His Thr Ile Gln Gln Gln Ser Leu His Ser Thr Thr Pro Glu
            260                 265                 270

Asn Thr Pro Asn Ser Thr Gln Thr Pro Thr Ala Ser Glu Pro Ser Thr
        275                 280                 285

Ser Asn Ser Thr Gln Asn Thr Gln Ser His Ala
    290                 295
```

<210> SEQ ID NO 50
<211> LENGTH: 234
<212> TYPE: PRT
<213> ORGANISM: respiratory syncytial virus

<400> SEQUENCE: 50

```
Asn His Lys Val Thr Leu Thr Thr Val Thr Val Gln Thr Ile Lys Asn
1               5                   10                  15

His Thr Glu Lys Asn Ile Thr Thr Tyr Leu Thr Gln Val Pro Pro Glu
                20                  25                  30

Arg Val Ser Ser Ser Lys Gln Pro Thr Thr Thr Ser Pro Ile His Thr
            35                  40                  45

Asn Ser Ala Thr Thr Ser Pro Asn Thr Lys Ser Glu Thr His His Thr
    50                  55                  60

Thr Ala Gln Thr Lys Gly Arg Thr Thr Thr Ser Thr Gln Thr Asn Lys
65                  70                  75                  80

Pro Ser Thr Lys Pro Arg Leu Lys Asn Pro Pro Lys Lys Pro Lys Asp
                85                  90                  95

Asp Tyr His Phe Glu Val Phe Asn Phe Val Pro Cys Ser Ile Cys Gly
                100                 105                 110

Asn Asn Gln Leu Cys Lys Ser Ile Cys Lys Thr Ile Pro Ser Asn Lys
            115                 120                 125

Pro Lys Lys Lys Pro Thr Ile Lys Pro Thr Asn Lys Pro Thr Thr Lys
    130                 135                 140

Thr Thr Asn Lys Arg Asp Pro Lys Thr Pro Ala Lys Thr Thr Lys Lys
145                 150                 155                 160

Glu Thr Thr Thr Asn Pro Thr Lys Lys Pro Thr Leu Thr Thr Thr Glu
                165                 170                 175

Arg Asp Thr Ser Thr Ser Gln Ser Thr Val Leu Asp Thr Thr Thr Leu
            180                 185                 190

Glu His Thr Ile Gln Gln Gln Ser Leu His Ser Thr Thr Pro Glu Asn
        195                 200                 205

Thr Pro Asn Ser Thr Gln Thr Pro Thr Ala Ser Glu Pro Ser Thr Ser
    210                 215                 220
```

```
Asn Ser Thr Gln Asn Thr Gln Ser His Ala
225                 230

<210> SEQ ID NO 51
<211> LENGTH: 321
<212> TYPE: PRT
<213> ORGANISM: respiratory syncytial virus

<400> SEQUENCE: 51

Met Ser Lys Thr Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Leu Thr Thr Ala Ile Ile Gln Asp Ala Thr
65                  70                  75                  80

Asn Gln Ile Lys Asn Thr Thr Pro Thr Tyr Leu Thr Gln Asn Pro Gln
                85                  90                  95

Leu Gly Ile Ser Phe Ser Asn Leu Ser Gly Thr Thr Ser Gln Ser Thr
            100                 105                 110

Thr Ile Leu Ala Ser Thr Thr Pro Ser Ala Glu Ser Thr Pro Gln Ser
        115                 120                 125

Thr Thr Val Lys Ile Lys Asn Thr Thr Thr Gln Ile Leu Pro Ser
    130                 135                 140

Lys Pro Thr Thr Lys Gln Arg Gln Asn Lys Pro Gln Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Pro Lys Glu
    210                 215                 220

Val Leu Thr Thr Lys Pro Thr Gly Lys Pro Thr Ile Asn Thr Thr Lys
225                 230                 235                 240

Thr Asn Ile Arg Thr Thr Leu Leu Thr Ser Asn Thr Lys Gly Asn Pro
                245                 250                 255

Glu His Thr Ser Gln Glu Glu Thr Leu His Ser Thr Thr Ser Glu Gly
            260                 265                 270

Tyr Leu Ser Pro Ser Gln Val Tyr Thr Thr Ser Gly Gln Glu Glu Thr
        275                 280                 285

Leu His Ser Thr Thr Ser Glu Gly Tyr Leu Ser Pro Ser Gln Val Tyr
    290                 295                 300

Thr Thr Ser Glu Tyr Leu Ser Gln Ser Leu Ser Ser Ser Asn Thr Thr
305                 310                 315                 320

Lys

<210> SEQ ID NO 52
<211> LENGTH: 256
<212> TYPE: PRT
<213> ORGANISM: respiratory syncytial virus
```

<400> SEQUENCE: 52

```
Asn His Lys Val Thr Leu Thr Thr Ala Ile Ile Gln Asp Ala Thr Asn
1               5                   10                  15

```
Thr Asn Ser Ala Thr Ile Ser Pro Asn Thr Lys Ser Glu Thr His His
            115                 120                 125
Thr Thr Ala Gln Thr Lys Gly Arg Thr Thr Pro Thr Gln Asn Asn
130             135                 140
Lys Pro Ser Thr Lys Pro Arg Pro Lys Asn Pro Pro Lys Lys Pro Lys
145                 150                 155                 160
Asp Asp Tyr His Phe Glu Val Phe Asn Phe Val Pro Cys Ser Ile Cys
                165                 170                 175
Gly Asn Asn Gln Leu Cys Lys Ser Ile Cys Lys Thr Ile Pro Ser Asn
            180                 185                 190
Lys Pro Lys Lys Pro Thr Ile Lys Pro Thr Asn Lys Pro Pro Thr
                195                 200                 205
Lys Thr Thr Asn Lys Arg Asp Pro Lys Lys Leu Ala Lys Thr Leu Lys
                210                 215                 220
Lys Glu Thr Thr Ile Asn Pro Thr Lys Lys Pro Thr Pro Lys Thr Thr
225                 230                 235                 240
Glu Arg Asp Thr Ser Thr Ser Gln Ser Thr Val Leu Asp Thr Thr Thr
                245                 250                 255
Ser Lys His Thr Glu Arg Asp Thr Ser Thr Ser Gln Ser Thr Val Leu
            260                 265                 270
Asp Thr Thr Thr Ser Lys His Thr Ile Gln Gln Ser Leu His Ser
            275                 280                 285
Thr Thr Pro Glu Asn Thr Pro Asn Ser Thr Gln Thr Pro Thr Ala Ser
            290                 295                 300
Glu Pro Ser Thr Ser Asn Ser Thr Gln Lys Leu
305                 310                 315

<210> SEQ ID NO 54
<211> LENGTH: 250
<212> TYPE: PRT
<213> ORGANISM: respiratory syncytial virus

<400> SEQUENCE: 54

Asn His Lys Val Thr Leu Thr Thr Val Thr Val Gln Thr Ile Lys Asn
1               5                   10                  15
His Thr Glu Lys Asn Ile Thr Thr Tyr Leu Thr Gln Val Ser Pro Glu
            20                  25                  30
Arg Val Ser Pro Ser Lys Gln Leu Thr Thr Pro Pro Ile Tyr Thr
            35                  40                  45
Asn Ser Ala Thr Ile Ser Pro Asn Thr Lys Ser Glu Thr His His Thr
50                  55                  60
Thr Ala Gln Thr Lys Gly Arg Thr Thr Pro Thr Gln Asn Asn Lys
65                  70                  75                  80
Pro Ser Thr Lys Pro Arg Pro Lys Asn Pro Pro Lys Lys Pro Lys Asp
                85                  90                  95
Asp Tyr His Phe Glu Val Phe Asn Phe Val Pro Cys Ser Ile Cys Gly
            100                 105                 110
Asn Asn Gln Leu Cys Lys Ser Ile Cys Lys Thr Ile Pro Ser Asn Lys
            115                 120                 125
Pro Lys Lys Lys Pro Thr Ile Lys Pro Thr Asn Lys Pro Thr Lys
            130                 135                 140
Thr Thr Asn Lys Arg Asp Pro Lys Lys Leu Ala Lys Thr Leu Lys Lys
145                 150                 155                 160
Glu Thr Thr Ile Asn Pro Thr Lys Lys Pro Thr Pro Lys Thr Thr Glu
```

```
                   165                 170                 175

Arg Asp Thr Ser Thr Ser Gln Ser Thr Val Leu Asp Thr Thr Thr Ser
                180                 185                 190

Lys His Thr Glu Arg Asp Thr Ser Thr Ser Gln Ser Thr Val Leu Asp
            195                 200                 205

Thr Thr Thr Ser Lys His Thr Ile Gln Gln Gln Ser Leu His Ser Thr
        210                 215                 220

Thr Pro Glu Asn Thr Pro Asn Ser Thr Gln Thr Pro Thr Ala Ser Glu
225                 230                 235                 240

Pro Ser Thr Ser Asn Ser Thr Gln Lys Leu
                245                 250

<210> SEQ ID NO 55
<211> LENGTH: 31
<212> TYPE: PRT
<213> ORGANISM: human parainfluenza virus 3

<400> SEQUENCE: 55

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys
            20                  25                  30

<210> SEQ ID NO 56
<211> LENGTH: 25
<212> TYPE: PRT
<213> ORGANISM: human parainfluenza virus 3

<400> SEQUENCE: 56

Ile Ile

```
Thr His Trp
        35

<210> SEQ ID NO 59
<211> LENGTH: 25
<212> TYPE: PRT
<213> ORGANISM: human parainfluenza virus 1

<400> SEQUENCE: 59

Ile Leu Leu Ile Ala Thr Thr Met His Thr Val Leu Ser Phe Ile Ile
1               5                   10                  15

Met Ile Leu Cys Ile Asp Leu Ile Ile
            20                  25

<210> SEQ ID NO 60
<211> LENGTH: 60
<212> TYPE: PRT
<213> ORGANISM: human parainfluenza virus 1

<400> SEQUENCE: 60

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile
    50                  55                  60

<210> SEQ ID NO 61
<211> LENGTH: 292
<212> TYPE: PRT
<213> ORGANISM: Artificial Sequence
<220> FEATURE:
<223> OTHER INFORMATION: Recombinant RSV G protein

<400> SEQUENCE: 61

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ala
            20                  25                  30

Gln Ile Ala Leu Ser Val Leu Ala Met Ile Ile Ser Thr Ser Leu Ile
        35                  40                  45

Ile Ala Ala Ile Ile Phe Ile Ile Ser Ala Asn His Lys Val Thr Leu
    50                  55                  60

Thr Thr Val Thr Val Gln Thr Ile Lys Asn His Thr Glu Lys Asn Ile
65              70                  75                  80

Thr Thr Tyr Leu Thr Gln Val Pro Pro Glu Arg Val Ser Ser Ser Lys
            85                  90                  95

Gln Pro Thr Thr Thr Ser Pro Ile His Thr Asn Ser Ala Thr Thr Ser
            100                 105                 110

Pro Asn Thr Lys Ser Glu Thr His His Thr Thr Ala Gln Thr Lys Gly
        115                 120                 125

Arg Thr Thr Thr Ser Thr Gln Thr Asn Lys Pro Ser Thr Lys Pro Arg
    130                 135                 140

Leu Lys Asn Pro Pro Lys Lys Pro Lys Asp Asp Tyr His Phe Glu Val
145                 150                 155                 160

Phe Asn Phe Val Pro Cys Ser Ile Cys Gly Asn Asn Gln Leu Cys Lys
                165                 170                 175
```

```
Ser Ile Cys Lys Thr Ile Pro Ser Asn Lys Pro Lys Lys Lys Pro Thr
            180                 185                 190

Ile Lys Pro Thr Asn Lys Pro Thr Lys Thr Thr Asn Lys Arg Asp
        195                 200                 205

Pro Lys Thr Pro Ala Lys Thr Thr Lys Lys Glu Thr Thr Thr Asn Pro
    210                 215                 220

Thr Lys Lys Pro Thr Leu Thr Thr Thr Glu Arg Asp Thr Ser Thr Ser
225                 230                 235                 240

Gln Ser Thr Val Leu Asp Thr Thr Thr Leu Glu His Thr Ile Gln Gln
                245                 250                 255

Gln Ser Leu His Ser Thr Thr Pro Glu Asn Thr Pro Asn Ser Thr Gln
            260                 265                 270

Thr Pro Thr Ala Ser Glu Pro Ser Thr Ser Asn Ser Thr Gln Asn Thr
        275                 280                 285

Gln Ser His Ala
    290

<210> SEQ ID NO 62
<211> LENGTH: 290
<212> TYPE: PRT
<213> ORGANISM: Artificial Sequence
<220> FEATURE:
<223> OTHER INFORMATION: Recombinant RSV G protein

<400> SEQUENCE: 62

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Leu Thr Thr
    50                  55                  60

Val Thr Val Gln Thr Ile Lys Asn His Thr Glu Lys Asn Ile Thr Thr
65                  70                  75                  80

Tyr Leu Thr Gln Val Pro Pro Glu Arg Val Ser Ser Lys Gln Pro
            85                  90                  95

Thr Thr Thr Ser Pro Ile His Thr Asn Ser Ala Thr Thr Ser Pro Asn
            100                 105                 110

Thr Lys Ser Glu Thr His His Thr Thr Ala Gln Thr Lys Gly Arg Thr
        115                 120                 125

Thr Thr Ser Thr Gln Thr Asn Lys Pro Ser Thr Lys Pro Arg Leu Lys
    130                 135                 140

Asn Pro Pro Lys Lys Pro Lys Asp Asp Tyr His Phe Glu Val Phe Asn
145                 150                 155                 160

Phe Val Pro Cys Ser Ile Cys Gly Asn Asn Gln Leu Cys Lys Ser Ile
            165                 170                 175

Cys Lys Thr Ile Pro Ser Asn Lys Pro Lys Lys Pro Thr Ile Lys
        180                 185                 190

Pro Thr Asn Lys Pro Thr Thr Lys Thr Thr Asn Lys Arg Asp Pro Lys
    195                 200                 205

Thr Pro Ala Lys Thr Thr Lys Lys Glu Thr Thr Thr Asn Pro Thr Lys
    210                 215                 220

Lys Pro Thr Leu Thr Thr Thr Glu Arg Asp Thr Ser Thr Ser Gln Ser
225                 230                 235                 240
```

```
Thr Val Leu Asp Thr Thr Thr Leu Glu His Thr Ile Gln Gln Gln Ser
            245                 250                 255

Leu His Ser Thr Thr Pro Glu Asn Thr Pro Asn Ser Thr Gln Thr Pro
            260                 265                 270

Thr Ala Ser Glu Pro Ser Thr Ser Asn Ser Thr Gln Asn Thr Gln Ser
            275                 280                 285

His Ala
    290

<210> SEQ ID NO 63
<211> LENGTH: 291
<212> TYPE: PRT
<213> ORGANISM: Artificial Sequence
<220> FEATURE:
<223> OTHER INFORMATION: Recombinant RSV G protein

<400> SEQUENCE: 63

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ala
            20                  25                  30

Gln Ile Thr Leu Ser Ile Leu Ala Met Ile Ile Ser Thr Ser Leu Ile
        35                  40                  45

Ile Ala Ala Ile Ile Phe Ile Ala Ser Ala Asn His Lys Val Thr Leu
    50                  55                  60

Thr Thr Ala Ile Ile Gln Asp Ala Thr Asn Gln Ile Lys Asn Thr Thr
65                  70                  75                  80

Pro Thr Tyr Leu Thr Gln Asn Pro Gln Leu Gly Ile Ser Leu Ser Asn
                85                  90                  95

Leu Ser Glu Thr Thr Ser Lys Pro Thr Thr Ile Leu Ala Leu Thr Thr
            100                 105                 110

Pro Asn Ala Glu Ser Thr Pro Gln Ser Thr Thr Val Lys Thr Lys Asn
        115                 120                 125

Thr Thr Thr Thr Gln Ile Gln Pro Ser Lys Pro Thr Thr Lys Gln Arg
    130                 135                 140

Gln Asn Lys Pro Gln Asn Lys Pro Asn Asn Asp Phe His Phe Glu Val
145                 150                 155                 160

Phe Asn Phe Val Pro Cys Ser Ile Cys Ser Asn Asn Pro Thr Cys Trp
                165                 170                 175

Ala Ile Cys Lys Arg Ile Pro Asn Lys Lys Pro Gly Arg Lys Thr Thr
            180                 185                 190

Thr Lys Pro Thr Lys Gln Pro Ala Ile Lys Thr Thr Lys Lys Asp Pro
        195                 200                 205

Lys Pro Gln Thr Thr Lys Pro Lys Glu Val Leu Thr Thr Lys Pro Thr
    210                 215                 220

Glu Lys Pro Thr Ile Asn Thr Thr Lys Thr Asn Ile Arg Thr Thr Leu
225                 230                 235                 240

Leu Thr Ser Asn Ile Thr Glu Asn Gln Glu His Thr Ser Gln Lys Glu
                245                 250                 255

Thr Leu His Ser Thr Thr Ser Glu Gly Asn Pro Ser Pro Ser Gln Val
            260                 265                 270

Tyr Thr Thr Ser Glu Tyr Leu Ser Gln Ser Leu Ser Pro Ser Asn Thr
        275                 280                 285

Thr Arg Trp
    290
```

<210> SEQ ID NO 64
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 64

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Leu Thr Thr
    50                  55                  60

Ala Ile Ile Gln Asp Ala Thr Asn Gln Ile Lys Asn Thr Thr Pro Thr
65                  70                  75                  80

Tyr Leu Thr Gln Asn Pro Gln Leu Gly Ile Ser Leu Ser Asn Leu Ser
                85                  90                  95

Glu Thr Thr Ser Lys Pro Thr Thr Ile Leu Ala Leu Thr Thr Pro Asn
            100                 105                 110

Ala Glu Ser Thr Pro Gln Ser Thr Thr Val Lys Thr Lys Asn Thr Thr
        115                 120                 125

Thr Thr Gln Ile Gln Pro Ser Lys Pro Thr Thr Lys Gln Arg Gln Asn
    130                 135                 140

Lys Pro Gln Asn Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Arg Lys Thr Thr Thr Lys
            180                 185                 190

Pro Thr Lys Gln Pro Ala Ile Lys Thr Thr Lys Lys Asp Pro Lys Pro
        195                 200                 205

Gln Thr Thr Lys Pro Lys Glu Val Leu Thr Thr Lys Pro Thr Glu Lys
    210                 215                 220

Pro Thr Ile Asn Thr Thr Lys Thr Asn Ile Arg Thr Thr Leu Leu Thr
225                 230                 235                 240

Ser Asn Ile Thr Glu Asn Gln Glu His Thr Ser Gln Lys Glu Thr Leu
                245                 250                 255

His Ser Thr Thr Ser Glu Gly Asn Pro Ser Pro Ser Gln Val Tyr Thr
            260                 265                 270

Thr Ser Glu Tyr Leu Ser Gln Ser Leu Ser Pro Ser Asn Thr Thr Arg
        275                 280                 285

Trp
```

<210> SEQ ID NO 65
<211> LENGTH: 314
<212> TYPE: PRT
<213> ORGANISM: Artificial Sequence
<220> FEATURE:
<223> OTHER INFORMATION: Recombinant RSV G protein

<400> SEQUENCE: 65

```
Met Glu Tyr Trp Lys His Thr Asn Ser Ile Asn Asn Thr Asn Asn Glu
1               5                   10                  15
```

```
Thr Glu Thr Ala Arg Gly Lys His Ser Ser Lys Val Thr Asn Ile Ala
            20                  25                  30

Gln Ile Thr Leu Ser Ile Leu Ala Met Ile Ile Ser Thr Ser Leu Ile
            35                  40                  45

Ile Ala Ala Ile Ile Phe Ile Ala Ser Ala Asn His Lys Val Thr Leu
50                  55                  60

Thr Thr Ala Ile Ile Gln Asp Ala Thr Asn Gln Ile Lys Asn Thr Thr
65                  70                  75                  80

Pro Thr Tyr Leu Thr Gln Asn Pro Gln Leu Gly Ile Ser Phe Ser Asn
                85                  90                  95

Leu Ser Gly Thr Thr Ser Gln Ser Thr Thr Ile Leu Ala Ser Thr Thr
            100                 105                 110

Pro Ser Ala Glu Ser Thr Pro Gln Ser Thr Thr Val Lys Ile Lys Asn
            115                 120                 125

Thr Thr Thr Thr Gln Ile Leu Pro Ser Lys Pro Thr Thr Lys Gln Arg
130                 135                 140

Gln Asn Lys Pro Gln Asn Lys Pro Asn Asn Asp Phe His Phe Glu Val
145                 150                 155                 160

Phe Asn Phe Val Pro Cys Ser Ile Cys Ser Asn Asn Pro Thr Cys Trp
                165                 170                 175

Ala Ile Cys Lys Arg Ile Pro Asn Lys Lys Pro Gly Lys Lys Thr Thr
            180                 185                 190

Thr Lys Pro Thr Lys Lys Pro Thr Leu Lys Thr Thr Lys Lys Asp Pro
            195                 200                 205

Lys Pro Gln Thr Thr Lys Pro Lys Glu Val Leu Thr Thr Lys Pro Thr
210                 215                 220

Gly Lys Pro Thr Ile Asn Thr Thr Lys Thr Asn Ile Arg Thr Thr Leu
225                 230                 235                 240

Leu Thr Ser Asn Thr Lys Gly Asn Pro Glu His Thr Ser Gln Glu Glu
                245                 250                 255

Thr Leu His Ser Thr Thr Ser Glu Gly Tyr Leu Ser Pro Ser Gln Val
            260                 265                 270

Tyr Thr Thr Ser Gly Gln Glu Glu Thr Leu His Ser Thr Thr Ser Glu
            275                 280                 285

Gly Tyr Leu Ser Pro Ser Gln Val Tyr Thr Thr Ser Glu Tyr Leu Ser
            290                 295                 300

Gln Ser Leu Ser Ser Ser Asn Thr Thr Lys
305                 310

<210> SEQ ID NO 66
<211> LENGTH: 312
<212> TYPE: PRT
<213> ORGANISM: Artificial Sequence
<220> FEATURE:
<223> OTHER INFORMATION: Recombinant RSV G protein

<400> SEQUENCE: 66

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
            35                  40                  45

Ile Met Ile Leu Thr Asn Leu Ile Asn His Lys Val Thr Leu Thr Thr
50                  55                  60
```

-continued

```
Ala Ile Ile Gln Asp Ala Thr Asn Gln Ile Lys Asn Thr Thr Pro Thr
 65                  70                  75                  80

Tyr Leu Thr Gln Asn Pro Gln Leu Gly Ile Ser Phe Ser Asn Leu Ser
                 85                  90                  95

Gly Thr Thr Ser Gln Ser Thr Thr Ile Leu Ala Ser Thr Thr Pro Ser
            100                 105                 110

Ala Glu Ser Thr Pro Gln Ser Thr Thr Val Lys Ile Lys Asn Thr Thr
        115                 120                 125

Thr Thr Gln Ile Leu Pro Ser Lys Pro Thr Thr Lys Gln Arg Gln Asn
    130                 135                 140

Lys Pro Gln Asn Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Lys Lys Thr Thr Thr Lys
            180                 185                 190

Pro Thr Lys Lys Pro Thr Leu Lys Thr Thr Lys Lys Asp Pro Lys Pro
        195                 200                 205

Gln Thr Thr Lys Pro Lys Glu Val Leu Thr Thr Lys Pro Thr Gly Lys
    210                 215                 220

Pro Thr Ile Asn Thr Thr Lys Thr Asn Ile Arg Thr Thr Leu Leu Thr
225                 230                 235                 240

Ser Asn Thr Lys Gly Asn Pro Glu His Thr Ser Gln Glu Glu Thr Leu
                245                 250                 255

His Ser Thr Thr Ser Glu Gly Tyr Leu Ser Pro Ser Gln Val Tyr Thr
            260                 265                 270

Thr Ser Gly Gln Glu Glu Thr Leu His Ser Thr Thr Ser Glu Gly Tyr
        275                 280                 285

Leu Ser Pro Ser Gln Val Tyr Thr Thr Ser Glu Tyr Leu Ser Gln Ser
    290                 295                 300

Leu Ser Ser Ser Asn Thr Thr Lys
305                 310
```

<210> SEQ ID NO 67
<211> LENGTH: 308
<212> TYPE: PRT
<213> ORGANISM: Artificial Sequence
<220> FEATURE:
<223> OTHER INFORMATION: Recombinant RSV G protein

<400> SEQUENCE: 67

```
Met Glu Tyr Trp Lys His Thr Asn Ser Ile Asn Asn Thr Asn Asn Glu
 1               5                  10                  15

Thr Glu Thr Ala Arg Gly Lys His Ser Ser Lys Val Thr Asn Ile Ala
                 20                  25                  30

Gln Ile Ala Leu Ser Val Leu Ala Met Ile Ile Ser Thr Ser Leu Ile
             35                  40                  45

Ile Ala Ala Ile Ile Phe Ile Ile Ser Ala Asn His Lys Val Thr Leu
         50                  55                  60

Thr Thr Val Thr Val Gln Thr Ile Lys Asn His Thr Glu Lys Asn Ile
 65                  70                  75                  80

Thr Thr Tyr Leu Thr Gln Val Ser Pro Glu Arg Val Ser Pro Ser Lys
                 85                  90                  95

Gln Leu Thr Thr Thr Pro Pro Ile Tyr Thr Asn Ser Ala Thr Ile Ser
            100                 105                 110
```

Pro Asn Thr Lys Ser Glu Thr His His Thr Thr Ala Gln Thr Lys Gly
            115                 120                 125

Arg Thr Thr Thr Pro Thr Gln Asn Asn Lys Pro Ser Thr Lys Pro Arg
130                 135                 140

Pro Lys Asn Pro Pro Lys Lys Pro Lys Asp Asp Tyr His Phe Glu Val
145                 150                 155                 160

Phe Asn Phe Val Pro Cys Ser Ile Cys Gly Asn Asn Gln Leu Cys Lys
                165                 170                 175

Ser Ile Cys Lys Thr Ile Pro Ser Asn Lys Pro Lys Lys Lys Pro Thr
            180                 185                 190

Ile Lys Pro Thr Asn Lys Pro Pro Thr Lys Thr Thr Asn Lys Arg Asp
            195                 200                 205

Pro Lys Lys Leu Ala Lys Thr Leu Lys Lys Glu Thr Thr Ile Asn Pro
210                 215                 220

Thr Lys Lys Pro Thr Pro Lys Thr Thr Glu Arg Asp Thr Ser Thr Ser
225                 230                 235                 240

Gln Ser Thr Val Leu Asp Thr Thr Thr Ser Lys His Thr Glu Arg Asp
                245                 250                 255

Thr Ser Thr Ser Gln Ser Thr Val Leu Asp Thr Thr Thr Ser Lys His
            260                 265                 270

Thr Ile Gln Gln Gln Ser Leu His Ser Thr Thr Pro Glu Asn Thr Pro
            275                 280                 285

Asn Ser Thr Gln Thr Pro Thr Ala Ser Glu Pro Ser Thr Ser Asn Ser
        290                 295                 300

Thr Gln Lys Leu
305

<210> SEQ ID NO 68
<211> LENGTH: 306
<212> TYPE: PRT
<213> ORGANISM: Artificial Sequence
<220> FEATURE:
<223> OTHER INFORMATION: Recombinant RSV G protein

<400> SEQUENCE: 68

Met Glu Tyr Trp Lys His Thr Asn Ser Ile Asn Asn Thr Asn Asn Glu
1               5                   10                  15

Thr Glu Thr Ala Arg Gly Lys Ser Ser Lys Val Thr Asn Ile Ile
            20                  25                  30

Met Tyr Thr Phe Trp Thr Ile Thr Leu Thr Ile Leu Ser Val Ile Phe
            35                  40                  45

Ile Met Ile Leu Thr Asn Leu Ile Asn His Lys Val Thr Leu Thr Thr
50                  55                  60

Val Thr Val Gln Thr Ile Lys Asn His Thr Glu Lys Asn Ile Thr Thr
65                  70                  75                  80

Tyr Leu Thr Gln Val Ser Pro Glu Arg Val Ser Pro Ser Lys Gln Leu
                85                  90                  95

Thr Thr Thr Pro Pro Ile Tyr Thr Asn Ser Ala Thr Ile Ser Pro Asn
            100                 105                 110

Thr Lys Ser Glu Thr His His Thr Thr Ala Gln Thr Lys Gly Arg Thr
            115                 120                 125

Thr Thr Pro Thr Gln Asn Asn Lys Pro Ser Thr Lys Pro Arg Pro Lys
130                 135                 140

Asn Pro Pro Lys Lys Pro Lys Asp Asp Tyr His Phe Glu Val Phe Asn
145                 150                 155                 160

```
Phe Val Pro Cys Ser Ile Cys Gly Asn Asn Gln Leu Cys Lys Ser Ile
                165                 170                 175
Cys Lys Thr Ile Pro Ser Asn Lys Pro Lys Lys Lys Pro Thr Ile Lys
            180                 185                 190
Pro Thr Asn Lys Pro Pro Thr Lys Thr Thr Asn Lys Arg Asp Pro Lys
        195                 200                 205
Lys Leu Ala Lys Thr Leu Lys Lys Glu Thr Thr Ile Asn Pro Thr Lys
    210                 215                 220
Lys Pro Thr Pro Lys Thr Thr Glu Arg Asp Thr Ser Thr Ser Gln Ser
225                 230                 235                 240
Thr Val Leu Asp Thr Thr Thr Ser Lys His Thr Glu Arg Asp Thr Ser
                245                 250                 255
Thr Ser Gln Ser Thr Val Leu Asp Thr Thr Thr Ser Lys His Thr Ile
            260                 265                 270
Gln Gln Gln Ser Leu His Ser Thr Thr Pro Glu Asn Thr Pro Asn Ser
        275                 280                 285
Thr Gln Thr Pro Thr Ala Ser Glu Pro Ser Thr Ser Asn Ser Thr Gln
    290                 295                 300
Lys Leu
305

<210> SEQ ID NO 69
<211> LENGTH: 292
<212> TYPE: PRT
<213> ORGANISM: Artificial Sequence
<220> FEATURE:
<223> OTHER INFORMATION: Recombinant RSV G protein

<400> SEQUENCE: 69

Met Glu Tyr Trp Lys His Thr Asn His Gly Lys Asp Ala Gly Asn Glu
1               5                   10                  15
Leu Glu Thr Ser Met Ala Thr His Gly Asn Lys Leu Thr Asn Lys Val
            20                  25                  30
Ala Gln Ile Thr Leu Ser Ile Leu Ala Met Ile Ile Ser Thr Ser Leu
        35                  40                  45
Ile Ile Ala Ala Ile Ile Phe Ile Ala Ser Ala Asn His Lys Val Thr
    50                  55                  60
Pro Thr Thr Ala Ile Ile Gln Asp Ala Thr Ser Gln Ile Lys Asn Thr
65                  70                  75                  80
Thr Pro Thr Tyr Leu Thr Gln Asn Pro Gln Leu Gly Ile Ser Pro Ser
                85                  90                  95
Asn Pro Ser Glu Ile Thr Ser Gln Ile Thr Thr Ile Leu Ala Ser Thr
            100                 105                 110
Thr Pro Gly Val Lys Ser Thr Leu Gln Ser Thr Thr Val Lys Thr Lys
        115                 120                 125
Asn Thr Thr Thr Thr Gln Thr Gln Pro Ser Lys Pro Thr Thr Lys Gln
    130                 135                 140
Arg Gln Asn Lys Pro Pro Ser Lys Pro Asn Asn Asp Phe His Phe Glu
145                 150                 155                 160
Val Phe Asn Phe Val Pro Cys Ser Ile Cys Ser Asn Asn Pro Thr Cys
                165                 170                 175
Trp Ala Ile Cys Lys Arg Ile Pro Asn Lys Lys Pro Gly Lys Lys Thr
            180                 185                 190
Thr Thr Lys Pro Thr Lys Lys Pro Thr Leu Lys Thr Thr Lys Lys Asp
        195                 200                 205
```

```
Pro Lys Pro Gln Thr Thr Lys Ser Lys Glu Val Pro Thr Thr Lys Pro
    210                 215                 220
Thr Glu Glu Pro Thr Ile Asn Thr Thr Lys Thr Asn Ile Ile Thr Thr
225                 230                 235                 240
Leu Leu Thr Ser Asn Thr Thr Gly Asn Pro Glu Leu Thr Ser Gln Met
                245                 250                 255
Glu Thr Phe His Ser Thr Ser Ser Glu Gly Asn Pro Ser Pro Ser Gln
            260                 265                 270
Val Ser Thr Thr Ser Glu Tyr Pro Ser Gln Pro Ser Ser Pro Pro Asn
        275                 280                 285
Thr Pro Arg Gln
    290

<210> SEQ ID NO 70
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 70

Met Glu Tyr Trp Lys His Thr Asn His Gly Lys Asp Ala Gly Asn Glu
1               5                   10                  15
Leu Glu Thr Ser Met Ala Thr His Gly Asn Lys Leu Thr Asn Lys Ile
            20                  25                  30
Ile Tyr Ile Leu Trp Thr Ile Ile Leu Val Leu Leu Ser Ile Val Phe
        35                  40                  45
Ile Ile Val Leu Ile Asn Ser Ile Asn His Lys Val Thr Pro Thr Thr
50                  55                  60
Ala Ile Ile Gln Asp Ala Thr Ser Gln Ile Lys Asn Thr Thr Pro Thr
65                  70                  75                  80
Tyr Leu Thr Gln Asn Pro Gln Leu Gly Ile Ser Pro Ser Asn Pro Ser
                85                  90                  95
Glu Ile Thr Ser Gln Ile Thr Thr Ile Leu Ala Ser Thr Thr Pro Gly
            100                 105                 110
Val Lys Ser Thr Leu Gln Ser Thr Thr Val Lys Thr Lys Asn Thr Thr
        115                 120                 125
Thr Thr Gln Thr Gln Pro Ser Lys Pro Thr Thr Lys Gln Arg Gln Asn
130                 135                 140
Lys Pro Pro Ser Lys Pro Asn Asn Asp Phe His Phe Glu Val Phe Asn
145                 150                 155                 160
Phe Val Pro Cys Ser Ile Cys Ser Asn Asn Pro Thr Cys Trp Ala Ile
                165                 170                 175
Cys Lys Arg Ile Pro Asn Lys Lys Pro Gly Lys Lys Thr Thr Thr Lys
            180                 185                 190
Pro Thr Lys Lys Pro Thr Leu Lys Thr Thr Lys Lys Asp Pro Lys Pro
        195                 200                 205
Gln Thr Thr Lys Ser Lys Glu Val Pro Thr Thr Lys Pro Thr Glu Glu
    210                 215                 220
Pro Thr Ile Asn Thr Thr Lys Thr Asn Ile Ile Thr Thr Leu Leu Thr
225                 230                 235                 240
Ser Asn Thr Thr Gly Asn Pro Glu Leu Thr Ser Gln Met Glu Thr Phe
                245                 250                 255
His Ser Thr Ser Ser Glu Gly Asn Pro Ser Pro Ser Gln Val Ser Thr
            260                 265                 270
```

```
Thr Ser Glu Tyr Pro Ser Gln Pro Ser Ser Pro Pro Asn Thr Pro Arg
        275                 280                 285
Gln
```

<210> SEQ ID NO 71
<211> LENGTH: 293
<212> TYPE: PRT
<213> ORGANISM: Artificial Sequence
<220> FEATURE:
<223> OTHER INFORMATION: Recombinant RSV G protein

<400> SEQUENCE: 71

```
Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ala Gln Ile Ala Leu Ser Val Leu Ala Met Ile Ile Ser Thr Ser Leu
        35                  40                  45

Ile Ile Ala Ala Ile Ile Phe Ile Ile Ser Ala Asn His Lys Val Thr
    50                  55                  60

Leu Thr Thr Val Thr Val Gln Thr Ile Lys Asn His Thr Glu Lys Asn
65                  70                  75                  80

Ile Thr Thr Tyr Leu Thr Gln Val Pro Pro Glu Arg Val Ser Ser Ser
                85                  90                  95

Lys Gln Pro Thr Thr Thr Ser Pro Ile His Thr Asn Ser Ala Thr Thr
            100                 105                 110

Ser Pro Asn Thr Lys Ser Glu Thr His His Thr Thr Ala Gln Thr Lys
        115                 120                 125

Gly Arg Thr Thr Thr Ser Thr Gln Thr Asn Lys Pro Ser Thr Lys Pro
    130                 135                 140

Arg Leu Lys Asn Pro Pro Lys Lys Pro Lys Asp Asp Tyr His Phe Glu
145                 150                 155                 160

Val Phe Asn Phe Val Pro Cys Ser Ile Cys Gly Asn Asn Gln Leu Cys
                165                 170                 175

Lys Ser Ile Cys Lys Thr Ile Pro Ser Asn Lys Pro Lys Lys Lys Pro
            180                 185                 190

Thr Ile Lys Pro Thr Asn Lys Pro Thr Thr Lys Thr Thr Asn Lys Arg
        195                 200                 205

Asp Pro Lys Thr Pro Ala Lys Thr Thr Lys Lys Glu Thr Thr Thr Asn
    210                 215                 220

Pro Thr Lys Lys Pro Thr Leu Thr Thr Thr Glu Arg Asp Thr Ser Thr
225                 230                 235                 240

Ser Gln Ser Thr Val Leu Asp Thr Thr Thr Leu Glu His Thr Ile Gln
                245                 250                 255

Gln Gln Ser Leu His Ser Thr Thr Pro Glu Asn Thr Pro Asn Ser Thr
            260                 265                 270

Gln Thr Pro Thr Ala Ser Glu Pro Ser Thr Ser Asn Ser Thr Gln Asn
        275                 280                 285

Thr Gln Ser His Ala
    290
```

<210> SEQ ID NO 72
<211> LENGTH: 290
<212> TYPE: PRT
<213> ORGANISM: Artificial Sequence
<220> FEATURE:

<223> OTHER INFORMATION: Recombinant RSV G protein

<400> SEQUENCE: 72

```
Met Glu Tyr Trp Lys His Thr Asn His

Ile Ile Ala Ala Ile Ile Phe Ile Ala Ser Ala Asn His Lys Val Thr
            50                  55                  60

Leu Thr Thr Ala Ile Ile Gln Asp Ala Thr Asn Gln Ile Lys Asn Thr
 65                  70                  75                  80

Thr Pro Thr Tyr Leu Thr Gln Asn Pro Gln Leu Gly Ile Ser Leu Ser
                    85                  90                  95

Asn Leu Ser Glu Thr Thr Ser Lys Pro Thr Thr Ile Leu Ala Leu Thr
                100                 105                 110

Thr Pro Asn Ala Glu Ser Thr Pro Gln Ser Thr Thr Val Lys Thr Lys
            115                 120                 125

Asn Thr Thr Thr Thr Gln Ile Gln Pro Ser Lys Pro Thr Thr Lys Gln
            130                 135                 140

Arg Gln Asn Lys Pro Gln Asn Lys Pro Asn Asn Asp Phe His Phe Glu
145                 150                 155                 160

Val Phe Asn Phe Val Pro Cys Ser Ile Cys Ser Asn Asn Pro Thr Cys
                165                 170                 175

Trp Ala Ile Cys Lys Arg Ile Pro Asn Lys Lys Pro Gly Arg Lys Thr
                180                 185                 190

Thr Thr Lys Pro Thr Lys Gln Pro Ala Ile Lys Thr Thr Lys Lys Asp
            195                 200                 205

Pro Lys Pro Gln Thr Thr Lys Pro Lys Glu Val Leu Thr Thr Lys Pro
210                 215                 220

Thr Glu Lys Pro Thr Ile Asn Thr Thr Lys Thr Asn Ile Arg Thr Thr
225                 230                 235                 240

Leu Leu Thr Ser Asn Ile Thr Glu Asn Gln Glu His Thr Ser Gln Lys
                245                 250                 255

Glu Thr Leu His Ser Thr Thr Ser Glu Gly Asn Pro Ser Pro Ser Gln
                260                 265                 270

Val Tyr Thr Thr Ser Glu Tyr Leu Ser Gln Ser Leu Ser Pro Ser Asn
                275                 280                 285

Thr Thr Arg Trp
    290

<210> SEQ ID NO 74
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 74

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
                20                  25                  30

Ile Tyr Ile Leu Trp Thr Ile Ile Leu Val Leu Leu Ser Ile Val Phe
            35                  40                  45

Ile Ile Val Leu Ile Asn Ser Ile Asn His Lys Val Thr Leu Thr Thr
        50                  55                  60

Ala Ile Ile Gln Asp Ala Thr Asn Gln Ile Lys Asn Thr Thr Pro Thr
65                  70                  75                  80

Tyr Leu Thr Gln Asn Pro Gln Leu Gly Ile Ser Leu Ser Asn Leu Ser
                85                  90                  95

Glu Thr Thr Ser Lys Pro Thr Thr Ile Leu Ala Leu Thr Thr Pro Asn
            100                 105                 110

Ala Glu Ser Thr Pro Gln Ser Thr Thr Val Lys Thr Lys Asn Thr Thr
            115                 120                 125

Thr Thr Gln Ile Gln Pro Ser Lys Pro Thr Thr Lys Gln Arg Gln Asn
        130                 135                 140

Lys Pro Gln Asn Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Arg Lys Thr Thr Thr Lys
                180                 185                 190

Pro Thr Lys Gln Pro Ala Ile Lys Thr Thr Lys Lys Asp Pro Lys Pro
            195                 200                 205

Gln Thr Thr Lys Pro Lys Glu Val Leu Thr Thr Lys Pro Thr Glu Lys
        210                 215                 220

Pro Thr Ile Asn Thr Thr Lys Thr Asn Ile Arg Thr Thr Leu Leu Thr
225                 230                 235                 240

Ser Asn Ile Thr Glu Asn Gln Glu His Thr Ser Gln Lys Glu Thr Leu
                245                 250                 255

His Ser Thr Thr Ser Glu Gly Asn Pro Ser Pro Ser Gln Val Tyr Thr
                260                 265                 270

Thr Ser Glu Tyr Leu Ser Gln Ser Leu Ser Pro Ser Asn Thr Thr Arg
            275                 280                 285

Trp

<210> SEQ ID NO 75
<211> LENGTH: 315
<212> TYPE: PRT
<213> ORGANISM: Artificial Sequence
<220> FEATURE:
<223> OTHER INFORMATION: Recombinant RSV G protein

<400> SEQUENCE: 75

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ala Gln Ile Thr Leu Ser Ile Leu Ala Met Ile Ile Ser Thr Ser Leu
        35                  40                  45

Ile Ile Ala Ala Ile Ile Phe Ile Ala Ser Ala Asn His Lys Val Thr
50                  55                  60

Leu Thr Thr Ala Ile Ile Gln Asp Ala Thr Asn Gln Ile Lys Asn Thr
65                  70                  75                  80

Thr Pro Thr Tyr Leu Thr Gln Asn Pro Gln Leu Gly Ile Ser Phe Ser
                85                  90                  95

Asn Leu Ser Gly Thr Thr Ser Gln Ser Thr Thr Ile Leu Ala Ser Thr
            100                 105                 110

Thr Pro Ser Ala Glu Ser Thr Pro Gln Ser Thr Thr Val Lys Ile Lys
        115                 120                 125

Asn Thr Thr Thr Thr Gln Ile Leu Pro Ser Lys Pro Thr Thr Lys Gln
    130                 135                 140

Arg Gln Asn Lys Pro Gln Asn Lys Pro Asn Asn Asp Phe His Phe Glu
145                 150                 155                 160

Val Phe Asn Phe Val Pro Cys Ser Ile Cys Ser Asn Asn Pro Thr Cys
                165                 170                 175

```
Trp Ala Ile Cys Lys Arg Ile Pro Asn Lys Lys Pro Gly Lys Lys Thr
            180                 185                 190

Thr Thr Lys Pro Thr Lys Pro Thr Leu Lys Thr Thr Lys Lys Asp
        195                 200                 205

Pro Lys Pro Gln Thr Thr Lys Pro Lys Glu Val Leu Thr Thr Lys Pro
210                 215                 220

Thr Gly Lys Pro Thr Ile Asn Thr Thr Lys Thr Asn Ile Arg Thr Thr
225                 230                 235                 240

Leu Leu Thr Ser Asn Thr Lys Gly Asn Pro Glu His Thr Ser Gln Glu
                245                 250                 255

Glu Thr Leu His Ser Thr Thr Ser Glu Gly Tyr Leu Ser Pro Ser Gln
            260                 265                 270

Val Tyr Thr Thr Ser Gly Gln Glu Glu Thr Leu His Ser Thr Thr Ser
        275                 280                 285

Glu Gly Tyr Leu Ser Pro Ser Gln Val Tyr Thr Thr Ser Glu Tyr Leu
290                 295                 300

Ser Gln Ser Leu Ser Ser Ser Asn Thr Thr Lys
305                 310                 315
```

<210> SEQ ID NO 76
<211> LENGTH: 312
<212> TYPE: PRT
<213> ORGANISM: Artificial Sequence
<220> FEATURE:
<223> OTHER INFORMATION: Recombinant RSV G protein

<400> SEQUENCE: 76

```
Met Glu Tyr

```
Pro Thr Ile Asn Thr Thr Lys Thr Asn Ile Arg Thr Thr Leu Leu Thr
225                 230                 235                 240

Ser Asn Thr Lys Gly Asn Pro Glu His Thr Ser Gln Glu Glu Thr Leu
            245                 250                 255

His Ser Thr Thr Ser Glu Gly Tyr Leu Ser Pro Ser Gln Val Tyr Thr
        260                 265                 270

Thr Ser Gly Gln Glu Glu Thr Leu His Ser Thr Thr Ser Glu Gly Tyr
            275                 280                 285

Leu Ser Pro Ser Gln Val Tyr Thr Thr Ser Glu Tyr Leu Ser Gln Ser
            290                 295                 300

Leu Ser Ser Ser Asn Thr Thr Lys
305                 310
```

<210> SEQ ID NO 77
<211> LENGTH: 309
<212> TYPE: PRT
<213> ORGANISM: Artificial Sequence
<220> FEATURE:
<223> OTHER INFORMATION: Recombinant RSV G protein

<400> SEQUENCE: 77

```
Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ala Gln Ile Ala Leu Ser Val Leu Ala Met Ile Ile Ser Thr Ser Leu
        35                  40                  45

Ile Ile Ala Ala Ile Ile Phe Ile Ile Ser Ala Asn His Lys Val Thr
    50                  55                  60

Leu Thr Thr Val Thr Val Gln Thr Ile Lys Asn His Thr Glu Lys Asn
65                  70                  75                  80

Ile Thr Thr Tyr Leu Thr Gln Val Ser Pro Glu Arg Val Ser Pro Ser
                85                  90                  95

Lys Gln Leu Thr Thr Thr Pro Pro Ile Tyr Thr Asn Ser Ala Thr Ile
            100                 105                 110

Ser Pro Asn Thr Lys Ser Glu Thr His His Thr Ala Gln Thr Lys
            115                 120                 125

Gly Arg Thr Thr Thr Pro Thr Gln Asn Asn Lys Pro Ser Thr Lys Pro
130                 135                 140

Arg Pro Lys Asn Pro Pro Lys Lys Pro Lys Asp Asp Tyr His Phe Glu
145                 150                 155                 160

Val Phe Asn Phe Val Pro Cys Ser Ile Cys Gly Asn Asn Gln Leu Cys
                165                 170                 175

Lys Ser Ile Cys Lys Thr Ile Pro Ser Asn Lys Pro Lys Lys Lys Pro
            180                 185                 190

Thr Ile Lys Pro Thr Asn Lys Pro Pro Thr Lys Thr Thr Asn Lys Arg
            195                 200                 205

Asp Pro Lys Lys Leu Ala Lys Thr Leu Lys Lys Glu Thr Thr Ile Asn
            210                 215                 220

Pro Thr Lys Lys Pro Thr Pro Lys Thr Thr Glu Arg Asp Thr Ser Thr
225                 230                 235                 240

Ser Gln Ser Thr Val Leu Asp Thr Thr Thr Ser Lys His Thr Glu Arg
            245                 250                 255

Asp Thr Ser Thr Ser Gln Ser Thr Val Leu Asp Thr Thr Thr Ser Lys
            260                 265                 270
```

```
His Thr Ile Gln Gln Gln Ser Leu His Ser Thr Thr Pro Glu Asn Thr
            275                 280                 285

Pro Asn Ser Thr Gln Thr Pro Thr Ala Ser Glu Pro Ser Thr Ser Asn
        290                 295                 300

Ser Thr Gln Lys Leu
305

<210> SEQ ID NO 78
<211> LENGTH: 306
<212> TYPE: PRT
<213> ORGANISM: Artificial Sequence
<220> FEATURE:
<223> OTHER INFORMATION: Recombinant RSV G protein

<400> SEQUENCE: 78

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Asn His Lys Val Thr Leu Thr Thr
    50                  55                  60

Val Thr Val Gln Thr Ile Lys Asn His Thr Glu Lys Asn Ile Thr Thr
65                  70                  75                  80

Tyr Leu Thr Gln Val Ser Pro Glu Arg Val Ser Pro Ser Lys Gln Leu
                85                  90                  95

Thr Thr Thr Pro Pro Ile Tyr Thr Asn Ser Ala Thr Ile Ser Pro Asn
            100                 105                 110

Thr Lys Ser Glu Thr His His Thr Thr Ala Gln Thr Lys Gly Arg Thr
        115                 120                 125

Thr Thr Pro Thr Gln Asn Asn Lys Pro Ser Thr Lys Pro Arg Pro Lys
    130                 135                 140

Asn Pro Pro Lys Lys Pro Lys Asp Asp Tyr His Phe Glu Val Phe Asn
145                 150                 155                 160

Phe Val Pro Cys Ser Ile Cys Gly Asn Asn Gln Leu Cys Lys Ser Ile
                165                 170                 175

Cys Lys Thr Ile Pro Ser Asn Lys Pro Lys Lys Pro Thr Ile Lys
            180                 185                 190

Pro Thr Asn Lys Pro Pro Thr Lys Thr Thr Asn Lys Arg Asp Pro Lys
        195                 200                 205

Lys Leu Ala Lys Thr Leu Lys Lys Glu Thr Thr Ile Asn Pro Thr Lys
    210                 215                 220

Lys Pro Thr Pro Lys Thr Thr Glu Arg Asp Thr Ser Thr Ser Gln Ser
225                 230                 235                 240

Thr Val Leu Asp Thr Thr Thr Ser Lys His Thr Glu Arg Asp Thr Ser
                245                 250                 255

Thr Ser Gln Ser Thr Val Leu Asp Thr Thr Thr Ser Lys His Thr Ile
            260                 265                 270

Gln Gln Gln Ser Leu His Ser Thr Thr Pro Glu Asn Thr Pro Asn Ser
        275                 280                 285

Thr Gln Thr Pro Thr Ala Ser Glu Pro Ser Thr Ser Asn Ser Thr Gln
    290                 295                 300

Lys Leu
305
```

```
<210> SEQ ID NO 79
<211> LENGTH: 296
<212> TYPE: PRT
<213> ORGANISM: Artificial Sequence
<220> FEATURE:
<223> OTHER INFORMATION: Recombinant RSV G protein

<400> SEQUENCE: 79

Met Ala Glu Lys Gly Lys Thr Asn Ser Ser Tyr Trp Ser Thr Thr Ar

```
Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile Asn His Lys Val
    50                  55                  60

Thr Pro Thr Thr Ala Ile Ile Gln Asp Ala Thr Ser Gln Ile Lys Asn
65                  70                  75                  80

Thr Thr Pro Thr Tyr Leu Thr Gln Asn Pro Gln Leu Gly Ile Ser Pro
                85                  90                  95

Ser Asn Pro Ser Glu Ile Thr Ser Gln Ile Thr Thr Ile Leu Ala Ser
            100                 105                 110

Thr Thr Pro Gly Val Lys Ser Thr Leu Gln Ser Thr Thr Val Lys Thr
        115                 120                 125

Lys Asn Thr Thr Thr Thr Gln Thr Gln Pro Ser Lys Pro Thr Thr Lys
    130                 135                 140

Gln Arg Gln Asn Lys Pro Pro Ser Lys Pro Asn Asn Asp Phe His Phe
145                 150                 155                 160

Glu Val Phe Asn Phe Val Pro Cys Ser Ile Cys Ser Asn Asn Pro Thr
                165                 170                 175

Cys Trp Ala Ile Cys Lys Arg Ile Pro Asn Lys Lys Pro Gly Lys Lys
            180                 185                 190

Thr Thr Thr Lys Pro Thr Lys Lys Pro Thr Leu Lys Thr Thr Lys Lys
        195                 200                 205

Asp Pro Lys Pro Gln Thr Thr Lys Ser Lys Glu Val Pro Thr Thr Lys
    210                 215                 220

Pro Thr Glu Glu Pro Thr Ile Asn Thr Thr Lys Thr Asn Ile Ile Thr
225                 230                 235                 240

Thr Leu Leu Thr Ser Asn Thr Thr Gly Asn Pro Glu Leu Thr Ser Gln
                245                 250                 255

Met Glu Thr Phe His Ser Thr Ser Ser Glu Gly Asn Pro Ser Pro Ser
            260                 265                 270

Gln Val Ser Thr Thr Ser Glu Tyr Pro Ser Gln Pro Ser Ser Pro Pro
        275                 280                 285

Asn Thr Pro Arg Gln
    290

<210> SEQ ID NO 81
<211> LENGTH: 297
<212> TYPE: PRT
<213> ORGANISM: Artificial Sequence
<220> FEATURE:
<223> OTHER INFORMATION: Recombinant RSV G protein

<400> SEQUENCE: 81

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Ala Gln Ile Ala Leu Ser Val Leu Ala Met Ile Ile
        35                  40                  45

Ser Thr Ser Leu Ile Ile Ala Ala Ile Ile Phe Ile Ile Ser Ala Asn
    50                  55                  60

His Lys Val Thr Leu Thr Thr Val Thr Val Gln Thr Ile Lys Asn His
65                  70                  75                  80
```

```
Thr Glu Lys Asn Ile Thr Thr Tyr Leu Thr Gln Val Pro Pro Glu Arg
                85                  90                  95

Val Ser Ser Ser Lys Gln Pro Thr Thr Thr Ser Pro Ile His Thr Asn
            100                 105                 110

Ser Ala Thr Thr Ser Pro Asn Thr Lys Ser Glu Thr His His Thr Thr
        115                 120                 125

Ala Gln Thr Lys Gly Arg Thr Thr Thr Ser Thr Gln Thr Asn Lys Pro
    130                 135                 140

Ser Thr Lys Pro Arg Leu Lys Asn Pro Pro Lys Lys Pro Lys Asp Asp
145                 150                 155                 160

Tyr His Phe Glu Val Phe Asn Phe Val Pro Cys Ser Ile Cys Gly Asn
                165                 170                 175

Asn Gln Leu Cys Lys Ser Ile Cys Lys Thr Ile Pro Ser Asn Lys Pro
            180                 185                 190

Lys Lys Lys Pro Thr Ile Lys Pro Thr Asn Lys Pro Thr Thr Lys Thr
            195                 200                 205

Thr Asn Lys Arg Asp Pro Lys Thr Pro Ala Lys Thr Thr Lys Lys Glu
        210                 215                 220

Thr Thr Thr Asn Pro Thr Lys Lys Pro Thr Leu Thr Thr Thr Glu Arg
225                 230                 235                 240

Asp Thr Ser Thr Ser Gln Ser Thr Val Leu Asp Thr Thr Thr Leu Glu
                245                 250                 255

His Thr Ile Gln Gln Gln Ser Leu His Ser Thr Thr Pro Glu Asn Thr
            260                 265                 270

Pro Asn Ser Thr Gln Thr Pro Thr Ala Ser Glu Pro Ser Thr Ser Asn
        275                 280                 285

Ser Thr Gln Asn Thr Gln Ser His Ala
    290                 295

<210> SEQ ID NO 82
<211> LENGTH: 294
<212> TYPE: PRT
<213> ORGANISM: Artificial Sequence
<220> FEATURE:
<223> OTHER INFORMATION: Recombinant RSV G protein

<400> SEQUENCE: 82

Met Ala Glu Lys Gly Lys Thr Asn Ser Ser Tyr Trp Ser Th

-continued

```
Pro Arg Leu Lys Asn Pro Lys Lys Pro Lys Asp Asp Tyr His Phe
145                 150                 155                 160

Glu Val Phe Asn Phe Val Pro Cys Ser Ile Cys Gly Asn Asn Gln Leu
            165                 170                 175

Cys Lys Ser Ile Cys Lys Thr Ile Pro Ser Asn Lys Pro Lys Lys Lys
        180                 185                 190

Pro Thr Ile Lys Pro Thr Asn Lys Pro Thr Thr Lys Thr Thr Asn Lys
            195                 200                 205

Arg Asp Pro Lys Thr Pro Ala Lys Thr Thr Lys Lys Glu Thr Thr Thr
        210                 215                 220

Asn Pro Thr Lys Lys Pro Thr Leu Thr Thr Thr Glu Arg Asp Thr Ser
225                 230                 235                 240

Thr Ser Gln Ser Thr Val Leu Asp Thr Thr Thr Leu Glu His Thr Ile
            245                 250                 255

Gln Gln Gln Ser Leu His Ser Thr Thr Pro Glu Asn Thr Pro Asn Ser
        260                 265                 270

Thr Gln Thr Pro Thr Ala Ser Glu Pro Ser Thr Ser Asn Ser Thr Gln
            275                 280                 285

Asn Thr Gln Ser His Ala
        290

<210> SEQ ID NO 83
<211> LENGTH: 296
<212> TYPE: PRT
<213> ORGANISM: Artificial Sequence
<220> FEATURE:
<223> OTHER INFORMATION: Recombinant RSV G protein

<400> SEQUENCE: 83

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Ala Gln Ile Thr Leu Ser Ile Leu Ala Met Ile Ile
        35                  40                  45

Ser Thr Ser Leu Ile Ile Ala Ala Ile Ile Phe Ile Ala Ser Ala Asn
    50                  55                  60

His Lys Val Thr Leu Thr Thr Ala Ile Ile Gln Asp Ala Thr Asn Gln
65                  70                  75                  80

Ile Lys Asn Thr Thr Pro Thr Tyr Leu Thr Gln Asn Pro Gln Leu Gly
            85                  90                  95

Ile Ser Leu Ser Asn Leu Ser Glu Thr Thr Ser Lys Pro Thr Thr Ile
            100                 105                 110

Leu Ala Leu Thr Thr Pro Asn Ala Glu Ser Thr Pro Gln Ser Thr Thr
        115                 120                 125

Val Lys Thr Lys Asn Thr Thr Thr Thr Gln Ile Gln Pro Ser Lys Pro
    130                 135                 140

Thr Thr Lys Gln Arg Gln Asn Lys Pro Gln Asn Lys Pro Asn Asn Asp
145                 150                 155                 160

Phe His Phe Glu Val Phe Asn Phe Val Pro Cys Ser Ile Cys Ser Asn
            165                 170                 175

Asn Pro Thr Cys Trp Ala Ile Cys Lys Arg Ile Pro Asn Lys Lys Pro
        180                 185                 190

Gly Arg Lys Thr Thr Thr Lys Pro Thr Lys Gln Pro Ala Ile Lys Thr
    195                 200                 205
```

```
Thr Lys Lys Asp Pro Lys Pro Gln Thr Thr Lys Pro Lys Glu Val Leu
        210                 215                 220

Thr Thr Lys Pro Thr Glu Lys Pro Thr Ile Asn Thr Thr Lys Thr Asn
225                 230                 235                 240

Ile Arg Thr Thr Leu Leu Thr Ser Asn Ile Thr Glu Asn Gln Glu His
                245                 250                 255

Thr Ser Gln Lys Glu Thr Leu His Ser Thr Thr Ser Glu Gly Asn Pro
        260                 265                 270

Ser Pro Ser Gln Val Tyr Thr Thr Ser Glu Tyr Leu Ser Gln Ser Leu
        275                 280                 285

Ser Pro Ser Asn Thr Thr Arg Trp
        290                 295

<210> SEQ ID NO 84
<211> LENGTH: 293
<212> TYPE: PRT
<213> ORGANISM: Artificial Sequence
<220> FEATURE:
<223> OTHER INFORMATION: Recombinant RSV G protein

<400> SEQUENCE: 84

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile Asn His Lys Val
    50                  55                  60

Thr Leu Thr Thr Ala Ile Ile Gln Asp Ala Thr Asn Gln Ile Lys Asn
65                  70                  75                  80

Thr Thr Pro Thr Tyr Leu Thr Gln Asn Pro Gln Leu Gly Ile Ser Leu
                85                  90                  95

Ser Asn Leu Ser Glu Thr Thr Ser Lys Pro Thr Thr Ile Leu Ala Leu
            100                 105                 110

Thr Thr Pro Asn Ala Glu Ser Thr Pro Gln Ser Thr Thr Val Lys Thr
        115                 120                 125

Lys Asn Thr Thr Thr Thr Gln Ile Gln Pro Ser Lys Pro Thr Thr Lys
    130                 135                 140

Gln Arg Gln Asn Lys Pro Gln Asn Lys Pro Asn Asn Asp Phe His Phe
145                 150                 155                 160

Glu Val Phe Asn Phe Val Pro Cys Ser Ile Cys Ser Asn Asn Pro Thr
                165                 170                 175

Cys Trp Ala Ile Cys Lys Arg Ile Pro Asn Lys Lys Pro Gly Arg Lys
            180                 185                 190

Thr Thr Thr Lys Pro Thr Lys Gln Pro Ala Ile Lys Thr Thr Lys Lys
        195                 200                 205

Asp Pro Lys Pro Gln Thr Thr Lys Pro Lys Glu Val Leu Thr Thr Lys
    210                 215                 220

Pro Thr Glu Lys Pro Thr Ile Asn Thr Thr Lys Thr Asn Ile Arg Thr
225                 230                 235                 240

Thr Leu Leu Thr Ser Asn Ile Thr Glu Asn Gln Glu His Thr Ser Gln
                245                 250                 255

Lys Glu Thr Leu His Ser Thr Thr Ser Glu Gly Asn Pro Ser Pro Ser
            260                 265                 270
```

Gln Val Tyr Thr Thr Ser Glu Tyr Leu Ser Gln Ser Leu Ser Pro Ser
            275                 280                 285

Asn Thr Thr Arg Trp
    290

<210> SEQ ID NO 85
<211> LENGTH: 319
<212> TYPE: PRT
<213> ORGANISM: Artificial Sequence
<220> FEATURE:
<223> OTHER INFORMATION: Recombinant RSV G protein

<400> SEQUENCE: 85

Met Ala Glu Lys Gly Lys Thr Asn Ser Ser Tyr Trp Ser Thr Thr Arg
1

<211> LENGTH: 316
<212> TYPE: PRT
<213> ORGANISM: Artificial Sequence
<220> FEATURE:
<223> OTHER INFORMATION: Recombinant RSV G protein

<400> SEQUENCE: 86

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile Asn His Lys Val
    50                  55                  60

Thr Leu Thr Thr Ala Ile Ile Gln Asp Ala Thr Asn Gln Ile Lys Asn
65                  70                  75                  80

Thr Thr Pro Thr Tyr Leu Thr Gln Asn Pro Gln Leu Gly Ile Ser Phe
                85                  90                  95

Ser Asn Leu Ser Gly Thr Thr Ser Gln Ser Thr Thr Ile Leu Ala Ser
            100                 105                 110

Thr Thr Pro Ser Ala Glu Ser Thr Pro Gln Ser Thr Thr Val Lys Ile
        115                 120                 125

Lys Asn Thr Thr Thr Thr Gln Ile Leu Pro Ser Lys Pro Thr Thr Lys
130                 135                 140

Gln Arg Gln Asn Lys Pro Gln Asn Lys Pro Asn Asn Asp Phe His Phe
145                 150                 155                 160

Glu Val Phe Asn Phe Val Pro Cys Ser Ile Cys Ser Asn Asn Pro Thr
                165                 170                 175

Cys Trp Ala Ile Cys Lys Arg Ile Pro Asn Lys Lys Pro Gly Lys Lys
            180                 185                 190

Thr Thr Thr Lys Pro Thr Lys Lys Pro Thr Leu Lys Thr Thr Lys Lys
        195                 200                 205

Asp Pro Lys Pro Gln Thr Thr Lys Pro Lys Glu Val Leu Thr Thr Lys
210                 215                 220

Pro Thr Gly Lys Pro Thr Ile Asn Thr Thr Lys Thr Asn Ile Arg Thr
225                 230                 235                 240

Thr Leu Leu Thr Ser Asn Thr Lys Gly Asn Pro Glu His Thr Ser Gln
                245                 250                 255

Glu Glu Thr Leu His Ser Thr Thr Ser Glu Gly Tyr Leu Ser Pro Ser
            260                 265                 270

Gln Val Tyr Thr Thr Ser Gly Gln Glu Glu Thr Leu His Ser Thr Thr
        275                 280                 285

Ser Glu Gly Tyr Leu Ser Pro Ser Gln Val Tyr Thr Thr Ser Glu Tyr
    290                 295                 300

Leu Ser Gln Ser Leu Ser Ser Asn Thr Thr Lys
305                 310                 315

<210> SEQ ID NO 87
<211> LENGTH: 313
<212> TYPE: PRT
<213> ORGANISM: Artificial Sequence
<220> FEATURE:
<223> OTHER INFORMATION: Recombinant RSV G protein

<400> SEQUENCE: 87

Met Ala Glu Lys Gly Lys Thr Asn Ser Ser Tyr Trp Ser Thr Thr Arg

```
  1               5                  10                 15
Asn Asp Asn Ser Thr Val Asn Thr His Ile Asn Thr Pro Ala Gly Arg
            20                 25                 30

Thr His Trp Ile Ala Gln Ile Ala Leu Ser Val Leu Ala Met Ile Ile
            35                 40                 45

Ser Thr Ser Leu Ile Ile Ala Ala Ile Ile Phe Ile Ile Ser Ala Asn
        50                 55                 60

His Lys Val Thr Leu Thr Thr Val Thr Val Gln Thr Ile Lys Asn His
65                 70                 75                 80

Thr Glu Lys Asn Ile Thr Thr Tyr Leu Thr Gln Val Ser Pro Glu Arg
                85                 90                 95

Val Ser Pro Ser Lys Gln Leu Thr Thr Thr Pro Pro Ile Tyr Thr Asn
            100                105                110

Ser Ala Thr Ile Ser Pro Asn Thr Lys Ser Glu Thr His His Thr Thr
            115                120                125

Ala Gln Thr Lys Gly Arg Thr Thr Thr Pro Thr Gln Asn Asn Lys Pro
130                135                140

Ser Thr Lys Pro Arg Pro Lys Asn Pro Pro Lys Lys Pro Lys Asp Asp
145                150                155                160

Tyr His Phe Glu Val Phe Asn Phe Val Pro Cys Ser Ile Cys Gly Asn
                165                170                175

Asn Gln Leu Cys Lys Ser Ile Cys Lys Thr Ile Pro Ser Asn Lys Pro
            180                185                190

Lys Lys Lys Pro Thr Ile Lys Pro Thr Asn Lys Pro Pro Thr Lys Thr
                195                200                205

Thr Asn Lys Arg Asp Pro Lys Lys Leu Ala Lys Thr Leu Lys Lys Glu
210                215                220

Thr Thr Ile Asn Pro Thr Lys Lys Pro Thr Pro Lys Thr Thr Glu Arg
225                230                235                240

Asp Thr Ser Thr Ser Gln Ser Thr Val Leu Asp Thr Thr Thr Ser Lys
                245                250                255

His Thr Glu Arg Asp Thr Ser Thr Ser Gln Ser Thr Val Leu Asp Thr
            260                265                270

Thr Thr Ser Lys His Thr Ile Gln Gln Gln Ser Leu His Ser Thr Thr
            275                280                285

Pro Glu Asn Thr Pro Asn Ser Thr Gln Thr Pro Thr Ala Ser Glu Pro
            290                295                300

Ser Thr Ser Asn Ser Thr Gln Lys Leu
305                310

<210> SEQ ID NO 88
<211> LENGTH: 310
<212> TYPE: PRT
<213> ORGANISM: Artificial Sequence
<220> FEATURE:
<223> OTHER INFORMATION: Recombinant RSV G protein

<400> SEQUENCE: 88

Met Ala Glu Lys Gly Lys Thr Asn Ser Ser Tyr Trp Ser Thr Thr Arg
1               5                  10                 15

Asn Asp Asn Ser Thr Val Asn Thr His Ile Asn Thr Pro Ala Gly Arg
            20                 25                 30

Thr His Trp Ile Leu Leu Ile Ala Thr Thr Met His Thr Val Leu Ser
            35                 40                 45

Phe Ile Ile Met Ile Leu Cys Ile Asp Leu Ile Ile Asn His Lys Val
```

```
        50                  55                  60
Thr Leu Thr Thr Val Thr Val Gln Thr Ile Lys Asn His Thr Glu Lys
 65                  70                  75                  80

Asn Ile Thr Thr Tyr Leu Thr Gln Val Ser Pro Glu Arg Val Ser Pro
                 85                  90                  95

Ser Lys Gln Leu Thr Thr Thr Pro Pro Ile Tyr Thr Asn Ser Ala Thr
            100                 105                 110

Ile Ser Pro Asn Thr Lys Ser Glu Thr His His Thr Thr Ala Gln Thr
        115                 120                 125

Lys Gly Arg Thr Thr Thr Pro Thr Gln Asn Asn Lys Pro Ser Thr Lys
    130                 135                 140

Pro Arg Pro Lys Asn Pro Pro Lys Lys Pro Lys Asp Asp Tyr His Phe
145                 150                 155                 160

Glu Val Phe Asn Phe Val Pro Cys Ser Ile Cys Gly Asn Asn Gln Leu
                165                 170                 175

Cys Lys Ser Ile Cys Lys Thr Ile Pro Ser Asn Lys Pro Lys Lys Lys
            180                 185                 190

Pro Thr Ile Lys Pro Thr Asn Lys Pro Pro Thr Lys Thr Thr Asn Lys
        195                 200                 205

Arg Asp Pro Lys Lys Leu Ala Lys Thr Leu Lys Lys Glu Thr Thr Ile
    210                 215                 220

Asn Pro Thr Lys Lys Pro Thr Pro Lys Thr Thr Glu Arg Asp Thr Ser
225                 230                 235                 240

Thr Ser Gln Ser Thr Val Leu Asp Thr Thr Thr Ser Lys His Thr Glu
                245                 250                 255

Arg Asp Thr Ser Thr Ser Gln Ser Thr Val Leu Asp Thr Thr Thr Ser
            260                 265                 270

Lys His Thr Ile Gln Gln Gln Ser Leu His Ser Thr Thr Pro Glu Asn
        275                 280                 285

Thr Pro Asn Ser Thr Gln Thr Pro Thr Ala Ser Glu Pro Ser Thr Ser
    290                 295                 300

Asn Ser Thr Gln Lys Leu
305                 310

<210> SEQ ID NO 89
<211> LENGTH: 897
<212> TYPE: DNA
<213> ORGANISM: Artificial Sequence
<220> FEATURE:
<223> OTHER INFORMATION: Recombinant RSV G protein

<400> SEQUENCE: 89
atgtcaaaga caaggatca gagaactgcc aagaccctgg aaagaacctg ggacaccctg      60
aaccacctgc tgtttatctc aagctgcctg tacaagctga atctgaaaag tgtggcccag     120 atcacccctgt caattctggc tatgatcatt tcaacaagcc tgatcattgc cgctatcatt    180
ttcatcgcaa gcgccaacca aaggtcacc cccaccacag ctatcattca ggacgcaaca      240
tcccagatta gaacactac ccccacctat ctgacacaga tcctcagct gggaatctcc       300 ccatctaacc cctcagagat taccagccag atcacaacta ttctggcctc caccacacct    360
ggcgtgaagt ccactctgca gtctactacc gtcaagacca aaatacaac taccacacag     420 acacagcctt ctaagccaac taccaaacag cggcagaata agccccctag taaaccaaac    480
aatgacttcc attttgaggt gttcaacttt gtccctgca gcatctgttc caacaatccc     540
acctgctggg ccatctgtaa agaattcca acaagaaac ccggcaagaa gaccactacc     600
```
aaacctacta agaaaccaac cctgaagaca actaagaaag atcctaaacc acagaccaca 660
aagtctaaag aagtgcccac taccaagcct acagaggaac caactatcaa cacaactaag 720
actaacatca tcaccacact gctgacaagc aacactaccg gcaatcccga gctgaccagc 780
cagatggaaa cctttcactc cacaagctcc gaggggaatc ccagtccttc acaggtgtct 840
acaactagtg aataccccag ccagccttct agtccaccca acacccctag gcagtga 897

<210> SEQ ID NO 90
<211> LENGTH: 899
<212> TYPE: DNA
<213> ORGANISM: Artificial Sequence
<220> FEATURE:
<223> OTHER INFORMATION: Recombinant RSV G protein

<400> SEQUENCE: 90
agtctaaaca caagaatcag cggaccgccc ggaccttgga aaagacttgg gataccctta 60
accaccttat cgtgatttcc tcctgcctgt accgcctcaa cctcaagagc attgctcaga 120
tcgcgctctc agtgctggcc atgataatct ccacttcctt gataattgcc gccattatct 180
tcattatttc tgcaaaccac aaagtcaccc tgaccaccgt taccgtgcaa accattaaaa 240
accacacgga gaagaacatc actacatacc tgactcaggt tcccccggag cgagtgagca 300
gctccaagca gcccacaaca acaagcccta tccatacaaa ttcagcaaca acaagtccaa 360
acacaaagtc tgaaacgcat cacacaaccg ctcagacgaa aggcaggacc acaacatcca 420
cccagactaa taaacccagt actaagccta gactgaagaa ccctcccaag aaacctaagg 480
acgactatca tttcgaggtg tttaattttg taccttgcag catctgtggc aacaatcagc 540
tctgcaaaag catctgtaag accatcccgt ctaataagcc aaagaagaag cccacgataa 600
aaccaacaaa taaaccaact accaagacaa caaataagag ggacccaaag acccccgcta 660
aaactaccaa gaaggagact accaccaacc cgacaaagaa acccaccctg acgactactg 720
agagagatac ttcaacttca caaagcaccg tcctggatac aactaccctg gagcacacaa 780
tccagcaaca gagcctgcat agtactacgc ctgaaaacac tccaaactct acccagacgc 840
ccacagcctc agaaccttct acctccaata gtacccaaaa tacccagagt catgcatag 899

<210> SEQ ID NO 91
<211> LENGTH: 16386
<212> TYPE: DNA
<213> ORGANISM: Artificial Sequence
<220> FEATURE:
<223> OTHER INFORMATION: Recombinant rB/HPIV3 sequence

<400> SEQUENCE: 91
accaaacaag agaagagact ggtttgggaa tattaattca aataaaaatt aacttaggat 60
taaagaactt taccgaaagg taaggggaaa gaaatcctaa gagcttagcc atgttgagtc 120
tattcgacac attcagtgcg cgtaggcagg agaacataac gaaatcagct ggtggggctg 180
ttattcccgg gcaaaaaaac actgtgtcta tatttgctct tggaccatca ataacagatg 240
acaatgataa aatgacattg gctcttctct ttttgtctca ttctttagac aatgaaaagc 300
agcatgcgca aagagctgga tttttagttt ctctgttatc aatggcttat gccaacccag 360
aattatattt aacatcaaat ggtagtaatg cagatgttaa atatgttatc tacatgatag 420
agaaagaccc aggaagacag aaatatggtg ggtttgtcgt caagactaga gagatggttt 480
atgaaaagac aactgattgg atgttcggga gtgatcttga gtatgatcaa gacaatatgt 540

-continued

```
tgcaaaatgg tagaagcact tctacaatcg aggatcttgt tcatacttttt ggatatccat    600 cgtgtcttgg agcccttata atccaagttt ggataatact tgttaaggct ataaccagta    660
tatcaggatt gaggaaagga ttctttactc ggttagaagc atttcgacaa gatggaacag    720
ttaaatccag tctagtgttg agcggtgatg cagtagaaca aattggatca attatgaggt    780
cccaacagag cttggtaaca ctcatggttg aaacactgat aacaatgaac acaggcagga    840
atgatctgac aacaatagaa aagaatatac agattgtagg aaactacatc agagatgcag    900
gtcttgcttc attttttcaac acaatcagat atggcattga gactagaatg gcagctctaa    960
ctctgtctac ccttagaccg gatatcaaca gactcaaggc actgatcgag ttatatctat   1020
caaaggggcc acgtgctcct tttatatgca ttttgagaga tcccgtgcat ggtgagtttg   1080
caccaggcaa ctatcctgcc ctctggagtt atgcgatggg tgtagcagtt gtacaaaaca   1140
aggccatgca acagtatgta acaggaaggt cttatctgga tattgaaatg ttccaacttg   1200
gtcaagcagt ggcacgtgat gccgagtcgc agatgagttc aatattagag gatgaactgg   1260
gggtcacaca agaagccaag caaagcttga agaaacacat gaagaacatc agcagttcag   1320
atacaacctt tcataagcct acaggggggat cagccataga aatggcgata gatgaagaag   1380
cagggcagcc tgaatccaga ggagatcagg atcaaggaga tgagcctcgg tcatccatag   1440
ttccttatgc atgggcagac gaaaccggga atgacaatca aactgaatca actacagaaa   1500
ttgacagcat caaaactgaa caaagaaaca tcagagacag gctgaacaaa agactcaacg   1560
agaaaaggaa acagagtgac ccgagatcaa ctgacatcac aaacaacaca aatcaaactg   1620
aaatagatga tttgttcagt gcattcggaa gcaactagtc acaaagagat gaccaggcgc   1680
gccaagtaag aaaaacttag gattaatgga cctgcaggat gtccaaaaac aaggaccaac   1740
gcaccgctaa gacattagaa aggacctggg acactctcaa tcatttatta ttcatatcat   1800
cgtgcttata taagttaaat cttaaatctg tagcacaaat cacattatcc attctggcaa   1860
tgataatctc aacttcactt ataattgcag ccatcatatt catagcctcg gcaaaccaca   1920
aagtcacacc aacaactgca atcatacaag atgcaacaag ccagatcaag aacacaaccc   1980
caacatacct cacccagaat cctcagcttg gaatcagtcc ctctaatccg tctgaaatta   2040
catcacaaat caccaccata ctagcttcaa caacaccagg agtcaagtca accctgcaat   2100
ccacaacagt caagaccaaa aacacaacaa caactcaaac acaacccagc aagcccacca   2160
caaaacaacg ccaaaacaaa ccaccaagca aacccaataa tgattttcac tttgaagtgt   2220
tcaactttgt accctgcagc atatgcagca acaatccaac ctgctgggct atctgcaaaa   2280
gaataccaaa caaaaaacca ggaaagaaaa ccactaccaa gcccacaaaa aaaccaaccc   2340
tcaagcaaac caaaaaagat cccaaacctc aaaccactaa atcaaaggaa gtacccacca   2400
ccaagcccac agaagagcca accatcaaca ccaccaaaac aaacatcata actacactac   2460
tcacctccaa caccacagga aatccagaac tcacaagtca aatggaaacc ttccactcaa   2520
cttcctccga aggcaatcca agcccttctc aagtctctac aacatccgag tacccatcac   2580
aaccttcatc tccacccaac acaccacgcc agtgatagct agcggcgcgc cagcaacaag   2640
taagaaaaac ttaggattaa tggaaattat ccaatccaga gacggaagga caaatccaga   2700
atccaaccac aactcaatca accaaagatt catggaagac aatgttcaaa acaatcaaat   2760
catggattct tgggaagagg gatcaggaga taaatcatct gacatctcat cggccctcga   2820
catcattgaa ttcatactca gcaccgactc ccaagagaac acggcagaca gcaatgaaat   2880
caacacagga accacaagac ttagcacgac aatctaccaa cctgaatcca aaacaacaga   2940
```

```
aacaagcaag gaaaatagtg gaccagctaa caaaaatcga cagtttgggg catcacacga    3000
acgtgccaca gagacaaaag atagaaatgt taatcaggag actgtacagg gaggatatag    3060
gagaggaagc agcccagata gtagaactga gactatggtc actcgaagaa tctccagaag    3120
cagcccagat cctaacaatg gaacccaaat ccaggaagat attgattaca atgaagttgg    3180
agagatggat aaggactcta ctaagaggga aatgcgacaa tttaaagatg ttccagtcaa    3240
ggtatcagga agtgatgcca ttcctccaac aaaacaagat ggagacggtg atgatgaag    3300 aggcctggaa tctatcagta catttgattc aggatatacc agtatagtga ctgccgcaac    3360
actagatgac gaagaagaac tccttatgaa gaacaacagg ccaagaaagt atcaatcaac    3420
accccagaac agtgacaagg gaattaaaaa aggggttgga aggccaaaag acacagacaa    3480
acaatcatca atattggact acgaactcaa cttcaaagga tcgaagaaga gccagaaaat    3540
cctcaaagcc agcacgaata caggagaacc aacaagacca cagaatggat cccaggggaa    3600
gagaatcaca tcctggaaca tcctcaacag cgagagcggc aatcgaacag aatcaacaaa    3660
ccaaacccat cagacatcaa cctcgggaca gaaccacaca atgggaccaa gcagaacaac    3720
ctccgaacca aggatcaaga cacaaaagac ggatggaaag gaaagagagg acacagaaga    3780
gagcactcga tttacagaaa gggcgattac attattacag aatcttggtg taatccaatc    3840
tgcagcaaaa ttagacctat accaagacaa gagagttgtg tgtgtggcga atgtcctaaa    3900
caatgcagat actgcatcaa agatagactt cctagcaggt ttgatgatag gagtgtcaat    3960
ggatcatgat accaaattaa atcagattca gaacgagata ttaagtttga aaactgatct    4020 taaaagatg gatgaatcac atagaagact aattgagaat caaaaagaac aattatcact    4080
gatcacatca ttaatctcaa atcttaaaat tatgacagag agaggaggga agaaggacca    4140
accagaacct agcgggagga catccatgat caagacaaaa gcaaagaag agaaaataaa    4200 gaaagtcagg tttgacccctc ttatggaaac acagggcatc gagaaaaaca tccctgacct    4260
ctatagatca atagagaaaa caccagaaaa cgacacacag atcaaatcag aaataaacag    4320
attgaatgat gaatccaatg ccactagatt agtacctaga agaataagca gtacaatgag    4380
atcattaata ataatcatta acaacagcaa tttatcatca aaagcaaagc aatcatacat    4440
caacgaactc aagctctgca agagtgacga ggaagtgtct gagttgatgg acatgttcaa    4500
tgaggatgtc agctcccagt aaaccgccaa ccaagggtca acaccaagaa accaatagc    4560 acaaaacagc caatcagaga ccaccccaat acaccaaacc aatcaacaca taacaaagat    4620
cgcggccgca tagatgatta agaaaaactt aggatgaaag gactaatcaa tcctccgaaa    4680
caatgagcat caccaactcc acaatctaca cattcccaga atcctctttc tccgagaatg    4740
gcaacataga gccgttacca ctcaaggtca atgaacagaa aaaggccata cctcatatta    4800
gggttgtcaa gataggagat ccgcccaaac atggatccag atatctggat gtcttttttac    4860 tgggcttctt tgagatggaa aggtcaaaag acaggtatgg gagcataagt gatctagatg    4920
atgatccaag ttacaaggtt tgtggctctg gatcattgcc acttgggttg gctagataca    4980
ccggaaatga tcaggaactc ctacaggctg caaccaagct cgatatagaa gtaagaagaa    5040
ctgtaaaggc tacggagatg atagtttaca ctgtacaaaa catcaaacct gaactatatc    5100
catggtccag tagattaaga aaagggatgt tatttgacgc taataaggtt gcacttgctc    5160
ctcaatgtct tccactagat agagggataa aattcagggt gatatttgtg aactgcacag    5220
caattggatc aataactcta ttcaaaatcc ctaagtccat ggcattgtta tcattgccta    5280
```

```
atacaatatc aataaatcta caagtacata tcaaaacagg agttcagaca gattccaaag    5340
gagtagttca gattctagat gaaaaaggtg aaaaatcact aaatttcatg gttcatctcg    5400
ggttgatcaa aaggaagatg ggcagaatgt actcagttga atattgtaag cagaagatcg    5460
agaagatgag attattattc tcattgggat tagttggagg gatcagcttc cacgtcaacg    5520
caactggctc tatatcaaag acattagcaa gtcaattagc attcaaaaga gaaatctgct    5580 atccctaat ggatctgaat ccacacttaa attcagttat atgggcatca tcagttgaaa    5640
ttacaagggt agatgcagtt ctccagcctt cattacctgg cgaattcaga tactacccaa    5700
acatcatagc aaaagggtc gggaaaatca gacagtaaaa tcaacaaccc tgatatccac     5760
cggtgtatta agccgaagca aataaaggat aatcaaaaac ttaggacaaa agaggtcaat    5820
accaacaact attagcagtc acactcgcaa gaataagaga gaaggacca aaaaagtcaa     5880 ataggagaaa tcaaaacaaa aggtacagaa caccagaaca acaaaatcaa acatccaac     5940 tcactcaaaa caaaaattcc aaaagagacc ggcaacacaa caagcactga acacaatgcc    6000
aacttcaata ctgctaatta ttacaaccat gatcatggca tctttctgcc aaatagatat    6060
cacaaaacta cagcacgtag gtgtattggt caacagtccc aaagggatga agatatcaca    6120
aaactttgaa acaagatatc taattttgag cctcatacca aaaatagaag actctaactc    6180
ttgtggtgac caacagatca agcaatacaa gaagttattg gatagactga tcatccctt    6240 atatgatgga ttaagattac agaaagatgt gatagtaacc aatcaagaat ccaatgaaaa    6300
cactgatccc agaacaaaac gattctttgg agggtaatt ggaaccattg ctctgggagt    6360
agcaacctca gcacaaatta cagcggcagt tgctctggtt gaagccaagc aggcaagatc    6420
agacatcgaa aaactcaaag aagcaattag ggacacaaac aaagcagtgc agtcagttca    6480
gagctccata ggaaatttaa tagtagcaat taaatcagtc caggattatg ttaacaaaga    6540
aatcgtgcca tcgattgcga ggctaggttg tgaagcagca ggacttcaat taggaattgc    6600
attaacacag cattactcag aattaacaaa catatttggt gataacatag atcgttaca    6660 agaaaaagga ataaaattac aaggtatagc atcattatac cgcacaaata tcacagaaat    6720
attcacaaca tcaacagttg ataaatatga tatctatgat ctgttattta cagaatcaat    6780
aaaggtgaga gttatagatg ttgacttgaa tgattactca atcaccctcc aagtcagact    6840
ccctttatta actaggctgc tgaacactca gatctacaaa gtagattcca tatcatataa    6900
catccaaaac agagaatggt atatccctct tcccagccat atcatgacga aagggcatt    6960 tctaggtgga gcagacgtca aagaatgtat agaagcattc agcagctata tatgcccttc    7020
tgatccagga tttgtattaa accatgaaat agagagctgc ttatcaggaa acatatccca    7080
atgtccaaga acaacggtca catcagacat tgttccaaga tatgcatttg tcaatggagg    7140
agtggttgca aactgtataa caaccacctg tacatgcaac ggaattggta atagaatcaa    7200
tcaaccacct gatcaaggag taaaaattat aacacataaa gaatgtagta caataggtat    7260
caacggaatg ctgttcaata caaataaaga aggaactctt gcattctata caccaaatga    7320
tataacacta aacaattctg ttgcacttga tccaattgac atatcaatcg agctcaacaa    7380
ggccaaatca gatctagaag aatcaaaaga atggataaga aggtcaaatc aaaaactaga    7440
ttctattgga aattggcatc aatctagcac tacaatcata attattttga taatgatcat    7500
tatattgttt ataattaata taacgataat tacaattgca attaagtatt acagaattca    7560
aaagagaaat cgagtggatc aaaatgacaa gccatatgta ctaacaaaca aataacatat    7620
ctacagatca ttagatatta aaattataaa aaacttagga gtaaagttac gcaatccaac    7680
```

```
tctactcata taattgagga aggacccaat agacaaatcc aaattcgaga tggaatactg   7740
gaagcatacc aatcacggaa aggatgctgg taatgagctg gagacgtcta tggctactca   7800
tggcaacaag ctcactaata agataatata catattatgg acaataatcc tggtgttatt   7860
atcaatagtc ttcatcatag tgctaattaa ttccatcaaa agtgaaaagg cccacgaatc   7920
attgctgcaa gacataaata atgagtttat ggaaattaca gaaagatccc aaatggcatc   7980
ggataatacc aatgatctaa tacagtcagg agtgaataca aggcttctta caattcagag   8040
tcatgtccag aattacatac caatatcatt gacacaacag atgtcagatc ttaggaaatt   8100
cattagtgaa attacaatta gaatgataaa tcaagaagtg ctgccacaaa gaataacaca   8160
tgatgtaggt ataaaaccttt aaatccaga tgattttttgg agatgcacgt ctggtcttcc   8220
atctttaatg aaaactccaa aaataaggtt aatgccaggg ccgggattat tagctatgcc   8280
aacgactgtt gatggctgtg ttagaactcc gtctttagtt ataaatgatc tgatttatgc   8340
ttatacctca aatctaatta ctcgaggttg tcaggatata ggaaaatcat atcaagtctt   8400
acagataggg ataataactg taaactcaga cttggtacct gacttaaatc ctaggatctc   8460
tcataccttt aacataaatg acaataggaa gtcatgttct ctagcactcc taaatacaga   8520
tgtatatcaa ctgtgttcaa ctcccaaagt tgatgaaaga tcagattatg catcatcagg   8580
catagaagat attgtacttg atattgtcaa ttatgatggt tcaatctcaa caacaagatt   8640
taagaataat aacataagct tgatcaacc atatgctgca ctatacccat ctgttggacc   8700
agggatatac tacaaaggca aaataatatt tctcgggtat ggaggtcttg aacatccaat   8760
aaatgagaat gtaatctgca acacaactgg gtgccccggg aaaacacaga gagactgtaa   8820
tcaagcatct catagtccat ggttttcaga taggaggatg gtcaactcca tcattgttgt   8880
tgacaaaggc ttaaactcaa ttccaaaatt gaaagtatgg acgatatcta tgcgacaaaa   8940
ttactggggg tcagaaggaa ggttacttct actaggtaac aagatctata tatatacaag   9000
atctacaagt tggcatagca agttacaatt aggaataatt gatattactg attacagtga   9060
tataaggata aaatggacat ggcataatgt gctatcaaga ccaggaaaca atgaatgtcc   9120
atggggacat tcatgtccag atggatgtat aacaggagta tatactgatg catatccact   9180
caatcccaca gggagcattg tgtcatctgt catattagac tcacaaaaat cgagagtgaa   9240
cccagtcata acttactcaa cagcaaccga aagagtaaac gagctggcca tcctaaacag   9300
aacactctca gctggatata caacaacaag ctgcattaca cactataaca aaggatattg   9360
ttttcatata gtagaaataa atcataaaag cttaaacaca tttcaaccca tgttgttcaa   9420
aacagagatt ccaaaaagct gcagttaatc ataattaacc ataatatgca tcaatctatc   9480
tataatacaa gtatatgata agtaatcagc aatcagacaa tagacgtacg gaataataaa   9540
aaaacttagg agaaaagtgt gcaagaaaaa tggacaccga gtcccacagc ggcacaacat   9600
ctgacattct gtaccctgaa tgtcacctca attctcctat agttaaagga aagatagcac   9660
aactgcatac aataatgagt ttgcctcagc cctacgatat ggatgatgat tcaatactga   9720
ttattactag acaaaaaatt aaactcaata aattagataa aagacaacgg tcaattagga   9780
aattaagatc agtcttaatg gaaagagtaa gtgatctagg taaatatacc tttatcagat   9840
atccagagat gtctagtgaa atgttccaat tatgtatacc cggaattaat aataaaatag   9900
atgaattgct aagtaaagca agtaaaacat ataatcaaat gactgatgga ttaagagatc   9960
tatgggttac tatactatcg aagttagcat cgaaaaatga tggaagtaat tatgatatca 10020
```

-continued

```
atgaagatat tagcaatata tcaaatgttc acatgactta tcaatcagac aaatggtata  10080
atccattcaa gacatggttt actattaagt atgacatgag aagattacaa aaagccaaaa  10140
atgagattac attcaatagg cataaagatt ataatctatt agaagaccaa aagaatatat  10200
tgctgataca tccagaactc gtcttaatat tagataaaca aaattacaat gggtatataa  10260
tgactcctga attggtacta atgtattgtg atgtagttga agggaggtgg aatataagtt  10320
catgtgcaaa attggatcct aagttacaat caatgtatta aagggtaac aatttatggg  10380 aaataataga tggactattc tcgaccttag gagaaagaac atttgacata atatcactat  10440
tagaaccact tgcattatcg ctcattcaaa cttatgaccc ggttaaacag ctcaggggggg  10500 cttttttaaa tcacgtgtta tcagaaatgg aattaatatt tgcagctgag tgtacaacag  10560
aggaaatacc taatgtggat tatatagata aaattttaga tgtgttcaaa gaatcaacaa  10620
tagatgaaat agcagaaatt ttctctttct tccgaactt tggacaccct ccattagagg  10680
cgagtatagc agcagagaaa gttagaaagt atatgtatac tgagaaatgc ttgaaatttg  10740
atactatcaa taaatgtcat gctatttttt gtacaataat tataaatgga tatagagaaa  10800
gacatggtgg tcaatggcct ccagttacat tacctgtcca tgcacatgaa tttatcataa  10860
atgcatacgg atcaaattct gccatatcat atgagaatgc tgtagattat tataagagct  10920
tcataggaat aaaatttgac aagtttatag agcctcaatt ggatgaagac ttaactattt  10980
atatgaaaga taaagcatta tccccaaaga aatcaaactg gcacacagtc tatccagctt  11040
caaacctgtt ataccgcact aatgtgtctc atgattcacg aagattggtt gaagtattta  11100
tagcagatag taaatttgat ccccaccaag tattagatta cgtagaatca ggatattggc  11160
tggatgatcc tgaatttaat atctcatata gtttaaaaga gaaagaaata aaacaagaag  11220 gtagacttt tgcaaaaatg acatacaaga tgagggctac acaagtatta tcagaaacat  11280
tattggcgaa taatataggg aaattcttcc aagagaatgg gatggttaaa ggagaaattg  11340
aattactcaa gagactaaca acaatatcta tgtctggagt tccgcggtat aatgaggtat  11400
acaataattc aaaaagtcac acagaagaac ttcaagctta taatgcaatt agcagttcca  11460
atttatcttc taatcagaag tcaaagaagt ttgaatttaa atctacagat atatacaatg  11520
atggatacga aaccgtaagc tgcttcttaa cgacagatct taaaaaatat tgtttaaatt  11580
ggaggtatga atcaacagct ttattcggtg atacttgtaa tcagatattt gggttaaagg  11640
aattatttaa ttggctgcac cctcgccttg aaaagagtac aatatatgtt ggagatcctt  11700
attgcccgcc atcagatatt gaacatttac cacttgatga ccatcctgat tcaggatttt  11760
atgttcataa tcctaaagga ggaatagaag ggtttttgcca aaagttatgg acactcatat  11820
ctatcagtgc aatacattta gcagctgtca aaatcggtgt aagagttact gcaatggttc  11880
aaggggataa tcaagccata gctgttacca caagagtacc taataattat gattataaag  11940
ttaagaaaga gattgtttat aaagatgtgg taagattttt tgattccttg agagaggtga  12000
tggatgatct gggtcatgag ctcaaactaa atgaaactat aataagtagt aaaatgttta  12060
tatatagcaa aaggatatac tatgacggaa gaatccttcc tcaggcatta aaagcattgt  12120
ctagatgtgt ttttggtct gaaacaatca tagatgagac aagatcagca tcctcaaatc  12180
tggctacatc gtttgcaaag gccattgaga atggctactc acctgtattg ggatatgtat  12240
gctcaatctt caaaaatatc caacagttgt atatagcgct tggaatgaat ataaacccaa  12300
ctataaccca aaatattaaa gatcaatatt tcaggaatat tcattggatg caatatgcct  12360
ccttaatccc tgctagtgtc ggaggattta attatatggc catgtcaagg tgttttgtca  12420
```

```
gaaacattgg agatcctaca gtcgctgcgt tagccgatat taaaagattt ataaaagcaa   12480
atttgttaga tcgaggtgtc ctttacagaa ttatgaatca agaaccaggc gagtcttctt   12540
ttttagactg ggcctcagat ccctattcat gtaacttacc acaatctcaa aatataacca   12600
ccatgataaa gaatataact gcaagaaatg tactacagga ctcaccaaac ccattactat   12660
ctggattatt tacaagtaca atgatagaag aggatgagga attagctgag ttcctaatgg   12720
acaggagaat aatcctccca agagttgcac atgacatttt agataattct cttactggaa   12780
ttaggaatgc tatagctggt atgttggata caacaaaatc actaattcga gtagggataa   12840
gcagaggagg attaacctat aacttattaa gaaagataag caactatgat cttgtacaat   12900
atgagacact tagtaaaact ttaagactaa tagtcagtga caagattaag tatgaagata   12960
tgtgctcagt agacctagcc atatcattaa gacaaaaaat gtggatgcat ttatcaggag   13020
gaagaatgat aaatggactt gaaactccag atcctttaga gttactgtct ggagtaataa   13080
taacaggatc tgaacattgt aggatatgtt attcaactga aggtgaaagc ccatatacat   13140
ggatgtattt accaggcaat cttaatatag gatcagctga gacaggaata gcatcattaa   13200
gggtccctta ctttggatca gttacagatg agagatctga agcacaatta gggtatatca   13260
aaaatctaag caaaccagct aaggctgcta taagaatagc aatgatatat acttgggcat   13320
ttgggaatga cgaaatatct tggatggaag catcacagat tgcacaaaca cgtgcaaact   13380
ttacattgga tagcttaaag attttgacac cagtgacaac atcaacaaat ctatcacaca   13440
ggttaaaaga tactgctact cagatgaaat tttctagtac atcacttatt agagtaagca   13500
ggttcatcac aatatctaat gataatatgt ctattaaaga agcaaatgaa actaaagata   13560
caaatcttat ttatcaacag gtaatgttaa caggattaag tgtatttgaa tatctatttta  13620 ggttagagga gagtacagga cataacccta tggtcatgca tctacatata gaggatggat   13680
gttgtataaa agagagttac aatgatgagc atatcaatcc ggagtctaca ttagagttaa   13740
tcaaataccc tgagagtaat gaatttatat atgataagga cccttttaaag gatatagatc   13800 tatcaaaatt aatggttata agagatcatt cttatacaat tgacatgaat tactgggatg   13860
acacagatat tgtacatgca atatcaatat gtactgcagt tacaatagca gatacaatgt   13920
cgcagctaga tcgggataat cttaaggagc tggttgtgat tgcaaatgat gatgatatta   13980
acagtctgat aactgaattt ctgacccctag atatactagt gtttctcaaa acatttggag   14040
ggttactcgt gaatcaattt gcatataccc tttatggatt gaaaatagaa ggaagggatc   14100
ccatttggga ttatataatg agaacattaa agcacacctc acattcagta cttaaagtat   14160
tatctaatgc actatctcat ccaaaagtgt ttaagagatt ttgggattgt ggagttttga   14220 atcctatttta tggtcctaat actgctagtc aagatcaagt taagcttgct ctctcgattt   14280
gcgagtactc cttggatcta tttatgagag aatggttgaa tggagcatca cttgagatct   14340
atatctgtga tagtgacatg gaaatagcaa atgacagaag acaagcattt ctctcaagac   14400
atcttgcctt tgtgtgttgt ttagcagaga tagcatcttt tggaccaaat ttattaaatc   14460
taacatatct agagagactt gatgaattaa aacaatactt agatctgaac atcaaagaag   14520
atcctactct taaatatgtg caagtatcag gactgttaat taaatcattc ccctcaactg   14580
ttacgtatgt aaggaaaact gcgattaagt atctgaggat tcgtggtatt aatccgcctg   14640
aaacgattga agattgggat cccatagaag atgagaaat cttagacaat attgttaaaa   14700
ctgtaaatga caattgcagt gataatcaaa agagaaataa agtagttat ttctggggat   14760
```

-continued

```
tagctctaaa gaattatcaa gtcgtgaaaa taagatccat aacgagtgat tctgaagtta  14820
atgaagcttc gaatgttact acacatggaa tgacacttcc tcagggagga agttatctat  14880
cacatcagct gaggttattt ggagtaaaca gtacaagttg tcttaaagct cttgaattat  14940
cacaaatctt aatgagggaa gttaaaaaag ataaagatag actcttttta ggagaaggag  15000
caggagctat gttagcatgt tatgatgcta cactcggtcc tgcaataaat tattataatt  15060
ctggtttaaa tattacagat gtaattggtc aacgggaatt aaaaatcttc ccatcagaag  15120
tatcattagt aggtaaaaaa ctaggaaatg taacacagat tcttaatcgg gtgagggtgt  15180
tatttaatgg gaatcccaat tcaacatgga taggaaatat ggaatgtgag agtttaatat  15240
ggagtgaatt aaatgataag tcaattggtt tagtacattg tgacatggag ggagcgatag  15300
gcaaatcaga agaaactgtt ctacatgaac attatagtat tattaggatt acatatttaa  15360
tcggggatga tgatgttgtc ctagtatcaa aaattatacc aactattact ccgaattggt  15420
ctaaaatact ctatctatac aagttgtatt ggaaggatgt aagtgtagtg tcccttaaaa  15480
catccaatcc tgcctcaaca gagctttatt taatttcaaa agatgcttac tgtactgtaa  15540
tggaacccag taatcttgtt ttatcaaaac ttaaaaggat atcatcaata gaagaaaata  15600
atctattaaa gtggataatc ttatcaaaaa ggaagaataa cgagtggtta cagcatgaaa  15660
tcaaagaagg agaaagggat tatgggataa tgaggccata tcatacagca ctgcaaattt  15720
ttggattcca aattaactta aatcacttag ctagagaatt tttatcaact cctgatttaa  15780
ccaacattaa taatataatt caaagtttta caagaacaat taaagatgtt atgttcgaat  15840
gggtcaatat cactcatgac aataaaagac ataaattagg aggaagatat aatctattcc  15900
cgcttaaaaa taaggggaaa ttaagattat tatcacgaag attagtacta agctggatat  15960
cattatcctt atcaaccaga ttactgacgg gccgttttcc agatgaaaaa tttgaaaata  16020
gggcacagac cggatatgta tcattggctg atattgattt agaatcctta aagttattat  16080
caagaaatat tgtcaaaaat tacaaagaac acataggatt aatatcatac tggtttttga  16140
ccaaagaggt caaaatacta atgaagctta taggaggagt caaactacta ggaattccta  16200
aacagtacaa agagttagag gatcgatcat ctcagggtta tgaatatgat aatgaatttg  16260
atattgatta atacataaaa acataaaata aaacacctat tcctcaccca ttcacttcca  16320
acaaaatgaa aagtaagaaa aacatgtaat atatatatac caaacagagt tttctcttg  16380
tttggt                                                             16386
```

<210> SEQ ID NO 92
<211> LENGTH: 16386
<212> TYPE: DNA
<213> ORGANISM: Artificial Sequence
<220> FEATURE:
<223> OTHER INFORMATION: Recombinant rB/HPIV3 sequence

<400> SEQUENCE: 92

```
accaaacaag agaagagact ggtttgggaa tattaattca aataaaaatt aacttaggat     60
taaagaactt taccgaaagg taaggggaaa gaaatcctaa gagcttagcc atgttgagtc    120
tattcgacac attcagtgcg cgtaggcagg agaacataac gaaatcagct ggtggggctg    180
ttattcccgg gcaaaaaaac actgtgtcta tatttgctct tggaccatca ataacagatg    240
acaatgataa aatgacattg gctcttctct tttgtctcta ttctttagac aatgaaaagc    300
agcatgcgca aagagctgga tttttagttt ctctgttatc aatggcttat gccaacccag    360
aattatattt aacatcaaat ggtagtaatg cagatgttaa atatgttatc tacatgatag    420
```

```
agaaagaccc aggaagacag aaatatggtg ggtttgtcgt caagactaga gagatggttt    480
atgaaaagac aactgattgg atgttcggga gtgatcttga gtatgatcaa gacaatatgt    540
tgcaaaatgg tagaagcact tctacaatcg aggatcttgt tcatactttt ggatatccat    600
cgtgtcttgg agcccttata atccaagttt ggataatact tgttaaggct ataaccagta    660
tatcaggatt gaggaaagga ttctttactc ggttagaagc atttcgacaa gatggaacag    720
ttaaatccag tctagtgttg agcggtgatg cagtagaaca aattggatca attatgaggt    780
cccaacagag cttggtaaca ctcatggttg aaacactgat aacaatgaac acaggcagga    840
atgatctgac aacaatagaa aagaatatac agattgtagg aaactacatc agagatgcag    900
gtcttgcttc attttttcaac acaatcagat atggcattga gactagaatg gcagctctaa    960
ctctgtctac ccttagaccg gatatcaaca gactcaaggc actgatcgag ttatatctat   1020
caaaggggcc acgtgctcct tttatatgca ttttgagaga tcccgtgcat ggtgagtttg   1080
caccaggcaa ctatcctgcc ctctggagtt atgcgatggg tgtagcagtt gtacaaaaca   1140
aggccatgca acagtatgta acaggaaggt cttatctgga tattgaaatg ttccaacttg   1200
gtcaagcagt ggcacgtgat gccgagtcgc agatgagttc aatattagag gatgaactgg   1260
gggtcacaca agaagccaag caaagcttga agaaacacat gaagaacatc agcagttcag   1320
atacaacctt tcataagcct acaggggat cagccataga aatggcgata gatgaagaag   1380
cagggcagcc tgaatccaga ggagatcagg atcaaggaga tgagcctcgg tcatccatag   1440
ttccttatgc atgggcagac gaaaccggga atgacaatca aactgaatca actacagaaa   1500
ttgacagcat caaaactgaa caaagaaaca tcagagacag gctgaacaaa agactcaacg   1560 agaaaggaa acagagtgac ccgagatcaa ctgacatcac aaacaacaca aatcaaactg   1620
aaatagatga tttgttcagt gcattcggaa gcaactagtc acaaagagat gaccaggcgc   1680
gccaagtaag aaaaacttag gattaatgga cctgcaggat gtcaaagaac aaggatcaga   1740
gaactgccaa gaccctggaa agaacctggg acaccctgaa ccacctgctg tttatctcaa   1800
gctgcctgta caagctgaat ctgaaaagtg tggcccagat caccctgtca attctggcta   1860
tgatcatttc aacaagcctg atcattgccg ctatcatttt catcgcaagc gccaaccaca   1920
aggtcacccc caccacagct atcattcagg acgcaacatc ccagattaag aacactaccc   1980
ccacctatct gacacagaat cctcagctgg gaatctcccc atctaacccc tcagagatta   2040
ccagccagat cacaactatt ctggcctcca ccacacctgg cgtgaagtcc actctgcagt   2100
ctactaccgt caagaccaaa aatacaacta ccacacagac acagccttct aagccaacta   2160
ccaaacagcg gcagaataag ccccctagta aaccaaacaa tgacttccat tttgaggtgt   2220
tcaactttgt cccatgcagc atctgttcca caatcccac tgctgggcc atctgtaaga   2280 gaattccaaa caagaaaccc ggcaagaaga ccactaccaa acctactaag aaaccaaccc   2340
tgaagacaac taagaaagat cctaaaccac agacacaaaa gtctaaagaa gtgcccacta   2400
ccaagcctac agaggaacca actatcaaca caactaagac taacatcatc accacactgc   2460
tgacaagcaa cactaccggc aatcccgagc tgaccagcca gatggaaacc tttcactcca   2520
caagctccga ggggaatccc agtccttcac aggtgtctac aactagtgaa taccccagcc   2580
agccttctag tccacccaac acccctaggc agtgatagct agcggcgcgc cagcaacaag   2640
taagaaaaac ttaggattaa tgaaattat ccaatccaga gacggaagga caatccaga   2700 atccaaccac aactcaatca accaaagatt catggaagac aatgttcaaa acaatcaaat   2760
```

```
catggattct tgggaagagg gatcaggaga taaatcatct gacatctcat cggccctcga    2820
catcattgaa ttcatactca gcaccgactc ccaagagaac acggcagaca gcaatgaaat    2880
caacacagga accacaagac ttagcacgac aatctaccaa cctgaatcca aaacaacaga    2940
aacaagcaag gaaaatagtg gaccagctaa caaaaatcga cagtttgggg catcacacga    3000
acgtgccaca gagacaaaag atagaaatgt taatcaggag actgtacagg gaggatatag    3060
gagaggaagc agcccagata gtagaactga gactatggtc actcgaagaa tctccagaag    3120
cagcccagat cctaacaatg gaacccaaat ccaggaagat attgattaca atgaagttgg    3180
agagatggat aaggactcta ctaagaggga aatgcgacaa tttaaagatg ttccagtcaa    3240
ggtatcagga agtgatgcca ttcctccaac aaaacaagat ggagacggtg atgatggaag    3300
aggcctggaa tctatcagta catttgattc aggatatacc agtatagtga ctgccgcaac    3360
actagatgac gaagaagaac tccttatgaa gaacaacagg ccaagaaagt atcaatcaac    3420
accccagaac agtgacaagg gaattaaaaa aggggttgga aggccaaaag acacagacaa    3480
acaatcatca atattggact acgaactcaa cttcaaagga tcgaagaaga gccagaaaat    3540
cctcaaagcc agcacgaata caggagaacc aacaagacca cagaatggat cccaggggaa    3600
gagaatcaca tcctggaaca tcctcaacag cgagagcggc aatcgaacag aatcaacaaa    3660
ccaaacccat cagacatcaa cctcgggaca gaaccacaca atgggaccaa gcagaacaac    3720
ctccgaacca aggatcaaga cacaaaagac ggatggaaag gaaagagagg acacagaaga    3780
gagcactcga tttacagaaa gggcgattac attattacag aatcttggtg taatccaatc    3840
tgcagcaaaa ttagacctat accaagacaa gagagttgtg tgtgtggcga atgtcctaaa    3900
caatgcagat actgcatcaa agatagactt cctagcaggt ttgatgatag gagtgtcaat    3960
ggatcatgat accaaattaa atcagattca gaacgagata ttaagtttga aaactgatct    4020
taaaaagatg gatgaatcac atagaagact aattgagaat caaaaagaac aattatcact    4080
gatcacatca ttaatctcaa atcttaaaat tatgacagag agaggaggga agaaggacca    4140
accagaacct agcgggagga catccatgat caagacaaaa gcaaagaag agaaaataaa    4200
gaaagtcagg tttgacccte ttatggaaac acagggcatc gagaaaaaca tccctgacct    4260
ctatagatca atagagaaaa caccagaaaa cgacacacag atcaaatcag aaataaacag    4320
attgaatgat gaatccaatg ccactagatt agtacctaga agaataagca gtacaatgag    4380
atcattaata ataatcatta caacagcaa tttatcatca aaagcaaagc aatcatacat    4440
caacgaactc aagctctgca agagtgacga ggaagtgtct gagttgatgg acatgttcaa    4500
tgaggatgtc agctcccagt aaaccgccaa ccaagggtca acaccaagaa aaccaatagc    4560
acaaaacagc caatcagaga ccacccccaat acaccaaacc aatcaacaca taacaaagat    4620
cgcggccgca tagatgatta agaaaaactt aggatgaaag gactaatcaa tcctccgaaa    4680
caatgagcat caccaactcc acaatctaca cattcccaga tcctctttc tccgagaatg    4740
gcaacataga gccgttacca ctcaaggtca atgaacagag aaaggccata cctcatatta    4800
gggttgtcaa gataggagat ccgcccaaac atggatccag atatctggat gtcttttac    4860
tgggcttctt tgagatggaa aggtcaaaag acaggtatgg gagcataagt gatcagatg    4920
atgatccaag ttacaaggtt tgtggctctg gatcattgcc acttgggttg gctagataca    4980
ccggaaatga tcaggaactc ctacaggctg caaccaagct cgatatagaa gtaagaagaa    5040
ctgtaaaggc tacggagatg atagtttaca ctgtacaaaa catcaaacct gaactatatc    5100
catggtccag tagattaaga aaagggatgt tatttgacgc taataaggtt gcacttgctc    5160
```

```
ctcaatgtct tccactagat agagggataa aattcagggt gatatttgtg aactgcacag   5220
caattggatc aataactcta ttcaaaatcc ctaagtccat ggcattgtta tcattgccta   5280
atacaatatc aataaatcta caagtacata tcaaaacagg agttcagaca gattccaaag   5340
gagtagttca gattctagat gaaaaaggtg aaaaatcact aaatttcatg gttcatctcg   5400
ggttgatcaa aaggaagatg ggcagaatgt actcagttga atattgtaag cagaagatcg   5460
agaagatgag attattattc tcattgggat tagttggagg gatcagcttc cacgtcaacg   5520
caactggctc tatatcaaag acattagcaa gtcaattagc attcaaaaga gaaatctgct   5580
atcccctaat ggatctgaat ccacacttaa attcagttat atgggcatca tcagttgaaa   5640
ttacaagggt agatgcagtt ctccagcctt cattacctgg cgaattcaga tactacccaa   5700
acatcatagc aaaaggggtc gggaaaatca gacagtaaaa tcaacaaccc tgatatccac   5760
cggtgtatta agccgaagca aataaggat  aatcaaaaac ttaggacaaa agaggtcaat   5820
accaacaact attagcagtc acactcgcaa gaataagaga gaagggacca aaaaagtcaa   5880
ataggagaaa tcaaaacaaa aggtacagaa caccagaaca acaaaatcaa acatccaac   5940 tcactcaaaa caaaaattcc aaaagagacc ggcaacacaa caagcactga acacaatgcc   6000
aacttcaata ctgctaatta ttacaaccat gatcatggca tctttctgcc aaatagatat   6060
cacaaaacta cagcacgtag gtgtattggt caacagtccc aaagggatga agatatcaca   6120
aaactttgaa acaagatatc taattttgag cctcatacca aaaatagaag actctaactc   6180
ttgtggtgac caacagatca agcaatacaa gaagttattg gatagactga tcatcccttt   6240
atatgatgga ttaagattac agaaagatgt gatagtaacc aatcaagaat ccaatgaaaa   6300
cactgatccc agaacaaaac gattctttgg aggggtaatt ggaaccattg ctctgggagt   6360
agcaacctca gcacaaatta cagcggcagt tgctctggtt gaagccaagc aggcaagatc   6420
agacatcgaa aaactcaaag aagcaattag ggacacaaac aaagcagtgc agtcagttca   6480
gagctccata ggaaatttaa tagtagcaat taaatcagtc caggattatg ttaacaaaga   6540
aatcgtgcca tcgattgcga ggctaggttg tgaagcagca ggacttcaat taggaattgc   6600
attaacacag cattactcag aattaacaaa catatttggt gataacatag gatcgttaca   6660
agaaaaagga ataaaattac aaggtatagc atcattatac cgcacaaata tcacagaaat   6720
attcacaaca tcaacagttg ataaatatga tatctatgat ctgttattta cagaatcaat   6780
aaaggtgaga gttatagatg ttgacttgaa tgattactca atcaccctcc aagtcagact   6840
ccctttatta actaggctgc tgaacactca gatctacaaa gtagattcca tatcatataa   6900
catccaaaac agagaatggt atatccctct tcccagccat atcatgacga aggggcatt   6960 tctaggtgga gcagacgtca aagaatgtat agaagcattc agcagctata tatgcccttc   7020
tgatccagga tttgtattaa accatgaaat agagagctgc ttatcaggaa acatatccca   7080
atgtccaaga acaacggtca catcagacat tgttccaaga tatgcatttg tcaatggagg   7140
agtggttgca aactgtataa caaccacctg tacatgcaac ggaattggta atagaatcaa   7200
tcaaccacct gatcaaggag taaaaattat aacacataaa gaatgtagta caataggtat   7260
caacggaatg ctgttcaata caaataaaga aggaactctt gcattctata caccaaatga   7320
tataacacta aacaattctg ttgcacttga tccaattgac atatcaatcg agctcaacaa   7380
ggccaaatca gatctagaag aatcaaaaga atggataaga aggtcaaatc aaaaactaga   7440
ttctattgga aattggcatc aatctagcac tacaatcata attattttga ataatgatcat   7500
```

```
tatattgttt ataattaata taacgataat tacaattgca attaagtatt acagaattca    7560
aaagagaaat cgagtggatc aaaatgacaa gccatatgta ctaacaaaca aataacatat    7620
ctacagatca ttagatatta aaattataaa aaacttagga gtaaagttac gcaatccaac    7680
tctactcata taattgagga aggacccaat agacaaatcc aaattcgaga tggaatactg    7740
gaagcatacc aatcacggaa aggatgctgg taatgagctg gagacgtcta tggctactca    7800
tggcaacaag ctcactaata agataatata catattatgg acaataatcc tggtgttatt    7860
atcaatagtc ttcatcatag tgctaattaa ttccatcaaa agtgaaaagg cccacgaatc    7920
attgctgcaa gacataaata atgagtttat ggaaattaca gaaaagatcc aaatggcatc    7980
ggataatacc aatgatctaa tacagtcagg agtgaataca aggcttctta caattcagag    8040
tcatgtccag aattacatac caatatcatt gacacaacag atgtcagatc ttaggaaatt    8100
cattagtgaa attacaatta gaaatgataa tcaagaagtg ctgccacaaa gaataacaca    8160
tgatgtaggt ataaaacctt taaatccaga tgattttttgg agatgcacgt ctggtcttcc    8220
atctttaatg aaaactccaa aaataaggtt aatgccaggg ccgggattat tagctatgcc    8280
aacgactgtt gatggctgtg ttagaactcc gtctttagtt ataaatgatc tgatttatgc    8340
ttatacctca aatctaatta ctcgaggttg tcaggatata ggaaaatcat atcaagtctt    8400
acagataggg ataataactg taaactcaga cttggtacct gacttaaatc ctaggatctc    8460
tcataccttt aacataaatg acaataggaa gtcatgttct ctagcactcc taaatacaga    8520
tgtatatcaa ctgtgttcaa ctcccaaagt tgatgaaaga tcagattatg catcatcagg    8580
catagaagat attgtacttg atattgtcaa ttatgatggt tcaatctcaa caacaagatt    8640
taagaataat aacataagct ttgatcaacc atatgctgca ctatacccat ctgttggacc    8700
agggatatac tacaaaggca aaataatatt tctcgggtat ggaggtcttg aacatccaat    8760
aaatgagaat gtaatctgca acacaactgg gtgccccggg aaaacacaga gagactgtaa    8820
tcaagcatct catagtccat ggttttcaga taggaggatg gtcaactcca tcattgttgt    8880
tgacaaaggc ttaaactcaa ttccaaaatt gaaagtatgg acgatatcta gcgacaaaa    8940
ttactggggg tcagaaggaa ggttacttct actaggtaac aagatctata tatatacaag    9000
atctacaagt tggcatagca agttacaatt aggaataatt gatattactg attacagtga    9060
tataaggata aaatggacat ggcataatgt gctatcaaga ccaggaaaca atgaatgtcc    9120
atggggacat tcatgtccag atggatgtat aacaggagta tatactgatg catatccact    9180
caatcccaca gggagcattg tgtcatctgt catattagac tcacaaaaat cgagagtgaa    9240
cccagtcata acttactcaa cagcaaccga aagagtaaac gagctggcca tcctaaacag    9300
aacactctca gctggatata caacaacaag ctgcattaca cactataaca aaggatattg    9360
ttttcatata gtagaaataa atcataaaag cttaaacaca tttcaaccca tgttgttcaa    9420
aacagagatt ccaaaaagct gcagttaatc ataattaacc ataatatgca tcaatctatc    9480
tataatacaa gtatatgata agtaatcagc aatcagacaa tagacgtacg gaaataataa    9540
aaaacttagg agaaaagtgt gcaagaaaaa tggacaccga gtcccacagc ggcacaacat    9600
ctgacattct gtaccctgaa tgtcacctca attctcctat agttaaagga aagatagcac    9660
aactgcatac aataatgagt ttgcctcagc cctacgatat ggatgatgat tcaatactga    9720
ttattactag acaaaaaatt aaactcaata aattagaaaa aagacaacgg tcaattagga    9780
aattaagatc agtcttaatg gaaagagtaa gtgatctagg taaatatacc tttatcagat    9840
atccagagat gtctagtgaa atgttccaat tatgtatacc cggaattaat aataaaatta    9900
```

```
atgaattgct aagtaaagca agtaaaacat ataatcaaat gactgatgga ttaagagatc    9960
tatgggttac tatactatcg aagttagcat cgaaaaatga tggaagtaat tatgatatca   10020
atgaagatat tagcaatata tcaaatgttc acatgactta tcaatcagac aaatggtata   10080
atccattcaa gacatggttt actattaagt atgacatgag aagattacaa aaagccaaaa   10140
atgagattac attcaatagg cataaagatt ataatctatt agaagaccaa aagaatatat   10200
tgctgataca tccagaactc gtcttaatat tagataaaca aaattacaat gggtatataa   10260
tgactcctga attggtacta atgtattgtg atgtagttga agggaggtgg aatataagtt   10320
catgtgcaaa attggatcct aagttacaat caatgtatta taagggtaac aatttatggg   10380
aaataataga tggactattc tcgaccttag agaaagaac atttgacata atatcactat    10440
tagaaccact tgcattatcg ctcattcaaa cttatgaccc ggttaaacag ctcagggggg   10500
cttttttaaa tcacgtgtta tcagaaatgg aattaatatt tgcagctgag tgtacaacag   10560
aggaaatacc taatgtggat tatatagata aaattttaga tgtgttcaaa gaatcaacaa   10620
tagatgaaat agcagaaatt ttctctttct tccgaacttt tggacaccct ccattagagg   10680
cgagtatagc agcagagaaa gttagaaagt atatgtatac tgagaaatgc ttgaaatttg   10740
atactatcaa taaatgtcat gctatttttt gtacaataat tataaatgga tatagagaaa   10800
gacatggtgg tcaatggcct ccagttacat tacctgtcca tgcacatgaa tttatcataa   10860
atgcatacgg atcaaattct gccatatcat atgagaatgc tgtagattat tataagagct   10920
tcataggaat aaaatttgac aagtttatag agcctcaatt ggatgaagac ttaactatt    10980
atatgaaaga taaagcatta tccccaaaga aatcaaactg ggacacagtc tatccagctt   11040
caaacctgtt ataccgcact aatgtgtctc atgattcacg aagattggtt gaagtattta   11100
tagcagatag taaatttgat ccccaccaag tattagatta cgtagaatca ggatattggc   11160
tggatgatcc tgaatttaat atctcatata gtttaaaaga gaaagaaata aaacaagaag   11220
gtagacttt tgcaaaaatg acatacaaga tgagggctac acaagtatta tcagaaacat   11280
tattggcgaa taatataggg aaattcttcc aagagaatgg gatggttaaa ggagaaattg   11340
aattactcaa gagactaaca acaatatcta tgtctggagt tccgcggtat aatgaggtat   11400
acaataattc aaaaagtcac acagaagaac ttcaagctta taatgcaatt agcagttcca   11460
atttatcttc taatcagaag tcaaagaagt ttgaatttaa atctacagat atatacaatg   11520
atggatacga aaccgtaagc tgcttcttaa cgacagatct taaaaaatat tgtttaaatt   11580
ggaggtatga atcaacagct ttattcggtg atacttgtaa tcagatattt gggttaaagg   11640
aattatttaa ttggctgcac cctcgccttg aaaagagtac aatatatgtt ggagatcctt   11700
attgcccgcc atcagatatt gaacatttac cacttgatga ccatcctgat tcaggatttt   11760
atgttcataa tcctaaagga ggaatagaag ggttttgcca aaagttatgg acactcatat   11820
ctatcagtgc aatacattta gcagctgtca aaatcggtgt aagagttact gcaatggttc   11880
aaggggataa tcaagccata gctgttacca caagagtacc taataattat gattataaag   11940
ttaagaaaga gattgtttat aaagatgtgg taagattttt tgattccttg agagaggtga   12000
tggatgatct gggtcatgag ctcaaactaa atgaaactat aataagtagt aaaatgttta   12060
tatatagcaa aaggatatac tatgacggaa gaatccttcc tcaggcatta aaagcattgt   12120
ctagatgtgt ttttttggtct gaaacaatca tagatgagac aagatcagca tcctcaaatc   12180
tggctacatc gtttgcaaag gccattgaga atggctactc acctgtattg ggatatgtat   12240
```

```
gctcaatctt caaaaatatc caacagttgt atatagcgct tggaatgaat ataaacccaa   12300
ctataaccca aaatattaaa gatcaatatt tcaggaatat tcattggatg caatatgcct   12360
ccttaatccc tgctagtgtc ggaggattta attatatggc catgtcaagg tgttttgtca   12420
gaaacattgg agatcctaca gtcgctgcgt tagccgatat taaaagattt ataaaagcaa   12480
atttgttaga tcgaggtgtc ctttacagaa ttatgaatca agaaccaggc gagtcttctt   12540
ttttagactg ggcctcagat ccctattcat gtaacttacc acaatctcaa aatataacca   12600
ccatgataaa gaatataact gcaagaaatg tactacagga ctcaccaaac ccattactat   12660
ctggattatt tacaagtaca atgatagaag aggatgagga attagctgag ttcctaatgg   12720
acaggagaat aatcctccca agagttgcac atgacatttt agataattct cttactggaa   12780
ttaggaatgc tatagctggt atgttggata caacaaaatc actaattcga gtagggataa   12840
gcagaggagg attaacctat aacttattaa gaaagataag caactatgat cttgtacaat   12900
atgagacact tagtaaaact ttaagactaa tagtcagtga caagattaag tatgaagata   12960
tgtgctcagt agacctagcc atatcattaa gacaaaaaat gtggatgcat ttatcaggag   13020
gaagaatgat aaatggactt gaaactccag atcctttaga gttactgtct ggagtaataa   13080
taacaggatc tgaacattgt aggatatgtt attcaactga aggtgaaagc ccatatacat   13140
ggatgtattt accaggcaat cttaatatag gatcagctga gacaggaata gcatcattaa   13200
gggtcccttt ctttggatca gttacagatg agagatctga agcacaatta gggtatatca   13260
aaaatctaag caaaccagct aaggctgcta taagaatagc aatgatatat acttgggcat   13320
ttgggaatga cgaaatatct tggatggaag catcacagat tgcacaaaca cgtgcaaact   13380
ttacattgga tagcttaaag attttgacac cagtgacaac atcaacaaat ctatcacaca   13440
ggttaaaaga tactgctact cagatgaaat tttctagtac atcacttatt agagtaagca   13500
ggttcatcac aatatctaat gataatatgt ctattaaaga agcaaatgaa actaaagata   13560
caaatcttat ttatcaacag gtaatgttaa caggattaag tgtatttgaa tatctatttta  13620 ggttagagga gagtacagga cataaaccta tggtcatgca tctacatata gaggatggat   13680
gttgtataaa agagagttac aatgatgagc atatcaatcc ggagtctaca ttagagttaa   13740
tcaaataccc tgagagtaat gaatttatat atgataagga cccctttaaag gatatagatc   13800 tatcaaaatt aatggttata agagatcatt cttatacaat tgacatgaat tactgggatg   13860
acacagatat tgtacatgca atatcaatat gtactgcagt tacaatagca gatacaatgt   13920
cgcagctaga tcgggataat cttaaggagc tggttgtgat tgcaaatgat gatgatatta   13980
acagtctgat aactgaattt ctgacccetag atatactagt gtttctcaaa acatttggag   14040
ggttactcgt gaatcaattt gcatataccc tttatggatt gaaaatagaa ggaagggatc   14100
ccatttggga ttatataatg agaacattaa aagacacctc acattcagta cttaaagtat   14160
tatctaatgc actatctcat ccaaaagtgt ttaagagatt ttgggattgt ggagttttga   14220 atcctatttta tggtcctaat actgctagtc aagatcaagt taagcttgct ctctcgattt   14280
gcgagtactc cttggatcta tttatgagag aatggttgaa tggagcatca cttgagatct   14340
atatctgtga tagtgacatg gaaatagcaa atgacagaag acaagcattt ctctcaagac   14400
atcttgcctt tgtgtgttgt ttagcagaga tagcatcttt tggaccaaat ttattaaatc   14460
taacatatct agagagactt gatgaattaa acaatacttt agatctgaac atcaaagaag   14520
atcctactct taaatatgtg caagtatcag gactgttaat taaatcattc ccctcaactg   14580
ttacgtatgt aaggaaaact gcgattaagt atctgaggat tcgtggtatt aatccgcctg   14640
```

```
aaacgattga agattgggat cccatagaag atgagaatat cttagacaat attgttaaaa  14700
ctgtaaatga caattgcagt gataatcaaa agagaaataa aagtagttat ttctggggat  14760
tagctctaaa gaattatcaa gtcgtgaaaa taagatccat aacgagtgat tctgaagtta  14820
atgaagcttc gaatgttact acacatggaa tgacacttcc tcagggagga agttatctat  14880
cacatcagct gaggttattt ggagtaaaca gtacaagttg tcttaaagct cttgaattat  14940
cacaaatctt aatgagggaa gttaaaaaag ataaagatag actctttttta ggagaaggag  15000 caggagctat gttagcatgt tatgatgcta cactcggtcc tgcaataaat tattataatt  15060
ctggtttaaa tattacagat gtaattggtc aacgggaatt aaaaatcttc ccatcagaag  15120
tatcattagt aggtaaaaaa ctaggaaatg taacacagat tcttaatcgg gtgagggtgt  15180
tatttaatgg gaatcccaat tcaacatgga taggaaatat ggaatgtgag agtttaatat  15240
ggagtgaatt aaatgataag tcaattggtt tagtacattg tgacatggag ggagcgatag  15300
gcaaatcaga agaaactgtt ctacatgaac attatagtat tattaggatt acatatttaa  15360
tcggggatga tgatgttgtc ctagtatcaa aaattatacc aactattact ccgaattggt  15420
ctaaaatact ctatctatac aagttgtatt ggaaggatgt aagtgtagtg tcccttaaaa  15480
catccaatcc tgcctcaaca gagctttatt taatttcaaa agatgcttac tgtactgtaa  15540
tggaacccag taatcttgtt ttatcaaaac ttaaaaggat atcatcaata gaagaaaata  15600
atctattaaa gtggataatc ttatcaaaaa ggaagaataa cgagtggtta cagcatgaaa  15660
tcaaagaagg agaaagggat tatgggataa tgaggccata tcatacagca ctgcaaattt  15720
ttggattcca aattaactta aatcacttag ctagagaatt tttatcaact cctgatttaa  15780
ccaacattaa taatataatt caaagtttta caagaacaat taaagatgtt atgttcgaat  15840
gggtcaatat cactcatgac aataaaagac ataaattagg aggaagatat aatctattcc  15900
cgcttaaaaa taaggggaaa ttaagattat tatcacgaag attagtacta agctggatat  15960
cattatcctt atcaaccaga ttactgacgg gccgttttcc agatgaaaaa tttgaaaata  16020
gggcacagac cggatatgta tcattggctg atattgattt agaatcctta aagttattat  16080
caagaaatat tgtcaaaaat tacaaagaac acataggatt aatatcatac tggtttttga  16140
ccaaagaggt caaaatacta atgaagctta taggaggagt caaactacta ggaattccta  16200
aacagtacaa agagttagag gatcgatcat ctcagggtta tgaatatgat aatgaatttg  16260
atattgatta atacataaaa acataaaata aaacacctat tcctcaccca ttcacttcca  16320
acaaaatgaa aagtaagaaa aacatgtaat atatatatac caaacagagt tttctcttg  16380 tttggt                                                             16386
```

<210> SEQ ID NO 93
<211> LENGTH: 16362
<212> TYPE: DNA
<213> ORGANISM: Artificial Sequence
<220> FEATURE:
<223> OTHER INFORMATION: Recombinant rB/HPIV3 sequence

<400> SEQUENCE: 93

```
accaaacaag agaagagact ggtttgggaa tattaattca aataaaaatt aacttaggat     60
taaagaactt taccgaaagg taaggggaaa gaaatcctaa gagcttagcc atgttgagtc    120
tattcgacac attcagtgcg cgtaggcagg agaacataac gaaatcagct ggtggggctg    180
ttattcccgg gcaaaaaaac actgtgtcta tatttgctct tggaccatca ataacagatg    240
```

```
acaatgataa aatgacattg gctcttctct ttttgtctca ttctttagac aatgaaaagc      300
agcatgcgca aagagctgga ttttagttt ctctgttatc aatggcttat gccaacccag       360
aattatattt aacatcaaat ggtagtaatg cagatgttaa atatgttatc tacatgatag      420
agaaagaccc aggaagacag aaatatggtg ggtttgtcgt caagactaga gagatggttt     480
atgaaaagac aactgattgg atgttcggga gtgatcttga gtatgatcaa gacaatatgt    540
tgcaaaatgg tagaagcact tctacaatcg aggatcttgt tcatacttt ggatatccat      600 cgtgtcttgg agcccttata atccaagttt ggataatact tgttaaggct ataaccagta    660
tatcaggatt gaggaaagga ttctttactc ggttagaagc atttcgacaa gatgaaacag    720
ttaaatccag tctagtgttg agcggtgatg cagtagaaca aattggatca attatgaggt    780
cccaacagag cttggtaaca ctcatggttg aaacactgat aacaatgaac acaggcagga   840
atgatctgac aacaatagaa aagaatatac agattgtagg aaactacatc agagatgcag    900
gtcttgcttc atttttcaac acaatcagat atggcattga gactagaatg gcagctctaa    960
ctctgtctac ccttagaccg gatatcaaca gactcaaggc actgatcgag ttatatctat   1020
caaaggggcc acgtgctcct tttatatgca ttttgagaga tcccgtgcat ggtgagtttg   1080
caccaggcaa ctatcctgcc ctctggagtt atgcgatggg tgtagcagtt gtacaaaaca   1140
aggccatgca acagtatgta acaggaaggt cttatctgga tattgaaatg ttccaacttg    1200
gtcaagcagt ggcacgtgat gccgagtcgc agatgagttc aatattagag gatgaactgg   1260
gggtcacaca agaagccaag caaagcttga agaaacacat gaagaacatc agcagttcag   1320
atacaacctt tcataagcct acaggggat cagccctaga aatggcgata gatgaagaag    1380
cagggcagcc tgaatccaga ggagatcagg atcaaggaga tgagcctcgg tcatccatag   1440
ttccttatgc atgggcagac gaaaccggga atgacaatca aactgaatca actacagaaa   1500
ttgacagcat caaaactgaa caaagaaaca tcagagacag gctgaacaaa agactcaacg   1560
agaaaaggaa acagagtgac ccgagatcaa ctgacatcac aaacaacaca aatcaaactg   1620
aaatagatga tttgttcagt gcattcggaa gcaactagtc acaaagagat gaccaggcgc   1680
gccaagtaag aaaaacttag gattaatgga cctgcaggat ggaatattgg aaacacacaa   1740
acagcataaa taacaccaac aatgaaaccg aaacagccag aggcaaacat agtagcaagg   1800
ttacaaatat cataatgtac accttctgga caataacatt aacaatatta tcagtcattt    1860
ttataatgat attgacaaac ttaattaacc acaaagtcac accaacaact gcaatcatac   1920
aagatgcaac aagccagatc aagaacacac ccccaacata cctcacccag aatcctcagc   1980
ttggaatcag tccctctaat ccgtctgaaa ttacatcaca aatcaccacc atactagctt   2040
caacaacacc aggagtcaag tcaaccctgc aatccacaac agtcaagacc aaaaacacaa   2100
caacaactca aacacaaccc agcaagccca ccacaaaaca cgccaaaac aaaccaccaa   2160 gcaaacccaa taatgatttt cactttgaag tgttcaactt tgtaccctgc agcatatgca   2220
gcaacaatcc aacctgctgg gctatctgca aaagaatacc aaacaaaaaa ccaggaagaa   2280
aaaccactac caagcccaca aaaaccaa ccctcaagac aaccaaaaaa gatcccaaac    2340
ctcaaaccac taaatcaaag gaagtaccca ccaccaagcc cacagaagag ccaaccatca   2400
acaccaccaa acaaacatc ataactacac tactcacctc caacaccaca ggaaatccag   2460
aactcacaag tcaaatggaa accttccact caacttcctc cgaaggcaat ccaagccctt    2520
ctcaagtctc tacaacatcc gagtacccat cacaaccttc atctccaccc aacacaccac   2580
gccagtagtg atagctagcg gcgcgccagc aacaagtaag aaaaacttag gattaatgga   2640
```

```
aattatccaa tccagagacg gaaggacaaa tccagaatcc aaccacaact caatcaacca    2700
aagattcatg gaagacaatg ttcaaaacaa tcaaatcatg gattcttggg aagagggatc    2760
aggagataaa tcatctgaca tctcatcggc cctcgacatc attgaattca tactcagcac    2820
cgactcccaa gagaacacgg cagacagcaa tgaaatcaac acaggaacca caagacttag    2880
cacgacaatc taccaacctg aatccaaaac aacagaaaca agcaaggaaa atagtggacc    2940
agctaacaaa aatcgacagt ttggggcatc acacgaacgt gccacagaga caaaagatag    3000
aaatgttaat caggagactg tacagggagg atataggaga ggaagcagcc cagatagtag    3060
aactgagact atggtcactc gaagaatctc cagaagcagc ccagatccta caatggaac     3120 ccaaatccag gaagatattg attacaatga agttggagag atggataagg actctactaa    3180
gagggaaatg cgacaattta agatgttcc agtcaaggta tcaggaagtg atgccattcc     3240
tccaacaaaa caagatggag acggtgatga tggaagaggc ctggaatcta tcagtacatt    3300
tgattcagga tataccagta tagtgactgc cgcaacacta gatgacgaag aagaactcct    3360
tatgaagaac aacaggccaa gaaagtatca atcaacaccc cagaacagtg acaagggaat    3420
taaaaagggg gttggaaggc caaaagacac agacaaacaa tcatcaatat tggactacga    3480
actcaacttc aaaggatcga agaagagcca gaaaatcctc aaagccagca cgaatacagg    3540
agaaccaaca agaccacaga atggatccca ggggaagaga atcacatcct ggaacatcct    3600
caacagcgag agcggcaatc gaacagaatc aacaaaccaa acccatcaga catcaacctc    3660
gggacagaac cacacaatgg gaccaagcag aacaacctcc gaaccaagga tcaagacaca    3720
aaagacggat ggaaaggaaa gagaggacac agaagagagc actcgattta cagaaagggc    3780
gattacatta ttacagaatc ttggtgtaat ccaatctgca gcaaaattag acctatacca    3840
agacaagaga gttgtgtgtg tggcgaatgt cctaaacaat gcagatactg catcaaagat    3900
agacttccta gcaggtttga tgataggagt gtcaatggat catgatacca aattaaatca    3960
gattcagaac gagatattaa gtttgaaaac tgatcttaaa aagatggatg aatcacatag    4020
aagactaatt gagaatcaaa aagaacaatt atcactgatc acatcattaa tctcaaatct    4080
taaaattatg acagagagag gagggaagaa ggaccaacca gaacctagcg ggaggacatc    4140
catgatcaag acaaaagcaa aagaagagaa aataaagaaa gtcaggtttg accctcttat    4200
ggaaacacag ggcatcgaga aaacatccc tgacctctat agatcaatag agaaaacacc     4260
agaaaacgac acacagatca aatcagaaat aaacagattg aatgatgaat ccaatgccac    4320
tagattagta cctagaagaa taagcagtac aatgagatca ttaataataa tcattaacaa    4380
cagcaattta tcatcaaaag caaagcaatc atacatcaac gaactcaagc tctgcaagag    4440
tgacgaggaa gtgtctgagt tgatggacat gttcaatgag gatgtcagct cccagtaaac    4500
cgccaaccaa gggtcaacac caagaaaacc aatagcacaa acagccaat cagagaccac      4560 cccaatacac caaaccaatc aacacataac aaagatcgcg gccgcataga tgattaagaa    4620
aaacttagga tgaaaggact aatcaatcct ccgaaacaat gagcatcacc aactccacaa    4680
tctacacatt cccagaatcc tctttctccg agaatggcaa catagagccg ttaccactca    4740
aggtcaatga acagagaaag gccataccctc atattagggt tgtcaagata ggagatccgc    4800
ccaaacatgg atccagatat ctggatgtct ttttactggg cttctttgag atggaaaggt     4860
caaaagacag gtatgggagc ataagtgatc tagatgatga tccaagttac aaggtttgtg    4920
gctctggatc attgccactt gggttggcta gatacaccgg aaatgatcag gaactcctac    4980
```

```
aggctgcaac caagctcgat atagaagtaa gaagaactgt aaaggctacg gagatgatag    5040
tttacactgt acaaaacatc aaacctgaac tatatccatg gtccagtaga ttaagaaaag    5100
ggatgttatt tgacgctaat aaggttgcac ttgctcctca atgtcttcca ctagatagag    5160
ggataaaatt cagggtgata tttgtgaact gcacagcaat tggatcaata actctattca    5220
aaatccctaa gtccatggca ttgttatcat tgcctaatac aatatcaata aatctacaag    5280
tacatatcaa aacaggagtt cagacagatt ccaaaggagt agttcagatt ctagatgaaa    5340
aaggtgaaaa atcactaaat ttcatggttc atctcgggtt gatcaaaagg aagatgggca    5400
gaatgtactc agttgaatat tgtaagcaga agatcgagaa gatgagatta ttattctcat    5460
tgggattagt tggagggatc agcttccacg tcaacgcaac tggctctata tcaaagacat    5520
tagcaagtca attagcattc aaaagagaaa tctgctatcc cctaatggat ctgaatccac    5580
acttaaattc agttatatgg gcatcatcag ttgaaattac aagggtagat gcagttctcc    5640
agccttcatt acctggcgaa ttcagatact acccaaacat catagcaaaa ggggtcggga    5700
aaatcagaca gtaaaatcaa caaccctgat atccaccggt gtattaagcc gaagcaaata    5760
aaggataatc aaaaacttag gacaaaagag gtcaatacca acaactatta gcagtcacac    5820
tcgcaagaat aagagagaag ggaccaaaaa agtcaaatag gagaaatcaa aacaaaaggt    5880
acagaacacc agaacaacaa aatcaaaaca tccaactcac tcaaaacaaa aattccaaaa    5940
gagaccggca acacaacaag cactgaacac aatgccaact tcaatactgc taattattac    6000
aaccatgatc atggcatctt tctgccaaat agatatcaca aaactacagc acgtaggtgt    6060
attggtcaac agtcccaaag ggatgaagat atcacaaaac tttgaaacaa gatatctaat    6120
tttgagcctc ataccaaaaa tagaagactc taactcttgt ggtgaccaac agatcaagca    6180
atacaagaag ttattggata gactgatcat ccctttatat gatggattaa gattacagaa    6240
agatgtgata gtaaccaatc aagaatccaa tgaaaacact gatcccagaa caaaacgatt    6300
ctttggaggg gtaattggaa ccattgctct gggagtagca acctcagcac aaattacagc    6360
ggcagttgct ctggttgaag ccaagcaggc aagatcagac atcgaaaaac tcaaagaagc    6420
aattagggac acaaacaaag cagtgcagtc agttcagagc tccataggaa atttaatagt    6480
agcaattaaa tcagtccagg attatgttaa caaagaaatc gtgccatcga ttgcgaggct    6540
aggttgtgaa gcagcaggac ttcaattagg aattgcatta acacagcatt actcagaatt    6600
aacaaacata tttggtgata acataggatc gttacaagaa aaaggaataa aattacaagg    6660
tatagcatca ttataccgca caaatatcac agaaatattc acaacatcaa cagttgataa    6720
atatgatatc tatgatctgt tatttacaga atcaataaag gtgagagtta tagatgttga    6780
cttgaatgat tactcaatca ccctccaagt cagactccct ttattaacta ggctgctgaa    6840
cactcagatc tacaaagtag attccatatc atataacatc aaaacagag aatggtatat    6900 ccctcttccc agccatatca tgacgaaagg ggcatttcta ggtggagcag acgtcaaaga    6960
atgtatagaa gcattcagca gctatatatg cccttctgat ccaggatttg tattaaacca    7020
tgaaatagag agctgcttat caggaaacat atcccaatgt ccaagaacaa cggtcacatc    7080
agacattgtt ccaagatatg catttgtcaa tggaggagtg gttgcaaact gtataacaac    7140
cacctgtaca tgcaacggaa ttggtaatag aatcaatcaa ccacctgatc aaggagtaaa    7200
aattataaca cataaagaat gtagtacaat aggtatcaac ggaatgctgt tcaatacaaa    7260
taaagaagga actcttgcat tctatacacc aaatgatata acactaaaca attctgttgc    7320
acttgatcca attgacatat caatcgagct caacaaggcc aaatcagatc tagaagaatc    7380
```

```
aaaagaatgg ataagaaggt caaatcaaaa actagattct attggaaatt ggcatcaatc    7440
tagcactaca atcataatta ttttgataat gatcattata ttgtttataa ttaatataac    7500
gataattaca attgcaatta agtattacag aattcaaaag agaaatcgag tggatcaaaa    7560
tgacaagcca tatgtactaa caaacaaata acatatctac agatcattag atattaaaat    7620
tataaaaaac ttaggagtaa agttacgcaa tccaactcta ctcatataat tgaggaagga    7680
cccaatagac aaatccaaat tcgagatgga atactggaag cataccaatc acggaaagga    7740
tgctggtaat gagctggaga cgtctatggc tactcatggc aacaagctca ctaataagat    7800
aatatacata ttatggacaa taatcctggt gttattatca atagtcttca tcatagtgct    7860
aattaattcc atcaaaagtg aaaaggccca cgaatcattg ctgcaagaca taaataatga    7920
gtttatggaa attacagaaa agatccaaat ggcatcggat aataccaatg atctaataca    7980
gtcaggagtg aatacaaggc ttcttacaat tcagagtcat gtccagaatt acataccaat    8040
atcattgaca caacagatgt cagatcttag gaaattcatt agtgaaatta caattagaaa    8100
tgataatcaa gaagtgctgc cacaaagaat aacacatgat gtaggtataa aacctttaaa    8160
tccagatgat ttttggagat gcacgtctgg tcttccatct ttaatgaaaa ctccaaaaat    8220
aaggttaatg ccagggccgg gattattagc tatgccaacg actgttgatg ctgtgttag     8280 aactccgtct ttagttataa atgatctgat ttatgcttat acctcaaatc taattactcg    8340
aggttgtcag gatataggaa aatcatatca agtcttacag atagggataa taactgtaaa    8400
ctcagacttg gtacctgact taaatcctag gatctctcat acctttaaca taaatgacaa    8460
taggaagtca tgttctctag cactcctaaa tacagatgta tatcaactgt gttcaactcc    8520
caaagttgat gaaagatcag attatgcatc atcaggcata gaagatattg tacttgatat    8580
tgtcaattat gatggttcaa tctcaacaac aagatttaag aataataaca taagctttga    8640
tcaaccatat gctgcactat acccatctgt tggaccaggg atatactaca aaggcaaaat    8700
aatatttctc gggtatggag gtcttgaaca tccaataaat gagaatgtaa tctgcaacac    8760
aactgggtgc cccgggaaaa cacagagaga ctgtaatcaa gcatctcata gtccatggtt    8820
ttcagatagg aggatggtca actccatcat tgttgttgac aaaggcttaa actcaattcc    8880
aaaattgaaa gtatggacga tatctatgcg acaaaattac tgggggtcag aaggaaggtt    8940
acttctacta ggtaacaaga tctatatata tacaagatct acaagttggc atagcaagtt    9000
acaattagga ataattgata ttactgatta cagtgatata aggataaaat ggacatggca    9060
taatgtgcta tcaagaccag gaaacaatga atgtccatgg ggacattcat gtccagatgg    9120
atgtataaca ggagtatata ctgatgcata tccactcaat cccacaggga gcattgtgtc    9180
atctgtcata ttagactcac aaaaatcgag agtgaaccca gtcataactt actcaacagc    9240
aaccgaaaga gtaaacgagc tggccatcct aaacagaaca ctctcagctg gatatacaac    9300
aacaagctgc attacacact ataacaaagg atattgtttt catatagtag aaataaatca    9360
taaaagctta aacacatttc aacccatgtt gttcaaaaca gagattccaa aaagctgcag    9420
ttaatcataa ttaaccataa tatgcatcaa tctatctata atacaagtat atgataagta    9480
atcagcaatc agacaataga cgtacggaaa taataaaaaa cttaggagaa aagtgtgcaa    9540
gaaaaatgga caccgagtcc cacagcggca caacatctga cattctgtac cctgaatgtc    9600
acctcaattc tcctatagtt aaaggaaaga tagcacaact gcatacaata atgagtttgc    9660
ctcagcccta cgatatggat gatgattcaa tactgattat tactagacaa aaaattaaac    9720
```

```
tcaataaatt agataaaaga caacggtcaa ttaggaaatt aagatcagtc ttaatggaaa    9780
gagtaagtga tctaggtaaa tatacctta tcagatatcc agagatgtct agtgaaatgt    9840
tccaattatg tatacccgga attaataata aaataaatga attgctaagt aaagcaagta    9900
aaacatataa tcaaatgact gatggattaa gagatctatg ggttactata ctatcgaagt    9960
tagcatcgaa aaatgatgga agtaattatg atatcaatga agatattagc aatatatcaa   10020
atgttcacat gacttatcaa tcagacaaat ggtataatcc attcaagaca tggtttacta   10080
ttaagtatga catgagaaga ttacaaaaag ccaaaaatga gattacattc aataggcata   10140
aagattataa tctattagaa gaccaaaaga atatattgct gatacatcca gaactcgtct   10200
taatattaga taaacaaaat tacaatgggt atataatgac tcctgaattg gtactaatgt   10260
attgtgatgt agttgaaggg aggtggaata taagttcatg tgcaaaattg gatcctaagt   10320
tacaatcaat gtattataag ggtaacaatt tatgggaaat aatagatgga ctattctcga   10380
ccttaggaga aagaacattt gacataatat cactattaga accacttgca ttatcgctca   10440
ttcaaactta tgacccggtt aaacagctca gggggctt ttaaatcac gtgttatcag    10500 aaatggaatt aatatttgca gctgagtgta caacagagga aatacctaat gtggattata   10560
tagataaaat tttagatgtg ttcaaagaat caacaataga tgaaatagca gaaattttct   10620
ctttcttccg aacttttgga caccctccat tagaggcgag tatagcagca gagaaagtta   10680
gaaagtatat gtatactgag aaatgcttga aatttgatac tatcaataaa tgtcatgcta   10740 tttttttgtac aataattata aatggatata gagaaagaca tggtggtcaa tggcctccag   10800
ttacattacc tgtccatgca catgaattta tcataaatgc atacggatca aattctgcca   10860
tatcatatga gaatgctgta gattattata agagcttcat aggaataaaa tttgacaagt   10920
ttatagagcc tcaattggat gaagacttaa ctatttatat gaaagataaa gcattatccc   10980
caaagaaatc aaactgggac acagtctatc cagcttcaaa cctgttatac cgcactaatg   11040
tgtctcatga ttcacgaaga ttggttgaag tattatagc agatagtaaa tttgatcccc   11100
accaagtatt agattacgta gaatcaggat attggctgga tgatcctgaa tttaatatct   11160
catatagttt aaaagagaaa gaaataaaac aagaaggtag actttttgca aaaatgacat   11220
acaagatgag ggctacacaa gtattatcag aaacattatt ggcgaataat atagggaaat   11280
tcttccaaga gaatgggatg gttaaaggag aaattgaatt actcaagaga ctaacaacaa   11340
tatctatgtc tggagttccg cggtataatg aggtatacaa taattcaaaa agtcacacag   11400
aagaacttca agcttataat gcaattagca gttccaattt atcttctaat cagaagtcaa   11460
agaagtttga atttaaatct acagatatat acaatgatgg atacgaaacc gtaagctgct   11520
tcttaacgac agatcttaaa aaatattgtt taaattggag gtatgaatca acagctttat   11580
tcggtgatac ttgtaatcag atatttgggt taaaggaatt atttaattgg ctgcacccctc   11640 gccttgaaaa gagtacaata tatgttggag atccttattg cccgccatca gatattgaac   11700
atttaccact tgatgaccat cctgattcag gattttatgt tcataatcct aaaggaggaa   11760
tagaagggtt ttgccaaaag ttatggacac tcatatctat cagtgcaata catttagcag   11820
ctgtcaaaat cggtgtaaga gttactgcaa tggttcaagg ggataatcaa gccatagctg   11880
ttaccacaag agtacctaat aattatgatt ataaagttaa gaaagagatt gtttataaag   11940
atgtggtaag attttttgat tccttgagag aggtgatgga tgatctgggt catgagctca   12000
aactaaatga aactataata agtagtaaaa tgtttatata tagcaaaagg atatactatg   12060
acggaagaat ccttcctcag gcattaaaag cattgtctag atgtgttttt tggtctgaaa   12120
```

```
caatcataga tgagacaaga tcagcatcct caaatctggc tacatcgttt gcaaaggcca    12180
ttgagaatgg ctactcacct gtattgggat atgtatgctc aatcttcaaa atatccaac    12240 agttgtatat agcgcttgga atgaatataa acccaactat aacccaaaat attaaagatc    12300
aatatttcag gaatattcat tggatgcaat atgcctcctt aatccctgct agtgtcggag    12360
gatttaatta tatggccatg tcaaggtgtt ttgtcagaaa cattggagat cctacagtcg    12420
ctgcgttagc cgatattaaa agatttataa aagcaaattt gttagatcga ggtgtccttt    12480
acagaattat gaatcaagaa ccaggcgagt cttcttttt agactgggcc tcagatccct    12540
attcatgtaa cttaccacaa tctcaaaata taaccaccat gataaagaat ataactgcaa    12600
gaaatgtact acaggactca ccaaacccat tactatctgg attatttaca agtacaatga    12660
tagaagagga tgaggaatta gctgagttcc taatggacag gagaataatc ctcccaagag    12720
ttgcacatga cattttagat aattctctta ctggaattag gaatgctata gctggtatgt    12780
tggatacaac aaaatcacta attcgagtag ggataagcag aggaggatta acctataact    12840
tattaagaaa gataagcaac tatgatcttg tacaatatga gacacttagt aaaactttaa    12900
gactaatagt cagtgacaag attaagtatg aagatatgtg ctcagtagac ctagccatat    12960
cattaagaca aaaaatgtgg atgcatttat caggaggaag aatgataaat ggacttgaaa    13020
ctccagatcc tttagagtta ctgtctggag taataataac aggatctgaa cattgtagga    13080
tatgttattc aactgaaggt gaaagcccat atacatggat gtatttacca ggcaatctta    13140 ataggatc agctgagaca ggaatagcat cattaagggt cccttacttt ggatcagtta    13200
cagatgagag atctgaagca caattagggt atatcaaaaa tctaagcaaa ccagctaagg    13260
ctgctataag aatagcaatg atatatactt gggcatttgg aatgacgaa atatcttgga    13320 tggaagcatc acagattgca caaacacgtg caaactttac attggatagc ttaaagattt    13380
tgacaccagt gacaacatca acaaatctat cacacaggtt aaaagatact gctactcaga    13440
tgaaattttc tagtacatca cttattagag taagcaggtt catcacaata tctaatgata    13500
atatgtctat taagaagca atgaaaacta aagatacaaa tcttatttat caacaggtaa    13560
tgttaacagg attaagtgta tttgaatatc tatttaggtt agaggagagt acaggacata    13620
accctatggt catgcatcta catatagagg atggatgttg tataaaagag agttacaatg    13680
atgagcatat caatccggag tctacattag agttaatcaa ataccctgag agtaatgaat    13740
ttatatatga taaggaccct ttaaaggata tagatctatc aaaattaatg gttataagag    13800
atcattctta tacaattgac atgaattact gggatgacac agatattgta catgcaatat    13860
caatatgtac tgcagttaca atagcagata caatgtcgca gctagatcgg gataatctta    13920
aggagctggt tgtgattgca aatgatgatg atattaacag tctgataact gaatttctga    13980
ccctagatat actagtgttt ctcaaaacat tggagggtt actcgtgaat caatttgcat    14040
atacccttta tggattgaaa atagaaggaa gggatcccat ttgggattat ataatgaaa    14100 cattaaaaga cacctcacat tcagtactta agtattatc taatgcacta tctcatccaa    14160
aagtgtttaa gagattttgg gattgtggag ttttgaatcc tatttatggt cctaatactg    14220
ctagtcaaga tcaagttaag cttgctctct cgatttgcga gtactccttg gatcatttta    14280
tgagagaatg gttgaatgga gcatcacttg agatctatat ctgtgatagt gacatggaaa    14340
tagcaaatga cagaagacaa gcatttctct caagacatct tgcctttgtg tgttgtttag    14400
cagagatagc atcttttgga ccaaatttat taaatctaac atatctagag agacttgatg    14460
```

-continued aattaaaaca atacttagat ctgaacatca aagaagatcc tactcttaaa tatgtgcaag 14520
tatcaggact gttaattaaa tcattcccct caactgttac gtatgtaagg aaaactgcga 14580
ttaagtatct gaggattcgt ggtattaatc cgcctgaaac gattgaagat tgggatccca 14640
tagaagatga gaatatctta gacaatattg ttaaaactgt aaatgacaat tgcagtgata 14700
atcaaaagag aaataaaagt agttatttct ggggattagc tctaaagaat tatcaagtcg 14760
tgaaaataag atccataacg agtgattctg aagttaatga agcttcgaat gttactacac 14820
atggaatgac acttcctcag ggaggaagtt atctatcaca tcagctgagg ttatttggag 14880
taaacagtac aagttgtctt aaagctcttg aattatcaca aatcttaatg agggaagtta 14940
aaaaagataa agatagactc tttttaggag aaggagcagg agctatgtta gcatgttatg 15000
atgctacact cggtcctgca ataaattatt ataattctgg tttaaatatt acagatgtaa 15060
ttggtcaacg ggaattaaaa atcttcccat cagaagtatc attagtaggt aaaaaactag 15120
gaaatgtaac acagattctt aatcgggtga gggtgttatt taatgggaat cccaattcaa 15180
catggatagg aaatatggaa tgtgagagtt taatatggag tgaattaaat gataagtcaa 15240
ttggtttagt acattgtgac atggagggag cgataggcaa atcagaagaa actgttctac 15300
atgaacatta tagtattatt aggattacat atttaatcgg ggatgatgat gttgtcctag 15360
tatcaaaaat tataccaact attactccga attggtctaa aatactctat ctatacaagt 15420
tgtattggaa ggatgtaagt gtagtgtccc ttaaaacatc caatcctgcc tcaacagagc 15480
tttatttaat ttcaaaagat gcttactgta ctgtaatgga acccagtaat cttgttttat 15540
caaaacttaa aaggatatca tcaatagaag aaaataatct attaaagtgg ataatcttat 15600
caaaaaggaa gaataacgag tggttacagc atgaaatcaa agaaggagaa agggattatg 15660
ggataatgag gccatatcat acagcactgc aaatttttgg attccaaatt aacttaaatc 15720
acttagctag agaatttttta tcaactcctg atttaaccaa cattaataat ataattcaaa 15780
gttttacaag aacaattaaa gatgttatgt tcgaatgggt caatatcact catgacaata 15840
aaagacataa attaggagga agatataatc tattcccgct taaaaataag gggaaattaa 15900
gattattatc acgaagatta gtactaagct ggatatcatt atccttatca accagattac 15960
tgacgggccg ttttccagat gaaaaatttg aaaatagggc acagaccgga tatgtatcat 16020
tggctgatat tgatttagaa tccttaaagt tattatcaag aaatattgtc aaaaattaca 16080
aagaacacat aggattaata tcatactggt ttttgaccaa agaggtcaaa atactaatga 16140
agcttatagg aggagtcaaa ctactaggaa ttcctaaaca gtacaaagag ttagaggatc 16200
gatcatctca gggttatgaa tatgataatg aatttgatat tgattaatac ataaaaacat 16260
aaaataaaac acctattcct cacccattca cttccaacaa aatgaaaagt aagaaaaaca 16320
tgtaatatat atataccaaa cagagttttt ctcttgtttg gt 16362

<210> SEQ ID NO 94
<211> LENGTH: 16368
<212> TYPE: DNA
<213> ORGANISM: Artificial Sequence
<220> FEATURE:
<223> OTHER INFORMATION: Recombinant rB/HPIV3 sequence

<400> SEQUENCE: 94
accaaacaag agaagagact ggtttgggaa tattaattca aataaaaatt aacttaggat 60
taaagaactt taccgaaagg taaggggaaa gaaatcctaa gagcttagcc atgttgagtc 120
tattcgacac attcagtgcg cgtaggcagg agaacataac gaaatcagct ggtggggctg 180

```
ttattcccgg gcaaaaaaac actgtgtcta tatttgctct tggaccatca ataacagatg    240
acaatgataa aatgacattg gctcttctct ttttgtctca ttctttagac aatgaaaagc    300
agcatgcgca aagagctgga tttttagttt ctctgttatc aatggcttat gccaacccag    360
aattatattt aacatcaaat ggtagtaatg cagatgttaa atatgttatc tacatgatag    420
agaaagaccc aggaagacag aaatatggtg ggtttgtcgt caagactaga gagatggttt    480
atgaaaagac aactgattgg atgttcggga gtgatcttga gtatgatcaa gacaatatgt    540
tgcaaaatgg tagaagcact tctacaatcg aggatcttgt tcatacttt ggatatccat     600 cgtgtcttgg agcccttata atccaagttt ggataatact tgttaaggct ataaccagta    660
tatcaggatt gaggaaagga ttctttactc ggttagaagc atttcgacaa gatggaacag    720
ttaaatccag tctagtgttg agcggtgatg cagtagaaca aattggatca attatgaggt    780
cccaacagag cttggtaaca ctcatggttg aaacactgat aacaatgaac acaggcagga    840
atgatctgac aacaatagaa aagaatatac agattgtagg aaactacatc agagatgcag    900
gtcttgcttc attttt caac acaatcagat atggcattga gactagaatg gcagctctaa    960
ctctgtctac ccttagaccg gatatcaaca gactcaaggc actgatcgag ttatatctat    1020
caaaggggcc acgtgctcct tttatatgca ttttgagaga tcccgtgcat ggtgagtttg    1080
caccaggcaa ctatcctgcc ctctggagtt atgcgatggg tgtagcagtt gtacaaaaca    1140
aggccatgca acagtatgta acaggaaggt cttatctgga tattgaaatg ttccaacttg    1200
gtcaagcagt ggcacgtgat gccgagtcgc agatgagttc aatattagag gatgaactgg    1260
gggtcacaca agaagccaag caaagcttga agaaacacat gaagaacatc agcagttcag    1320
atacaacctt tcataagcct acaggggat cagccataga aatggcgata gatgaagaag    1380
cagggcagcc tgaatccaga ggagatcagg atcaaggaga tgagcctcgg tcatccatag    1440
ttccttatgc atgggcagac gaaaccggga atgacaatca aactgaatca actacagaaa    1500
ttgacagcat caaaactgaa caaagaaaca tcagagacag gctgaacaaa agactcaacg    1560 agaaaggaa acagagtgac ccgagatcaa ctgacatcac aaacaacaca atcaaaactg    1620
aaatagatga tttgttcagt gcattcggaa gcaactagtc acaaagagat gaccaggcgc    1680
gccaagtaag aaaaacttag gattaatgga cctgcaggat ggaatattgg aaacacacaa    1740
acagcataaa taacaccaac aatgaaaccg aaacagccag aggcaaacat agtagcaagg    1800
ttacaaatgt agcacaaatc acattatcca ttctggcaat gataatctca acttcactta    1860
taattgcagc catcatattc atagcctcgg caaaccacaa agtcacacca acaactgcaa    1920
tcatacaaga tgcaacaagc cagatcaaga acacaacccc aacatacctc acccagaatc    1980
ctcagcttgg aatcagtccc tctaatccgt ctgaaattac atcacaaatc accaccatac    2040
tagcttcaac aacaccagga gtcaagtcaa ccctgcaatc acaacagtc aagaccaaaa     2100 acacaacaac aactcaaaca caacccagca agcccaccac aaaacaacgc aaaacaaac     2160 caccaagcaa acccaataat gattttcact ttgaagtgtt caactttgta ccctgcagca    2220
tatgcagcaa caatccaacc tgctgggcta tctgcaaaag aataccaaac aaaaaaccag    2280
gaaagaaaac cactaccaag cccacaaaaa accaaccct caagacaacc aaaaaagatc      2340
ccaaacctca aaccactaaa tcaaaggaag tacccaccac caagcccaca gaagagccaa    2400
ccatcaacac caccaaaaca aacatcataa ctacactact cacctccaac accacaggaa    2460
atccagaact cacaagtcaa atggaaacct tccactcaac ttcctccgaa ggcaatccaa    2520
```

```
gcccttctca agtctctaca acatccgagt acccatcaca accttcatct ccacccaaca      2580
caccacgcca gtagtgatag ctagcggcgc gccagcaaca agtaagaaaa acttaggatt      2640
aatggaaatt atccaatcca gagacggaag gacaaatcca gaatccaacc acaactcaat      2700
caaccaaaga ttcatggaag acaatgttca aaacaatcaa atcatggatt cttgggaaga      2760
gggatcagga gataaatcat ctgacatctc atcggccctc gacatcattg aattcatact      2820
cagcaccgac tcccaagaga acacggcaga cagcaatgaa atcaacacag gaaccacaag      2880
acttagcacg acaatctacc aacctgaatc caaaacaaca gaaacaagca aggaaaatag      2940
tggaccagct aacaaaaatc gacagtttgg ggcatcacac gaacgtgcca cagagacaaa      3000
agatagaaat gttaatcagg agactgtaca gggaggatat aggagaggaa gcagcccaga      3060
tagtagaact gagactatgg tcactcgaag aatctccaga agcagcccag atcctaacaa      3120
tggaacccaa atccaggaag atattgatta caatgaagtt ggagagatgg ataaggactc      3180
tactaagagg gaaatgcgac aatttaaaga tgttccagtc aaggtatcag gaagtgatgc      3240
cattcctcca acaaaacaag atggagacgg tgatgatgga agaggcctgg aatctatcag      3300
tacatttgat tcaggatata ccagtatagt gactgccgca acactagatg acgaagaaga      3360
actccttatg aagaacaaca ggccaagaaa gtatcaatca acaccccaga acagtgacaa      3420
gggaattaaa aaaggggttg gaaggccaaa agacacagac aaacaatcat caatattgga      3480
ctacgaactc aacttcaaag gatcgaagaa gagccagaaa atcctcaaag ccagcacgaa      3540
tacaggagaa ccaacaagac cacagaatgg atcccagggg aagagaatca catcctggaa      3600
catcctcaac agcgagagcg gcaatcgaac agaatcaaca aaccaaaccc atcagacatc      3660
aacctcggga cagaaccaca caatgggacc aagcagaaca acctccgaac caaggatcaa      3720
gacacaaaag acgatggaa aggaaagaga ggacacagaa gagagcactc gatttacaga      3780
aagggcgatt acattattac agaatcttgg tgtaatccaa tctgcagcaa aattagacct      3840
ataccaagac aagagagttg tgtgtgtggc gaatgtccta acaatgcag atactgcatc      3900
aaagatagac ttcctagcag gtttgatgat aggagtgtca atggatcatg ataccaaatt      3960
aaatcagatt cagaacgaga tattaagttt gaaaactgat cttaaaaaga tggatgaatc      4020
acatagaaga ctaattgaga atcaaaaaga acaattatca ctgatcacat cattaatctc      4080
aaatcttaaa attatgacag agagggagg gaagaaggac caaccagaac ctagcgggag      4140
gacatccatg atcaagacaa aagcaaaaga agagaaaata aagaaagtca ggtttgaccc      4200
tcttatggaa acacagggca tcgagaaaaa catccctgac ctctatagat caatagagaa      4260
aacaccagaa aacgacacac agatcaaatc agaaataaac agattgaatg atgaatccaa      4320
tgccactaga ttagtaccta agaataag cagtacaatg agatcattaa taataatcat      4380
taacaacagc aatttatcat caaaagcaaa gcaatcatac atcaacgaac tcaagctctg      4440
caagagtgac gaggaagtgt ctgagttgat ggacatgttc aatgaggatg tcagctccca      4500
gtaaaccgcc aaccaagggt caacaccaag aaaaccaata gcacaaaaca gccaatcaga      4560
gaccacccca atacaccaaa ccaatcaaca cataacaaag atcgcggccg catagatgat      4620
taagaaaaac ttaggatgaa aggactaatc aatcctccga acaatgagc atcaccaact      4680
ccacaatcta cacattccca gaatcctctt tctccgagaa tggcaacata gagccgttac      4740
cactcaaggt caatgaacag agaaaggcca tacctcatat tagggttgtc aagataggag      4800
atccgcccaa acatggatcc agatatctgg atgtcttttt actgggcttc tttgagatgg      4860
aaaggtcaaa agacaggtat gggagcataa gtgatctaga tgatgatcca agttacaagg      4920
```

-continued

```
tttgtggctc tggatcattg ccacttgggt tggctagata caccggaaat gatcaggaac    4980
tcctacaggc tgcaaccaag ctcgatatag aagtaagaag aactgtaaag gctacggaga    5040
tgatagttta cactgtacaa aacatcaaac ctgaactata tccatggtcc agtagattaa    5100
gaaaagggat gttatttgac gctaataagg ttgcacttgc tcctcaatgt cttccactag    5160
atagagggat aaaattcagg gtgatatttg tgaactgcac agcaattgga tcaataactc    5220
tattcaaaat ccctaagtcc atggcattgt tatcattgcc taatacaata tcaataaatc    5280
tacaagtaca tatcaaaaca ggagttcaga cagattccaa aggagtagtt cagattctag    5340
atgaaaaagg tgaaaaatca ctaaatttca tggttcatct cgggttgatc aaaaggaaga    5400
tgggcagaat gtactcagtt gaatattgta agcagaagat cgagaagatg agattattat    5460
tctcattggg attagttgga gggatcagct tccacgtcaa cgcaactggc tctatatcaa    5520
agacattagc aagtcaatta gcattcaaaa gagaaatctg ctatcccctc atggatctga    5580
atccacactt aaattcagtt atatgggcat catcagttga aattacaagg gtagatgcag    5640
ttctccagcc ttcattacct ggcgaattca gatactaccc aaacatcata gcaaaggggg    5700
tcgggaaaat cagacagtaa aatcaacaac cctgatatcc accggtgtat taagccgaag    5760
caaataaagg ataatcaaaa acttaggaca aaagaggtca ataccaacaa ctattagcag    5820
tcacactcgc aagaataaga gagaagggac caaaaaagtc aaataggaga aatcaaaaca    5880
aaggtacag aacaccagaa caacaaaatc aaaacatcca actcactcaa aacaaaaatt    5940
ccaaaagaga ccggcaacac aacaagcact gaacacaatg ccaacttcaa tactgctaat    6000
tattcaaacc atgatcatgg catctttctg ccaaatagat atcacaaaac tacagcacgt    6060
aggtgtattg gtcaacagtc ccaaagggat gaagatatca caaaactttg aaacaagata    6120
tctaattttg agcctcatac caaaaataga agactctaac tcttgtggtg accaacagat    6180
caagcaatac aagaagttat tggatagact gatcatccct ttatatgatg gattaagatt    6240
acagaaagat gtgatagtaa ccaatcaaga atccaatgaa acactgatc ccagaacaaa    6300
acgattcttt ggaggggtaa ttggaaccat tgctctggga gtagcaacct cagcacaaat    6360
tacagcggca gttgctctgg ttgaagccaa gcaggcaaga tcagacatcg aaaaactcaa    6420
agaagcaatt agggacacaa acaaagcagt gcagtcagtt cagagctcca taggaaattt    6480
aatagtagca attaaatcag tccaggatta tgttaacaaa gaaatcgtgc catcgattgc    6540
gaggctaggt tgtgaagcag caggacttca attaggaatt gcattaacac agcattactc    6600
agaattaaca aacatatttg gtgataacat aggatcgtta caagaaaaag gaataaaatt    6660
acaaggtata gcatcattat accgcacaaa tatcacagaa atattcacaa catcaacagt    6720
tgataaatat gatatctatg atctgttatt tacagaatca ataaaggtga gagttataga    6780
tgttgacttg aatgattact caatcacccct ccaagtcaga ctccctttat taactaggct    6840
gctgaacact cagatctaca agtagattc catatcatat aacatccaaa acagagaatg    6900
gtatatccct cttcccagcc atatcatgac gaaagggca tttctaggtg gagcagacgt    6960
caaagaatgt atagaagcat tcagcagcta tatgcccct tctgatccag gatttgtatt    7020
aaaccatgaa atagagagct gcttatcagg aaacatatcc caatgtccaa gaacaacggt    7080
cacatcagac attgttccaa gatatgcatt tgtcaatgga ggagtggttg caaactgtat    7140
aacaaccacc tgtacatgca acggaattgg taatagaatc aatcaaccac ctgatcaagg    7200
agtaaaaatt ataacacata aagaatgtag tacaataggt atcaacggaa tgctgttcaa    7260
```

```
tacaaataaa gaaggaactc ttgcattcta tacaccaaat gatataacac taaacaattc     7320
tgttgcactt gatccaattg acatatcaat cgagctcaac aaggccaaat cagatctaga     7380
agaatcaaaa gaatggataa gaaggtcaaa tcaaaaacta gattctattg gaaattggca     7440
tcaatctagc actacaatca taattatttt gataatgatc attatattgt ttataattaa     7500
tataacgata attacaattg caattaagta ttacagaatt caaagagaaa atcgagtgga     7560
tcaaaatgac aagccatatg tactaacaaa caaataacat atctacagat cattagatat     7620
taaaattata aaaacttag gagtaaagtt acgcaatcca actctactca tataattgag      7680
gaaggaccca atagacaaat ccaaattcga gatggaatac tggaagcata ccaatcacgg     7740
aaaggatgct ggtaatgagc tggagacgtc tatggctact catggcaaca agctcactaa     7800
taagataata tacatattat ggacaataat cctggtgtta ttatcaatag tcttcatcat     7860
agtgctaatt aattccatca aaagtgaaaa ggcccacgaa tcattgctgc aagacataaa     7920
taatgagttt atggaaatta cagaaaagat ccaaatggca tcggataata ccaatgatct     7980
aatacagtca ggagtgaata caaggcttct tacaattcag agtcatgtcc agaattacat     8040
accaatatca ttgacacaac agatgtcaga tcttaggaaa ttcattagtg aaattacaat     8100
tagaaatgat aatcaagaag tgctgccaca agaataaca catgatgtag gtataaaacc       8160
tttaaatcca gatgattttt ggagatgcac gtctggtctt ccatctttaa tgaaaactcc     8220
aaaaataagg ttaatgccag ggccgggatt attagctatg ccaacgactg ttgatggctg     8280
tgttagaact ccgtctttag ttataaatga tctgatttat gcttatacct caaatctaat     8340
tactcgaggt tgtcaggata taggaaaatc atatcaagtc ttacagatag ggataataac     8400
tgtaaactca gacttggtac ctgacttaaa tcctaggatc tctcatacct ttaacataaa     8460
tgacaatagg aagtcatgtt ctctagcact cctaaataca gatgtatatc aactgtgttc     8520
aactcccaaa gttgatgaaa gatcagatta tgcatcatca ggcatagaag atattgtact     8580
tgatattgtc aattatgatg gttcaatctc aacaacaaga tttaagaata taacataag      8640 ctttgatcaa ccatatgctg cactataccc atctgttgga ccagggatat actacaaagg     8700
caaaataata tttctcgggt atggaggtct tgaacatcca ataaatgaga atgtaatctg     8760
caacacaact gggtgccccg ggaaaacaca gagagactgt aatcaagcat ctcatagtcc     8820
atggttttca gataggagga tggtcaactc catcattgtt gttgacaaag cttaaactc      8880 aattccaaaa ttgaaagtat ggacgatatc tatgcgacaa aattactggg ggtcagaagg     8940
aaggttactt ctactaggta acaagatcta tatatataca agatctacaa gttggcatag     9000
caagttacaa ttaggaataa ttgatattac tgattacagt gatataagga taaaatggac     9060
atggcataat gtgctatcaa gaccaggaaa caatgaatgt ccatggggac attcatgtcc     9120
agatggatgt ataacaggag tatatactga tgcatatcca ctcaatccca caggagcat       9180 tgtgtcatct gtcatattag actcacaaaa atcgagagtg aacccagtca taacttactc     9240
aacagcaacc gaaagagtaa acgagctggc catcctaaac agaacactct cagctggata     9300
tacaacaaca agctgcatta cacactataa caaggatat tgttttcata tagtagaaat       9360
aaatcataaa agcttaaaca catttcaacc catgttgttc aaaacagaga ttccaaaaag     9420
ctgcagttaa tcataattaa ccataatatg catcaatcta tctataatac aagtatatga     9480
taagtaatca gcaatcagac aatagacgta cggaaataat aaaaaactta ggagaaaagt      9540
gtgcaagaaa aatggacacc gagtcccaca gcggcacaac atctgacatt ctgtaccctg     9600
aatgtcacct caattctcct atagttaaag gaaagatagc acaactgcat acaataatga     9660
```

```
gtttgcctca gccctacgat atggatgatg attcaatact gattattact agacaaaaaa    9720
ttaaactcaa taaattagat aaaagacaac ggtcaattag gaaattaaga tcagtcttaa    9780
tggaaagagt aagtgatcta ggtaaatata cctttatcag atatccagag atgtctagtg    9840
aaatgttcca attatgtata cccggaatta ataataaaat aaatgaattg ctaagtaaag    9900
caagtaaaac atataatcaa atgactgatg gattaagaga tctatgggtt actatactat    9960
cgaagttagc atcgaaaaat gatggaagta attatgatat caatgaagat attagcaata   10020
tatcaaatgt tcacatgact tatcaatcag acaaatggta taatccattc aagacatggt   10080
ttactattaa gtatgacatg agaagattac aaaaagccaa aaatgagatt acattcaata   10140
ggcataaaga ttataatcta ttagaagacc aaaagaatat attgctgata catccagaac   10200
tcgtcttaat attagataaa caaaattaca atgggtatat aatgactcct gaattggtac   10260
taatgtattg tgatgtagtt gaagggaggt ggaatataag ttcatgtgca aaattggatc   10320
ctaagttaca atcaatgtat tataagggta acaatttatg ggaaataata gatggactat   10380
tctcgacctt aggagaaaga acatttgaca taatatcact attagaacca cttgcattat   10440
cgctcattca aacttatgac ccggttaaac agctcagggg ggcttttttta aatcacgtgt   10500 tatcagaaat ggaattaata tttgcagctg agtgtacaac agaggaaata cctaatgtgg   10560
attatataga taaaatttta gatgtgttca aagaatcaac aatagatgaa atagcagaaa   10620
ttttctcttt cttccgaact tttggacacc ctccattaga ggcgagtata gcagcagaga   10680
aagttagaaa gtatatgtat actgagaaat gcttgaaatt tgatactatc aataaatgtc   10740
atgctatttt ttgtacaata attataaatg gatatagaga aagacatggt ggtcaatggc   10800
ctccagttac attacctgtc catgcacatg aatttatcat aaatgcatac ggatcaaatt   10860
ctgccatatc atatgagaat gctgtagatt attataagag cttcatagga ataaaatttg   10920
acaagtttat agagcctcaa ttggatgaag acttaactat ttatatgaaa gataaagcat   10980
tatccccaaa gaaatcaaac tgggacacag tctatccagc ttcaaacctg ttataccgca   11040
ctaatgtgtc tcatgattca cgaagattgg ttgaagtatt tatagcagat agtaaatttg   11100
atccccacca agtattagat tacgtagaat caggatattg gctggatgat cctgaattta   11160
atatctcata tagtttaaaa gagaaagaaa taaaacaaga aggtagactt tttgcaaaaa   11220
tgacatacaa gatgagggct acacaagtat tatcagaaac attattggcg aataatatag   11280
ggaaattctt ccaagagaat gggatggtta aaggagaaat tgaattactc aagagactaa   11340
caacaatatc tatgtctgga gttccgcggt ataatgaggt atacaataat tcaaaaagtc   11400
acacagaaga acttcaagct tataatgcaa ttagcagttc caatttatct tctaatcaga   11460
agtcaaagaa gtttgaattt aaatctacag atatatacaa tgatggatac gaaaccgtaa   11520
gctgcttctt aacgacagat cttaaaaaat attgtttaaa ttggaggtat gaatcaacag   11580
ctttattcgg tgatacttgt aatcagatat ttgggttaaa ggaattattt aattggctgc   11640
accctcgcct tgaaaagagt acaatatatg ttggagatcc ttattgcccg ccatcagata   11700
ttgaacattt accacttgat gaccatcctg attcaggatt ttatgttcat aatcctaaag   11760
gaggaataga agggttttgc caaaagttat ggacactcat atctatcagt gcaatacatt   11820
tagcagctgt caaaatcggt gtaagagtta ctgcaatggt tcaagggggat aatcaagcca   11880 tagctgttac cacaagagta cctaataatt atgattataa agttaagaaa gagattgttt   11940
ataaagatgt ggtaagattt tttgattcct tgagagaggt gatggatgat ctgggtcatg   12000
```

```
agctcaaact aaatgaaact ataataagta gtaaaatgtt tatatatagc aaaaggatat    12060
actatgacgg aagaatcctt cctcaggcat taaaagcatt gtctagatgt gttttttggt    12120
ctgaaacaat catagatgag acaagatcag catcctcaaa tctggctaca tcgtttgcaa    12180
aggccattga gaatggctac tcacctgtat tgggatatgt atgctcaatc ttcaaaaata    12240
tccaacagtt gtatatagcg cttggaatga atataaaccc aactataacc caaaatatta    12300
aagatcaata tttcaggaat attcattgga tgcaatatgc ctccttaatc cctgctagtg    12360
tcggaggatt taattatatg gccatgtcaa ggtgttttgt cagaaacatt ggagatccta    12420
cagtcgctgc gttagccgat attaaaagat ttataaaagc aaatttgtta gatcgaggtg    12480
tcctttacag aattatgaat caagaaccag gcgagtcttc ttttttagac tgggcctcag    12540
atccctattc atgtaactta ccacaatctc aaaatataac caccatgata aagaatataa    12600
ctgcaagaaa tgtactacag gactcaccaa acccattact atctggatta tttacaagta    12660
caatgataga agaggatgag gaattagctg agttcctaat ggacaggaga ataatcctcc    12720
caagagttgc acatgacatt ttagataatt ctcttactgg aattaggaat gctatagctg    12780
gtatgttgga tacaacaaaa tcactaattc gagtagggat aagcagagga ggattaaccc    12840
ataacttatt aagaaagata agcaactatg atcttgtaca atatgagaca cttagtaaaa    12900
ctttaagact aatagtcagt gacaagatta agtatgaaga tatgtgctca gtagacctag    12960
ccatatcatt aagacaaaaa atgtggatgc atttatcagg aggaagaatg ataaatggac    13020
ttgaaactcc agatcctttta gagttactgt ctggagtaat aataacagga tctgaacatt    13080
gtaggatatg ttattcaact gaaggtgaaa gcccatatac atggatgtat ttaccaggca    13140
atcttaatat aggatcagct gagacaggaa tagcatcatt aagggtccct tactttggat    13200
cagttacaga tgagagatct gaagcacaat tagggtatat caaaaatcta agcaaaccag    13260
ctaaggctgc tataagaata gcaatgatat atacttgggc atttgggaat gacgaaatat    13320
cttggatgga agcatcacag attgcacaaa cacgtgcaaa ctttacattg gatagcttaa    13380
agattttgac accagtgaca acatcaacaa atctatcaca caggttaaaa gatactgcta    13440
ctcagatgaa attttctagt acatcactta ttagagtaag caggttcatc acaatatcta    13500
atgataatat gtctattaaa gaagcaaatg aaactaaaga tacaaatctt atttatcaac    13560
aggtaatgtt aacaggatta agtgtatttg aatatctatt taggttagag gagagtacag    13620
gacataaccc tatggtcatg catctacata tagaggatgg atgttgtata aaagagagtt    13680
acaatgatga gcatatcaat ccggagtcta cattagagtt aatcaaatac cctgagagta    13740
atgaatttat atatgataag gacccttaa aggatataga tctatcaaaa ttaatggtta    13800
taagagatca ttcttataca attgacatga attactggga tgacacagat attgtacatg    13860
caatatcaat atgtactgca gttacaatag cagatacaat gtcgcagcta gatcgggata    13920
atctaaggga gctggttgtg attgcaaatg atgatgatat taacagtctg ataactgaat    13980 ttctgacccct agatatacta gtgtttctca aaacatttgg agggttactc gtgaatcaat    14040
ttgcatatac cctttatgga ttgaaaatag aaggaaggga tcccatttgg gattatataa    14100
tgagaacatt aaaagacacc tcacattcag tacttaaagt attatctaat gcactatctc    14160
atccaaaagt gtttaagaga ttttgggatt gtggagtttt gaatcctatt tatggtccta    14220
atactgctag tcaagatcaa gttaagcttg ctctctcgat ttgcgagtac tccttggatc    14280
tatttatgag agaatggttg aatggagcat cacttgagat ctatatctgt gatagtgaca    14340
tggaaatagc aaatgacaga agacaagcat ttctctcaag acatctttgcc tttgtgtgtt    14400
```

```
gtttagcaga gatagcatct tttggaccaa atttattaaa tctaacatat ctagagagac    14460
ttgatgaatt aaaacaatac ttagatctga acatcaaaga agatcctact cttaaatatg    14520
tgcaagtatc aggactgtta attaaatcat tcccctcaac tgttacgtat gtaaggaaaa    14580
ctgcgattaa gtatctgagg attcgtggta ttaatccgcc tgaaacgatt gaagattggg    14640
atcccataga agatgagaat atcttagaca atattgttaa aactgtaaat gacaattgca    14700
gtgataatca aaagagaaat aaaagtagtt atttctgggg attagctcta aagaattatc    14760
aagtcgtgaa aataagatcc ataacgagtg attctgaagt taatgaagct tcgaatgtta    14820
ctacacatgg aatgacactt cctcagggag gaagttatct atcacatcag ctgaggttat    14880
ttggagtaaa cagtacaagt tgtcttaaag ctcttgaatt atcacaaatc ttaatgagggg   14940 aagttaaaaa agataaagat agactctttt taggagaagg agcaggagct atgttagcat    15000
gttatgatgc tacactcggt cctgcaataa attattataa ttctggttta aatattacag    15060
atgtaattgg tcaacgggaa ttaaaaatct tcccatcaga agtatcatta gtaggtaaaa    15120
aactaggaaa tgtaacacag attcttaatc gggtgagggt gttatttaat gggaatccca    15180
attcaacatg gataggaaat atggaatgtg agagtttaat atggagtgaa ttaaatgata    15240
agtcaattgg tttagtacat tgtgacatgg agggagcgat aggcaaatca gaagaaactg    15300
ttctacatga acattatagt attattagga ttacatattt aatcggggat gatgatgttg    15360
tcctagtatc aaaaattata ccaactatta ctccgaattg gtctaaaata ctctatctat    15420
acaagttgta ttggaaggat gtaagtgtag tgtcccttaa aacatccaat cctgcctcaa    15480
cagagcttta tttaattcta aaagatgctt actgtactgt aatggaaccc agtaatcttg    15540
ttttatcaaa acttaaaagg atatcatcaa tagaagaaaa taatctatta agtggataa    15600 tcttatcaaa aaggaagaat aacgagtggt tacagcatga aatcaaagaa ggagaaaggg    15660
attatgggat aatgaggcca tatcatacag cactgcaaat ttttggattc caaattaact    15720
taaatcactt agctagagaa ttttttatcaa ctcctgattt aaccaacatt aataatataa    15780
ttcaaagttt tacaagaaca attaaagatg ttatgttcga atgggtcaat atcactcatg    15840
acaataaaag acataaatta ggaggaagat ataatctatt cccgcttaaa aataggggaa    15900
aattaagatt attatcacga agattagtac taagctggat atcattatcc ttatcaacca    15960
gattactgac gggccgtttt ccagatgaaa aatttgaaaa tagggcacag accggatatg    16020
tatcattggc tgatattgat ttagaatcct taaagttatt atcaagaaat attgtcaaaa    16080
attacaaaga acacatagga ttaatatcat actggttttt gaccaaagag gtcaaaatac    16140
taatgaagct tataggagga gtcaaactac taggaattcc taaacagtac aaagagttag    16200
aggatcgatc atctcagggt tatgaatatg ataatgaatt tgatattgat taatacataa    16260
aaacataaaa taaaacacct attcctcacc cattcacttc caacaaaatg aaaagtaaga    16320
aaaacatgta atatatatat accaaacaga gttttctctc tgtttggt                 16368
```

<210> SEQ ID NO 95
<211> LENGTH: 897
<212> TYPE: DNA
<213> ORGANISM: Artificial Sequence
<220> FEATURE:
<223> OTHER INFORMATION: Recombinant RSV G protein

<400> SEQUENCE: 95

```
atgtctaaga caaaggatca gcggacagcc aaaacactgg aacggacatg ggataccctg    60
```

```
aatcacctcc tcttcatcag cagttgcctg tacaagctca atctgaagtc catcgcccag    120
atcactctct ccatccttgc catgatcatc tctacaagcc tcatcattgc cgcaattatc    180
ttcatcgcca gcgctaacca caaggtcacc cttaccacag ccattattca ggatgccacc    240
aaccagatca agaacacaac ccctacctac ctgacacaga accctcagct tggaatttca    300
ctgagcaacc tgtccgaaac cacatctaaa cctacaacca tcttggctct gaccacacca    360
aacgccgagt ccaccccaca aagtaccaca gtgaagacca aaaacaccac aaccacacag    420
attcagccaa gcaagcctac aactaagcaa aggcagaaca agccacagaa caaacccaac    480
aacgactttc actttgaggt gttcaacttt gtgccctgct ccatttgctc caacaaccct    540
acctgttggg ctatctgcaa gaggatcccc aacaagaagc ccggcaggaa gactactact    600
aagcctacta aacagccagc cattaagacc actaagaagg acccaaagcc acagacaacc    660
aagccaaagg aggtgctcac taccaagccc actgagaagc ccaccattaa caccactaaa    720
accaacatcc gcacaacatt gctgacatca aacattacag agaaccagga gcacacaagc    780
cagaaggaga cactgcatag cactacatcc gaaggcaatc ccagcccaag ccaggtctat    840
actacctcag agtacctgtc ccagagcctg agccctagca acactactag atggtag      897
```